US007788045B2

(12) United States Patent
Andrijauskas

(10) Patent No.: US 7,788,045 B2
(45) Date of Patent: Aug. 31, 2010

(54) SYSTEMS AND METHOD FOR HOMEOSTATIC BLOOD STATES

(75) Inventor: Audrius Andrijauskas, Vilnius (LT)

(73) Assignee: Meditasks, LLC, Tenafly, NJ (US)

( * ) Notice: Subject to any disclaimer, the term of this patent is extended or adjusted under 35 U.S.C. 154(b) by 881 days.

(21) Appl. No.: 11/514,667

(22) Filed: Sep. 1, 2006

(65) Prior Publication Data

US 2007/0178167 A1    Aug. 2, 2007

Related U.S. Application Data

(60) Provisional application No. 60/712,809, filed on Sep. 1, 2005.

(51) Int. Cl.
    *G01N 33/49* (2006.01)
(52) U.S. Cl. ...................................................... 702/21
(58) Field of Classification Search ................... None
    See application file for complete search history.

(56) References Cited

OTHER PUBLICATIONS

Holme, et al. Prediction of Red Cell and Blood Volumes Distribution by Various Nomograms: Do Current Nomograms Overestimate?; Transfusion, vol. 48 (2008) pp. 910-916.*
Andrijauskas, A and Ivaskevicius, J. New Method of Tracing Blood Hemoglobin Concentration to Hematocrit Ratio for Monitoring Plasma Dilution and Osmotic Origin Shifts in Blood; Medicina(Kaunas), vol. 42, No. 3 (2006) pp. 181-186.*
Andrijauskas A, Ivaskevicius J. Zidinaviciute J. Immediate postoperative transfusions after total hip arthroplasty: retrospective analysis comparing two methods of predicting post-transfusion hematocrit. Lietuvos chirurgija. 2006;4(1): 13-21.
Andrijauskas A, Ivaskevicius J. New method of tracing blood hemoglobin concentration to hematocrit ratio for monitoring plasma dilution and osmotic origin shifts in blood. Medicina (Kaunas). 2006;42(3): 181-186.
Barker S.J. Blood volume measurement: the next intraoperative monitor? Anesthesiology. 1998;89:1310-2.
Boldt J. New light on intravascular volume replacement regimens: what did we learn from the past three years? Anesth Analg. 2003;97:1595-604.
Brauer PL, Svensen H, Hahn RG, Kilicturgay S, Kramer GC, Prough DS. Influence of rate and volume of infusion on the kinetics of 0.9% Saline and 7.5% Saline/6.0% Dextran 70 in sheep. Anesth Analg. 2002;95:1547-56.
Brauer K, Svensen C, Hahn RG, Traber LD, Prough DS. Volume kinetic analysis of the distribution of 0.9% Saline in conscious versus Isoflurane-anesthetized sheep. Anesthesiology 2002;96:442-449.
Carson JL, Duff A, Berlin JA, et al. Perioperative blood transfusion and postoperative mortality. JAMA. 1998;279:199-205.
Carson JL, Hill S, Carless P, et al. Transfusion triggers: A systematic review of the literature. Trans Med Rev. 2002;16:187-199.
Corwin HL, Krantz SB. Anemia of the critically ill: "Acute" anemia of chronic disease. Crit Care Med. 2000;28:3098-3099.
Drobin D, Hahn RG. Time course of increased haemodilution in hypotension induced by extradural anaesthesia. Br J Anaesth. 1996,77:213-226.
Drobin D, Hahn RG. Volume Kinetics of Ringer's Solution in Hypovolemic Volunteers. Anesthesiology. 1999;90:81-91.
Drobin D, Hahn R. Kinetics of isotonic and hypertonic plasma volume expanders. Anesthesiology. 2002; 96:1371-80.
Ewaldson CA, Hahn RG. Volume kinetics of Ringer's solution during induction of spinal and general anaesthesia. Br J Anaesth. 2001;87:406-414.
Hahn RG, Drobin D, Stahle L. Volume kinetics of Ringer's solution in female volunteers. Br J Anaesth. 1997;78:144-148.
Hahn RG; Svensen C. Plasma dilution and the rate of infusion of Ringer's solution. Br J Anaesth. 1997;79(1):64-7.
Hahn, RG, Resby M. Volume kinetics of Ringer's solution and dextran 3% during induction of spinal anaesthesia for Caesarean section. Can J Anaesth. 1998;45:443-45.
Hahn RG, Drobin D. Urinary excretion as an input variable in volume kinetic analysis of Ringer's solution. Br J Anaesth. 1998;80:183-188.
Hahn RG. Physiological or functional fluid spaces. Anesth Analg.; A letter to the editor, 2002;95(1)251-252.
Hahn RG, Edsberg L, Sjostrand F. Volume kinetic analysis of fluid shifts accompanying intravenous infusions of glucose solution. Cell Biochem Biophys. 2003;39(3):211-22.
Hahn RG. The use of volume kinetics to optimize fluid therapy. J Trauma. 2003;54(5 Suppl):S 155-8.
Hahn RG, Drobin D. Rapid water and slow sodium excretion of acetated Ringer's solution dehydrates cells. Anesth Analg 2003;97:1590-4.
Haruna M, Kumon K, Yahagi N et al. Blood measurement at the bedside using ICG Pulse Spectrometry. Anesthesiology. 1998;89:1322-8.
Hebert PC, Yetisir E, Martin C, et al. Is a low transfusion threshold safe in critically ill patients with cardiovascular disease? Crit Care Med. 2001;29:227-234.
Hebert PC, Fergusson DA: Red blood cell transfusions in critically ill patients. JAMA. 2002;288:1525-1526.

(Continued)

*Primary Examiner*—Rebecca E. Prouty
*Assistant Examiner*—Paul C. Martin
(74) *Attorney, Agent, or Firm*—Gary J. Gershik; Cooper & Dunham LLP

(57) ABSTRACT

Decades of investigations were focused on finding "gold standard" for evaluation of plasma dilution and osmolality, blood loss evaluation and prediction of bleeding or transfusion induced changes in hematocrit and hemoglobin concentration. Addressing deficiencies of existing methods, the current invention created new combined mathematical-physiological model applicable to manually operated nomograms and software in medical monitors. The mathematical model HBS Trends is used in blood transfusion and infusion therapy nomogram—HBS Nomogram—which is based on blood hemoglobin concentration and hematocrit. It is also an easy and practical tool for recording and dynamical interpretation of plasma osmolality, blood hemoglobin concentration, hematocrit and mean corpuscular hemoglobin concentration. The HBS Nomogram is a practical system for organizing blood test results in a patient's medical records. It can be used alone or, in line with existing guidelines for infusion and transfusion therapy making them more practical, cost effective and time saving in decision making.

9 Claims, 58 Drawing Sheets

OTHER PUBLICATIONS

Hedin A; Hahn RG. Volume expansion and plasma protein clearance during intravenous infusion of 5% albumin and autologous plasma. Clin Sci (Lond). 2005; 108(3):217-24.

Heidegger T, Kreienbuhl G. Unsuccessful Resuscitation Under Hypotensive Epidural Anesthesia During Elective Hip Arthroplasty. Anesth Analg. 1998;86:847-9.

Hoeft A, Schorn B, Weyland A, et al. Bedside assessment of intravascular volume status in patients undergoing coronary bypass surgery. Anesthesiology. 1994;81:76-86.

Holte K, Foss NB, Svensen C, Lund C, Madsen JL, Kehlet H. Epidural anesthesia, hypotension, and changes in intravascular volume. Anesthesiology. 2004; 100(2):281-6.

Iijima T, Iwao Y, Sankawa H. Circulating Blood Volume Measured by Pulse Dye-Densitometry: Comparison with 1311-HSA Analysis. Anesthesiology. 1998;89:1329-35.

Meier J, Kleen M, Habler O, Kemming G, Messmer K. New mathematical model for the correct prediction of the exchangeable blood volume during acute normovolemic hemodilution. Acta Anaesthesiol Scand. 2003;47(1):37-45.

Norberg A, Brauer KI, Prough DS, Gabrielsson J, Hahn RG, Uchida T, et al. Volume turnover kinetics of fluid shifts after hemorrhage, fluid infusion, and the combination of hemorrhage and fluid infusion in sheep. Anesthesiology. 2005;102(5):985-94.

Obata H, Goto F, Nara T, et al. High predictive value of red cell volume measurement using carboxy-haemoglobin in a rabbit model of haemorrahage. Br J Anaesth. 1998;81:940-4.

Ohki S, Kunimoto F, Isa Y, Obata H. Accuracy of carboxy-haemoglobin dilution method for the measurement of circulating blood volume. Can J Anesth. 2000;47:150-154.

Pearson TC, Guthrie DL, Simpson J et al. Interpretation of measured red cell mass and plasma volume in adults: Expert Panel on Radionuclides of the International Council for Standardization in Haematology. Br J Haematol. 1995;89(4):748-56.

Quon CF. Clinical pharmacokinetics and pharmacodynamics of colloidal plasma volume expanders. J Cardiothorac Anesth. 1988;2 (Suppl 1):S13-23.

Rehm M, Orth V, Kreimeier U et al. Four cases of radical hysterectomy with acute normovolemic hemodilution despite low preoperative hematocrit values. Anesth Analg. 2000;90:852-5.

Rehm M, Haller M, Orth V et al. Changes in Blood Volume and Hematocrit during Acute Preoperative Volume Loading with 5% Albumin or 6% Hetastarch Solutions in Patients before Radical Hysterectomy. Anesthesiology. 2001;95:849-856.

Sjostrand F, Edsberg L, Hahn RG. Volume kinetics of glucose solutions given by intravenous infusion. Br J Anaesth. 2001;87(6):834-43.

Sjostrand F, Hahn RG. Validation of volume kinetic analysis of glucose 2.5% solution given by intravenous infusion. Br J Anaesth. 2003;90(5): 600-7.

Stahle L, Nilsson A, Hahn RG. Modelling the volume of expandable body fluid spaces during i.v. fluid therapy. Br J Anaesth. 1997;78:138-143.

Stanski DR. The pharmacokinetics of intravenous fluids. Anesthesiology. 1997;87:200-l.

Strandberg P, Hahn RR. Volume kinetics of glucose 2.5% solution and insulin resistance after abdominal hysterectomy. Br J Anaesth. 2005;94(1):30-8.

Svensen C, Ponzer S, Hahn RG. Volume kinetics of Ringer solution after surgery for hip fracture. Can J Anesth. 1999; 46:133-141.

Svensen CH, Brauer KP, Hahn RG, Uchida T, Traber LD, Traber DL, Prough DS. Elimination rate constant describing clearance of infused fluid from plasma is independent of large infusion volumes of 0.9% saline in sheep. Anesthesiology. 2004;101(3): 666-74.

Vincent JL, Baron J-F, Reinhart K, et al: Anemia and blood transfusion in critically ill patients. JAMA. 2002;288:1499-1507.

Welch HG, Meehan KR, Goodnough LT. Prudent strategies for elective red blood cell transfusion. Ann Intern Med. 1992; 116:393-402.

Young JD, McQuillan P. Comparison of thoracic electrical bioimpedance and thermodilution for the measurement of cardiac index in patients with severe sepsis. Br J Anaesth. 1993:70:58.

American Society of Anesthesiologists Task Force on Blood Component Therapy: Practice guidelines for blood component therapy. Anesthesiology 1996; 84:732-747.

An Updated Report by the American Society of Anesthesiologists Task Force on Perioperative Blood Transfusion and Adjuvant Therapies;2006. Available from: http://www.asahq.org/publicationsAnd Services/sgstoc.htm.

* cited by examiner

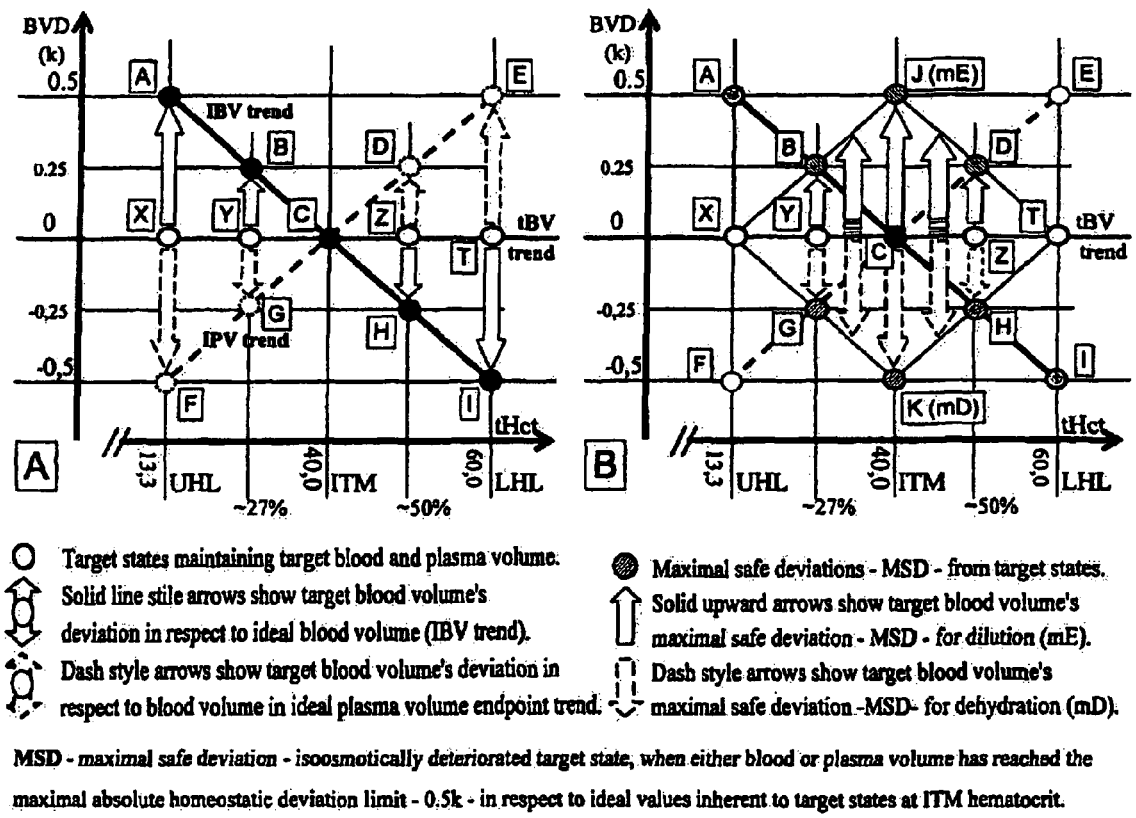

FIG. 4

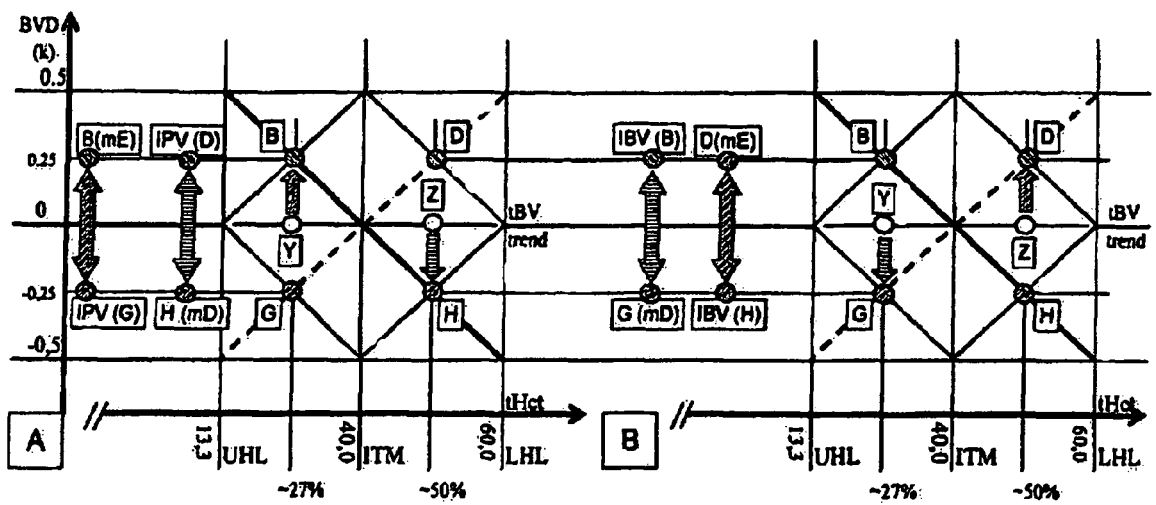

A Maximal safe deviations - B and H - maintain ideal blood volume.   B Maximal safe deviations - G and D - maintain ideal plasma volume.

○ Target states maintaining target blood and plasma volume.
⇧ Solid upward arrows show target blood volume's maximal safe deviation - MSD - for dilution (mE).

In A:
⇧ Target state (Y) diluted to maximal safe deviation (B) maintains
⇩ plasma volume that exceeds ideal value by maximal volume [0.5k].
⇧ Target state (Z) dehydrated to MSD state (H) maintains
⇩ depleted plasma volume in respect to ideal by max [0.5k].

⊙ Maximal safe deviations - MSD - from target states.
⇧ Striated style arrows show target blood volume's maximal safe deviation - MSD - for dehydration (mD).

In B:
⇧ Target state (Z) diluted to MSD state (D) maintains
⇩ blood volume exceeding ideal by maximal value [0.5k].
⇧ Target state (Y) dehydrated to MSD state (G) maintains
⇩ blood volume below ideal value by maximal volume [0.5k].

*Example 3*

3a
Open hyperosmotic MCV shift
calculation summary:
50,0 tHct % (tZ)
3,50 IBV
2,10 IPV
53,9 mD-Hct % (H)
50,3 HyD-Hct % (K)
58,1 excD-Hct % (no Osm shifts)
  92 tMCV (normal)
1,87 RCM (k) at tOsm (tZ and B)
0,25 absolute osmotic RCM deviation (k)
1,62 RCM (k) at HyOsm (J) [13%]
  80 HyMCV (normal)
285 tOsm (mnOsm)
329 HyOsm (cmHyOsm-320)

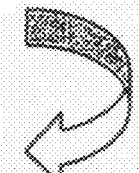

3b
Open hyperosmotic MCV shift
calculation summary:
60,0 tHct % (tT)
3,50 IBV
2,10 IPV
60,0 mD-Hct % (tT)
57,3 HyD-Hct % (H)
64,0 excD-Hct % (no Osm shifts)
  90 tMCV (normal)
2,40 RCM (k) at tOsm (tT)
0,25 absolute osmotic RCM deviation (k)
2,15 RCM (k) at HyOsm (H) [10%]
  81 HyMCV (normal)
285 tOsm (mnOsm)
318 HyOsm (cmHyOsm-320)

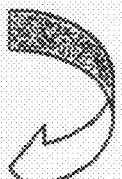

3c
Open hyperosmotic MCV shift
calculation summary (within normal Osm):
60,0 tHct % (tT)
3,50 IBV
2,10 IPV
60,0 mD-Hct % (tT)
61,0 HyD-Hct % (H)
64,0 excD-Hct % (no Osm shifts)
  90 tMCV (normal)
2,40 RCM (k) at tOsm (tT)
2,32 RCM (k) at HyOsm
  87 HyMCV (normal)
285 tOsm (normal - mnOsm)
295 HyOsm (normal - mxnOsm)

*Example 4*

4a
Open hypoosmotic MCV shift
calculation summary:
27,0 tHct % (tY)
3,50 IBV
2,10 IPV
25,1 mE-Hct % (B)
30,1 oE-Hct % (J)
23,4 excE-Hct % (no Osm shifts)
  80 tMCV (normal)
0,87 RCM (k) at tOsm (tY)
0,25 absolute osmotic RCM deviation
1,12 RCM (k) at HyOsm (J) [29%]
 103 HyMCV (macrocytic)
295 tOsm (mxnOsm)
229 HoOsm (cmHoOsm-265)

4b
Open hypoosmotic MCV shift
calculation summary:
13,3 tHct % (tX)
3,50 IBV
2,10 IPV
13,3 mE-Hct % (tX)
20,0 oE-Hct % (B)
12,3 excE-Hct % (no Osm shifts)
  80 tMCV (normal)
0,4 RCM (k) at tOsm (tX)
0,25 absolute osmotic RCM deviation
0,65 RCM (k) at HyOsm (B) [63%]
 130 HyMCV (macrocytic)
295 tOsm (mxnOsm)
182 HoOsm (cmHoOsm-265)

4c
Open hypoosmotic MCV shift
calculation summary (within normal Osm):
13,3 tHct % (tX)
3,50 IBV
2,10 IPV
20,0 mD-Hct % (H)
13,9 HyD-Hct % (K)
22,9 excE-Hct % (no Osm shifts)
  90 tMCV (normal)
0,40 RCM (k) at tOsm (B)
0,41 RCM (k) at HyOsm
  87 HyMCV (normal)
285 tOsm (normal - mnOsm)
295 HyOsm (normal - mxnOsm)

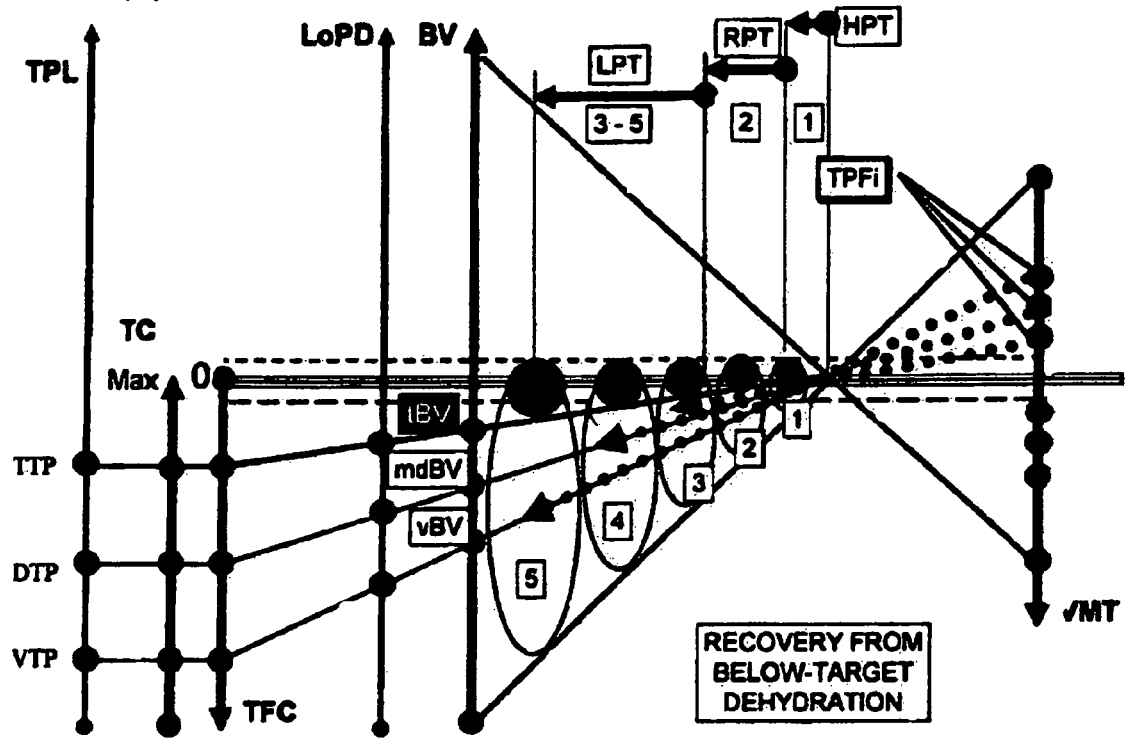
FIG. 10 (B) RECOVERY FROM BELOW-TARGET DEHYDRATION
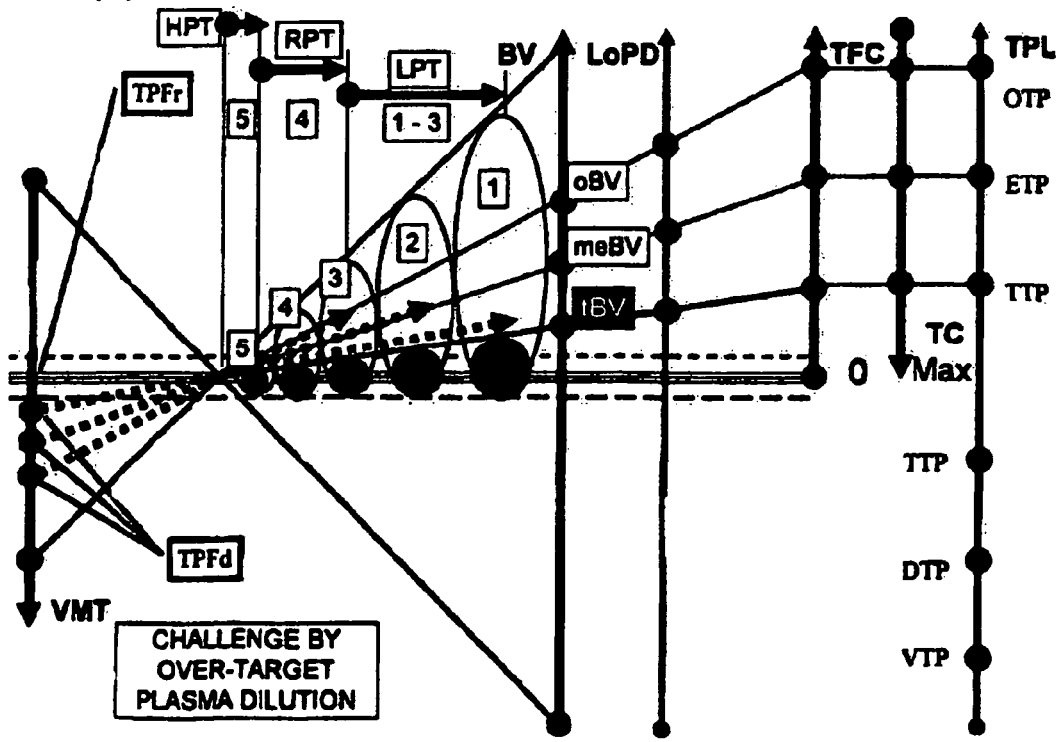
FIG. 10 (C) CHALLENGE BY OVER-TARGET PLASMA DILUTION

FIG. 13 (A-B)
B
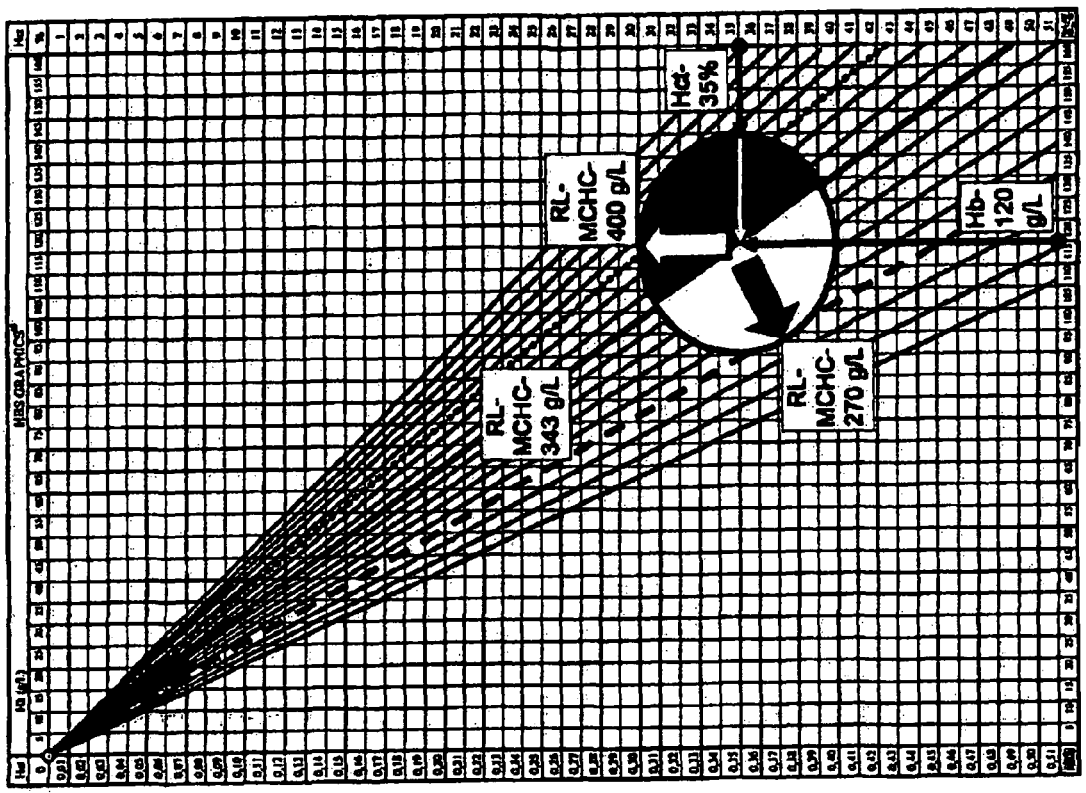
A
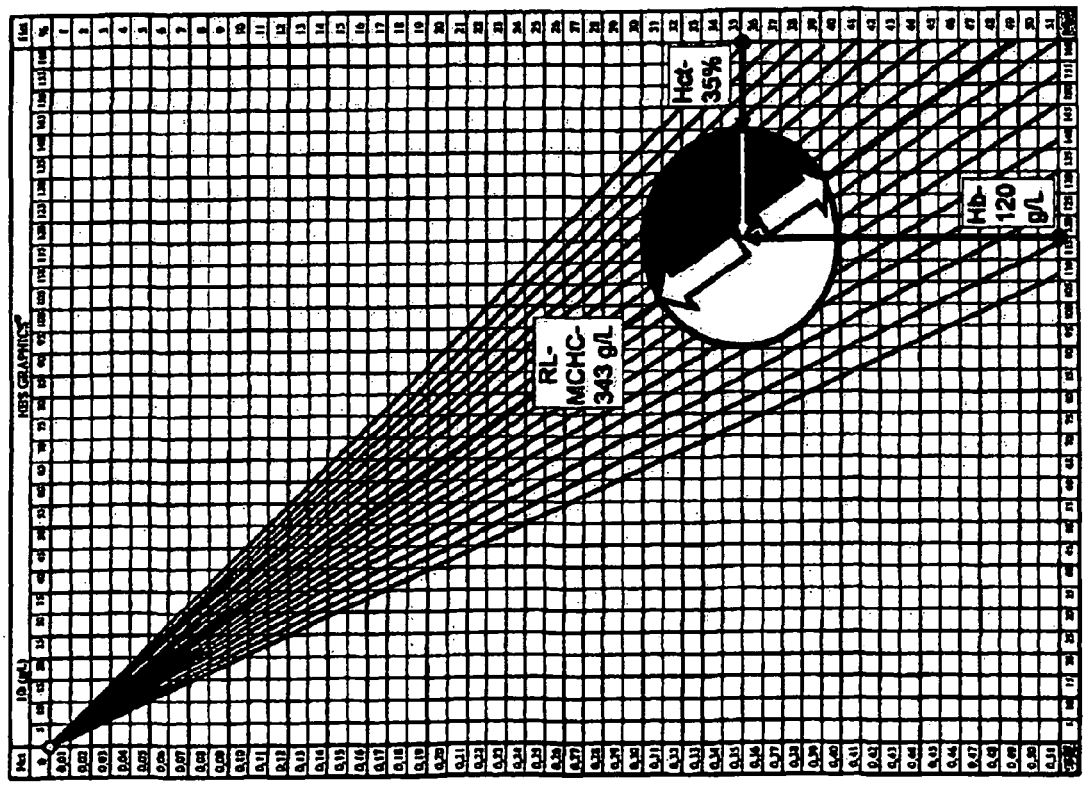

FIG. 14 (A-B)
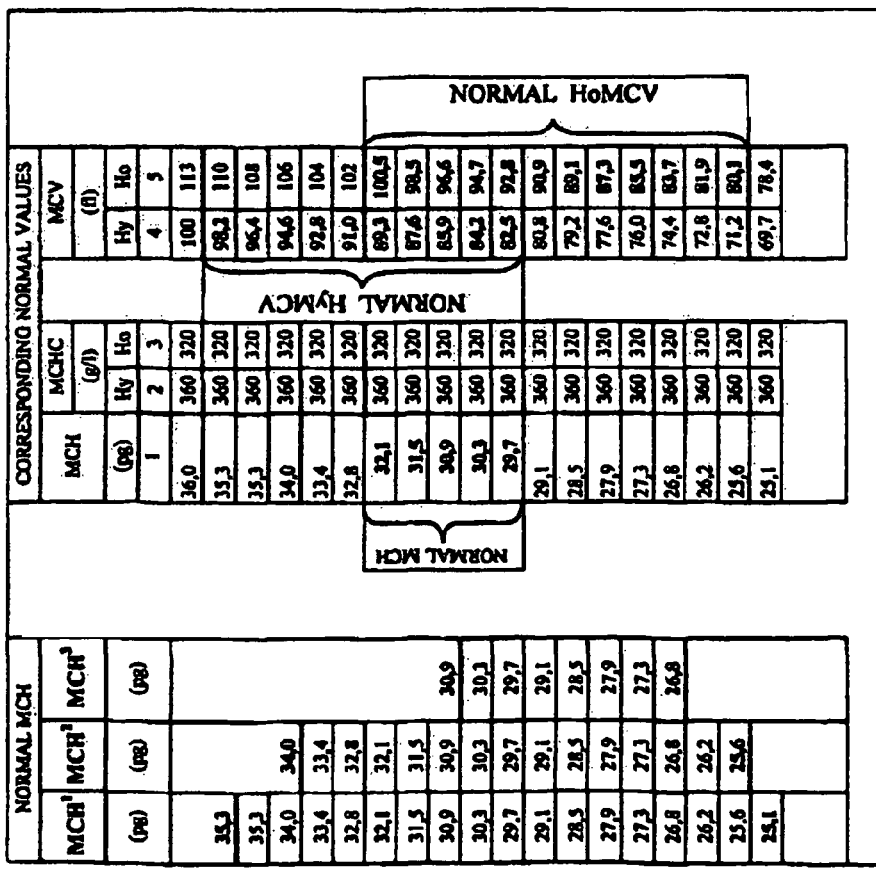
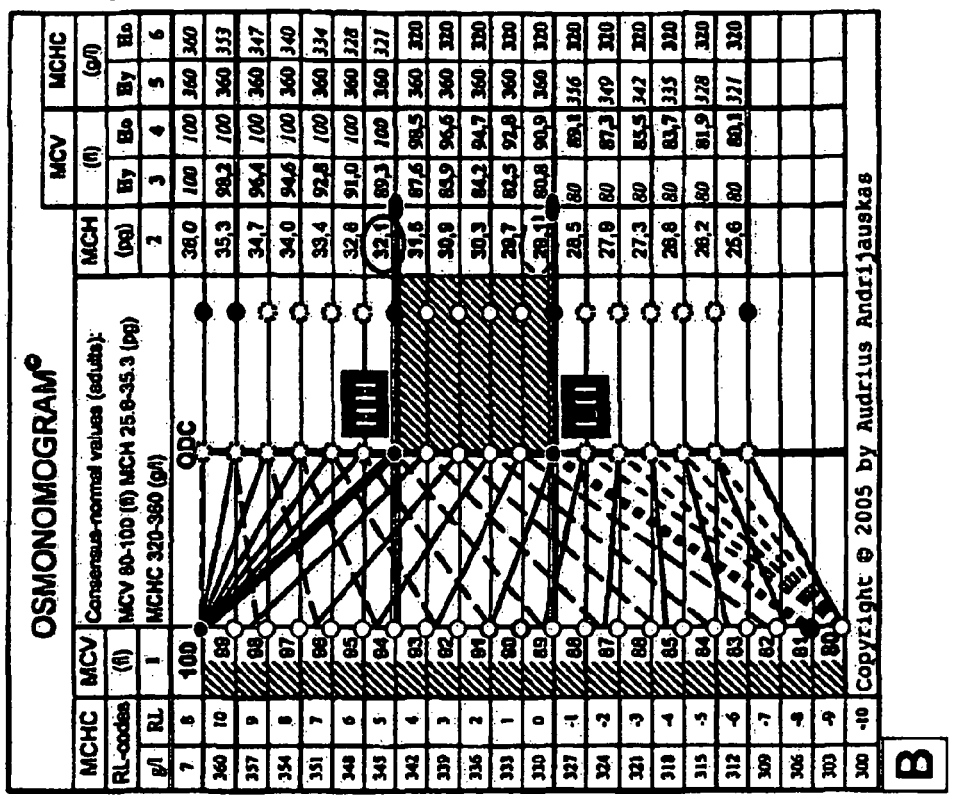
MCH[1] - Manual of laboratory tests [Laboratoriniu tyrimu zinynas]. Kucinskienė ZA. Vaistų Zinios Inc. Vilnius, Lithuania; 2001.
MCH[2] - Oxford Handbook of Clinical and Laboratory Investigation. 2nd ed. Provan D. editor. London, UK; 2005.
MCH[3] - Mosby's manual of diagnostic and laboratory tests. 3rd ed. Pagana KD, Pagana TJ, eds. Mosby Inc. USA; 2006.

FIG. 14 (C-D)
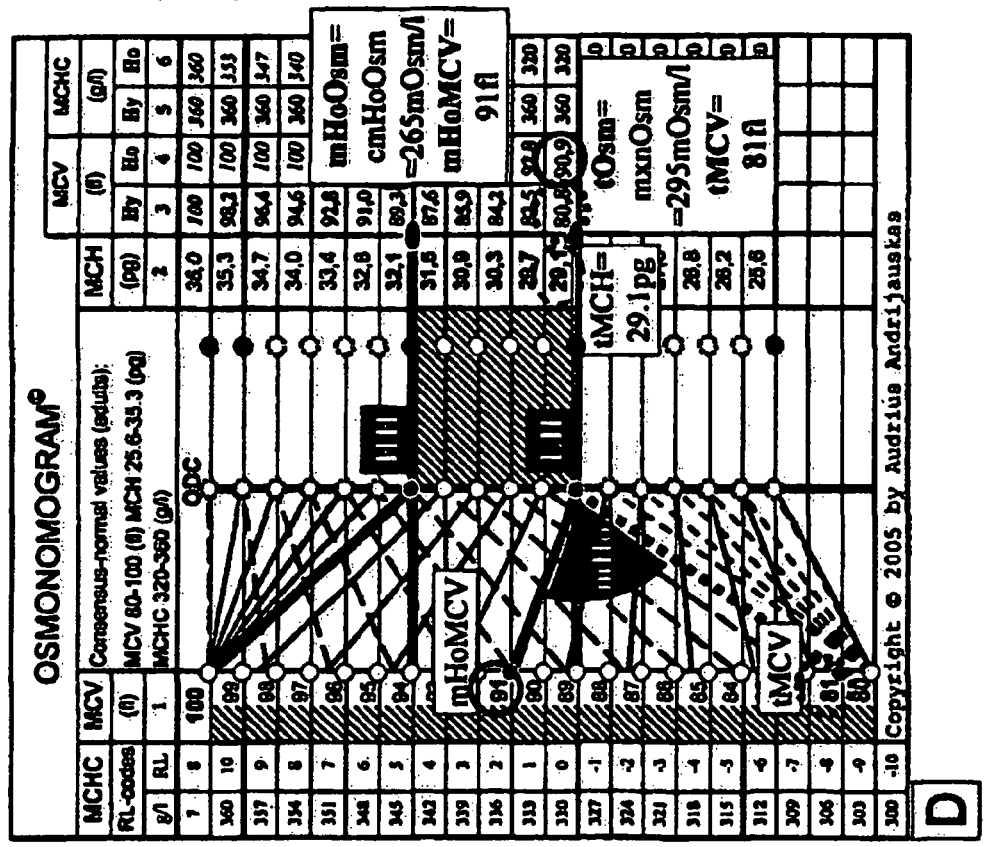
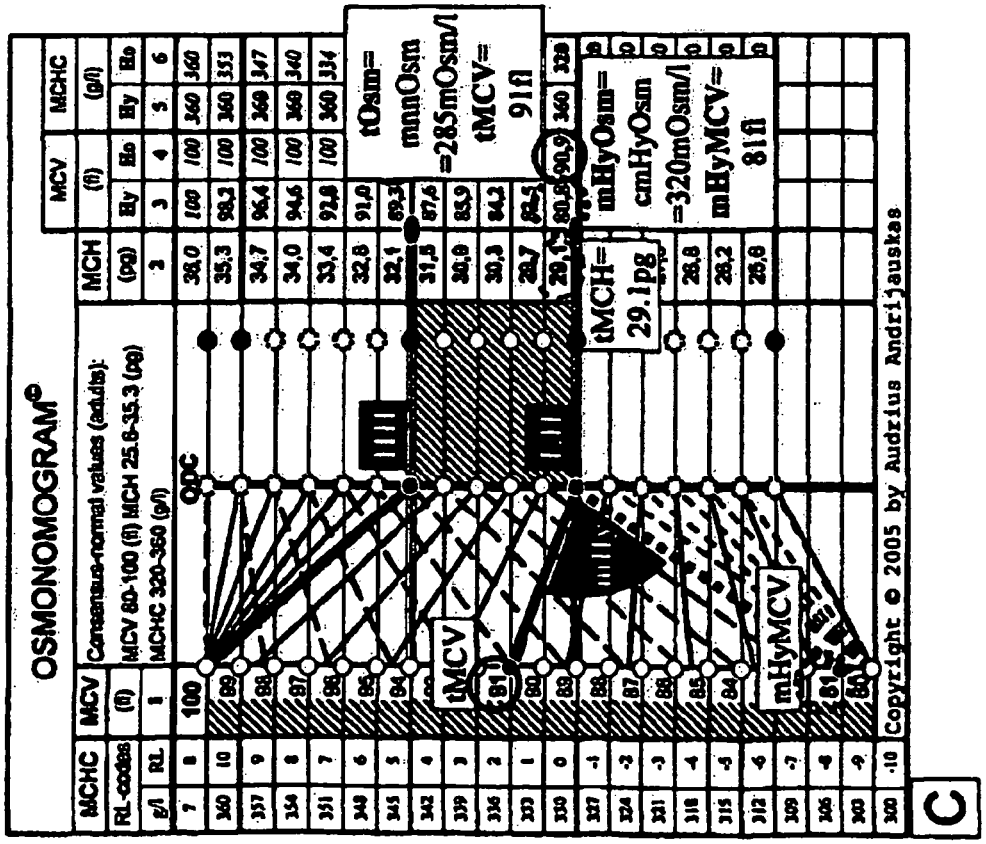

FIG. 14 (E-F)
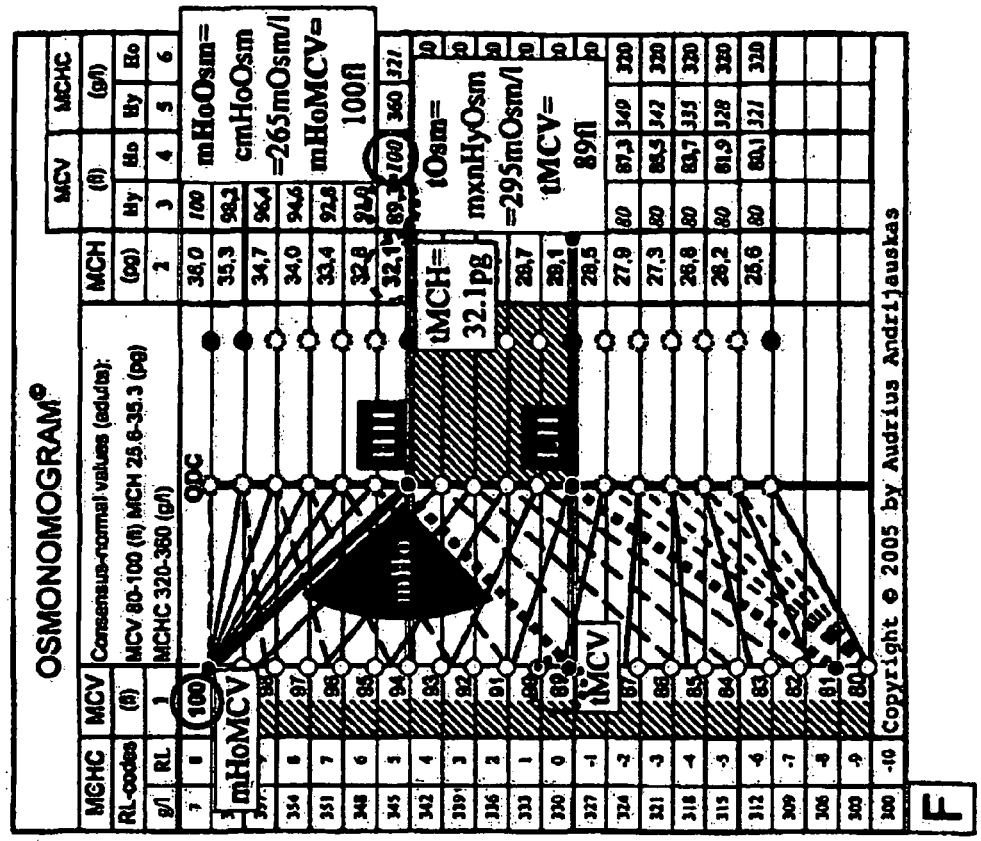
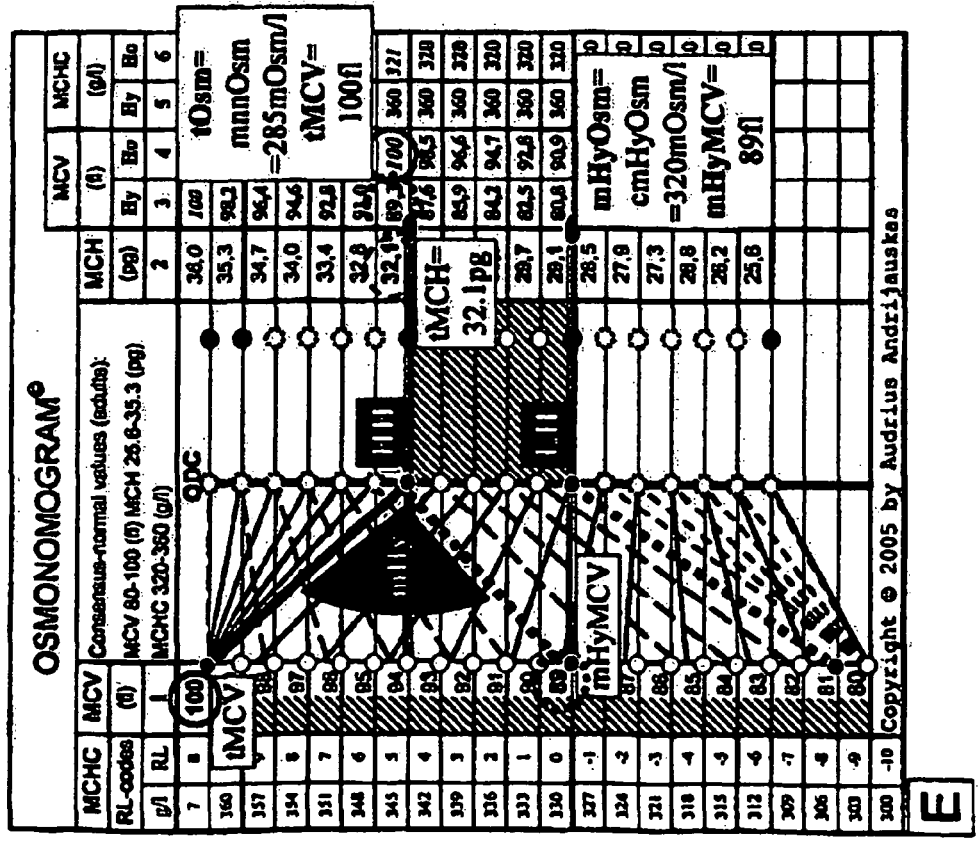

FIG. 23 A

Distribution of baseline packed cell volume (PCV) in orthopaedic surgical patients operated on at the Gaetano Pini Orthopaedic Institute in 1997

|  | Baseline PCV | | | | |
| --- | --- | --- | --- | --- | --- |
|  | 20.5–29.9% | 30–33.9% | 34–39.9% | 40–55.9% | Total |
| No. of pts | 129 | 252 | 1010 | 792 | 2183 |
| (% of total) | (6) | (12) | (46) ✓ | (36) ✓ |  |
| Female | 99 | 203 | 831 | 389 | 1522 |
|  | (6.5%) | (13.3%) | (54.6%) | (25.6%) |  |
| Male | 30 | 49 | 179 | 403 | 661 |
|  | (4.5%) | (7.5%) | (27%) | (61%) |  |
| Osteoarthritis | 19 | 70 | 624 | 585 | 1298 |
|  | (1.5%) | (5.5%) | (48%) | (45%) |  |
| Rheumatoid arthritis | 6 | 16 | 42 | 19 | 82 |
|  | (7%) | (18%) | (52%) | (23%) |  |
| Cancer | 14 | 17 | 39 | 33 | 103 |
|  | (14%) | (16%) | (38%) | (32%) |  |
| Sepsis | 8 | 16 | 17 | 16 | 57 |
|  | (14%) | (28%) | (30%) | (28%) |  |
| Trauma | 78 | 126 | 264 | 113 | 581 |
|  | (13%) | (22%) | (45%) | (20%) |  |
| Other | 4 | 8 | 24 | 26 | 62 |
|  | (6%) | (13%) | (39%) | (42%) |  |

TABLE 1

| | BASIC VALUES | | | | TARGET BLOOD VOLUME TREND IDEAL | | DEVIATION | | | MAXIMAL SAFE DEVIATIONS FROM TARGET STATES DILUTION | | | | DEHYDRATION | | |
|---|---|---|---|---|---|---|---|---|---|---|---|---|---|---|---|---|
| tHct | tRCM | tPV | Cn | tBV | IPV | IBV | IPVE | IBVE | mE | mE-Hct | mE-PV | mE-BV | mD | mD-Hct | mD-PV | mD-BV |
| % | k | k | coef | k | k | k | k | k | % | k | k | k | % | k | k | k |
| 1 | 2 | 4 | 5 | 6 | A | B | C | D | 7 | 8 | 9 | 10 | 11 | 12 | 13 | 14 |
| 13,3 | 0,40 | 2,6 | 0,506 | 3,00 | 2,1 | 3,5 | 0,50 | -0,50 | 0,0 | 13,3 | 2,6 | 3,0 | 0,0 | 13,4 | 2,6 | 3,0 |
| 14 | 0,42 | 2,6 | 0,507 | 3,01 | 2,1 | 3,5 | 0,49 | -0,49 | 0,02 | 13,9 | 2,6 | 3,0 | -0,02 | 14,1 | 2,6 | 3,0 |
| 15 | 0,45 | 2,6 | 0,507 | 3,03 | 2,1 | 3,5 | 0,47 | -0,47 | 0,03 | 14,8 | 2,6 | 3,1 | -0,03 | 15,2 | 2,5 | 3,0 |
| 16 | 0,49 | 2,6 | 0,507 | 3,05 | 2,1 | 3,5 | 0,46 | -0,46 | 0,05 | 15,7 | 2,6 | 3,1 | -0,05 | 16,3 | 2,5 | 3,0 |
| 17 | 0,52 | 2,5 | 0,507 | 3,06 | 2,1 | 3,5 | 0,44 | -0,44 | 0,07 | 16,6 | 2,6 | 3,1 | -0,07 | 17,4 | 2,5 | 3,0 |
| 18 | 0,55 | 2,5 | 0,508 | 3,08 | 2,1 | 3,5 | 0,42 | -0,42 | 0,08 | 17,5 | 2,6 | 3,2 | -0,08 | 18,5 | 2,4 | 3,0 |
| 19 | 0,59 | 2,5 | 0,508 | 3,10 | 2,1 | 3,5 | 0,41 | -0,41 | 0,10 | 18,4 | 2,6 | 3,2 | -0,10 | 19,6 | 2,4 | 3,0 |
| 20 | 0,62 | 2,5 | 0,508 | 3,11 | 2,1 | 3,5 | 0,39 | -0,39 | 0,12 | 19,3 | 2,6 | 3,2 | -0,12 | 20,8 | 2,4 | 3,0 |
| 21 | 0,66 | 2,5 | 0,508 | 3,13 | 2,1 | 3,5 | 0,37 | -0,37 | 0,14 | 20,1 | 2,6 | 3,3 | -0,14 | 22,0 | 2,3 | 3,0 |
| 22 | 0,69 | 2,5 | 0,508 | 3,15 | 2,1 | 3,5 | 0,35 | -0,35 | 0,15 | 21,0 | 2,6 | 3,3 | -0,15 | 23,1 | 2,3 | 3,0 |
| 23 | 0,73 | 2,4 | 0,508 | 3,17 | 2,1 | 3,5 | 0,34 | -0,34 | 0,17 | 21,8 | 2,6 | 3,3 | -0,17 | 24,3 | 2,3 | 3,0 |
| 24 | 0,76 | 2,4 | 0,508 | 3,18 | 2,1 | 3,5 | 0,32 | -0,32 | 0,19 | 22,7 | 2,6 | 3,4 | -0,19 | 25,5 | 2,2 | 3,0 |
| 25 | 0,80 | 2,4 | 0,508 | 3,20 | 2,1 | 3,5 | 0,30 | -0,30 | 0,21 | 23,5 | 2,6 | 3,4 | -0,21 | 26,7 | 2,2 | 3,0 |
| 26 | 0,84 | 2,4 | 0,508 | 3,22 | 2,1 | 3,5 | 0,28 | -0,28 | 0,23 | 24,3 | 2,6 | 3,4 | -0,23 | 28,0 | 2,2 | 3,0 |
| 27 | 0,87 | 2,4 | 0,508 | 3,24 | 2,1 | 3,5 | 0,26 | -0,26 | 0,24 | 25,1 | 2,6 | 3,5 | -0,24 | 29,2 | 2,1 | 3,0 |
| 28 | 0,91 | 2,3 | 0,507 | 3,26 | 2,1 | 3,5 | 0,24 | -0,24 | 0,26 | 25,9 | 2,6 | 3,5 | -0,26 | 30,5 | 2,1 | 3,0 |
| 29 | 0,95 | 2,3 | 0,507 | 3,28 | 2,1 | 3,5 | 0,23 | -0,23 | 0,28 | 26,7 | 2,6 | 3,6 | -0,28 | 31,7 | 2,0 | 3,0 |
| 30 | 0,99 | 2,3 | 0,507 | 3,30 | 2,1 | 3,5 | 0,21 | -0,21 | 0,30 | 27,5 | 2,6 | 3,6 | -0,30 | 33,0 | 2,0 | 3,0 |
| 31 | 1,03 | 2,3 | 0,506 | 3,32 | 2,1 | 3,5 | 0,19 | -0,19 | 0,32 | 28,3 | 2,6 | 3,6 | -0,32 | 34,3 | 2,0 | 3,0 |
| 32 | 1,07 | 2,3 | 0,506 | 3,34 | 2,1 | 3,5 | 0,17 | -0,17 | 0,34 | 29,0 | 2,6 | 3,7 | -0,34 | 35,6 | 1,9 | 3,0 |
| 33 | 1,11 | 2,2 | 0,505 | 3,36 | 2,1 | 3,5 | 0,15 | -0,15 | 0,36 | 29,8 | 2,6 | 3,7 | -0,36 | 37,0 | 1,9 | 3,0 |
| 34 | 1,15 | 2,2 | 0,505 | 3,38 | 2,1 | 3,5 | 0,13 | -0,13 | 0,38 | 30,5 | 2,6 | 3,8 | -0,38 | 38,3 | 1,8 | 3,0 |
| 35 | 1,19 | 2,2 | 0,504 | 3,40 | 2,1 | 3,5 | 0,11 | -0,11 | 0,40 | 31,3 | 2,6 | 3,8 | -0,40 | 39,7 | 1,8 | 3,0 |
| 36 | 1,23 | 2,2 | 0,504 | 3,42 | 2,1 | 3,5 | 0,09 | -0,09 | 0,42 | 32,0 | 2,6 | 3,8 | -0,42 | 41,1 | 1,8 | 3,0 |
| 37 | 1,27 | 2,2 | 0,503 | 3,44 | 2,1 | 3,5 | 0,06 | -0,06 | 0,44 | 32,8 | 2,6 | 3,9 | -0,44 | 42,5 | 1,7 | 3,0 |
| 38 | 1,31 | 2,1 | 0,502 | 3,46 | 2,1 | 3,5 | 0,04 | -0,04 | 0,46 | 33,5 | 2,6 | 3,9 | -0,46 | 43,9 | 1,7 | 3,0 |
| 39 | 1,36 | 2,1 | 0,501 | 3,48 | 2,1 | 3,5 | 0,02 | -0,02 | 0,49 | 34,2 | 2,6 | 4,0 | -0,49 | 45,3 | 1,6 | 3,0 |
| 40 | 1,40 | 2,1 | 0,500 | 3,50 | 2,1 | 3,5 | 0,00 | 0,00 | 0,51 | 34,9 | 2,6 | 4,0 | -0,51 | 46,8 | 1,6 | 3,0 |
| 41 | 1,45 | 2,1 | 0,499 | 3,53 | 2,1 | 3,5 | -0,02 | 0,02 | 0,49 | 36,0 | 2,6 | 4,0 | -0,49 | 47,6 | 1,6 | 3,0 |
| 42 | 1,49 | 2,1 | 0,498 | 3,55 | 2,1 | 3,5 | -0,04 | 0,04 | 0,46 | 37,1 | 2,5 | 4,0 | -0,46 | 48,3 | 1,6 | 3,1 |
| 43 | 1,54 | 2,0 | 0,496 | 3,57 | 2,1 | 3,5 | -0,07 | 0,07 | 0,44 | 38,3 | 2,5 | 4,0 | -0,44 | 49,1 | 1,6 | 3,1 |
| 44 | 1,58 | 2,0 | 0,495 | 3,59 | 2,1 | 3,5 | -0,09 | 0,09 | 0,42 | 39,4 | 2,4 | 4,0 | -0,42 | 49,8 | 1,6 | 3,2 |
| 45 | 1,63 | 2,0 | 0,494 | 3,62 | 2,1 | 3,5 | -0,11 | 0,11 | 0,39 | 40,6 | 2,4 | 4,0 | -0,39 | 50,5 | 1,6 | 3,2 |
| 46 | 1,67 | 2,0 | 0,492 | 3,64 | 2,1 | 3,5 | -0,14 | 0,14 | 0,37 | 41,7 | 2,3 | 4,0 | -0,37 | 51,2 | 1,6 | 3,3 |
| 47 | 1,72 | 1,9 | 0,490 | 3,66 | 2,1 | 3,5 | -0,16 | 0,16 | 0,35 | 42,9 | 2,3 | 4,0 | -0,35 | 51,9 | 1,6 | 3,3 |
| 48 | 1,77 | 1,9 | 0,489 | 3,69 | 2,1 | 3,5 | -0,18 | 0,18 | 0,32 | 44,1 | 2,2 | 4,0 | -0,32 | 52,6 | 1,6 | 3,4 |
| 49 | 1,82 | 1,9 | 0,487 | 3,71 | 2,1 | 3,5 | -0,21 | 0,21 | 0,30 | 45,3 | 2,2 | 4,0 | -0,30 | 53,3 | 1,6 | 3,4 |
| 50 | 1,87 | 1,9 | 0,485 | 3,74 | 2,1 | 3,5 | -0,23 | 0,23 | 0,27 | 46,6 | 2,1 | 4,0 | -0,27 | 54,0 | 1,6 | 3,5 |
| 51 | 1,92 | 1,8 | 0,483 | 3,76 | 2,1 | 3,5 | -0,26 | 0,26 | 0,25 | 47,8 | 2,1 | 4,0 | -0,25 | 54,6 | 1,6 | 3,5 |
| 52 | 1,97 | 1,8 | 0,480 | 3,79 | 2,1 | 3,5 | -0,28 | 0,28 | 0,22 | 49,1 | 2,0 | 4,0 | -0,22 | 55,3 | 1,6 | 3,6 |
| 53 | 2,02 | 1,8 | 0,478 | 3,81 | 2,1 | 3,5 | -0,31 | 0,31 | 0,20 | 50,4 | 2,0 | 4,0 | -0,20 | 55,9 | 1,6 | 3,6 |
| 54 | 2,07 | 1,8 | 0,476 | 3,84 | 2,1 | 3,5 | -0,34 | 0,34 | 0,17 | 51,7 | 1,9 | 4,0 | -0,17 | 56,5 | 1,6 | 3,7 |
| 55 | 2,13 | 1,7 | 0,473 | 3,87 | 2,1 | 3,5 | -0,36 | 0,36 | 0,15 | 53,0 | 1,9 | 4,0 | -0,15 | 57,2 | 1,6 | 3,7 |
| 56 | 2,18 | 1,7 | 0,470 | 3,89 | 2,1 | 3,5 | -0,39 | 0,39 | 0,12 | 54,3 | 1,8 | 4,0 | -0,12 | 57,8 | 1,6 | 3,8 |
| 57 | 2,23 | 1,7 | 0,467 | 3,92 | 2,1 | 3,5 | -0,42 | 0,42 | 0,09 | 55,7 | 1,8 | 4,0 | -0,09 | 58,4 | 1,6 | 3,8 |
| 58 | 2,29 | 1,7 | 0,464 | 3,95 | 2,1 | 3,5 | -0,44 | 0,44 | 0,06 | 57,1 | 1,7 | 4,0 | -0,06 | 59,0 | 1,6 | 3,9 |
| 59 | 2,35 | 1,6 | 0,461 | 3,98 | 2,1 | 3,5 | -0,47 | 0,47 | 0,04 | 58,5 | 1,7 | 4,0 | -0,04 | 59,5 | 1,6 | 3,9 |
| 60,0 | 2,40 | 1,6 | 0,457 | 4,00 | 2,1 | 3,5 | -0,50 | 0,50 | 0,0 | 59,9 | 1,6 | 4,0 | 0,0 | 60,1 | 1,6 | 4,0 |

| MTD | 1,0 | k |
|---|---|---|
| IBV | 3,503 | k |

| mE-BV | 4,0 | k |
|---|---|---|
| mE-PV | 2,6 | k |

| mD-BV | 3,0 | k |
|---|---|---|
| mD-PV | 1,6 | k |

ITM 0,40 (Hct/SI units)    $k = 0.2855 \cdot IBV$

TABLE 2

TABLE 2-A

| MCV/hMCV (fL) | Hypoosmotic shift N1 Plasma osmolality 2* mOsm/kg H₂O | Plasma osmolality 3* cmHo mOsm/kg H₂O | MCV 4* mHo (fL) | Hyperosmotic shift N1 Plasma osmolality 5* mOsm/kg H₂O | Plasma osmolality 6* mOsm/kg H₂O | MCV 7* mHy (fL) |
|---|---|---|---|---|---|---|
| 100 | 285 | 265 | 111.2 | 285 | 320 | 88.9 |
| 99 | 285 | 265 | 110.0 | 285 | 320 | 88.0 |
| 98 | 285 | 265 | 108.9 | 285 | 320 | 87.1 |
| 97 | 285 | 265 | 107.8 | 285 | 320 | 86.2 |
| 96 | 285 | 265 | 106.7 | 285 | 320 | 85.3 |
| 95 | 285 | 265 | 105.6 | 285 | 320 | 84.4 |
| 94 | 285 | 265 | 104.5 | 285 | 320 | 83.6 |
| 93 | 285 | 265 | 103.4 | 285 | 320 | 82.7 |
| 92 | 285 | 265 | 102.3 | 285 | 320 | 81.8 |
| 91 | 285 | 265 | 101.1 | 285 | 320 | 80.9 |
| 90 | 285 | 265 | 100.0 | 285 | 320 | 80.0 |
| 89 | 285 | 265 | 98.9 | 285 | 320 | 79.1 |
| 88 | 285 | 265 | 97.8 | 285 | 320 | 78.2 |
| 87 | 285 | 265 | 96.7 | 285 | 320 | 77.3 |
| 86 | 285 | 265 | 95.6 | 285 | 320 | 76.4 |
| 85 | 285 | 265 | 94.5 | 285 | 320 | 75.6 |
| 84 | 285 | 265 | 93.4 | 285 | 320 | 74.7 |
| 83 | 285 | 265 | 92.3 | 285 | 320 | 73.8 |
| 82 | 285 | 265 | 91.1 | 285 | 320 | 72.9 |
| 81 | 285 | 265 | 90.0 | 285 | 320 | 72.0 |
| 80 | 285 | 265 | 88.9 | 285 | 320 | 71.1 |

TABLE 2-B

| MCV/hMCV (fL) | Hypoosmotic shift N2 Plasma osmolality 2* mOsm/kg H₂O | Plasma osmolality 3* mean nOsr mOsm/kg H₂O | MCV 4* mHo (fL) | Hyperosmotic shift N2 Plasma osmolality 5* mOsm/kg H₂O | Plasma osmolality 6* mOsm/kg H₂O | MCV 7* mHy (fL) |
|---|---|---|---|---|---|---|
| 100 | 320 | 288 | 111.1 | 265 | 298 | 88.9 |
| 99 | 320 | 288 | 110.0 | 265 | 298 | 88.0 |
| 98 | 320 | 288 | 108.9 | 265 | 298 | 87.1 |
| 97 | 320 | 288 | 107.8 | 265 | 298 | 86.3 |
| 96 | 320 | 288 | 106.7 | 265 | 298 | 85.4 |
| 95 | 320 | 288 | 105.6 | 265 | 298 | 84.5 |
| 94 | 320 | 288 | 104.4 | 265 | 298 | 83.6 |
| 93 | 320 | 288 | 103.3 | 265 | 298 | 82.7 |
| 92 | 320 | 288 | 102.2 | 265 | 298 | 81.8 |
| 91 | 320 | 288 | 101.1 | 265 | 298 | 80.9 |
| 90 | 320 | 288 | 100.0 | 265 | 298 | 80.0 |
| 89 | 320 | 288 | 98.9 | 265 | 298 | 79.1 |
| 88 | 320 | 288 | 97.8 | 265 | 298 | 78.3 |
| 87 | 320 | 288 | 96.7 | 265 | 298 | 77.4 |
| 86 | 320 | 288 | 95.6 | 265 | 298 | 76.5 |
| 85 | 320 | 288 | 94.4 | 265 | 298 | 75.6 |
| 84 | 320 | 288 | 93.3 | 265 | 298 | 74.7 |
| 83 | 320 | 288 | 92.2 | 265 | 298 | 73.8 |
| 82 | 320 | 288 | 91.1 | 265 | 298 | 72.9 |
| 81 | 320 | 288 | 90.0 | 265 | 298 | 72.0 |
| 80 | 320 | 288 | 88.9 | 265 | 298 | 71.1 |

TABLE 2-C

| MCV/hMCV (fL) | Hypoosmotic shift N3 Plasma osmolality 2* mOsm/kg H₂O | Plasma osmolality 3* mOsm/kg H₂O | MCV 4* mHo (fL) | Hyperosmotic shift N3 Plasma osmolality 5* mOsm/kg H₂O | Plasma osmolality 6* mOsm/kg H₂O | MCV 7* mHy (fL) |
|---|---|---|---|---|---|---|
| 100 | 295 | 285 | 103.5 | 285 | 295 | 96.6 |
| 99 | 295 | 285 | 102.5 | 285 | 295 | 95.6 |
| 98 | 295 | 285 | 101.4 | 285 | 295 | 94.7 |
| 97 | 295 | 285 | 100.4 | 285 | 295 | 93.7 |
| 96 | 295 | 285 | 99.4 | 285 | 295 | 92.7 |
| 95 | 295 | 285 | 98.3 | 285 | 295 | 91.8 |
| 94 | 295 | 285 | 97.3 | 285 | 295 | 90.8 |
| 93 | 295 | 285 | 96.3 | 285 | 295 | 89.8 |
| 92 | 295 | 285 | 95.2 | 285 | 295 | 88.9 |
| 91 | 295 | 285 | 94.2 | 285 | 295 | 87.9 |
| 90 | 295 | 285 | 93.2 | 285 | 295 | 86.9 |
| 89 | 295 | 285 | 92.1 | 285 | 295 | 86.0 |
| 88 | 295 | 285 | 91.1 | 285 | 295 | 85.0 |
| 87 | 295 | 285 | 90.1 | 285 | 295 | 84.1 |
| 86 | 295 | 285 | 89.0 | 285 | 295 | 83.1 |
| 85 | 295 | 285 | 88.0 | 285 | 295 | 82.1 |
| 84 | 295 | 285 | 86.9 | 285 | 295 | 81.2 |
| 83 | 295 | 285 | 85.9 | 285 | 295 | 80.2 |
| 82 | 295 | 285 | 84.9 | 285 | 295 | 79.2 |
| 81 | 295 | 285 | 83.8 | 285 | 295 | 78.3 |
| 80 | 295 | 285 | 82.8 | 285 | 295 | 77.3 |

* Mosby's manual of diagnostic and laboratory tests, 3rd edition
Pagana KD, Pagana TJ, eds. Mosby Inc. USA 2006

TABLE 3

| RL Nr | MCHC g/l | Hb g/l | Hct dec | Hb g/l | Hct dec | Hb g/l | Hct dec |
|---|---|---|---|---|---|---|---|
| 1 | 2 | 3 | 4 | 5 | 6 | 7 | 8 |
| 15 | 375 | 75 | 0,20 | 150 | 0,40 | 225 | 0,60 |
| 14 | 372 | 74 | 0,20 | 149 | 0,40 | 223 | 0,60 |
| 13 | 369 | 74 | 0,20 | 148 | 0,40 | 221 | 0,60 |
| 12 | 366 | 73 | 0,20 | 146 | 0,40 | 220 | 0,60 |
| 11 | 363 | 73 | 0,20 | 145 | 0,40 | 218 | 0,60 |
| 10 | 360 | 72 | 0,20 | 144 | 0,40 | 216 | 0,60 |
| 9 | 357 | 71 | 0,20 | 143 | 0,40 | 214 | 0,60 |
| 8 | 354 | 71 | 0,20 | 142 | 0,40 | 212 | 0,60 |
| 7 | 351 | 70 | 0,20 | 140 | 0,40 | 211 | 0,60 |
| 6 | 348 | 70 | 0,20 | 139 | 0,40 | 209 | 0,60 |
| 5 | 345 | 69 | 0,20 | 138 | 0,40 | 207 | 0,60 |
| 4 | 342 | 68 | 0,20 | 137 | 0,40 | 205 | 0,60 |
| 3 | 339 | 68 | 0,20 | 136 | 0,40 | 203 | 0,60 |
| 2 | 336 | 67 | 0,20 | 134 | 0,40 | 202 | 0,60 |
| 1 | 333 | 67 | 0,20 | 133 | 0,40 | 200 | 0,60 |
| 0 | 330 | 66 | 0,20 | 132 | 0,40 | 198 | 0,60 |
| -1 | 327 | 65 | 0,20 | 131 | 0,40 | 196 | 0,60 |
| -2 | 324 | 65 | 0,20 | 130 | 0,40 | 194 | 0,60 |
| -3 | 321 | 64 | 0,20 | 128 | 0,40 | 193 | 0,60 |
| -4 | 318 | 64 | 0,20 | 127 | 0,40 | 191 | 0,60 |
| -5 | 315 | 63 | 0,20 | 126 | 0,40 | 189 | 0,60 |
| -6 | 312 | 62 | 0,20 | 125 | 0,40 | 187 | 0,60 |
| -7 | 309 | 62 | 0,20 | 124 | 0,40 | 185 | 0,60 |
| -8 | 306 | 61 | 0,20 | 122 | 0,40 | 184 | 0,60 |
| -9 | 303 | 61 | 0,20 | 121 | 0,40 | 182 | 0,60 |
| -10 | 300 | 60 | 0,20 | 120 | 0,40 | 180 | 0,60 |
| -11 | 297 | 59 | 0,20 | 119 | 0,40 | 178 | 0,60 |
| -12 | 294 | 59 | 0,20 | 118 | 0,40 | 176 | 0,60 |
| -13 | 291 | 58 | 0,20 | 116 | 0,40 | 175 | 0,60 |
| -14 | 288 | 58 | 0,20 | 115 | 0,40 | 173 | 0,60 |
| -15 | 285 | 57 | 0,20 | 114 | 0,40 | 171 | 0,60 |

Radiating line specific mean cell hemoglobin concentration, hematocrit and hemoglobin concentration values.

TAB. 4 (A-C)

MBI=20

| Body height m | Body weight kg | Pre-bleeding (baseline) hematocrit bHct1 (tHct1) % | Std-method Calculated IBV (Nadler's formula) bBV (IBV) mL | HBS-method Target volume tBV1 mL | HBS-method Target volume tRCM1 mL | Protocol 1 (Withdrawing of 1 unit of Whole Blood) Blood withdrawal Whole blood EBV mL | Protocol 1 Blood withdrawal Red cells wRCM mL | HBS-method Postbleed target volume tBV2 mL | HBS-method Postbleed target volume tRCM2 mL | Hematocrit Post-bleeding (donation) HBS-method % | Hematocrit Post-bleeding (donation) std-method % | Post-bleeding (donation) hematocrit decrease HBS-method Hct% | Post-bleeding (donation) hematocrit decrease Std-method Hct% |
|---|---|---|---|---|---|---|---|---|---|---|---|---|---|
| 1 | 2 | 3 | 4 | 5 | 6 | 7 | 8 | 9 | 10 | 11 | 12 | 13 | 14 |
| 1,85 | 70 | 34,0 | 5.180 | 4.993 | 1.698 | -458 | -149 | 0 | 0 | 31,6 | 31,1 | -2,4 | -2,9 |
| 1,85 | 70 | 35,0 | 5.180 | 5.023 | 1.758 | -474 | -159 | 0 | 0 | 32,4 | 31,9 | -2,6 | -3,1 |
| 1,85 | 70 | 36,0 | 5.180 | 5.054 | 1.819 | -490 | -169 | 0 | 0 | 33,3 | 32,7 | -2,7 | -3,3 |
| 1,85 | 70 | 37,0 | 5.180 | 5.085 | 1.881 | -505 | -179 | 0 | 0 | 34,1 | 33,5 | -2,9 | -3,5 |
| 1,85 | 70 | 38,0 | 5.180 | 5.117 | 1.944 | -521 | -190 | 0 | 0 | 35,0 | 34,3 | -3,0 | -3,7 |
| 1,85 | 70 | 39,0 | 5.180 | 5.148 | 2.008 | -536 | -201 | 0 | 0 | 35,8 | 35,1 | -3,2 | -3,9 |
| 1,85 | 70 | 40,0 | 5.180 | 5.180 | 2.072 | -552 | -212 | 0 | 0 | 36,7 | 35,9 | -3,3 | -4,1 |
| BMI | 20 | | | | | | | | | | | | |

MBI=24

| Body height m | Body weight kg | Pre-bleeding (baseline) hematocrit bHct1 (tHct1) % | Std-method Calculated IBV (Nadler's formula) bBV (IBV) mL | HBS-method Target volume tBV1 mL | HBS-method Target volume tRCM1 mL | Protocol 1 (Withdrawing of 1 unit of Whole Blood) Blood withdrawal Whole blood EBV mL | Protocol 1 Blood withdrawal Red cells wRCM mL | HBS-method Postbleed target volume tBV2 mL | HBS-method Postbleed target volume tRCM2 mL | Hematocrit Post-bleeding (donation) HBS-method % | Hematocrit Post-bleeding (donation) std-method % | Post-bleeding (donation) hematocrit decrease HBS-method Hct% | Post-bleeding (donation) hematocrit decrease Std-method Hct% |
|---|---|---|---|---|---|---|---|---|---|---|---|---|---|
| 1 | 2 | 3 | 4 | 5 | 6 | 7 | 8 | 9 | 10 | 11 | 12 | 13 | 14 |
| 1,70 | 70 | 34,0 | 4.660 | 4.492 | 1.527 | -412 | -134 | 0 | 0 | 31,6 | 31,1 | -2,4 | -2,9 |
| 1,70 | 70 | 35,0 | 4.660 | 4.519 | 1.582 | -426 | -143 | 0 | 0 | 32,4 | 31,9 | -2,6 | -3,1 |
| 1,70 | 70 | 36,0 | 4.660 | 4.546 | 1.637 | -440 | -152 | 0 | 0 | 33,3 | 32,7 | -2,7 | -3,3 |
| 1,70 | 70 | 37,0 | 4.660 | 4.574 | 1.692 | -454 | -161 | 0 | 0 | 34,1 | 33,5 | -2,9 | -3,5 |
| 1,70 | 70 | 38,0 | 4.660 | 4.602 | 1.749 | -468 | -171 | 0 | 0 | 35,0 | 34,3 | -3,0 | -3,7 |
| 1,70 | 70 | 39,0 | 4.660 | 4.631 | 1.806 | -482 | -181 | 0 | 0 | 35,8 | 35,1 | -3,2 | -3,9 |
| 1,70 | 70 | 40,0 | 4.660 | 4.660 | 1.864 | -496 | -191 | 0 | 0 | 36,7 | 35,9 | -3,3 | -4,1 |
| BMI | 24 | | | | | | | | | | | | |

MBI=29

| Body height m | Body weight kg | Pre-bleeding (baseline) hematocrit bHct1 (tHct1) % | Std-method Calculated IBV (Nadler's formula) bBV (IBV) mL | HBS-method Target volume tBV1 mL | HBS-method Target volume tRCM1 mL | Protocol 1 (Withdrawing of 1 unit of Whole Blood) Blood withdrawal Whole blood EBV mL | Protocol 1 Blood withdrawal Red cells wRCM mL | HBS-method Postbleed target volume tBV2 mL | HBS-method Postbleed target volume tRCM2 mL | Hematocrit Post-bleeding (donation) HBS-method % | Hematocrit Post-bleeding (donation) std-method % | Post-bleeding (donation) hematocrit decrease HBS-method Hct% | Post-bleeding (donation) hematocrit decrease Std-method Hct% |
|---|---|---|---|---|---|---|---|---|---|---|---|---|---|
| 1 | 2 | 3 | 4 | 5 | 6 | 7 | 8 | 9 | 10 | 11 | 12 | 13 | 14 |
| 1,70 | 85 | 34,0 | 5.143 | 4.957 | 1.685 | -455 | -148 | 0 | 0 | 31,6 | 31,1 | -2,4 | -2,9 |
| 1,70 | 85 | 35,0 | 5.143 | 4.987 | 1.745 | -471 | -158 | 0 | 0 | 32,4 | 31,9 | -2,6 | -3,1 |
| 1,70 | 85 | 36,0 | 5.143 | 5.017 | 1.806 | -486 | -168 | 0 | 0 | 33,3 | 32,7 | -2,7 | -3,3 |
| 1,70 | 85 | 37,0 | 5.143 | 5.048 | 1.868 | -501 | -178 | 0 | 0 | 34,1 | 33,5 | -2,9 | -3,5 |
| 1,70 | 85 | 38,0 | 5.143 | 5.079 | 1.930 | -517 | -189 | 0 | 0 | 35,0 | 34,3 | -3,0 | -3,7 |
| 1,70 | 85 | 39,0 | 5.143 | 5.111 | 1.993 | -532 | -200 | 0 | 0 | 35,8 | 35,1 | -3,2 | -3,9 |
| 1,70 | 85 | 40,0 | 5.143 | 5.143 | 2.057 | -548 | -211 | 0 | 0 | 36,7 | 35,9 | -3,3 | -4,1 |
| BMI | 29 | | | | | | | | | | | | |

TAB. 4-D

Any MBI

| Pre-bleeding (baseline) hematocrit bHct (dHct1) % | Std IBV-method Calculated IBV (Nadler's formula) bBV (IBV) mL | Protocol I (Withdrawing of 1 unit of Whole Blood) ||||||| Post-bleeding (donation) hematocrit decrease ||
|---|---|---|---|---|---|---|---|---|---|---|---|
| | | HBS-method Target volume || Blood withdrawal || HBS-method Postbleed target volume || Hematocrit Post-bleeding (donation) || | |
| | | tBV1 mL | tRCM1 mL | EBV mL | wRCM mL | tBV2 mL | tRCM2 mL | HBS-method % | std-method % | HBS-method Hct% | Std-method Hct% |
| 3 | 4 | 5 | 6 | 7 | 8 | 9 | 10 | 11 | 12 | 13 | 14 |
| 44,0 | 5.180 | 5.313 | 2.338 | -1.865 | -793 | 4.917 | 1.545 | 31,4 | 28,7 | -12,6 | -15,3 |
| 45,0 | 5.180 | 5.348 | 2.406 | -1.917 | -834 | 4.931 | 1.573 | 31,9 | 28,9 | -13,1 | -16,1 |
| 46,0 | 5.180 | 5.382 | 2.476 | -1.969 | -876 | 4.944 | 1.600 | 32,4 | 29,1 | -13,6 | -16,9 |
| 47,0 | 5.180 | 5.417 | 2.546 | -2.020 | -919 | 4.958 | 1.627 | 32,8 | 29,3 | -14,2 | -17,7 |
| 48,0 | 5.180 | 5.453 | 2.618 | -2.072 | -964 | 4.971 | 1.654 | 33,3 | 29,4 | -14,7 | -18,6 |
| 49,0 | 5.180 | 5.489 | 2.690 | -2.124 | -1.009 | 4.985 | 1.681 | 33,7 | 29,5 | -15,3 | -19,5 |
| 50,0 | 5.180 | 5.526 | 2.763 | -2.176 | -1.055 | 4.998 | 1.708 | 34,2 | 29,6 | -15,8 | -20,4 |
| 51,0 | 5.180 | 5.563 | 2.837 | -2.228 | -1.103 | 5.012 | 1.734 | 34,6 | 29,7 | -16,4 | -21,3 |
| 52,0 | 5.180 | 5.601 | 2.912 | -2.279 | -1.151 | 5.025 | 1.761 | 35,0 | 29,8 | -17,0 | -22,2 |
| 53,0 | 5.180 | 5.639 | 2.988 | -2.331 | -1.201 | 5.038 | 1.788 | 35,5 | 29,8 | -17,5 | -23,2 |
| 54,0 | 5.180 | 5.677 | 3.066 | -2.383 | -1.251 | 5.052 | 1.815 | 35,9 | 29,9 | -18,1 | -24,2 |
| 55,0 | 5.180 | 5.716 | 3.144 | -2.435 | -1.303 | 5.065 | 1.841 | 36,4 | 29,9 | -18,6 | -25,1 |
| 56,0 | 5.180 | 5.756 | 3.223 | -2.487 | -1.355 | 5.078 | 1.868 | 36,8 | 29,8 | -19,2 | -26,2 |

TAB. 4-E

| Units | Hct | N | Method | Mean Hct↓ | SD | Deviance | Diff. |
|---|---|---|---|---|---|---|---|
| 1 | 34-40 | 181 | HBS | -3,089 | 0,250 | -0,089 | <0,001 |
| | | 181 | Std | -3,753 | 0,332 | -0,753 | |
| 3 | 44-56 | 139 | HBS | -13,875 | 1,279 | -3,875 | <0,001 |
| | | 139 | Std | -17,304 | 2,033 | -7,304 | |

P-1 (Supplement to TAB. 4-E)
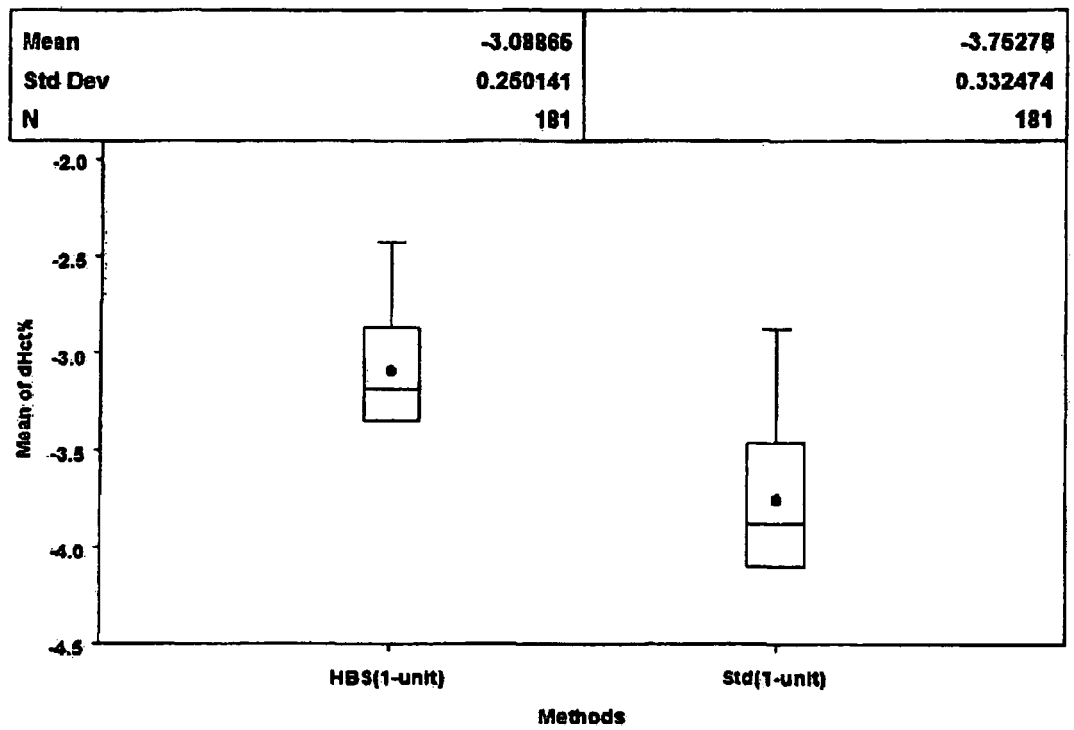
P-2 (Supplement to TAB. 4-E)
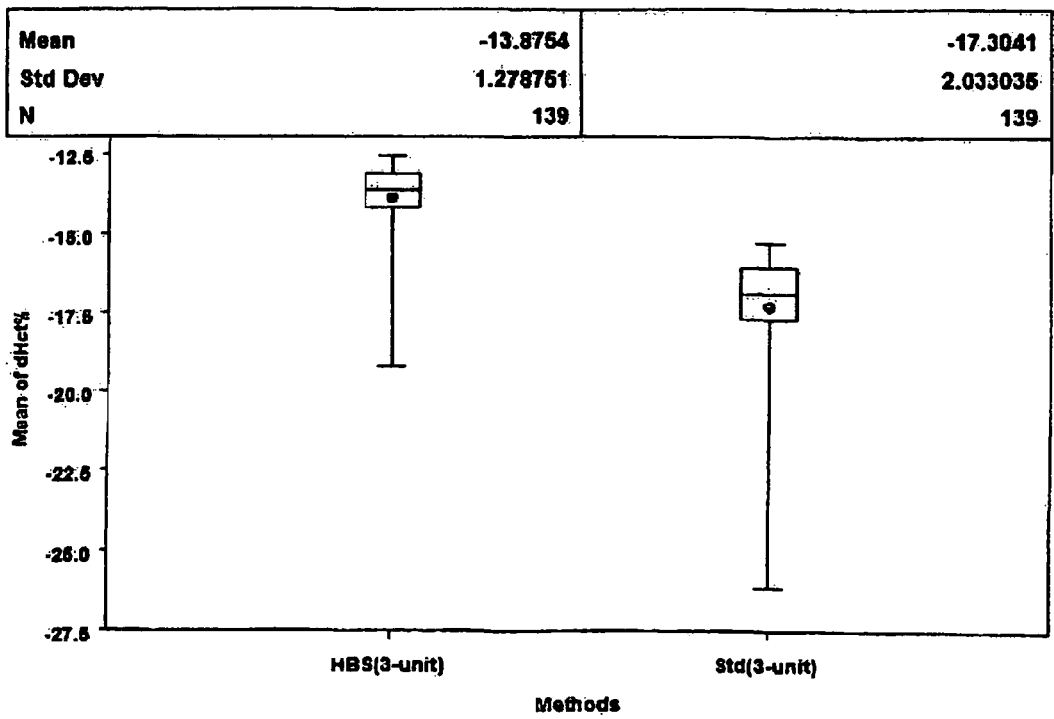

TAB. 5 (A-C)

BMI 20

| Body height m | Body weight kg | Pre-bleeding (baseline) hematocrit bHct1 (tHct1) % | Std-method Calculated IBV (Nadler's formula) bBV (fBV) mL | HBS-method Target volume tBV1 mL | HBS-method Target volume tRCM1 mL | Protocol 1 (Withdrawing of 1 unit of Whole Blood) Blood withdrawal Whole blood EBV mL | Red cells wRCM mL | Postbleed target volume tBV2 mL | Postbleed target volume tRCM2 mL | Hematocrit Post-bleeding (donation) HBS-method % | Hematocrit Post-bleeding (donation) std-method % | Post-bleeding (donation) hematocrit decrease HBS-method Hct% | Post-bleeding (donation) hematocrit decrease Std-method Hct% |
|---|---|---|---|---|---|---|---|---|---|---|---|---|---|
| 1 | 2 | 3 | 4 | 5 | 6 | 7 | 8 | 9 | 10 | 11 | 12 | 13 | 14 |
| 1,85 | 70 | 34,0 | 5.180 | 4.993 | 1.698 | -450 | -146 | 0 | 0 | 31,5 | 31,2 | -2,5 | -2,8 |
| 1,85 | 70 | 35,0 | 5.180 | 5.023 | 1.758 | -450 | -151 | 0 | 0 | 32,5 | 32,1 | -2,5 | -2,9 |
| 1,85 | 70 | 36,0 | 5.180 | 5.054 | 1.819 | -450 | -155 | 0 | 0 | 33,4 | 33,0 | -2,6 | -3,0 |
| 1,85 | 70 | 37,0 | 5.180 | 5.085 | 1.881 | -450 | -160 | 0 | 0 | 34,4 | 33,9 | -2,6 | -3,1 |
| 1,85 | 70 | 38,0 | 5.180 | 5.117 | 1.944 | -450 | -164 | 0 | 0 | 35,4 | 34,8 | -2,6 | -3,2 |
| 1,85 | 70 | 39,0 | 5.180 | 5.148 | 2.008 | -450 | -169 | 0 | 0 | 36,3 | 35,7 | -2,7 | -3,3 |
| 1,85 | 70 | 40,0 | 5.180 | 5.180 | 2.072 | -450 | -173 | 0 | 0 | 37,3 | 36,7 | -2,7 | -3,3 |

BMI 24

| Body height m | Body weight kg | Pre-bleeding (baseline) hematocrit bHct1 (tHct1) % | Std-method Calculated IBV (Nadler's formula) bBV (fBV) mL | HBS-method Target volume tBV1 mL | HBS-method Target volume tRCM1 mL | Protocol 1 (Withdrawing of 1 unit of Whole Blood) Blood withdrawal Whole blood EBV mL | Red cells wRCM mL | Postbleed target volume tBV2 mL | Postbleed target volume tRCM2 mL | Hematocrit Post-bleeding (donation) HBS-method % | Hematocrit Post-bleeding (donation) std-method % | Post-bleeding (donation) hematocrit decrease HBS-method Hct% | Post-bleeding (donation) hematocrit decrease Std-method Hct% |
|---|---|---|---|---|---|---|---|---|---|---|---|---|---|
| 1 | 2 | 3 | 4 | 5 | 6 | 7 | 8 | 9 | 10 | 11 | 12 | 13 | 14 |
| 1,70 | 70 | 34,0 | 4.660 | 4.492 | 1.527 | -450 | -146 | 0 | 0 | 31,3 | 30,9 | -2,7 | -3,1 |
| 1,70 | 70 | 35,0 | 4.660 | 4.519 | 1.582 | -450 | -151 | 0 | 0 | 32,2 | 31,8 | -2,8 | -3,2 |
| 1,70 | 70 | 36,0 | 4.660 | 4.546 | 1.637 | -450 | -155 | 0 | 0 | 33,2 | 32,7 | -2,8 | -3,3 |
| 1,70 | 70 | 37,0 | 4.660 | 4.574 | 1.692 | -450 | -160 | 0 | 0 | 34,1 | 33,6 | -2,9 | -3,4 |
| 1,70 | 70 | 38,0 | 4.660 | 4.602 | 1.749 | -450 | -164 | 0 | 0 | 35,1 | 34,5 | -2,9 | -3,5 |
| 1,70 | 70 | 39,0 | 4.660 | 4.631 | 1.806 | -450 | -169 | 0 | 0 | 36,0 | 35,4 | -3,0 | -3,6 |
| 1,70 | 70 | 40,0 | 4.660 | 4.660 | 1.864 | -450 | -173 | 0 | 0 | 37,0 | 36,3 | -3,0 | -3,7 |

BMI 29

| Body height m | Body weight kg | Pre-bleeding (baseline) hematocrit bHct1 (tHct1) % | Std-method Calculated IBV (Nadler's formula) bBV (fBV) mL | HBS-method Target volume tBV1 mL | HBS-method Target volume tRCM1 mL | Protocol 1 (Withdrawing of 1 unit of Whole Blood) Blood withdrawal Whole blood EBV mL | Red cells wRCM mL | Postbleed target volume tBV2 mL | Postbleed target volume tRCM2 mL | Hematocrit Post-bleeding (donation) HBS-method % | Hematocrit Post-bleeding (donation) std-method % | Post-bleeding (donation) hematocrit decrease HBS-method Hct% | Post-bleeding (donation) hematocrit decrease Std-method Hct% |
|---|---|---|---|---|---|---|---|---|---|---|---|---|---|
| 1 | 2 | 3 | 4 | 5 | 6 | 7 | 8 | 9 | 10 | 11 | 12 | 13 | 14 |
| 1,70 | 85 | 34,0 | 5.143 | 4.957 | 1.685 | -450 | -146 | 0 | 0 | 31,3 | 31,2 | -2,7 | -2,8 |
| 1,70 | 85 | 35,0 | 5.143 | 4.987 | 1.745 | -450 | -151 | 0 | 0 | 32,2 | 32,1 | -2,8 | -2,9 |
| 1,70 | 85 | 36,0 | 5.143 | 5.017 | 1.806 | -450 | -155 | 0 | 0 | 33,2 | 33,0 | -2,8 | -3,0 |
| 1,70 | 85 | 37,0 | 5.143 | 5.048 | 1.868 | -450 | -160 | 0 | 0 | 34,1 | 33,9 | -2,9 | -3,1 |
| 1,70 | 85 | 38,0 | 5.143 | 5.079 | 1.930 | -450 | -164 | 0 | 0 | 35,1 | 34,8 | -2,9 | -3,2 |
| 1,70 | 85 | 39,0 | 5.143 | 5.111 | 1.993 | -450 | -169 | 0 | 0 | 36,0 | 35,7 | -3,0 | -3,3 |
| 1,70 | 85 | 40,0 | 5.143 | 5.143 | 2.057 | -450 | -173 | 0 | 0 | 37,0 | 36,6 | -3,0 | -3,4 |

TAB. 5 (D-E)

D

Protocol 1 (Withdrawing of 1 unit of Whole Blood)

| Body height | Body weight | Pre-bleeding (baseline) hematocrit bHct1 | Std-method Calculated IBV (Nadler's formula) bBV (IBV) | HBS-method Target volume tBV1 | HBS-method tRCM1 | Blood withdrawal Whole blood EBV | Red cells wRCM | HBS-method Postbleed target volume tBV2 | HBS-method tRCM2 | Hematocrit Post-bleeding (donation) HBS-method % | Hematocrit std-method % | Post-bleeding (donation) hematocrit decrease HBS-method Hct% | Std-method Hct% |
|---|---|---|---|---|---|---|---|---|---|---|---|---|---|
| m | kg | % | mL | mL | mL | mL | mL | mL | mL | % | % | Hct% | Hct% |
| 1 | 2 | 3 | 4 | 5 | 6 | 7 | 8 | 9 | 10 | 11 | 12 | 13 | 14 |
| 1,85 | 70 | 44,0 | 5.180 | 5.313 | 2.338 | -1.350 | -574 | 0 | 0 | 35,1 | 32,9 | -8,9 | -11,1 |
| 1,85 | 70 | 45,0 | 5.180 | 5.348 | 2.406 | -1.350 | -587 | 0 | 0 | 36,0 | 33,7 | -9,0 | -11,3 |
| 1,85 | 70 | 46,0 | 5.180 | 5.382 | 2.476 | -1.350 | -601 | 0 | 0 | 36,9 | 34,4 | -9,1 | -11,6 |
| 1,85 | 70 | 47,0 | 5.180 | 5.417 | 2.546 | -1.350 | -614 | 0 | 0 | 37,8 | 35,1 | -9,2 | -11,9 |
| 1,85 | 70 | 48,0 | 5.180 | 5.453 | 2.618 | -1.350 | -628 | 0 | 0 | 38,7 | 35,9 | -9,3 | -12,1 |
| 1,85 | 70 | 49,0 | 5.180 | 5.489 | 2.690 | -1.350 | -641 | 0 | 0 | 39,6 | 36,6 | -9,4 | -12,4 |
| 1,85 | 70 | 50,0 | 5.180 | 5.526 | 2.763 | -1.350 | -655 | 0 | 0 | 40,6 | 37,4 | -9,4 | -12,6 |
| 1,85 | 70 | 51,0 | 5.180 | 5.563 | 2.837 | -1.350 | -668 | 0 | 0 | 41,5 | 38,1 | -9,5 | -12,9 |
| 1,85 | 70 | 52,0 | 5.180 | 5.601 | 2.912 | -1.350 | -682 | 0 | 0 | 42,4 | 38,8 | -9,6 | -13,2 |
| 1,85 | 70 | 53,0 | 5.180 | 5.639 | 2.988 | -1.350 | -695 | 0 | 0 | 43,3 | 39,6 | -9,7 | -13,4 |
| 1,85 | 70 | 54,0 | 5.180 | 5.677 | 3.066 | -1.350 | -709 | 0 | 0 | 44,3 | 40,3 | -9,7 | -13,7 |
| 1,85 | 70 | 55,0 | 5.180 | 5.716 | 3.144 | -1.350 | -722 | 0 | 0 | 45,2 | 41,1 | -9,8 | -13,9 |
| 1,85 | 70 | 56,0 | 5.180 | 5.756 | 3.223 | -1.350 | -736 | 0 | 0 | 46,2 | 41,8 | -9,8 | -14,2 |

BMI 20

E

Protocol 1 (Withdrawing of 1 unit of Whole Blood)

| Body height | Body weight | Pre-bleeding (baseline) hematocrit bHct1 | Std-method Calculated IBV (Nadler's formula) bBV (IBV) | HBS-method Target volume tBV1 | HBS-method tRCM1 | Blood withdrawal Whole blood EBV | Red cells wRCM | HBS-method Postbleed target volume tBV2 | HBS-method tRCM2 | Hematocrit Post-bleeding (donation) HBS-method % | Hematocrit std-method % | Post-bleeding (donation) hematocrit decrease HBS-method Hct% | Std-method Hct% |
|---|---|---|---|---|---|---|---|---|---|---|---|---|---|
| m | kg | % | mL | mL | mL | mL | mL | mL | mL | % | % | Hct% | Hct% |
| 1 | 2 | 3 | 4 | 5 | 6 | 7 | 8 | 9 | 10 | 11 | 12 | 13 | 14 |
| 1,70 | 70 | 44,0 | 4.660 | 4.779 | 2.103 | -1.350 | -574 | 0 | 0 | 34,0 | 31,7 | -10,0 | -12,3 |
| 1,70 | 70 | 45,0 | 4.660 | 4.810 | 2.165 | -1.350 | -587 | 0 | 0 | 34,9 | 32,4 | -10,1 | -12,6 |
| 1,70 | 70 | 46,0 | 4.660 | 4.842 | 2.227 | -1.350 | -601 | 0 | 0 | 35,8 | 33,1 | -10,2 | -12,9 |
| 1,70 | 70 | 47,0 | 4.660 | 4.873 | 2.290 | -1.350 | -614 | 0 | 0 | 36,7 | 33,8 | -10,3 | -13,2 |
| 1,70 | 70 | 48,0 | 4.660 | 4.905 | 2.355 | -1.350 | -628 | 0 | 0 | 37,6 | 34,5 | -10,4 | -13,5 |
| 1,70 | 70 | 49,0 | 4.660 | 4.938 | 2.419 | -1.350 | -641 | 0 | 0 | 38,5 | 35,2 | -10,5 | -13,8 |
| 1,70 | 70 | 50,0 | 4.660 | 4.971 | 2.485 | -1.350 | -655 | 0 | 0 | 39,4 | 35,9 | -10,6 | -14,1 |
| 1,70 | 70 | 51,0 | 4.660 | 5.004 | 2.552 | -1.350 | -668 | 0 | 0 | 40,3 | 36,7 | -10,7 | -14,3 |
| 1,70 | 70 | 52,0 | 4.660 | 5.038 | 2.620 | -1.350 | -682 | 0 | 0 | 41,3 | 37,4 | -10,7 | -14,6 |
| 1,70 | 70 | 53,0 | 4.660 | 5.072 | 2.688 | -1.350 | -695 | 0 | 0 | 42,2 | 38,1 | -10,8 | -14,9 |
| 1,70 | 70 | 54,0 | 4.660 | 5.107 | 2.758 | -1.350 | -709 | 0 | 0 | 43,1 | 38,8 | -10,9 | -15,2 |
| 1,70 | 70 | 55,0 | 4.660 | 5.142 | 2.828 | -1.350 | -722 | 0 | 0 | 44,0 | 39,5 | -11,0 | -15,5 |
| 1,70 | 70 | 56,0 | 4.660 | 5.178 | 2.900 | -1.350 | -736 | 0 | 0 | 45,0 | 40,2 | -11,0 | -15,8 |

BMI 24

TAB. 5 (F)

| | | | | | | Protocol 1 (Withdrawing of 1 unit of Whole Blood) | | | | | | | | |
|---|---|---|---|---|---|---|---|---|---|---|---|---|---|---|
| | | Pre-bleeding (baseline) | Std-method Calculated IBV (Nadler's formula) | HBS-method Target volume | | Blood withdrawal Whole blood | Red cells | HBS-method Postbleed target volume | | Hematocrit Post-bleeding (donation) | | Post-bleeding (donation) hematocrit decrease | |
| Body height | Body weight | hematocrit bHct1 | bBV (IBV) | tBV1 | tRCM1 | EBV | wRCM | tBV2 | tRCM2 | HBS-method | std-method | HBS-method Hct% | Std-method Hct% |
| m | kg | % | mL | mL | mL | mL | mL | mL | mL | % | % | | |
| 1 | 2 | 3 | 4 | 5 | 6 | 7 | 8 | 9 | 10 | 11 | 12 | 13 | 14 |
| 1,70 | 85 | 44,0 | 5.143 | 5.275 | 2.321 | -1.350 | -574 | 0 | 0 | 34,0 | 32,8 | -10,0 | -11,2 |
| 1,70 | 85 | 45,0 | 5.143 | 5.309 | 2.389 | -1.350 | -587 | 0 | 0 | 34,9 | 33,6 | -10,1 | -11,4 |
| 1,70 | 85 | 46,0 | 5.143 | 5.343 | 2.458 | -1.350 | -601 | 0 | 0 | 35,8 | 34,3 | -10,2 | -11,7 |
| 1,70 | 85 | 47,0 | 5.143 | 5.378 | 2.528 | -1.350 | -614 | 0 | 0 | 36,7 | 35,1 | -10,3 | -11,9 |
| 1,70 | 85 | 48,0 | 5.143 | 5.414 | 2.598 | -1.350 | -628 | 0 | 0 | 37,6 | 35,8 | -10,4 | -12,2 |
| 1,70 | 85 | 49,0 | 5.143 | 5.449 | 2.670 | -1.350 | -641 | 0 | 0 | 38,5 | 36,5 | -10,5 | -12,5 |
| 1,70 | 85 | 50,0 | 5.143 | 5.486 | 2.743 | -1.350 | -655 | 0 | 0 | 39,4 | 37,3 | -10,6 | -12,7 |
| 1,70 | 85 | 51,0 | 5.143 | 5.523 | 2.816 | -1.350 | -668 | 0 | 0 | 40,3 | 38,0 | -10,7 | -13,0 |
| 1,70 | 85 | 52,0 | 5.143 | 5.560 | 2.891 | -1.350 | -682 | 0 | 0 | 41,3 | 38,7 | -10,7 | -13,3 |
| 1,70 | 85 | 53,0 | 5.143 | 5.598 | 2.967 | -1.350 | -695 | 0 | 0 | 42,2 | 39,5 | -10,8 | -13,5 |
| 1,70 | 85 | 54,0 | 5.143 | 5.636 | 3.043 | -1.350 | -709 | 0 | 0 | 43,1 | 40,2 | -10,9 | -13,8 |
| 1,70 | 85 | 55,0 | 5.143 | 5.675 | 3.121 | -1.350 | -722 | 0 | 0 | 44,0 | 41,0 | -11,0 | -14,0 |
| 1,70 | 85 | 56,0 | 5.143 | 5.714 | 3.200 | -1.350 | -736 | 0 | 0 | 45,0 | 41,7 | -11,0 | -14,3 |

BMI 29

TAB.5 (G)
| BMI | Expect. Hct↓ | mL | Hct | N | Method | Mean Hct↓ | SD | Deviance | Diff. |
|---|---|---|---|---|---|---|---|---|---|
| 20 | -3 | 450 | 34-40 | 181 | HBS | -2,655 | 0,065 | 0,345 | <0,001 |
| | | | | 181 | Controls | -3,202 | 0,138 | -0,202 | |
| | -10 | 1350 | 44-56 | 139 | HBS | -9,129 | 0,199 | 0,871 | <0,001 |
| | | | | 139 | Controls | -11,703 | 0,608 | -1,703 | |
| 24 | -3 | 450 | 34-40 | 181 | HBS | -2,957 | 0,073 | 0,043 | <0,001 |
| | | | | 181 | Controls | -3,560 | 0,154 | -0,560 | |
| | -10 | 1350 | 44-56 | 139 | HBS | -10,216 | 0,226 | -0,216 | <0,001 |
| | | | | 139 | Controls | -13,010 | 0,676 | -3,010 | |
| 29 | -3 | 450 | 34-40 | 181 | HBS | -2,957 | 0,073 | 0,043 | <0,001 |
| | | | | 181 | Controls | -3,226 | 0,139 | -0,226 | |
| | -10 | 1350 | 44-56 | 139 | HBS | -10,216 | 0,226 | -0,216 | <0,001 |
| | | | | 139 | Controls | -11,789 | 0,613 | -1,789 | |
P-3 (Supplement to TAB.5-G)
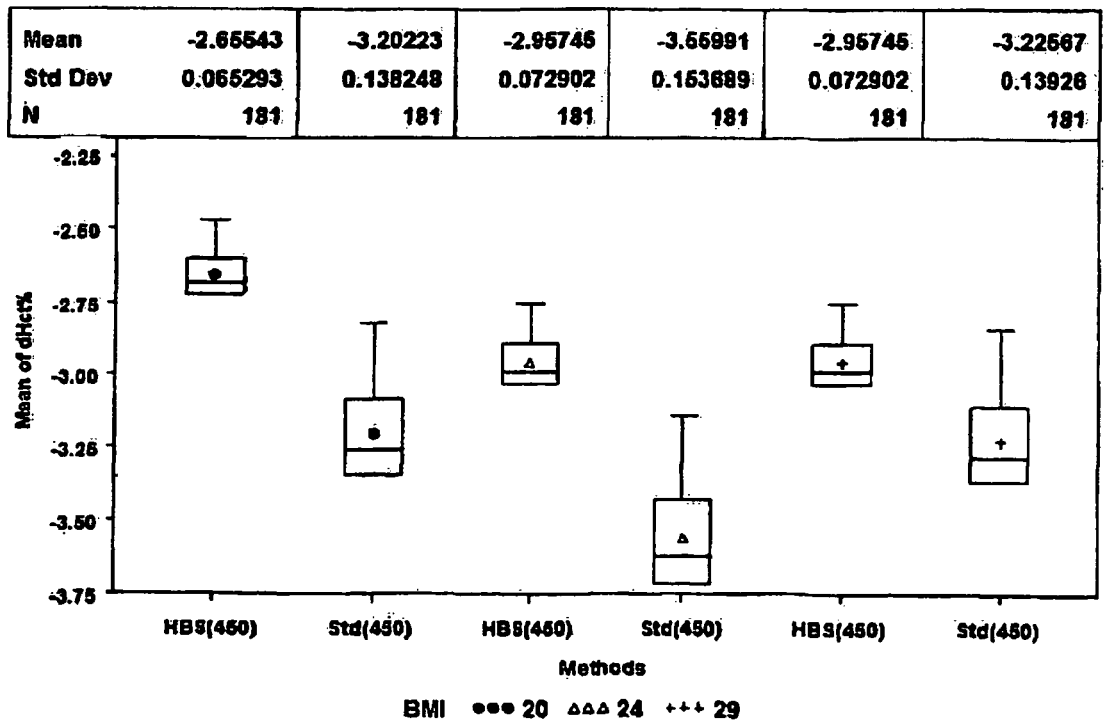

P-4 (Supplement to TAB.5-G)
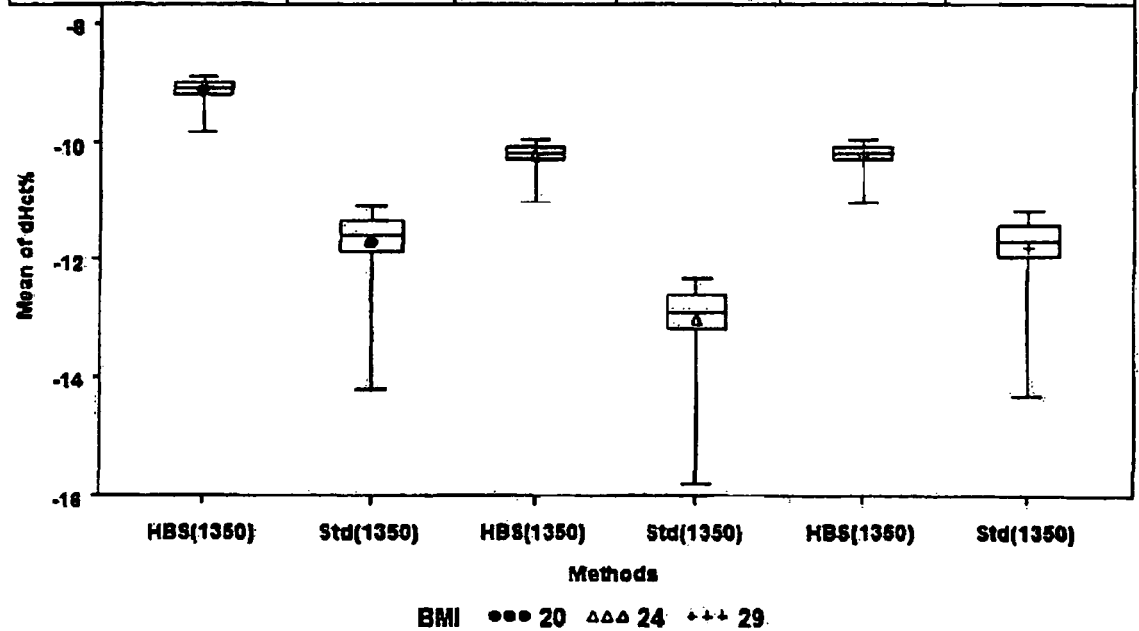

TAB.5 (H)
| Expect. Hct↓ | mL | Hct | N | Method | Mean Hct↓ | SD | Deviance | Diff. |
|---|---|---|---|---|---|---|---|---|
| -3 | 450 | 34-40 | 543 | HBS | -2,857 | 0,159 | 0,143 | <0,001 |
| | | | | | -3,329 | 0,218 | -0,329 | |
| -10 | 1350 | 44-56 | 417 | HBS | -9,854 | 0,557 | 0,146 | <0,001 |
| | | | | | -12,168 | 0,870 | -2,168 | |
P-5 (Supplement to TAB.4-H)
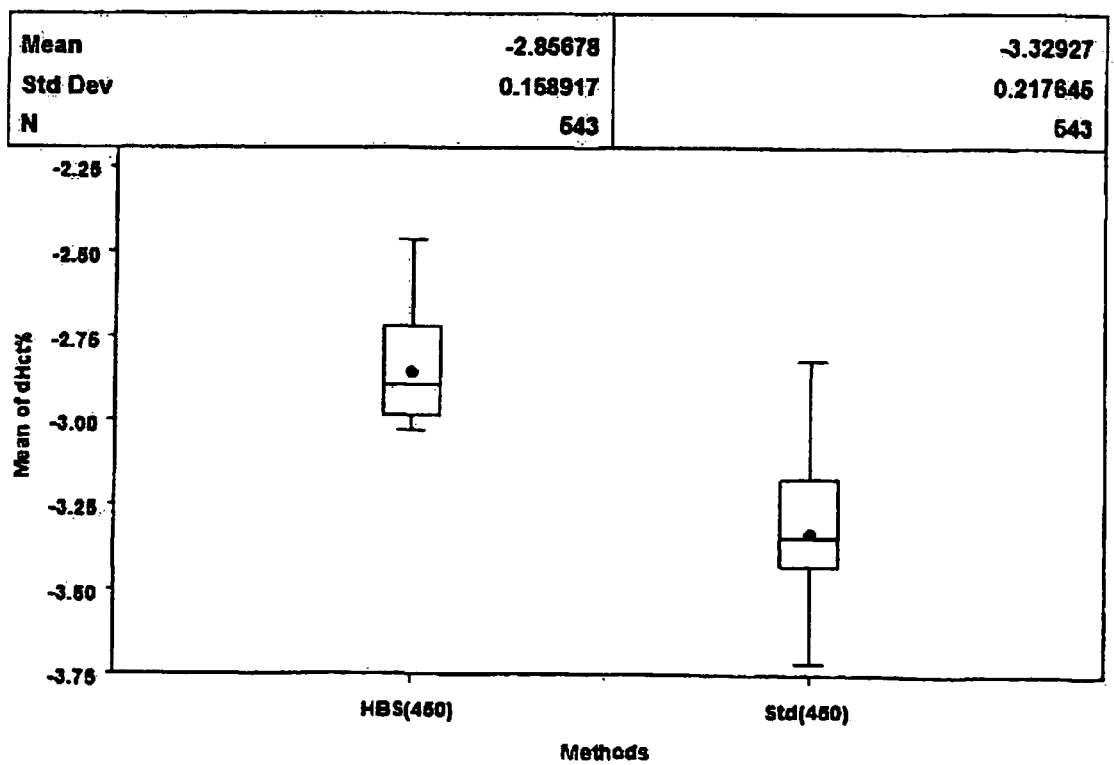

P-6 (Supplement to TAB.4-H)
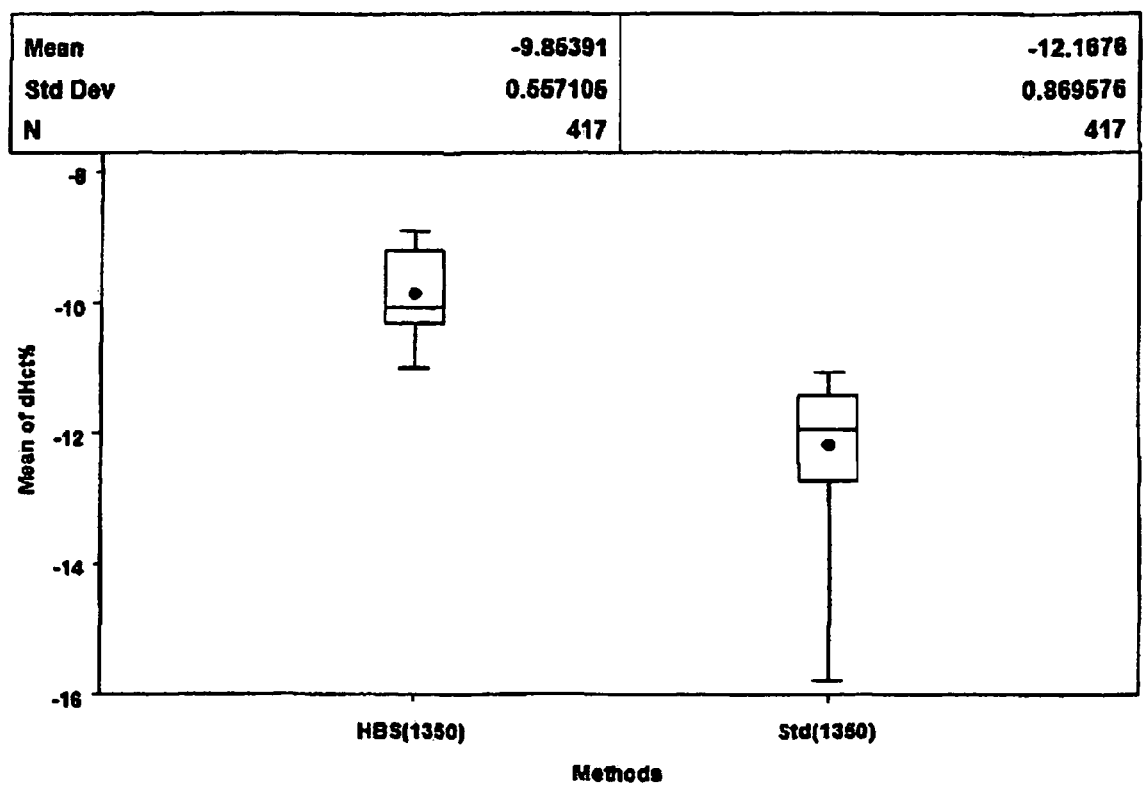

TAB. 6

| | PATIENT SPECIFIC PHYSICAL PARAMETERS | | | | | POST-OPERATIVE PRBC TRANSFUSION PROTOCOL | | | | | BLOOD TEST TIMING | BLOOD HEMATOCRIT | | BLOOD LOSS DURING TRANSFUSION | | | | METHOD A CALCULATED VALUES | | | | | METHOD B CALCULATED VALUES | | |
|---|---|---|---|---|---|---|---|---|---|---|---|---|---|---|---|---|---|---|---|---|---|---|---|---|---|
| Row | GENDER | Age | H | W | | PRBC | Duration | TU | Day | Time interval | tHct | pHct | MDM | dmHct | dLEM | | iRCM | | pIRCM | | cPRBC | | eHctAeHctA-cor | eHctB-1 eHctB-2 eHctB-3 |
| N | M F | yrs | m | kg | k | ml | 30' 60' | units | Nr | <60min >12h | % | % | ml | % | ml k | ml | ml | k | ml | k | ml | k | % % | % % % |
| 1 | M | 52 | 1.68 | 65 | 5 | 243 | 0.19 | 7 | 8 | 9 10 11 12 13 14 | 15 16 | 17 | 18 19 20 | 21 | 22 23 | 24 25 | 26 27 | 28 29 | 30 31 32 |
| 1 | 1 M | 52 | 1.68 | 65 | | 243 | 0.19 | 1 | 0 | 1 | 33.7 | 36.1 | 230 | 35 | 80 0.09 | 1,297 | 1,438 | 1.14 | 1,563 | 1.23 | 125 | 0.10 | 38.3 38.8 | 36.7 37.7 36.7 |
| 2 | 1 M | 47 | 1.76 | 88 | | 209 | 0.13 | 1 | 0 | 1 | 35.0 | 38.9 | 135 | 37 | 50 0.03 | 1,534 | 1,823 | 1.19 | 2,076 | 1.35 | 252 | 0.18 | 38.2 37.4 | 38.0 39.0 40.0 |
| 3 | 1 M | 72 | 1.75 | 100 | | 193 | 0.12 | 1 | 0 | 1 | 38.9 | 38.2 | 140 | 36 | 53 0.03 | 1,653 | 2,098 | 1.27 | 2,258 | 1.37 | 162 | 0.10 | 39.6 38.8 | 39.9 40.9 41.9 |
| 4 | 1 M | 61 | 1.58 | 88 | | 213 | 0.15 | 1 | 0 | 1 | 31.2 | 36.3 | 115 | 34 | 39 0.03 | 1,376 | 1,425 | 1.04 | 1,710 | 1.24 | 285 | 0.21 | 35.0 34.4 | 34.2 39.2 39.2 |
| 5 | 1 M | 61 | 1.70 | 79 | | 233 | 0.18 | 1 | 0 | 1 | 35.2 | 37.7 | 216 | 38 | 76 0.09 | 1,413 | 1,692 | 1.20 | 1,840 | 1.30 | 148 | 0.10 | 39.1 37.8 | 38.2 39.2 40.2 |
| 6 | 1 M | 73 | 1.80 | 83 | | 233 | 0.17 | 1 | 0 | 1 | 30.9 | 33.4 | 205 | 32 | 68 0.05 | 1,364 | 1,397 | 1.02 | 1,533 | 1.12 | 136 | 0.10 | 35.1 34.0 | 33.9 34.9 35.9 |
| 7 | 1 M | 67 | 1.59 | 79 | | 229 | 0.17 | 1 | 0 | 1 | 34.9 | 37.8 | 125 | 36 | 45 0.03 | 1,310 | 1,552 | 1.18 | 1,711 | 1.31 | 159 | 0.12 | 38.9 38.1 | 37.9 38.9 39.9 |
| 8 | 1 M | 74 | 1.60 | 60 | | 193 | 0.17 | 1 | 0 | 1 | 32.6 | 34.0 | 275 | 33 | 92 0.08 | 1,153 | 1,258 | 1.08 | 1,323 | 1.15 | 65 | 0.06 | 36.7 34.8 | 35.6 36.6 37.8 |
| 9 | 1 M | 68 | 1.64 | 83 | | 406 | 0.27 | 2 | 0 | 1 | 35.6 | 40.8 | 280 | 38 | 107 0.07 | 1,489 | 1,807 | 1.21 | 2,139 | 1.44 | 332 | 0.22 | 41.9 40.3 | 41.8 43.6 45.6 |
| 10 | 1 M | 45 | 1.70 | 80 | | 423 | 0.30 | 2 | 0 | 1 | 39.0 | 47.0 | 120 | 43 | 52 0.04 | 1,422 | 1,931 | 1.36 | 2,449 | 1.72 | 518 | 0.36 | 45.8 44.8 | 45.0 47.0 49.0 |
| 11 | 1 M | 79 | 1.50 | 89 | | 406 | 0.30 | 2 | 0 | 1 | 39.9 | 44.8 | 280 | 42 | 119 0.09 | 1,344 | 1,877 | 1.40 | 2,174 | 1.62 | 297 | 0.22 | 46.5 44.6 | 45.9 47.9 49.9 |
| 12 | 1 M | 74 | 1.62 | 70 | | 416 | 0.33 | 2 | 0 | 1 | 34.7 | 39.9 | 320 | 37 | 119 0.09 | 1,261 | 1,494 | 1.18 | 1,745 | 1.39 | 251 | 0.21 | 42.4 40.3 | 40.7 42.7 44.7 |
| 13 | 1 M | 55 | 1.81 | 95 | | 353 | 0.21 | 2 | 0 | 1 | 35.4 | 38.7 | 285 | 37 | 106 0.06 | 1,667 | 2,009 | 1.21 | 2,241 | 1.34 | 232 | 0.14 | 40.4 38.9 | 41.4 43.4 45.4 |
| 14 | 1 M | 68 | 1.69 | 79 | | 368 | 0.29 | 2 | 0 | 1 | 38.3 | 42.0 | 385 | 40 | 155 0.12 | 1,328 | 1,762 | 1.33 | 1,978 | 1.49 | 215 | 0.16 | 44.8 42.3 | 44.3 46.3 48.3 |
| 15 | 1 M | 76 | 1.83 | 84 | | 378 | 0.24 | 2 | 0 | 1 | 43.5 | 48.8 | 105 | 46 | 48 0.03 | 1,596 | 2,471 | 1.55 | 2,654 | 1.66 | 183 | 0.24 | 49.5 47.0 | 49.5 51.5 53.5 |
| 16 | 1 F | 66 | 1.50 | 60 | | 478 | 0.44 | 2 | 0 | 1 | 35.5 | 41.1 | 420 | 38 | 161 0.15 | 1,077 | 1,303 | 1.21 | 1,562 | 1.45 | 259 | 0.24 | 45.5 42.3 | 41.5 43.5 45.5 |

M- male gender
F- female gender
W- body weight
H- body height
k- Constant k
iRCM- pretransfusion volume of circulating PRBCs PRBC- actual volume of transfused packed RBC
k- volume value expressed in fractions of Constant k
TU- units of transfused packed red blood cells
NA- data not available
Day- postoperative day (0- means day of surgery)
pIRCM- post-transfusion volume of RBC tHct- measured baseline hematocrit
pHct- post-transfusion hematocrit
MDM- measured drainage mass volume
dmHct- drainage mass hematocrit
cLEM- calculated loss of erythrocyte mass
dPRBC- calculated volume of transfused PRBCs eHctA- expected Hct after transfusion of PRBCs volume (column N7)
ceHctA-cor- the same, but corrected to loss of RBC volume (column N18)
eHctB1- expected Hct value, assuming 3% increase per PRBC unit
eHctB2- expected Hct value, assuming 4% increase per PRBC unit
eHctB3- expected Hct value, assuming 5% increase per PRBC unit P-7 (Supplement to TAB.6)
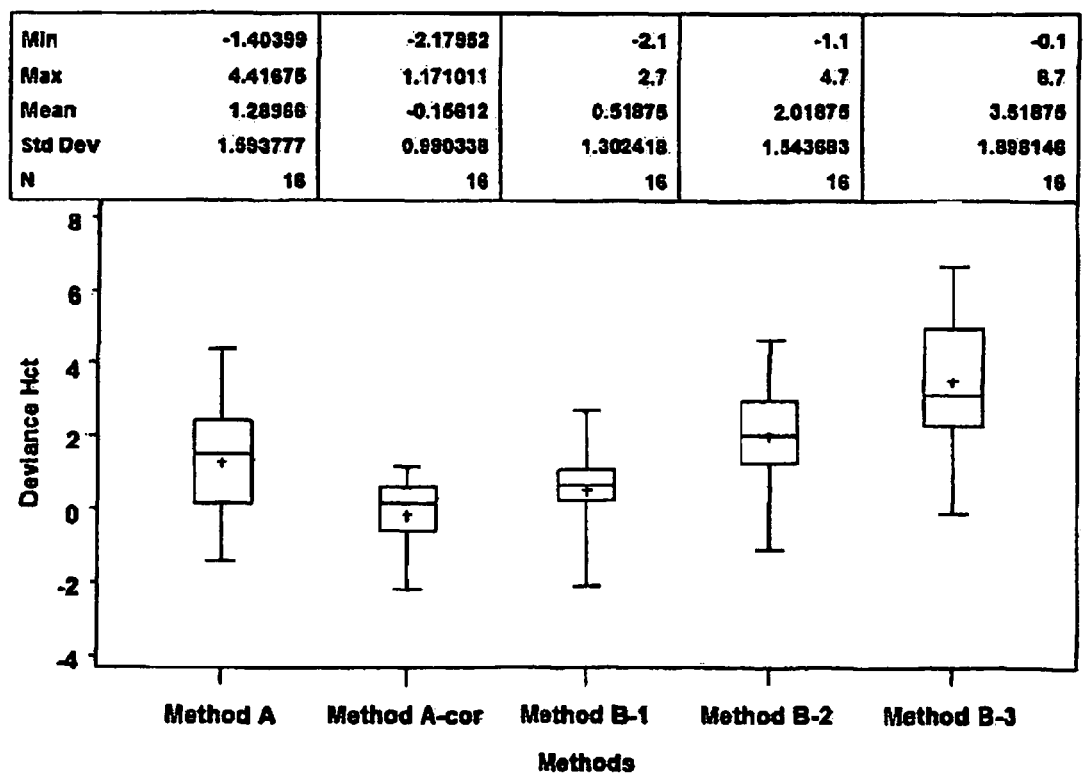

SYSTEMS AND METHOD FOR HOMEOSTATIC BLOOD STATES

CROSS-REFERRENCE TO RELATED APPLICATIONS

This application claims provisional priority to U.S. Provisional Patent Application Ser. No. 60/712,809 filed Sep. 1, 2005, incorporated herein by reference.

BACKGROUND OF THE INVENTION

1. Field of Endeavor 1.1. Intravenous fluid and red cell mass resuscitation are an integral part of modern medicine practice in a variety of medical fields. The administration of intravenous fluid and red cell mass replacement measures is a common practice during surgery and is indispensable in the management of many nonsurgical medical conditions. It is often a crucial component in areas such as (1) patients undergoing elective, urgent or emergent surgical or obstetrical procedures, (2) patients who elect not to be transfused, (3) patients undergoing treatment in intensive care and toxicology units, (4) critically-ill patients (5) dehydrated patients, and so on.

1.2. The present invention is focused on the administration of blood transfusion therapy for patients with preexisting blood loss or massive bleeding, also for patients undergoing surgery and other procedures in which significant blood loss occurs or is expected. This includes but is not limited to: (1) patients undergoing major urgent or emergent surgery and obstetrical procedures, major surgery or organ transplantation (2) patients with preexisting blood disorders or acquired deficiency states secondary to bleeding, (3) critically-ill patients.

1.3. The present invention applies to both inpatient and outpatient surgical or hematology settings, and to procedures performed in operating rooms, intensive care units and other locations (e.g., interventional radiology or surgery wards) where blood transfusion therapy is indicated. This new invention is directly applicable to the care administered by anesthesiologists, intensive care doctors, surgeons and individuals who deliver care under their medical direction or supervision.

1.4. The present invention relates to the mathematical model for determining the hemoglobin concentration and hematocrit specific circulating red cell mass and total blood volume that are crucial in plasma dilution evaluation, also calculating rates of intravenous fluid infusions and amounts of packed red blood cell transfusion.

1.5. More specifically, the present invention relates to a method and apparatus for determining the total blood volume, circulating red cell mass and plasma hydration from blood hemoglobin concentration and hematocrit deployed in a nomogram (i,ii) (See references listed after Abstract on Pg.) as trends of hemoglobin concentration and hematocrit ratio (iii) known as mean cell hemoglobin concentration.

2. Description of the Related Art 2.1. Under the existing processes, blood hematocrit and hemoglobin concentration are probably the most frequently obtained blood tests in both outpatients and inpatients. They are the classic parameters used for tracing plasma dilution in evaluation of infusion therapy and serving as indirect criteria of blood erythrocyte content and oxygen carrying capacity in evaluation of bleeding and guiding blood transfusion strategies. The ratio blood hemoglobin concentration to hematocrit is referred to as mean cell hemoglobin concentration (MCHC) in red blood test results.

Existing Art 1

Measures and Estimates of Blood Volume and its Components 2.1.1. Hemoglobin dilution-time curves are used for the dynamical investigation of blood volume and plasma dilution in human and animal studies.(iv) Hemoglobin concentration serves as endogenous tracer of plasma dilution.

(a) Traditional methods for estimating fluid distribution are based on mass balance. They use baseline measured or assume normal calculated blood volume for the evaluation of plasma dilution reflected by changes in blood hemoglobin concentration or hematocrit. (iv)

(b) Under the existing art, the most accurate blood volume values are obtained by the direct measurements, especially simultaneous measuring of red cell mass and plasma volume.

(c) Under the existing art, formulas for calculating normal blood and plasma volumes are conventionally used in research and clinical practice. (xiv-xvii) Expert Panel on Radionuclides of the International Council for Standardization in Haematology reported that there was insufficient data in any single publication to make recommendations for calculating normal RCM and PV for adults, so they were aggregated together to provide normal red cell mass and plasma volume predictions in adults. The standardization has been achieved since no single publication biased the results. (xvii) Thus, the mean predictions of red cell mass and plasma volume proposed by the Expert Panel on Radionuclides of the International Council for Standardization in Haematology (ICSH) were shown being closer to the direct measurements than predictions based on calculated normal values (Nadler and Hurley for male red cell mass; Nadler, Hurley and Wennesland for male plasma volume; Nadler and Hurley for female red cell mass and plasma volume). The recommendations carried out by the panel are as follows:

For Males:

Mean normal RCM (ml)=(1486×S)−825 [98% limits=plus/minus 25%]

Mean normal PV (ml)=1578×S[99 percent limits=plus/minus 25 percent]

For Females:

Mean normal RCM ml=(1.06×age)+(822×S)[99% limits=plus/minus 25%]

Mean normal PV ml=1395×S[99% limits=plus/minus 25%]

Where RCM is red cell mass, PV—plasma volume, S=surface area $(m^2)$,=$W^0.425 \times h^0.725 \times 0.007184$; age=age (years); h=height (cm); W=weight (kg).

As to the best knowledge of the author, no further advance in the development of normal blood volume related calculations was made.

(d) Under the existing art, bioelectrical impedance (bioimpedance) analysis is a noninvasive method most frequently used to obtain an accurate reproducible estimates of cardiac index that are comparable to thermodilution methods. (xx) A similar technique is used to assess the overall body composition and volume of different parts, i.e. limbs or intracellular and extracellular space. Therefore this method is used for obtaining the body fluid volumes in studies on volume kinetics of parenterally infused solutions. Svensen and his colleagues used Xitron 4000B Spectrum Analyser (Xitron Technologies Inc., San Diego, Calif., USA) for measurings before surgery, after surgery, and just before and after the experimental infusion of Ringer's solution to evaluate an intercompartment fluid distribution. (xxi) The bioelectrical analysis involved sending small currents in a series of 50 frequencies between 5 kHz to 500 kHz through the patient via four electrodes placed on the right foot and right arm. The obtained data indirectly suggested the intravascular volume (total blood volume) calculated by the software supplied with an apparatus.

(e) Under the existing art, the most accurate methods for dynamically investigating plasma volume as part of central expandable fluid space are based on volume kinetic analysis (xxii-xlvi) and its latest elaboration—volume turnover kinetics. (xlvii) These methods—the most advanced processes investigating intravascular fluid handling—explain the movement of fluid between functional body tissue compartments in relation to their expandability. The method has been applied for infused intravenous solutions by Drs. Svensen and Hahn in 1997. (xlviii) It was a new innovative application of pharmacokinetic data analysis, earlier applied to drug disposition. The distribution of the fluid infused is modeled separately for each subject using a kinetic model based on the assumption that the volume of the fluid space expanded by the infused fluid strives to be maintained in a way similar to an elastic balloon. A fluid given by iv infusion at a rate ki is distributed in a virtual expandable fluid space with a volume (v) which the fluid space strives to maintain at a baseline (target) volume (V). Fluid leaves the space at a basal rate, representing perspiration from the expanded body fluid space and baseline diuresis (kb) and at a controlled rate proportional by a constant (kr) to the deviation from the target volume. Serial changes in hemoglobin concentration serve as indicators of plasma dilution. After infusing the test fluids, the non-linear regression of fluid-induced changes in hemoglobin concentration is used to cathegorize mathematically the clearance curves as one, two or three volume of fluid space (1,2,3-VOFS) models. (xxv) Mathematical models were built on that basis to represent the changes in volume of the body fluid spaces associated with intravenous administration of different solutions. Input data for mathematical parameter estimations were dilution of blood, measured as reduction of blood hemoglobin concentration. In contrast to mass balance, baseline plasma volume measurement is not necessary for volume kinetic analysis. (xxi,xlv) Fitting the kinetic model to an index of plasma dilution makes it possible to estimate the intravascular and extravascular volume expanded by the parenteral fluid infusion. (xxi) Theoretical value of baseline blood volume is used in all models for corrections of dilution due to blood sampling, and theoretical volume of intracellular fluid space is used by the most sophisticated 3-VOFS model for evaluation of osmotic fluid shifts. (xlv) Both the effect of fluid bolus on plasma dilution and rate of infusion needed to maintain the given level of dilution are predicted by kinetic modeling. (v)

(f) Numerous studies investigating plasma dilution by different intravenous solutions reported that plasma fluid equilibration with peripheral tissues and induced increase in renal elimination are over in 15 to 20 minutes after the end of infusion. Similar findings were published by Ruttmann et al., who reported that hemodilution enhanced onset of coagulation measured by the thrombelastogram is transient, with values returning towards baseline within 15 min after finishing the infusion. Blood samples were taken prior to, and immediately after (30 min) the rapid normal saline infusion was completed (30 min). They were then repeated at regular intervals up to 120 min. Hematocrit and platelet counts were taken to determine the degree of dilution. The hematocrit and platelet count showed a rapid dilutional decrease at 30 min (mean of −12.2% and −14.4%, respectively), with values returning towards baseline within 15 minutes. Infusion therapy manuals for nurses alert that blood samples should be obtained from the arm without an IV or infusion should be stopped for 1 or 2 minutes.

Below Follow the Deficiencies Related to Existing Art 1 [2.1.1]

2.1.2. However, the total blood volume is unknown in most clinical settings (v), therefore limiting the clinical value of hemoglobin concentration and hematocrit in the evaluation of infusion therapy measures. No mathematical model provides the hematocrit and red cell mass specific homeostatic target blood volume trends. That is because:

(a) Methods for the direct measurement of blood volume have limited clinical applicability due to numerous limitations, such as radiation hazard, steady state requirements, long period required between consequent measurements and others. (vi-xiii)

(b) Calculations of the normal blood volume are continuously debated as the calculations nearly match the values obtained by direct measurements (xviii,xix) or data from volume kinetic analysis. Expert Panel on Radionuclides of the International Council for Standardization in Haematology reported that comparison of red cell mass and plasma volume predictions by the various published methods showed clearly that predictions based solely on body weight were inappropriate. Although there was reasonable agreement in the prediction values given by the formulate based on both height and weight, it was not possible to establish which formulae could be recommended. (xvii)

(c) The proposed reference ranges plus/minus 25 percent in the recommendations carried out by the Expert Panel on Radionuclides of the International Council for Standardization in Haematology (xvii) have been selected to include at least 98 percent of the population. It was recognized that these limits are wide, and significant changes in both RCM and PV may occur in some individuals without their measured values falling outside their normal range.

(d) Although offering clinicians a simple, quick method with minimal direct patient risk bioimpedance has not gained wide acceptance. Hundreds of validation studies reported both poor and good correlations between bioimpedance and reference methods. The major limitations of bioimpedance technique are as following: (1) electrode placement is an important source of error (2) subject must not move, because alterations in body posture may alter baseline impedance readings and thus invalidate the recording (3) other factors include inner-compartment fluid shifts and changes in hematocrit. Intravascular volume (total blood volume) is not measured, but calculated from readings of extracellular volume by the preset mathematical ratio which is debatable.

(e) Methods based on volume kinetics have limited clinical applicability, mainly due to steady state requirements (no intravenous infusion or any other origin plasma dilution present) during the postinfusion period when serial blood samples are taken. Volume kinetic parameters are vulnerable to loss of hemoglobin and postbleeding capillary refill origin plasma dilution. (xliv) The predictions of fluid disposition with further infusions can be deteriorated by the naturally changing fluid balance and transcapillary fluid shifts. Although volume kinetic models do not require baseline blood volume for major estimates, they apply assumptions of normal calculated blood volume for corrections of dilution due to blood sampling, and theoretical volume of intracellular fluid space in the most sophisticated 3-VOFS model for evaluation of osmotic fluid shifts. (xlv) As described earlier in the text, assumption of normal theoretically calculated values is a potential source of error.

Existing Art 2

Blood Volume Homeostasis: Issue of Normal or Physiologic Target Volume 2.1.3. Under the existing art, normal blood volume is conventionally assumed being the homeostatic target that the body strives to maintain regardless of circulating red cell mass.

(a) Mathematical methods (xvi,xlix) are used to predict hemoglobin concentration and hematocrit changes resulting from blood withdrawal and plasma dilution in acute normovolemic hemodilution that serves to reduce allogeneic transfusions. Methods rely on the assumption of baseline normal calculated blood volume, and intravenous replacement infusions are targeted to restore normal blood volume. (xlix)

(b) Under the existing art, over the last decade, there was a significant advance in blood transfusion decision making so the transfusion triggers and targets are well established. (l-lxi) Draft new ASA (American Society of Anesthesiologists) Guidelines 2005 for transfusion of allogeneic red blood cells or autologous blood has defined the following process: (1) maintain adequate intravascular volume and blood pressure with crystalloids or colloids until the criteria for red blood cell transfusion is met; (2) Adequate quantities of red blood cells should be transfused to maintain organ perfusion. (lviii) Obviously, blood loss and blood transfusion induced changes in hemoglobin concentration and hematocrit can be calculated on the assumption of baseline normal calculated blood volume similarly to the above described methods used in acute normovolemic hemodilution. There are several methods that ignore the assumption of baseline normal blood volume for estimating the amount of packed red blood cell transfusion for proper hematocrit and hemoglobin concentration increase. The "Rule of Thumb" by Habibi et al. (lxii,lxiii) that is probably the most popular in clinical practice for predicting post-transfusion hematocrit tells that transfusing one unit causes hematocrit increase in a range from 3% to 5%. Other recommendations suggest that transfusing one unit causes hemoglobin concentration increase by approximately 10 g/L. Similarly, predonation of one unit is reported to cause the mean hemoglobin concentration decrease by 10 g/l and hematocrit by 3%, and these values are increasing with the number of predonated units. (lxiv) This progressively increasing drop of hematocrit and hemoglobin concentration with increasing number of predonated units suggests that the drop is baseline hematocrit and hemoglobin concentration specific.

(c) Under the existing art, the body carefully controls a seemingly endless list of vital parameters by means of homeostasis. Homeostasis acts similarly at the level of a single cell and systemic parameters that affect the whole body, i.e. blood volume and arterial pressure. (lxv) The blood volume that is necessary to achieve adequate perfusion of key organs is referred to as the effective circulating volume. For homeostasis of effective circulating volume, changes in extracellular volume are important, because they are accompanied by proportional changes in plasma volume, which in turn affects the adequacy with which the circulatory system can perfuse vital organs with blood. (lxvi-lxviii) Note that the same effective circulating volume can be maintained by different patterns of total blood volume. The 1,2,3-VOFS models used in volume kinetic analysis are based on the assumption that the body strives to maintain volume homeostasis of functional fluid spaces and that the rate of restoration is a function of deviation from resting volume. (xlviii) These methods use the sophisticated mathematical models and software (initially MatLab Version 3, later MatLab Version 4.2 and 5.3 by Math Works Inc., Notich, Mass.) for modeling the kinetics of the fluid infused intravenously. Initial or baseline blood volume, blood dilution marker's dynamics obtained from serial blood sampling, the basal urine output, which is estimated, and induced (controlled) urine output, which is measured, are the variables deployed by that software. (xxvii) With some limitations, the baseline blood volume and its dynamics following intravenous fluid load is obtained without direct measures or assumption of normal calculated blood volume. The most powerful concept (v) of volume kinetic analysis is the mathematical demonstration of a physiologic target blood volume that intravascular volume will approach, usually quite rapidly after perturbation following the intravascular volume load. Most likely it can be considered as homeostatic target volume, although it was not reported to match the normal calculated blood volume.

Below Follow the Deficiencies Related to Existing Art 2 [2.1.3]

2.1.4. However, assumption of normal calculated blood volume regardless of circulating red cell mass is debatable as it leads to significant errors in estimates, such as calculating an exchangeable blood amount and measures of volume resuscitation with intravenous solutions during acute normovolemic hemodilution, also calculating an amount of blood transfusion for proper targets of hemoglobin concentration and hematocrit increase.

(a) Assumption of normal calculated blood volume usually leads to overestimation of the 'true' exchangeable blood volume in acute normovolemic hemodilution. It endangers patients, because target hemoglobin concentration is usually missed and normovolemic anemia appears to be more severe than intended. Normal calculated blood volume targeted withdrawn blood volume replacement by intravenous crystalloids and/or colloids results in transitory circulatory overload, dilution coagulopathy and advanced edema. (xlix)

(b) Evaluating blood loss and calculating the right blood transfusion amount for targets of hematocrit and hemoglobin concentration increase in relationship with parenteral fluid resuscitation remains challenging as guidelines are very approximate. (lviii,lxii) Draft new ASA Guidelines 2006 for transfusion of allogeneic red blood cells or autologous blood has defined the amount of transfusion as adequate quantities of red blood cells should be transfused to maintain organ perfusion. (lviii) Therefore, practicing physicians are further facing the dilemma of calculating the transfusion amount for the desired hematocrit increase without having access to simple and accurate tools or procedures. Under the prior art, the rule of thumb as suggested by Habibi et al is that the administration of one unit of packed RBCs will increase hematocrit by 3-5%. (lxii) Inaccurate estimates of total blood volume and circulating red cell mass based on assumption of normal calculated blood volume result in clinical errors reported to be even fatal. (lx,lxiii) Existing methods of predicting post-transfusion hematocrit and hemoglobin concentration increase do not account for the volume of PRBC transfusion, thus indirectly acknowledging that blood volume is unknown in most clinical settings. The influence of pre-transfusion plasma dilution, especially achieved with colloid solutions, is also ignored. It results in post-transfusion coagulopathy, transitory circulatory overload and edema. Clinical dillemas are also frequent with methods that ignore assumption of baseline normal blood volume for estimating the amount of packed red blood cell transfusion for proper hematocrit and hemoglobin concentration increase: how many units are to be transfused when the needed increase in hematocrit is >15% or hemoglobin concentration increase for >30 g/L: is it 3, 4 or 5? Therefore, blood tests are adviced to be made after each unit. To the best knowledge of the author, clinically approved nomograms providing detailed progressive trends of hematocrit and hemoglobin concentration increase following transfusion or decrese due to donation are not available yet.

(c) Existing mathematical models based on volume kinetics do not provide the definition of the physiologic (homeostatic) target blood volume that would allow its clinical calculation. Clinical detection of physiologic (homeostatic) target blood volume is not proposed. Target blood volume's red cell mass specificity was not investigated. Methods based on volume kinetics use sophisticated mathematical models and software that deploy numerous variables to derive nomograms reflecting or simulating proper infusion specific kinetics. Entering numerous variables into a computer takes time and detracts a physician's attention from the patient. Finally, the derived kinetic modeling results have limited clinical applicability, because they are easily affected by a changing clinical setting. For example, various intensity perioperative bleeding and capillary leaks make preoperative kinetic predictions useless, while offering no method for adjusting that data to the changing clinical conditions. Meanwhile simplified clinically applicable nomograms were not proposed. In addition, limits of iso-osmotic plasma hydration in respect to physiologic (homeostatic) target blood volume were not established. These limits were not investigated in relationship with homeostatic (non-artificial) osmotic changes in red cell mass and consequently mean cell volume (MCV) and mean cell hemoglobin concentration (MCHC). Therefore, clinically it is still hard to differentiate hematocrit and hemoglobin concentration changes resulting from mild or initial bleeding and those induced by isoosmotic plasma dilution.

Existing Art 3

2.1.5. Under the prior art, the basic characteristics of red blood cell specific erythropoietic brand is the mean cell volume (MCV), mean cell hemoglobin content (MCH) and mean cell hemoglobin concentration (MCHC). (1) hemoglobin concentration (Hb) to hematocrit (Hct) ratio provides MCHC value; (2) two coordinate—hemoglobin concentration and hematocrit—systems are used for tracing plasma dilution; (3) plasma osmolality shifts are reflected by non-erythropoietic origin changes in MCV; (4) blood test results for Hb, Hct, MCHC, MCH and MCV are obtained from a single blood test, and results are printed in a numerical form and stored this way in medical records. Different literature sources provide slightly different normal intervals. The most recent manuals—American [Mosby, 2006] and Great Britain's [Oxford, 2005]—unanimously claim MCV>100 fl as macrocytic and MCV<80 fl as microcytic thresholds. The normal MCHC intervals are also very much similar—320-360 and 310-360 (g/L) accordingly.

(a) The MCHC value is mathematically derived from the existing formulae of MCHC and MCH and MCV relationship (lxix-lxxi), as follows:

$$MCHC = Hb \cdot Hct^{-1} \quad (1)$$

MCHC—mean cell hemoglobin concentration (g/dL)
Hb—blood hemoglobin concentration (g/dL)
Hct—blood hematocrit (SI)

(b) Under the prior art, two coordinate—hemoglobin concentration and hematocrit—systems for tracing plasma dilution is used by the prior processes. Iso-osmotic plasma dilution is reflected by linear graphical trends, meanwhile osmotic shifts induce proper deviations from it.

(c) Under the prior processes, red blood cells (RBCs) in the human body are produced by erythropoiesis and released into blood circulation as normal or abnormal forms that are referred to as erythropoietic brands. There is a continuous release of new cells to replace worn-out cells that are withdrawn from circulation. Normally there are negligible differences in brands that are typically released in the body of the same person. However pathologic states and blood transfusions can change this status quo. The main characteristics of the erythropoietic brand are mean cell volume (MCV), mean cell hemoglobin content (MCH) and osmotic fragility or resistance. Like Hb, Hct and their derivative MCHC, both MCV and MCH are obtained by conventional blood tests. Red cell mass (RCM) acts as fluid compartment in osmotic fluid shifts. Its volume deviations are directly proportional to appropriate osmotic origin MCV shifts. Consequently plasma osmolality deviations can be traced by mean cell volume dynamics, too. Only MCV is specifically sensitive to osmotic erythrocyte volume shifts, while MCH is not sensitive to these shifts. Under the prior processes, the MCV value is in direct proportion with ratio Hct to the red cell (erythrocyte) concentration (EC) in the following formula:

$$MVC = 1000 \cdot Hct \cdot EC^{-1} \quad (2)$$

MCV—mean cell volume (pf)
Hct—blood hematocrit (SI)
EC—blood erythrocyte concentration (mln/mcL)

The MCH value is in direct proportion with ratio Hb to RBCs concentration (EC) in the following formula:

$$MCH = 10 \cdot Hb \cdot EC^{-1} \quad (3)$$

MCH—mean cell hemoglobin content (pg)
Hb—blood hemoglobin concentration (g/dL)
EC—blood erythrocyte concentration (mln/mcL)

A direct relationship of MCHC, MCV and MCH is expressed as follows:

$$MCHC = (0.1 \cdot MCH \cdot EC) \times (0.001 \cdot MCV \cdot EC)^{-1} = 100 \cdot MCH \cdot MCV^{-1} \quad (*4)$$

where MCHC—mean cell hemoglobin concentration (g/dL)
MCH—mean cell hemoglobin content (pg)
EC—blood erythrocyte concentration (mln/mcL)

MCV—mean cell volume (fl) The MCH parameter is not changing if no RBCs are transfused when erythropoietic erythrocyte brand content stays the same, which normally does. Obviously, in such a setting, MCHC and MCV ratio is shown in the following formula:

$$MCHC = 100 \cdot MCV^{-1} \quad (5)$$

Following is an equation of deviation proportions:

$$MCHC_2 \div MCHC_1 = MCV_1 \div MCV_2 \quad (6)$$

or $$\Delta MCHC = MCHC \times (\Delta MCV)^{-1} \quad (7)$$

MCHC₁—pre-osmotic shift mean cell hemoglobin concentration

MCHC₂—post-osmotic shift mean cell hemoglobin concentration

MCV₁—pre-osmotic shift mean cell volume

MCV₂—post-osmotic shift mean cell volume (d) Under the prior art, plasma osmolality values are obtained by means of special blood tests. These values and especially their dynamics are of great importance in many fields of treatment such as cerebral hypertension, when osmotic diuretics are being administered and plasma osmolality needs to be constantly verified. Shifts of plasma osmolality are also important in tracing effects of osmotically active plasma volume expanders such as hypertonic intravenous saline solution and others used for infusion therapy.

(e) With the prior art, results of blood tests for Hb, Hct, MCH, MCV and MCHC are recorded on multiple pages or files in medical records, making evaluations and dynamical investigations tedious and time consuming. The limitations of the existing two coordinate Hb/Hc graphical systems make it unsuitable for medical records, too.

Below Follow the Deficiencies Related to Existing Art 3 [2.1.5.]

All together Hb, Hct, MCH, MCV and MCHC parameters are not used in existing nomograms for evaluation of their interfering dynamics for the needs of infusion and blood transfusion therapies. Existing applications have limited clinical applicability.

(a) However, conventional interpretation of plasma dilution data derived from two coordinate—hemoglobin concentration and hematocrit—systems is limited both in clinical and research applications, because it does not account for osmotic deviations related hematocrit shifts due to related changes in red cell mass, while this information is of major importance for infusion therapy. It has never been applied for tracing the dynamics of plasma osmolality and erythrpoietic content either. Thus, two coordinate Hb/Hct graphical systems has no clinical value. To the best knowledge of the author, standardized MCHC specific trends were never added to the two coordinate Hb/Hct graphical systems.

(b) Plasma osmolality tests are costly, require patient's blood loss and in many cases, especially for critically injured patients, they go along with a separate blood test for Hb and Hct. Lowering the overall number of blood sampling in critically ill patients would favor the results of treatment. To the best knowledge of the author, all together the MCH, MCV and MCHC parameters were never used in nomograms for tracing dynamics of plasma osmolality and erythropietic red blood cell content in blood. Investigation of interfering plasma dilution and osmolality dynamics by means of Hb, Hct and MCHC parameters has never been undertaken in one graphical system or nomogram.

(c) Red blood test results for hematocrit (Hct), hemoglobin concentration (Hb), mean cell volume (MCV), mean cell hemoglobin (MCH) and mean cell hemoglobin concentration (MCHC) conventionally recorded on multiple pages or files in medical records make evaluations and dynamical investigations tedious and time consuming.

In conclusion, It is generally acknowledged that in everyday clinical practice we still can't accurately evaluate blood volume, can't accurately identify fluid overload and define the correct rate of fluid volume resuscitation. (v) Inaccurate estimates and incomplete definitions of physiological target blood volume along with missing limits of baseline specific isoosmotic plasma dilution are the major deficiencies of the existing methods. To the best knowledge of the author, there is no mathematical model and clinical method for determining the physiologic target blood volume, hematocrit and hemoglobin concentration specific circulating red cell mass and state of plasma hydration. Definition of the "ideal" intravascular fluid volume replacement strategy remains a critical problem and 'gold standard' is still missing. (liv,lv) Sophisticated monitoring like measuring the adequacy of preload, level of systemic oxygen delivery, gastric intramucosal pHi and others do not provide the blood volume estimates, also they depend on their on-site availability and induce intervention related risk. (xxv-xli) Relying on indirect classic signs of body hydration (i-ii), tissue oxygenation and adequacy of effective circulating volume (iii-vii) is a common clinical practice. Therefore, current infusion and blood transfusion therapy methods are challenged by coagulation disorders and deleterious circulatory overload that is associated with significant increase in morbidity and mortality. (xxiv) Thus, there is a need in the art for conventionally available, inexpensive and less invasive methods preferably using data obtained from measuring hemoglobin concentration and hematocrit as they are inexpensive and conventionally available. Technique for obtaining these parameters is expected to become noninvasive as methods of non-invasive, real-time, accurate and continuous monitoring of hemoglobin concentration and hematocrit are on the way. (lvii,lviii)

BRIEF SUMMARY OF THE INVENTION

The present invention provides solutions to those deficiencies identified under the "Prior Art" in the BACKGROUND section of this application.

The present invention provides a mathematical model—HBS Trends.

It Provides a Solution for Deficiencies #2.1.2. and 2.1.4., as Follows

The present inventor discovered that normal ideal values of blood and plasma volume—IBV and IPV—are met only once along Hct scale. That unique Hct value is referred to as Ideal Total Match hematocrit (ITM-Hct).

The present inventor declares that ITM-Hct is the universal hematocrit countdown value for calculation of hematocrit (Hct) specific homeostatic target blood volume, plasma volume, red cell mass and related limits of maximal isoosmotic plasma dilution origin deviations from target values. That is of major importance for planning and evaluation of infusion therapy and blood transfusion measures.

An input variables for the new mathematical model are individual calculated normal blood volume (IBV), ITM-Hct value and either lowest (UHL) or highest (LHL) homoestatic Hct value.

The discovered universal volume expansion constant k is described as ITM-Hct and homeostatic hematocrit limits specific. It is used for calculating hematocrit specific limits of maximal isoosmotic plasma dilution origin deviations from target values. These limits are of major importance for planning and evaluation of infusion therapy measures.

The volume expansion constant k is also used as a new unit of measure for volume estimates specifically in the new mathematical model. That unit is used in the discovered mathematical relationship allowing an easy on-site calculation of proper individual specific values. The hematocrit specific target blood volume, plasma volume, red cell mass and values of plasma volume expansion consistent with limits of maximal isoosmotic dilution are expressed in fractions of constant k. These values are used in HBS Nomogram providing a simple on-site tool for planning and evaluation of infusion therapy and blood transfusion measures. Advanced calculations based on the new mathematical model can be deployed in software for medical monitors providing an easy access to individual values for planning and evaluation of infusion therapy and blood transfusion measures.

The mathematical model is desribed by formulae and numerical tables. It is also explained by schematic models of Blood Component Compartments (BCC model), Homeostatic Hematocrit Limits (HHL model) and Osmotic Deviation Limits (ODL model).

The model's precision depends on the (1) mode of Hct value registration (manual or PC) and margin of error inherent to their measuring devices and procedures; (2) precision inherent to method of calculating individual normal blood volume (IBV); (3) precision of TM-Hct value; and (4) precision of either lowest (UHL) or highest (LHL) homoestatic Hct value depending on which of them is used in calculations.

The HBS-trends model is an alternative to calculations of the normal blood volume.

The present invention provides a detailed mathematical, physiological and clinical description of homeostatic target state offering a method of its verification—the Volume Loading Test (VLT-test).

It Provides a Solution for Deficiencies #2.1.2. and 2.1.4., as Follows

In contrast to conventional approach considering normal calculated blood volume (IBV) as homeostatic target regardless of circulating red cell mass (RCM), the present inventor proposed a concept of circulating RCM specific homeostatic target blood volume (tBV) maintained by homeostatic target states.

The homeostatic target state description as combination of RCM specific target values—hematocrit (tHct), blood volume (tBV), plasma volume (tPV), mean cell volume (tMCV), mean cell hemoglobin concentration (tMCHC) and plasma osmolality (tOsm)—is introduced for the first time. The new process states that tBV homeostatically accommodates to fit different RCM patterns in keeping the optimal balance of BV and PV. The RCM specific absolute BV deviation from ideal value is considered equal to corresponding absolute PV deviation, assuming ideal values (IBV and IPV) are met only once along Hct scale—at ITM-Hct. The mathematical formulae describing this trend is part of the earlier described new mathematical model—HBS Trends.

The present inventor described the role of vasomotor tone and tissue expansion-compliance in the homeostasis of target blood volume, also proposed the stratification of Homeostatic Tissue Perfusion Levels (TPL model) and model of Body Fluid Equilibration (BFE) for explaining physiologic processes of maintaining the homeostatic target states.

The maximal safe or iso-osmotic plasma hydration limits in respect to target states are described as threshold for induction of compensatory osmotic deviations in plasma. The present inventor is the first to investigate compensatory oncotic accommodations that strive to preserve plasma viscosity in advanced deteriorations of plasma hydration. For the first time, the lymphatics are described as independent expandable fluid compartment with an exceptional role in plasma oncotic state regulation and accommodations during advanced deteriorations affecting blood volume.

The proposed Patterns of homeostatic stability offer the process of encoding the homeostatic blood states in respect to plasma hydration state and osmolality allowing simplified states' description in research and clinical practice.

The proposed homeostatic target states' identification method—Volume Loading Test (VLT-test) is based on evaluation of the effect of small parenteral fluid infusion on plasma dilution as reflected by Hct and Hb changes in consecutive blood tests. It is also useful for evaluation of plasma hydration. Steady state (equilibration pause) is described as deployed in the VLT-test. Target state's verification is of major importance in guiding infusion and blood transfusion measures.

This study is the first to propose tissue homeostatic priority stratification in relation to perfusion patterns. Changes in tissue perfusion with corresponding changes in tissue fluid compliance are described as major factors deployed by homeostasis in maintaining target states and opposing deteriorating plasma hydration shifts.

As shown by the author's investigation, assumption of the homeostatic target blood volume instead of normal calculated blood volume increases the precision in prediction of blood transfusion induced Hb and Hct increase, similarly allowing better estimates of blood transfusion amount for proper Hct and Hb increase, also calculation of exchangeable blood volume in acute normovolemic dilution used to decrease the blood loss during major surgery.

In contrast to the existing methods based on volume kinetic the VLT-test and the HBS Trends derived values of the hematocrit specific target blood volume, plasma volume, red cell mass and values of plasma volume expansion consistent with limits of maximal isoosmotic dilution provide a solution for Deficiencies #2.1.2.(e) and 2.1.4.(c), as follows:

(1) the requirement of steady state without parenteral fluid infusion is limited to the procedure of VLT-tests; later Hct and Hb dynamics derived evaluations of red cell mass and plasma dilution for infusion therapy and blood transfusions are based on results of previous VLT-test; the new method is sensitive, but not vulnerable to changing physiological and clinical conditions—it reflects these changes allowing proper evaluations.

(2) the new method is sensitive, but not vulnerable to changing blood hemoglobin content—it reflects these changes allowing proper evaluation of bleeding and transfusion amount for proper Hb and Hct increase.

(3) the new method is sensitive, but not vulnerable to changing plasma hydration—it reflects these changes allowing proper evaluation of the body fluid balance.

(4) the new method uses the calculated Hct and RCM specific target blood volume instead of normal calculated blood volume regardless of circulating red cell mass.

(5) the new method does not need estimates of extracellular fluid space.

(6) the author of the present invention considers that physiologic target blood volume demonstrated in studies on volume kinetics is the homeostatic target blood volume described in the present invention; in contrast to the studies on volume kinetics, the present invention provides a method of calculating target blood volume, describes its red cell mass and Hct specificity, explains physiologic-homeostatic processes of maintaining it, describes Hct specific limits of maximal iso-osmotic deviations from target states and offers a process of its clinical verification.

The present invention provides a method of tracing the simultaneous plasma dilution and osmolality changes by following the dynamics of mean cell hemoglobin concentration (MCHC) in nomograms.

It Provides a Solution for Deficiency # 2.1.6., as Follows

The linear graphical relationship Hb to Hct ratio is well known to reflect the dynamics of plasma dilution, but inclusion of MCHC parameter specific trends has never been considered in nomograms. The present invention proposed a graphical triple factor—Hb/Hct/MCHC—relationship referred to as HBS Graphics© serving as a background part of HBS Nomogram©.

Safe (isoosmotic) plasma hydration shifts take part in the setting of unchanging tMCHC. Therefore, isoosmotic shifts can be graphically traced in HBS Graphics© by shifts along one MCHC trend-projection or radiating line (RL).

The present invention provides Osmonomogram for the more specific evaluation of osmolality shifts. It is used to separated pure plasma osmolality dependent MCHC changes from ereythropoietic changes in MCHC resulting from changes in generic red cell brands.

The present invention provides a nomogram—the HBS Nomogram. It is a new method of Hb and Hct evaluation for obtaining BV, PV, RCM, plasma hydration and osmolality estimates in dynamically changing clinical and experimental settings fiting the needs of infusion and blood transfusion therapies. It incorporates all the above mentioned components of the present invention.

It Provides a Solution for all Deficiencies, as Follows

The present invention provides the HBS Nomogram, which is made on the basis of the mathematical model HBS Trends and complements one basic and two optional components: the graphical background provided by HBS Graphics (basic component), Osmonomogram and Devi-safe nomograms (optional components). The basic version of the HBS Nomogram does not have optional components. Optional components can be used independently from the HBS Nomogram.

The HBS Nomogram uses Hb and Hct as variables for obtaining BV, PV, RCM, plasma hydration and osmolality estimates in dynamically changing clinical and experimental settings fiting the needs of infusion and blood transfusion therapies. This method deploys the VLT-test algorithm.

The Devi-safe nomogram provides an easy and fast evaluation of proper target state (and consequently tHct) specific limits of isoosmotic deviations. It is also more accurate than basic version of the HBS Nomogram, which accounts for maximal isoosmotic Hct deviation limits mE and mD on every 1% step of target Hct, meanwhile Devi-safe provides all intermediate values. The modified version of HBS Nomogram also provides intermediate limits, because Devi-safe specific trends are overlaping the background MCHC-trends.

Osmonomogram may serve as an independent nomogram. It enables more reliable and accurate nomographic evaluation of plasma osmolality shifts, because it traces MCH stability in consequent blood test results as indicator of stability in eryhropoietic blood content. It also traces the corresponding MCV dynamics.

The invented manually operated HBS Nomogram or software for application in medical monitors are both based on the same mathematical model (HBS Trends) providing valuable options of clinical applicability and flexibility in respect to on-site availability. Both applications use the same variables to be entered for individualizing readings of monitors: patient height and weight or body surface area.

Variables traced by both applications are the same—BV, PV, RCM, plasma hydration and osmolality estimates. They are derived from blood hemoglobin concentration (Hb) and hematocrit (Hct) or, in addition, from mean cell volume (MCV) and mean cell hemoglobin (MCH) if optional verification of plasma osmolality dynamics and eryhropoietic content of blood is used. All parameters are available from a single conventional blood test. The method is applicable to dynamically changing clinical settings.

Both applications provide plasma volume expansion needed to reach proper targets of plasma hydration in infusion therapy and suggest an amount of packed red blood cell transfusion for proper Hb and Hct increase or similarly provide an amount of blood volume donation for proper Hb and Hct decrease. These values are of greatest importance for infusion and transfusion therapies.

Finally, the HBS Nomogram is a practical system for organizing and dynamical evaluation of blood test results in a patient's medical records.

BRIEF DESCRIPTION OF FIGURES AND TABLES IN THE APPENDIX

FIG. 1 depicts the Blood component Compartment model (BCC model): an equal red cell mass (RCM) specific patterns of blood and plasma volume in three different endpoints trends: Ideal Blood Volume (IBV), Target Blood Volume (TBV) and Ideal Plasma Volume (IPV) trends. All trends maintain equal volumes and structure only at Hct-37.5%. A. The Ideal Blood Volume endpoint trend (IBV-trend) maintains ideal blood volume (IBV) at any hematocrit. Plasma volume (vertical coordinate axis) changes accordingly. B. The Target Blood Volume endpoint trend (TBV-trend) at any hematocrit maintains equal absolute blood and plasma volume deviations from appropriate values at Hct-37.5%. Plasma and blood volume both change accordingly. C. The Ideal Plasma Volume endpoint trend (IPV-trend) maintains ideal plasma volume at any hematocrit. Blood volume (vertical coordinate axis) changes accordingly.

FIG. 2 depicts the Homeostatic Hematocrit Limits model (HHL). A. Target state specific plasma volume (tPV), blood volume (BV) and the corresponding limits (E,D) of safe—isoosmotic—and osmotic ideal-blood-volume-targeted (tE, tD) deviations from target states. Heavy black dots mark the target states. (B). Target states specific red cell mass (RCM), blood volume (tBV) and corresponding plasma volume deviations from ideal value. Limits (mE and mD) of maximal safe (iso-osmotic) deviations (MSD) from target states decrease to both directions from Hct of Ideal Total Match (ITM). Any safe deviations are homeostatically allowed at critical Hct limits—UHL and LHL—as MSD states reach the value of maximal target deviation (MTD) equal to 0.5 k (k—is for Constant k, which is equal to 0.25·IBV, if assumed ITM-Hct is equal to 37.5% and assumed UHL-Hct is 14.4%). Vasomotor tone is adjusting to maintain adequate or target tissue perfusion consistent with effective circulating volume fitting the different patterns of target blood volume: TPFd-target perfusion focused decreased tone, TPFd-resting and TPFi-increased.

FIG. 3 depicts the Homeostatic Hematocrit Limits model (HHL). A. Target states specific blood volume deviations in respect to Ideal Blood Volume (IBV) and Ideal Plasma Volume (IPV) endpoints at different target hematocrit (tHct) values along the physiological range. B. Limits (E,D) of safe (iso-osmotic) blood volume deviations from target states at different target hematocrit (tHct) values along the physiological range. Target states specific red cell mass (RCM), blood volume (tBV) and corresponding plasma volume deviations from ideal value. Limits (mE and mD) of maximal safe (isoosmotic) deviations (MSD) from target states decrease to both directions from Hct of Ideal Total Match (ITM). Any safe deviations are homeostatically allowed at critical Hct limits—upper homeostatic limit (UHL) and lower homeostatic limit (LHL)—as MSD states reach the value of maximal target deviation (MTD) equal to 0.5 k (k—is for Constant k, which is equal to 0.25 IBV, if assumed ITM-Hct is equal to 37.5% and assumed UHL-Hct is 14.4%). BVD is target state's blood volume deviation in respect to either ideal blood (IBV) or plasma (IPV) volume endpoint trends. IBV trend is ideal blood volume endpoint trend's heavy solid projection line. IPV trend is ideal plasma volume endpoint trend's dash style projection line.

FIG. 4 depicts the Homeostatic Hematocrit Limits model (HHL). The maximal safe (isoosmotic) deviations (MSD), B and H maintain ideal blood volume and G and D maintain ideal plasma volume, in respect to target states can result in homeostatically unstable ideal blood volume (IBV) and ideal plasma volume (IPV) maintaining states only in the following settings: A. The maximal safe dilution in respect to target state Y at target hematocrit (tHct)~27% and maximal safe dehydration in respect to target state Z at target hematocrit (tHct) ~50%, both result in IBV states; B. The maximal safe dehydration in respect to target state Y at target hematocrit (tHct) ~27% and maximal safe dilution in respect to target state Z at target hematocrit (tHct)~50%, both result in IPV states. MSD is isoosmotically deteriorated target state, where either blood or plasma volume has reached the maximal absolute homeostatic deviation limit, 0.5 k, in respect to ideal values (IBV and IPV) inherent to target state at ideal total match (ITM) hematocrit. mE indicates maximal safe (isoosmotic) plasma dilution, mD indicates maximal safe (isoosmotic) plasma dehydration. UHL and LHL represents upper and lower homeostatic limits, respectively. IBV trend is ideal blood volume endpoint trend's heavy solid projection line. IPV trend is ideal plasma volume endpoint trend's dash style projection line. K is for Constant k.

FIG. 5 depicts the plasma osmolality shifts affecting target states at ITM-Hct-40%, when limits of maximal safe deviations (MSD) are overridden by the overwhelming plasma hydration deteriorations. A. Hypoosmotic shift from J to D and hyperosmotic from K to G, both recover IPV in an "isolated" case (no intravascular fluid exchange with extravascular space), therefore BV is not changing. Osmotic plasma volume shifts are considered as a sole result of fluid osmotically released from or absorbed by RBCs (or RCM); B. Hypoosmotic and hyperosmotic shifts, both preserve the plasma volume in an "open" case conditions (active intercompartment fluid exchange); the heavy arrow going upward from J (mE) shows that overwhelming plasma dilution in already diluted to MSD plasma, promotes BV increase, while RBC swelling preserves PV by absorbing excessive fluid. Heavy arrow going downward from K (mD) shows that overwhelming dehydration in already dehydrated to MSD plasma, decreases BV, but RBC shrinking preserves plasma volume fixed at [IPV-0.5 k]. Mean cell volume (MCV) increases from target tMCV to hypoosmotic HoMCV or decreases to hyperosmotic HyMCV; mean cell hemoglobin concentration (MCHC) decreases from target tMCHC to hypoosmotic HoMCHC or increases to hyperosmotic HyMCHC. BVD is target state's blood volume deviation in respect to either ideal blood (IBV) or plasma (IPV) volume endpoint trends. UHL and LHL represent upper and lower homeostatic limit, respectively. IBV trend is ideal blood volume endpoint trend's heavy solid projection line. IPV trend is ideal plasma volume endpoint trend's dash style projection line.

FIG. 6 depicts compensatory and artificial plasma osmolality shifts affecting target states.

A. Target states affected: tY at tHct~27% and tZ at tHct~50%; RBC volume changes are equal to blood volume deviations; plasma volume is not affected; a) compensatory hypoosmotic shift from B to J-HoE affects tY; plasma volume is constant—[IPV+0.5 k]; b) artificial hypoosmotic shift from D to S-HoE affects tZ; plasma volume is constant—ideal (IPV); c) artificial hyperosmotic shift from G to R-HyD affects tY; plasma vol. is const.—ideal; d) compensatory hyperosmotic shift from H to K-HyD affects tZ; plasma vol. is const.—[IPV−0.5 k]. B. Target states affected: tX at UHL-Hct-13.3% and tT at LHL-Hct-60.0%; RBC vol. changes equal blood vol. deviations; plasma vol. not affected; a) compensatory hypoosmotic shift from tY to B-HoE; plasma volume is constant—[IPV+0.5 k ]; b) compensatory hyperosmotic shift from tT to H-HyD; plasma volume is constant—[IPV−0.5 k]. C. Examples. tMCHC is target mean cell Hb concentration. HoMCHC and HyMCHC are hypoosmotic and hyperosmotic mean cell hemoglobin concentration, respectively. tMCV is target mean cell volume, HoMCV is hypoosmotic mean cell volume and HyMCV is hyperosmotic mean cell volume. BVD is target state's blood volume deviation in respect to either ideal blood (IBV) or plasma (IPV) volume endpoint trends. UHL and LHL represent upper and lower homestatic limit, respectively. ITM is ideal total match Hct (target states maintain IBV and IPV). K is Constant k. HoBVE and HyBVE are hypoosmotic and hyperosmotic blood volume expansion, respectively. mE indicates maximal safe (isoosmotic) plasma dilution, mD indicates maximal safe (isoosmotic) plasma dehydration.

FIG. 7 depicts tissue compartments in the extravascular fluid space. Stratification of the body tissue specific homeostatic perfusion priority and fluid compliance. Tissue fluid compliance increases with the decreasing perfusion priority, except low perfusion priority non-expandable tissues. Red blood cells (RBCs) are considered as specific, independent and expandable fluid compartment that equilibrates with plasma in the very similar way like extravascular space. Thus, osmotic RBCs volume fluctuations can reflect the corresponding volume shifts in the superior FIG. 8 depicts major patterns of blood volume and tissue perfusion levels (TPLS) in the setting of immobile ("frozen") vasomotor tone or target-perfusion-ignored resting vasomotor tone (TPIr) Homeostatic vasomotor tone increase is required to maintain target tissue perfusion (TTP) with depleted by maximal safe dehydration blood volume (mdBV or mD); this volume is sufficient to maintain only the depleted tissue perfusion level (DTP). Lower blood volume patterns induce compensatory plasma hyperosmolality. Target blood volume (tBV) maintains TTP without homeostatic strain. Homeostatic vasomotor tone decrease is required to maintain TTP with the expanded by maximal safe dilution blood volume (meBV or mE); in this setting, the resulting expanded tissue perfusion level (ETP) induces edema of the higher priority tissues. Higher blood volume patterns induce compensatory plasma hypoosmolality. OTP is overloading tissue perfusion where all tissues are maximally expanded and fluid enters body cavities. oE and oD are osmotically deteriorated advanced plasma dilution and dehydration, respectively. oBV is overloading blood volume (volume increase over MSD limits and osmolality deteriorations are present). VTP is vital tissue perfusion where all tissues are maximally volume depleted and vBV is vital blood volume where volume decrease below MSD limits and osmolality deteriorations are present). HNA indicates homeostatically not available.

FIG. 9 depicts Patterns of blood volume, vasomotor tone and tissue perfusion level. oE is osmotically compensated advanced plasma dilution, oBV is overloading blood volume (volume increase over MSD limits), and vBV is vital blood volume (volume decrease below MSD limits). HNA is homeostatically not available. A shows depleted blood volume (mdBV) and target-perfusion-ignored resting vasomotor tone (TPIr) maintains depleted tissue perfusion (DTP). B shows depleted blood volume (mdBV) and target-perfusion-focused increased vasomotor tone (TPFi) maintains target tissue perfusion (TTP). C shows depleted blood volume (mdBV) and target-perfusion-ignored decreased vasomotor tone (TPId) maintains vital tissue perfusion (VTP). D shows target blood volume (tBV) and target-perfusion-ignored resting vasomotor tone (TPIr) maintains target tissue perfusion (TTP). E shows target blood volume (tBV) and target-perfusion-ignored increased vasomotor tone (TPIi) maintains excessive tissue perfusion (ETP). F shows target blood volume (tBV) and target-perfusion-ignored decreased vasomotor tone (TPId) maintains depleted tissue perfusion (DTP). G shows expanded blood volume (meBV) and target-perfusion-ignored resting vasomotor tone (TPIr) maintains expended tissue perfusion (ETP). H shows expanded blood volume (meBV) and target-perfusion-ignored increased vasomotor tone (TPIi) maintains overloading tissue perfusion (OTP). I shows expanded blood volume (meBV) and target-perfusion-focused decreased vasomotor tone (TPFd) maintains target tissue perfusion (TTP). J shows overloading blood volume (oBV) and life-saving-focused decreased vasomotor tone (LSFd) maintains excessive tissue perfusion (ETP).

FIG. 10 depicts (A). Tissue compartment specific compliance and patterns of tissue perfusion in relationship with circulating blood volume and vasomotor tone. (B). Tissue perfusion sequence (in numbers) during rehydration. Fluid demands of lower priority tissues (LPT) are satisfied after the higher priority tissues and regular priority tissues (HPT, RPT); (C). Tissue perfusion sequence (in numbers) during safe (isoosmotic) over-the-target state plasma dilution (excessive hydration). Fluid overload is "drained" by the lower priority tissues (LPT) before affecting the higher priority tissues and regular priority tissues (HPT, RPT). BR is circulating blood volume, VMT is vasomotor tone. LoPD is level of tissue perfusion decentralization. TC is tissue compliance (tissue resistance to expansion) and TFC is tissue fluid compliance (tissue expandability by fluid). OTP is overloading tissue perfusion (all tissues are critically expanded, fluid enters body cavity), ETP is excessive perfusion (tissue swelling: high priority tissues—moderate, regular—submax, lowest—max), TTP is homestatic target tissue perfusion (all tissues are at their target expansion state), DTP is depleted tissue perfusion (tissue shrinking: highest priority—moderate, regular—submax, lowest—max), and VTP is minimal-vital tissue perfusion (critical shrinking of all tissues). TPF is target perfusion focused vasomotor tone, TPFi-increased, TPFd-decreased, TPFr-resting (no homeostatic tension forces.) oBV is overloading blood volume (over-MSD or over-MTD states), tBV is homeostatic target blood volume, mdBV is maximally depleted blood volume (MTD or MSD states), vBV is minimal or vital blood volume (over-MSD or over-MTD states), oBV is overloading blood volume (over-MSD or over-MTD states), and meBV is maximally expanded blood volume (MTD or MSD states). Note the numbers show the sequence of blood flow distribution priority with proper blood volume.

FIG. 11 depicts the body fluid equilibration model (BFE). Body fluid compartments: intracellular space, extravascular extracellular space, lymphatic loop, circulation and urinary tract. Size of the horizontal arrows represents the volume and intensity of intercompartment fluid shifts corresponding to patterns of tissue perfusion and urine output. The high priority tissues (HPT) do not have lymphatic vessels, therefore, only regular (RPT) and low priority tissues (LPT) in appropriate compartment or spaces are considered taking part in the lymphatic loop's fluid and protein turnover. Lymphatic loop's turnover and urine output are both dependant on tissue perfusion: they are most intense at target tissue perfusion (TTP) and decreasing with either increasing (ETP, OTP) or decreasing (DTP, VTP) levels of perfusion. Lymphatic vessels expand proportionately to the increasing tissue perfusion (dot-style linings), but lymphatic return to circulation decreases, because of increasing lymphatic fluid retention that results from obstructive effects of interstitial edema and decreasing compliance of lymphatic vessels. Tissue perfusion levels do not represent the blood volume patterns.

FIG. 12 depicts the body fluid equilibration model (BFE). Corresponding patterns of circulating blood volume, plasma hydration, tissue perfusion and expansion, lymphatic loop's fluid and protein turnover, also the urine output. tOsm is target plasma osmolality. HoOsm and HyOsm are plasma hypoosmolality and hyperosmolality, respectively, in respect to target osmolality. HoE is critically advanced plasma dilution with advanced compensatory hypoosmolality. meBV and mdBV are maximally expanded and depleted, respectively, blood volume (MTD or MSD states). mE and mD are maximal isoosmotic plasma dilution and dehydration, respectively, with normal close to target osmolality. tBV is target blood volume (optimal or target plasma dilution and target osmolality), vBV is vital blood volume (over-MSD or over-MTD states) and oBV is overloading blood volume (over-MSD or over-MTD states). HyD is critically advanced plasma dehydration with advanced compensatory hyperosmolality. OTP is over loading tissue perfusion (all tissues are critically expanded, fluid enters body cavities), ETP is excessive perfusion (disproportionate tissues expansion-swelling: high priority tissues—maximal, regular—submaximal, lowest—moderate), TTP is homestatic target tissue perfusion (all tissues are at their target expansion state), and DTP is depleted tissue perfusion (tissue shrinking: highest priority—maximal, regular—submaximal, lowest—moderate).

FIG. 13 depicts radiating MCHC-Lines (RL) in HBS Graphics. A Isoosmotic shifts (heavy white arrows; B hyperosmotic (heavy white arrow) and hypoosmotic (heavy black arrow); C The HBS Nomogram as part of clinical chart in patient's medical records. Calculation of PRBC transfusion volume and blood loss evaluation considering lost RCM.

FIG. 14 depicts an Osmonomogram. A,B show the corresponding normal MCH, MCV and MCHC values; C shows the pure hyperosmotic shifts; D shows pure hypoosmotic MCV and MCHC shifts affecting target states with erythropoietic MCH-29.1 pg value; E shows pure hyperosmotic and F shows pure hypoosmotic MCV and MCHC shifts affecting target states with erythropoietic MCH-32.1 pg value; G Osmonomogram for independent use or as an optional component of the HBS Nomogram. HH is homeostatic high mean cell hemoglobin (MCH-32.1 pg), LH is low homeostatic mean cell hemoglobin (MCH-29.1 pg). tMCV and tOsm are target state specific mean cell volume and plasma osmolality, respectively. mHyMCV and mHyOsm are target state specific maximal hyperosmotic mean cell volume and corresponding hyperosmolality in respect to tOsm. mHoMCV and mHoOsm are target state specific maximal hypoosmotic mean cell volume and corresponding hypoosmolality in respect to tOsm. mnnOsm and mxn0sm are minimal and maximal normal osmolality (286-295 mOsm/l). cmHyOsm and cmHoOsm are crtical high (maximal) and low osmolality (320-265 mOsm/l).

FIG. 15 depicts HBS Nomogram in clinical record chart with optional Osmonomograrn.

FIG. 16 depicts the development of the Devi-safe nomogram.: A Target state specific hematocrit and volume characteristics with corresponding values of maximal safe (isoosmotic) deviations—dilution (mE) and dehydration (mD)—are displayed in the nomogram. In the left part of the nomogram, plasma volume expansion—PVE—equal to [0.1 k] is applicable to every 1% Hct deviation from target states. Similarly, mean PVE [0.025 k] is consistent with one column-wide horizontal plasma volume shift in the right part of the nomogram. The same step-values (0.1 k and 0.025 k) are applicable to target states specific blood and plasma volume deviations from normal (ideal); B target states that can reach normal blood volume (IBV) differently: t4,t5—by isoosmotic plasma dilution below maximal (E4,E5), t5—by maximal (mE3), t1—by sum of max. isoosmotic and osmotic (oE1), tA—only osmotic (oEA); tC—only osmotic dehydration, t8—sum isoosmotic (within MSD) and osmotic dehydration, t7—totally by maximal isoosmotic dehydration (MSD state). Meanwhile tB (tBe and tBd) maintains IBV itself. Mean plasma volume expansion PVE-[0.025 k] per one column-step is applicable to these shifts traced by appropriate horizontal arrows; C target state t1 (tHct1-20%) is shown capable of reaching normal blood volume (IBV) by sum of maximal isoosmotic (mE1) and osmotic (oE1) dilution, while target state t2 (tHct2-27%) reaches IBV by maximal isoosmotic (mE2) dilution, and target state tB (tBe) at tHctB-40% (ITM) maintains IBV itself. These plasma dilution shifts traced by horizontal arrows can be evaluated as follows: a) maximal isoosmotic dilution PVE1 from t1 to mE1 needs plasma expansion by 5 horizontal nomographic steps, while 1 step is equal to one vertical column and it represents PVE-0.025 k, where k=0.29·IBV; therefore PVE1=0.125 k; b) an additional osmotic expansion from mE1 to oE1 requires oPVE1=10× 0.025 k=0.25 k; c) oPVE1 is equal to maximal isoosmotic dilution PVE2 from t1 to mE2 and from tBe to E-B, but mE2 reaches IBV, meanwhile E-B overcomes IBV by 0.25 k. Circulating red cell mass difference between target states t1 (RCM-1) and t2 (RCM-2) is: 0.87-0.62=0.25 (k); D target state t8 at tHct-55% that has specific maximal isoosmotic deviation—dehydration—limit mD8 that maintains blood volume, which is by 0.25 k higher than normal; thus, osmotic dehydration up to oD8 would be needed to reach normal blood volume, but it would be catastrophic to plasma viscosity as plasma volume at target state is already by 0.375 k less than normal (IPV).

Figure 23A:
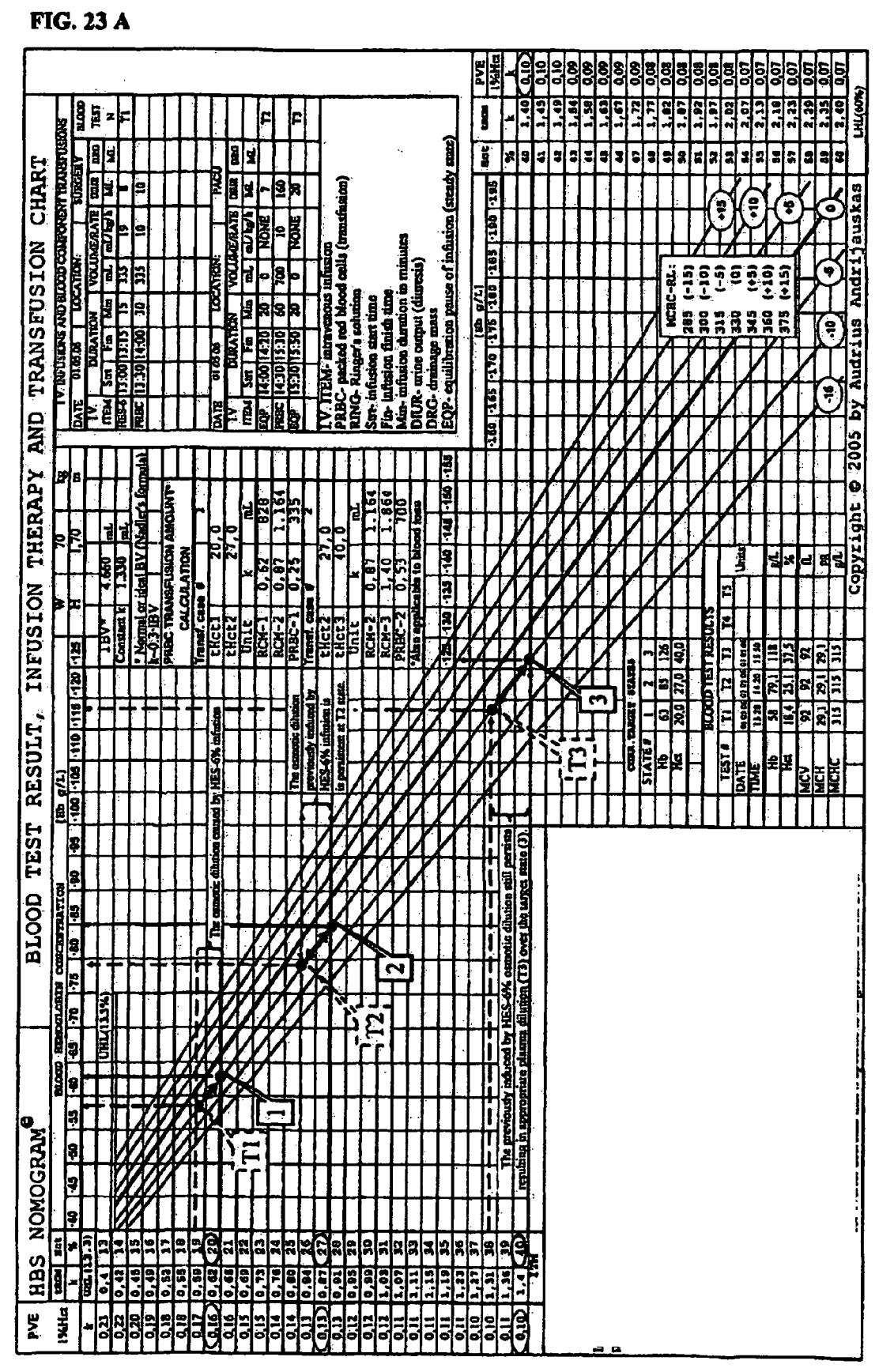
Figure 23:
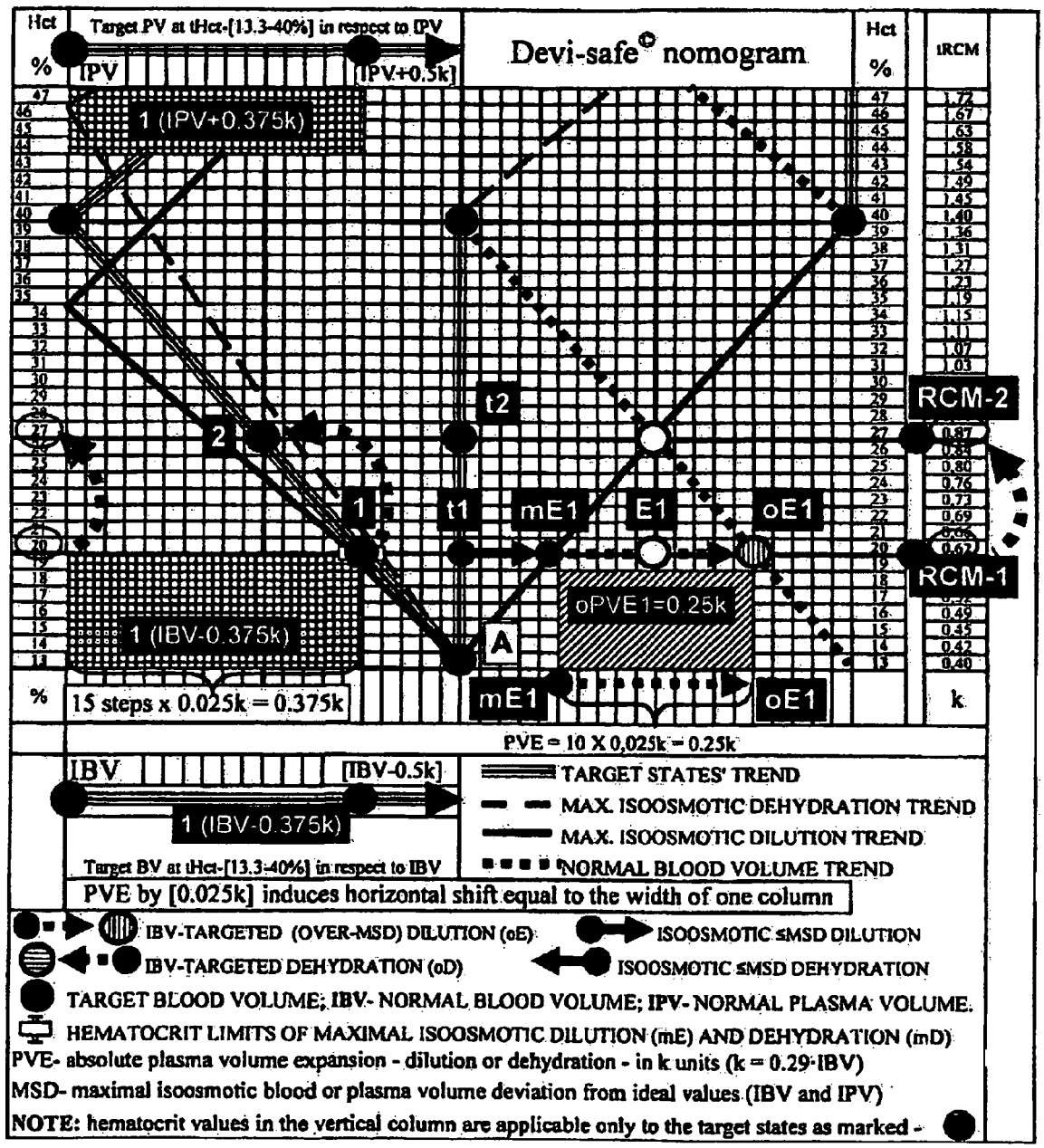
Figure 23:
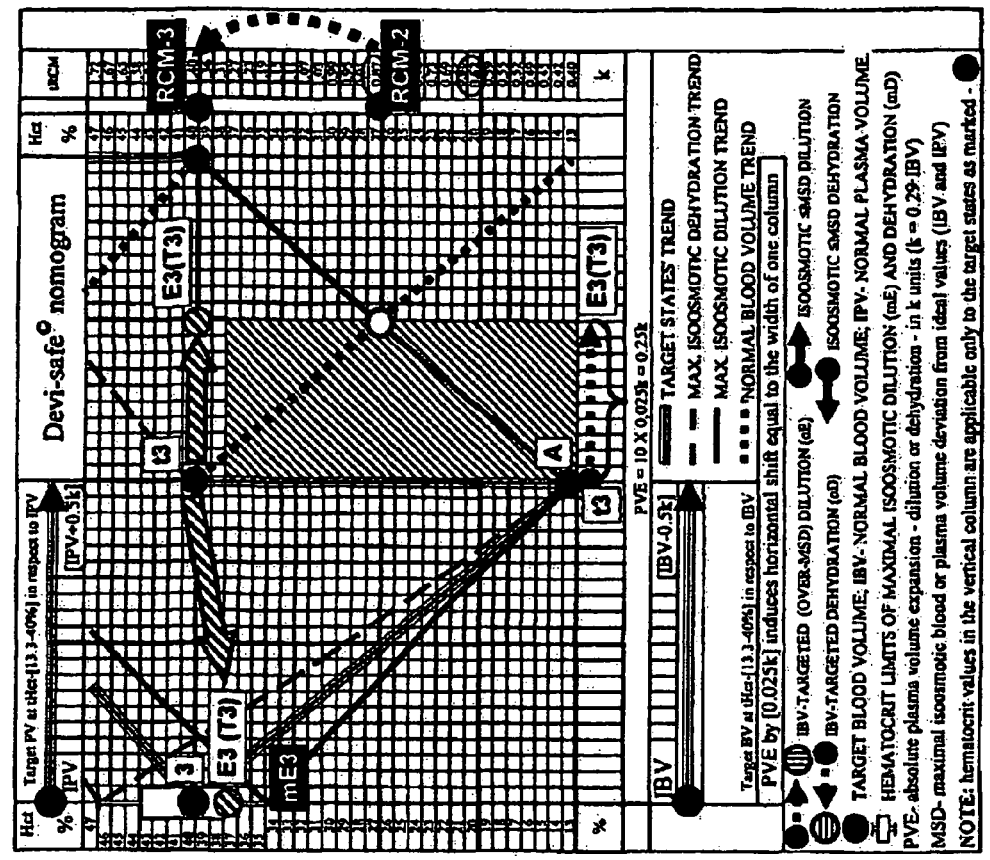
Figure 23:
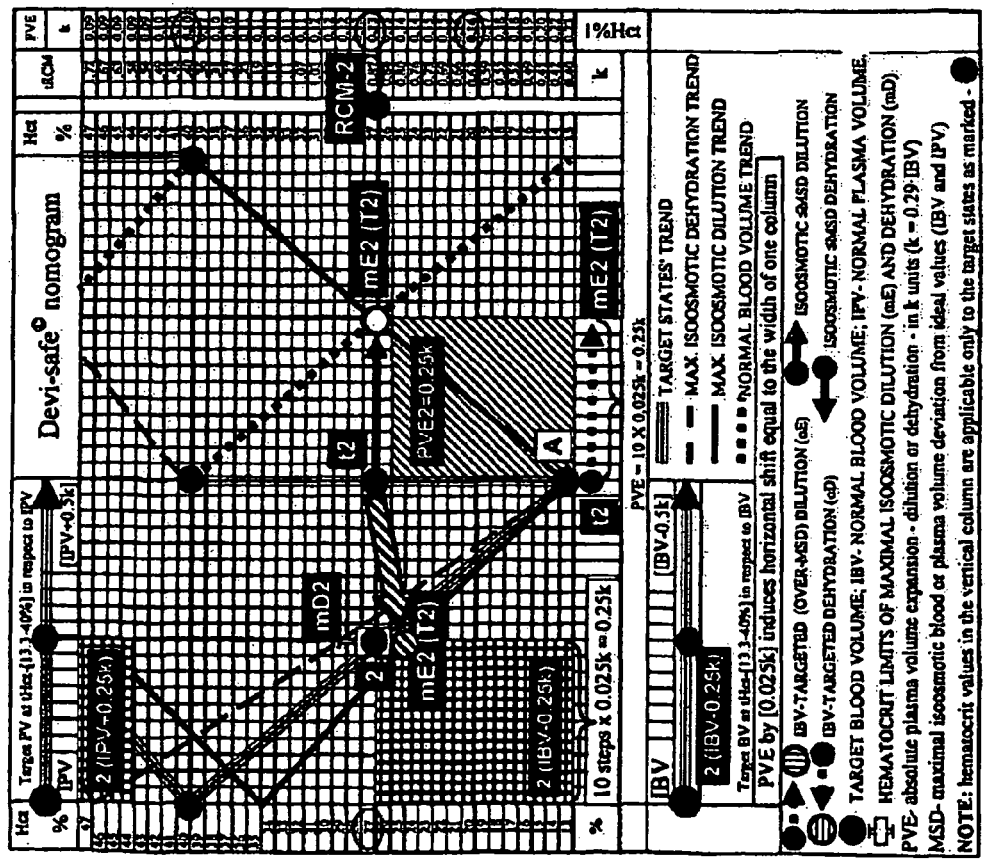

FIG. 23 depicts clinical case example #1. A The basic HBS Nomogram application; B independent Devi-safe application for plasma dilution and blood transfusion evaluation; C independent Devi-safe application for evaluation of residual plasma dilution; D independent Devi-safe application for evaluation of blood transfusion interfering with residual plasma dilution. Initially infused HES-6% 335 ml (equivalent to 0.25 k) volume induced persistent plasma dilution origin deviation from target states following PRBC transfusions. T1, initial dilution from target state 1. Blood test (T1) was obtained after HES infusion, therefore revealed Hct-18.4%, which is 1.6% lower than corresponding target state 1 Hct-20: deviation is consistent with mean PVE-0.16 k for 1% Hct decrease that is specific to target state at tHct-20%. T2, persistent dilution from target state 2. Blood test (T2) was obtained after PRBC transfusion, and revealed Hct-25.1%, which is 1.9% lower than corresponding target state-2 Hct-27%: deviation is consistent with mean PVE-0.19 k for 1% Hct decrease that is specific to target state at tHct-27%. T3, persistent dilution from target state 3. Blood test (T3) obtained after another PRBC transfusin revealed Hct-37.5%, which is 2.5% lower than corresponding target state-3 Hct-40%: deviation is consistent with mean PVE-0.19 k for 1% Hct decrease that is specific to target state at tHct-27%.

Figure 25:
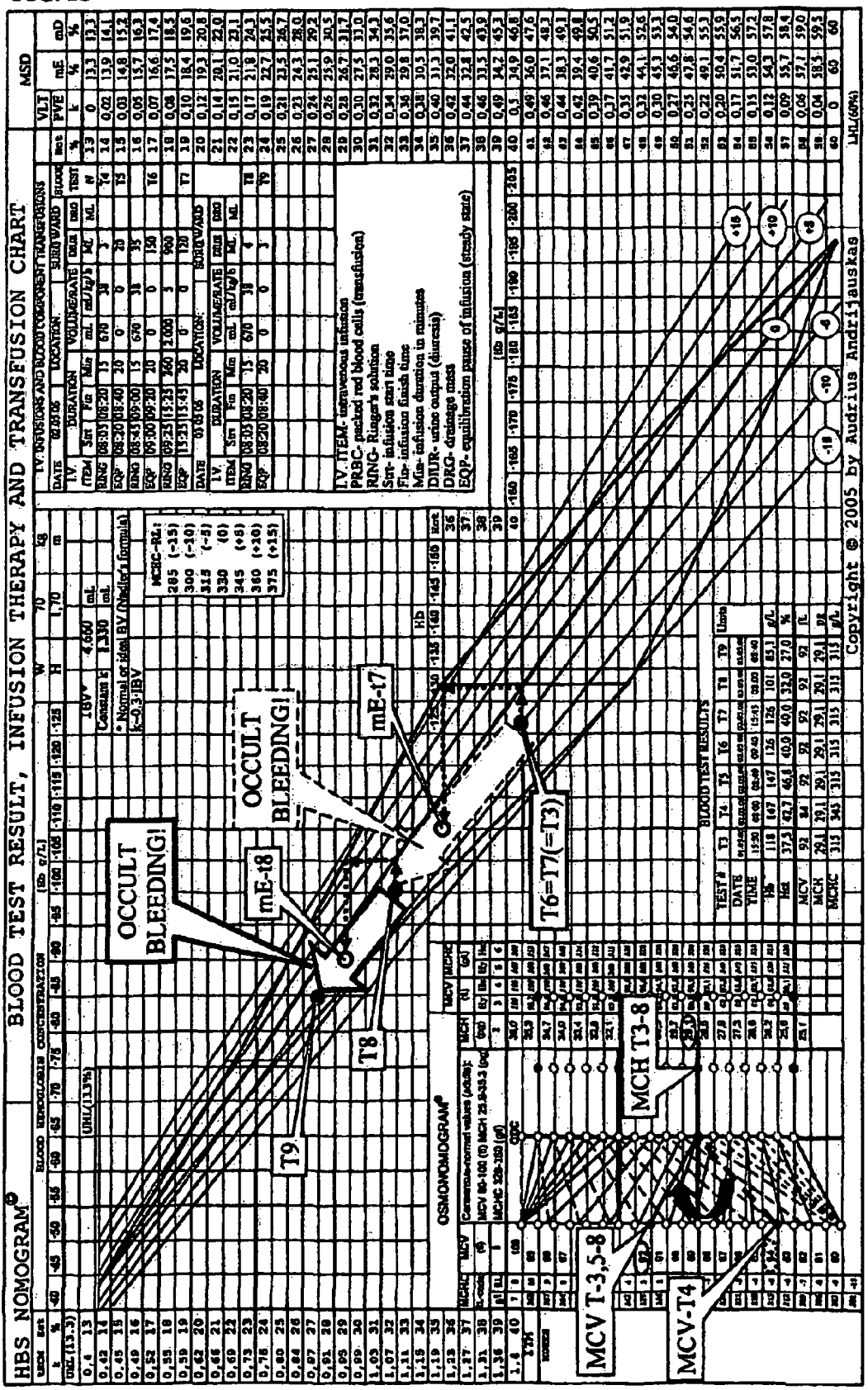

FIG. 25 depicts clinical case example #3. The basic HBS Nomogram application.

Figure 26:
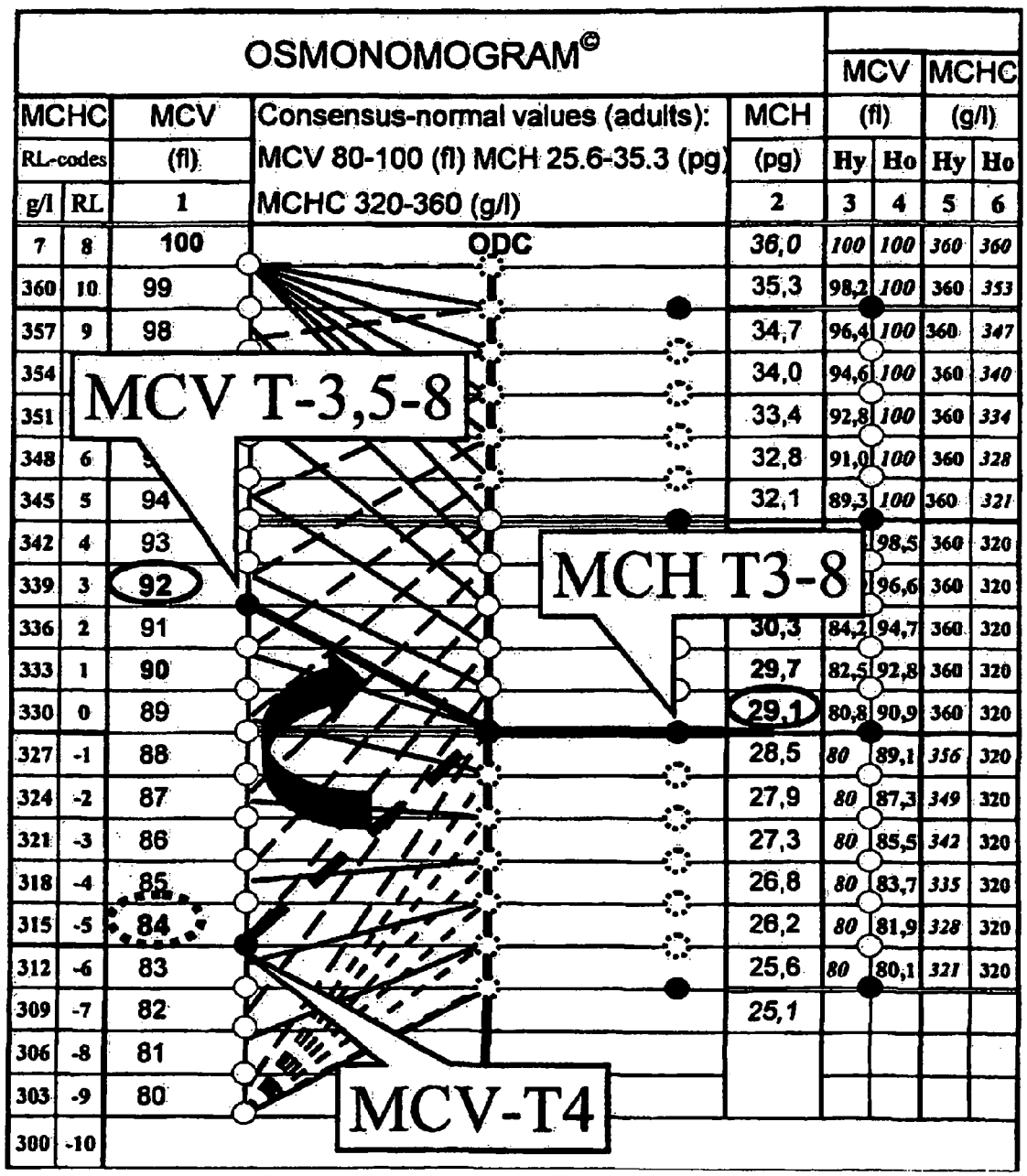

FIG. 26 depicts Osmonomogram© in clinical case example #2. The MCH parameter stayed unchanged during isoosmotic plasma dilution shifts reflected by blood tests T3, T5-8 and also during hyperosmotic shift from T3 to T4 and hypoosmotic shift from T4 to T5 during volume loading test or VLT-test (isotonic crystalloid infusion recovered target plasma osmolality, target plasma dilution and MCV value). Plasma hyperosmolality as a result of patient's overnight dehydration has induced hyperosmotic mean cell volume (MCV) decrease from target 92 fl to hyperosmotic 84 fl value. The target MCV has been recovered by the isotonic crystalloid infusion in the morning.

Figure 27:
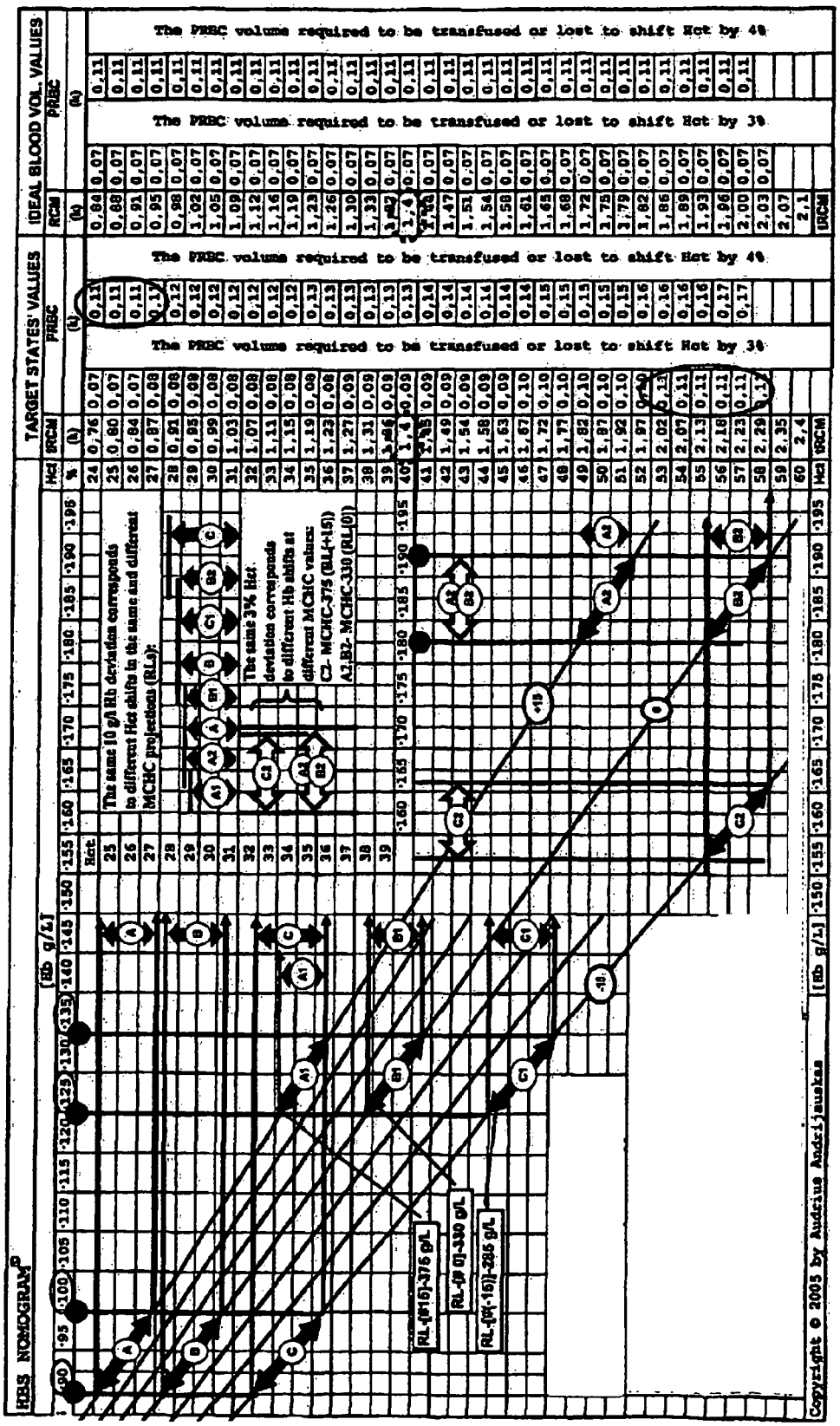

FIG. 27 depicts calculated expected baseline hematocrit decrease after collection of donor's blood. Calculations by HBS method assumed target states specific blood volume at any baseline Hct value, meanwhile control values assumed ideal or normal baseline volume instead. The HBS method showed progressive Hct decrease with donation of consecutive units, while controls defined equal decrease, which is not consistent with published reports. Donor blood donation standards quote that each unit of collected whole blood should contain 50-60 g of total Hbl therefore collecting 350-450 ml of whole blood per unit in approved. HBS method shows that removal of the same packed red blood cell volume (PRBC) causes increasing hematocrit and Hb decrease, i.e., removal of 0.11 k PRBC volume result in Hct decrease by 3% from baseline tHct 24-27% and by 3% from baseline tHct 53-58%. It is inconsistent with numerous published data recorded during collection of consecutive whole blood units in donor and surgery patients population. The same PRBC volume would result in equal Hct shifts regardless of baseline Hct if ideal basedline blood volume was assumed.

Figure 28:
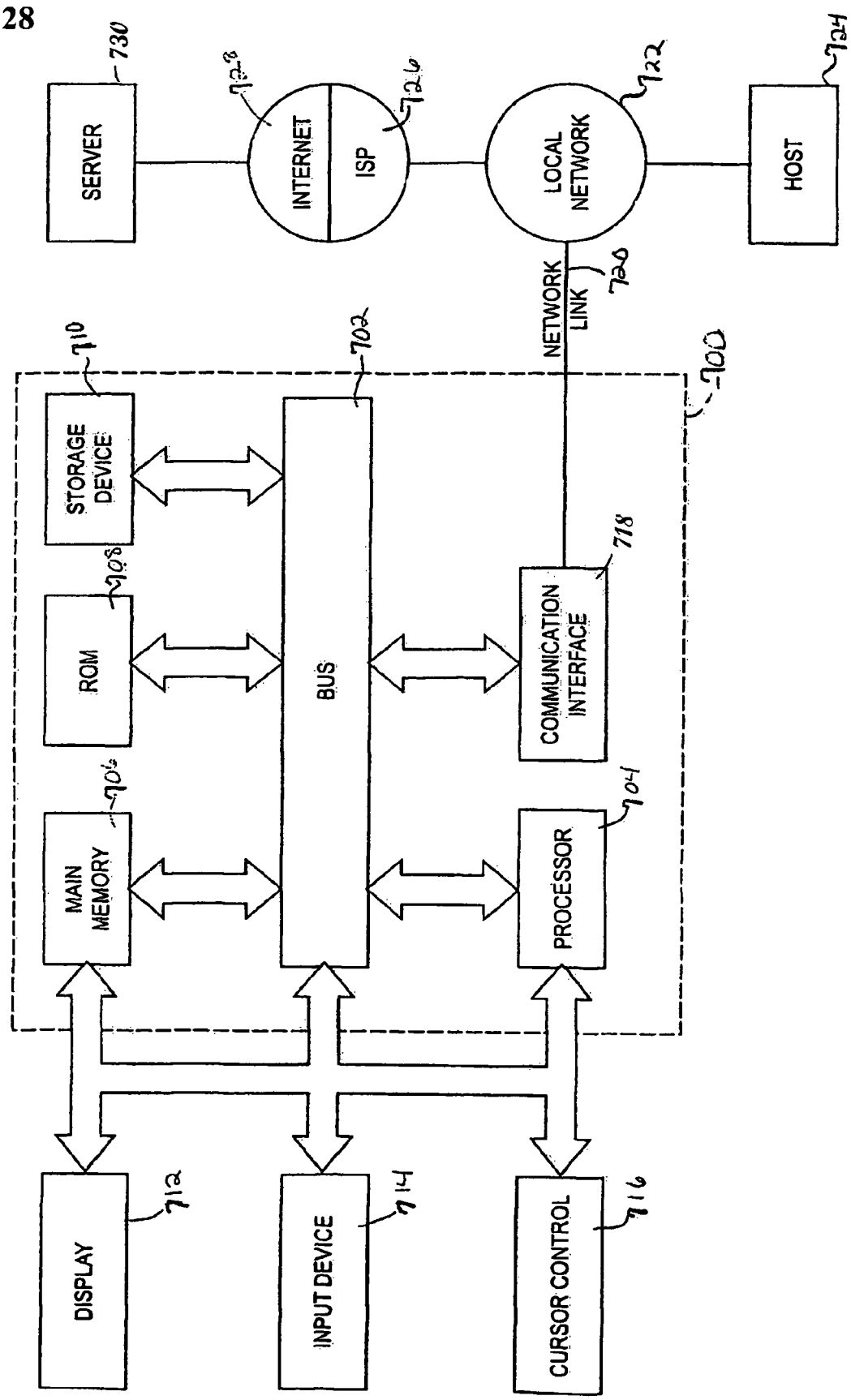

FIG. 28 depicts a computer system 700 upon which an embodiment of the invention may be implemented. Computer system 700 includes a bus 702 or other communication mechanism for communicating information, and a processor 704 coupled with bus 702 for processing information. Computer system 700 also includes a main memory 706, coupled to bus 702 for storing information and instructions to be executed by processor 704. Main memory 706 also may be used for storing temporary variables or other intermediate information during execution of instructions to be executed by processor 704. Computer system 700 further includes a read only memory (ROM) 708 or other static storage device coupled to bus 702 for storing static information and instructions for processor 704. A storage device 710 is provided and coupled to bus 702 for storing information and instructions. Computer system 700 may be coupled via bus 702 to a display 712 for displaying information to a computer user. An input device 714 is coupled to bus 702 for communicating information and command selections to processor 704. A cursor control 716 is also provided. Computer system 700 also includes a communication interface 718 coupled to bus 702. Communication interface 718 provides a two-way data communication coupling to a network line 720 that is connected to a local network 722. Network link 720 may provide a connection through local network 722 to a host 724 or to an ISP 726. ISP 726 provides data communication through the Internet 728 to a Server 730.

Figures 29, 30:
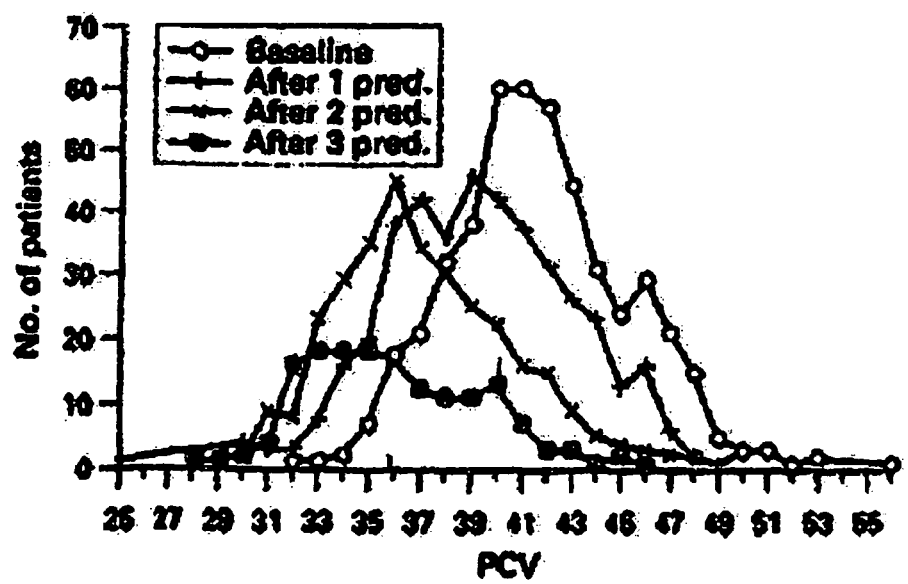

FIG. 29 depicts a table showing distribution of baseline packed cell volume (PCV) in orthopaedic surgical patients operated on at the Gaetano Pino Orthopaedic Institute in 1997 as reported in the study of Mercuriali et al.

FIG. 30 depicts the relationship between units of autologous blood collected and the baseline packed cell volume (PCV or Hct) in the study of Mercuriali et al.

Table 1 depicts numeric values in HBS Trends: target hematocrit (tHct) specific target values: red cell mass (tRCM), plasma vol. (PV), coefficient (Cn), blood vol. (tBV), plasma vol. (tPV), normal blood vol. (IBV) and plasma vol. (IPV), target state specific PV deviation from normal (IPVE), similar BV deviation in from normal (IBVE), maximal isoosmotic (safe) volume deviation—dilution—from target state specific plasma dilution and blood volume (mE) and its Hct (mE-Hct), PV at its maximal isoosmotic dilution (mE-PV), BV at its maximal safe dilution (mE-BV), maximal isoosmotic (safe) volume deviation—dehydration—from target state specific plasma dilution and blood volume (mD) and its Hct (mD-Hct), plasma volume at its maximal safe or isoosmotic dehydration (mD-PV), blood volume at its maximal safe dehydration (mD-BV).

Table 2 depicts corresponding mean cell volume (MCV) and osmolality (osm) fluctuations. A. Osmotic mean cell volume (MCV) fluctuations within osmolality intervals from normal to critical values. B. Osmotic mean cell volume (MCV) fluctuations within osmolality intervals from critical to normal values. C. Osmotic mean cell volume (MCV) fluctuations within limits of normal osmolality values. In each table, column 1 is homeostatic mean cell volume (hMCV). Column 2 is maximal normal plasma osmolality (mxn0sm). Column 3 is critically minimal (low) plasma osmolality (cmHo). Column 4 is maximal hypoosmotic mean cell volume (mHo-MCV). Column 5 is minimal normal plasma osmolality (mnnOsm). Column 6 is critically high plasma osmolality (cmHy). Column 7 is minimal hyperosmotic mean cell volume (mHy-MCV).

Table 3 depicts the interfering numeric MCHC, Hb and Hct as background for drawing the MCHC specific radiating lines (RL) in the HBS Graphics, i.e. on its pace downwards from point-zero-Hct/Hb, the RL#15 (RL-MCHC-375 g/L) crosses three corresponding check-points or "blood points" (BP) in the Graphics: the BP-Hb/Hct —75/0.20, BP-Hb/Hct—150/0.40 and BP-Hb/Hct—225/0.60 (where Hb is in g/L and Hct in decimal SI units). The RL numbers from (−15) to (+15) are applied for practical purpose of making the system user-friendly and time saving: proper RLs can be easier found in the Nomogram by their attached number. RL is radiating line, Hb is hemoglobin concentration, MCHC is radiating line specific mean cell hemoglobin concentration, and Hct is blood hematocrit in decimal values. Column 1 is radiating line specific identical number. Column 2 is radiating line specific mean cell hemoglobin concentration. Columns 3-8 are check-points for drawing radiating lines. Vertical Hb projections [3,5,7] meet horizontal Hct projections [4,6,8] in RL (MCHC) projections [1,2].

Table 4 depicts (A-C) Hematocrit decrease in three body mass index groups (BMI-20, 24 and 29) after whole blood donation predicted by two methods. The exchangeable blood volume was calculated for the target Hct decrease by 3% from any baseline Hct value. The baseline Hct specific EBV was expected to decrease Hct by approximately 3% (decrease associated with predonation of 1 unit of whole blood). Hematocrit decrease in all BMI groups is the same in respect to the same initial Hct values, although volumes of withdrawal are different; (D) Hematocrit decrease in any body mass index (BMI) groups after whole blood donation predicted by two methods. The exchangeable blood volume was calculated for the target Hct decrease by 10% from any baseline Hct value. Baseline Hct specific EBV was expected to decrease Hct by approx. 10% (associated with predonation of 3 units of whole blood). The total volume of donated blood was calculated individually for every baseline Hct value depending on the expected Hct decrease by 10%; (E) The new method (HBS) predicted hematocrit decrease significantly better than IBV-method, when donation volume was calculated individually for every baseline hematocrit value, calculations being targeted to Hct decrease of 3% after one and 10% after three donated units of whole blood. (See the statistical charts in Supplement-1 pictures P-1 and 2 that follow: P-1

Prognostic stability and accuracy of new method (HBS) is significantly better than IBV-method's (Std) in predicting Hct decrease with donation of 1 unit of whole blood. P-2 Prognostic stability and accuracy of new method (HBS) is significantly better than IBV-method's (Std) in predicting Hct decrease with donation of 3 units of whole blood.)

Table 5 depicts (A-C) hematocrit decrease in three body mass index groups (BMI-20, 24 and 29) after 1 unit (450 mL) whole blood donation predicted by two methods. The exchangeable blood volume was equal to 450 mL and expected Hct decrease was 3% at all baseline Hct values; (D-E) Hematocrit decrease predicted by two methods in body mass index groups BMI-20 and 24 after donation of 3 units (1350 mL) whole blood. The exchangeable blood volume was equal to 1350 mL and expected Hct decrease was 10% at all baseline Hct values; (F) Hematocrit decrease predicted by two methods in body mass index BMI-29 group after donation of 3 units (1350 mL) whole blood. The exchangeable blood volume was equal to 1350 mL and expected Hct decrease was 10% at all baseline Hct values; TAB. 5-G The new method (HBS) predicted Hct decrease significantly better than IBV-method in all BMI groups (BMI-20, 24 and 29 groups), when donation volume was 450 ml or 1350 ml at any baseline Hct value. Predicted values were compared to conceptual 3% decrease after 1 (450 ml) and 10%—after 3 (1350 ml) donated units of whole blood. (See the statistical charts in a Supplement-2 pictures P-3 and 4 that follow: P-3 Prognostic stability and accuracy of new method (HBS) in all BMI groups was significantly better than IBV-method's (Std) in predicting Hct decrease with donation of 1 unit of whole blood; P-4 Prognostic stability and accuracy of new method (HBS) in all BMI groups was better than IBV-method's (Std)

in predicting Hct decrease with donation of 3 units of whole blood.); H The new method (HBS) predicted Hct decrease significantly better than IBV-method, when donation volume was 450 ml or 1350 ml at any baseline Hct value. Predicted values were compared to conceptual 3% decrease after one (450 ml) and 10%—after three (1350 ml) donated units of whole blood, regardless of body mass index BMI. (See the statistical charts in a Supplement-3 pictures P-5 and 6 that follow: P-5 Prognostic stability and accuracy of new method (HBS) was significantly better than IBV-method's (Std) in predicting Hct decrease with donation of one unit of whole blood; P-6 Prognostic stability and accuracy of new method (HBS) is significantly better than IBV-method's (Std) in predicting Hct decrease with donation of 3 units of whole blood.)

Table 6 depicts how the new method (HBS) predicted Hct decrease significantly better than IBV-method, when donation volume was 450 ml or 1350 ml at any baseline Hct value. (See the statistical charts in a Supplement picture P-7 that follow: P-7 Prognostic stability and accuracy of the corrected for simultaneous bleeding HBS—method (A-cor) is significantly better than method-A (HBS method) without correction and rule of thumb (B1-3) in predicting Hct increase after PRBC transfusion. Predictions of method-A are significantly better than rule of thumb (B2-3).

DETAILED DESCRIPTION OF THE INVENTION

ABBREVIATIONS

BV—Circulating blood volume
tBV—Circulating red cell mass specific homeostatic target blood volume
ECF—Extracellular fluid
EQP—Equilibration pause (steady state without any intravenous infusion)
Hb—Blood hemoglobin concentration
Hct—Blood hematocrit (packed cell volume)
NS—Normal saline (0.9% solution of NaCl in water for intravenous infusion)
HES—Hydroxyethylstarch preparations for intravenous infusion
HHL—Homeostatic hematocrit limits
HPT—High and superior homeostatic priority tissues
IBV—Normal/ideal circulating blood volume (calculated by conventional formulas)
IPV—Normal or ideal circulating plasma volume (calculated by new formulas)
tPV—Homeostatic target state specific plasma volume
ICF—Intracellular fluid
k or Constant k—New unit of measure for blood and plasma volume, etc.
LHL—Lower homeostatic hematocrit limit (highest physiologically critical value)
LPT—Low homeostatic priority tissues
MCH—Mean cell hemoglobin content (non-specific to target states)
tMCHC—Homeostatic target state specific mean cell hemoglobin concentration
tMCV—Homeostatic target state specific mean cell volume
mE—Maximal expansion (maximal safe or isoosmotic plasma dilution)
mD—maximal depletion (maximal safe or isoosmotic plasma dehydration)
MSD—Maximal safe deviation
MTD—Maximal target deviation
ODC—Osmotic deviation center (vertical MCH projection in Osmonomogram©)
tOsm—Homeostatic target state specific plasma osmolality
POP—Preset osmotic potential
PVP—Preset volume potential
PRBC—Packed red blood cells (collected for transfusion purposes)
PV—Circulating plasma volume
PVE—Plasma volume expansion
PVEE—Plasma volume expansion efficacy
RCM—Red cell mass (volume)
tRCM—Homeostatic target state specific red cell mass (volume)
RL—Radiating Line (the MCHC value specific graphical projection)
RPT—Regular homeostatic priority tissues
SDL—Safe deviation line (MSD-mE-mD projections in Devi-safe© nomogram)
iTPF—Ideal target tissue perfusion focused vasomotor tone
TPFi—Target tissue perfusion focused increased vasomotor tone
TPFd—Target tissue perfusion focused decreased vasomotor tone
TPL—Tissue priority levels (homeostatic perfusion priority levels)
TPF—Target tissue perfusion focused vasomotor tone
TVL—Test volume load (isotonic crystalloid solution volume for VLT-test)
UHL—Upper homeostatic hematocrit limit (lowest physiologically critical value)
VLT-test—Volume loading test (for verifying target plasma hydration)
VLT-test—Volume loading test (clinical verification of target states)

DEFINITIONS

Ideal Total Match (ITM) hematocrit is the unique Hct value, where both—blood and plasma—maintain normal or ideal volume (IBV and IPV) as homeostatic target. It is the countdown Hct value in the new mathematical model (HBS trends).
Homeostatic target state or target state is the homeostatically maintained target combination of circulating red cell mass specific homeostatic target values—tHct, tBV, tPV, tMCV, tMCHC and tOsm. Case specific homeostatic target plasma hydration and osmolality are the major conditions for the maintenance of tBV.
Homeostatic Hematocrit Limits (HHL) are physiologically critical Hct values: the new method argues the lowest Hct-13.3% (UHL) and highest Hct-60.0% (LHL).
Maximal target deviation (MTD) is the sum absolute blood and plasma volume deviation from normal values applicable to target states.
Constant k or k is the sum of absolute tBV and tPV deviations from IBV and IPV at critically low and high Hct values (HHL). It is expressed as MTD to IBV ratio.
Maximal safe deviations (MSD) are target Hct specific limits of maximal safe or isoosmotic plasma hydration origin deviations from target. These limits are reached when either BV or PV reaches maximal deviation 0.5 k in respect to IBV or IPV.

Maximal safe plasma dilution (mE) is the target state specific maximal isoosmotic plasma volume expansion from target state. The MSD consistent state.

Maximal safe plasma dehydration (mD) is target state specific maximal isoosmotic plasma volume decrease from target state. The MSD consistent state.

IBV-target plasma deviations are plasma hydration origin deviations from target states in attempt to reach the normal (ideal) blood volume.

Target tissue perfusion focused (TPF) or normal vasomotor tone is present under the control of intact sympathetic stimulation and homeostatic guidance.

Ideal target tissue perfusion focused (iTPF) vasomotor tone is present only with ideal blood volume, which is maintained by target states only at ITM-tHct, but also may be reached in dilution origin deviation from target states with other tHct values.

Increased (TPFi) or decreased (TPFd) target tissue perfusion focused vasomotor tone is meant in respect to ideal pattern (iTPF). It adjusts in maintaining homeostatic targets of tissue perfusion with the ever-changing blood volume.

Homeostatic stability patterns (HSP) is predisposition to retain in or eliminate from circulation an additional load of isotonic non-colloid fluid.

Pre-set potentials describe the HSP: osmotic and volemic predisposition to plasma dilution for maintaining adequate effective circulating volume and osmolality.

Pre-set volume potential [$PVP^{-/0/+}$] describes predisposition of proper homeostatic blood state to isotonic plasma hydration solely for blood volume increase.

Pre-set osmotic potential [$POP^{-/0/+}$] describes predisposition to isotonic plasma hydration solely for decreasing osmolality (dilution).

Volume Loading Test (VLT-test) is an algorithm for clinical verification of target states.

Test volume load (TVL) is the volume of isotonic crystalloid solution that has a primary purpose to recover the target state in case of preexisting dehydration.

Maximal Functional Osmotic Deviations (MFOD)—standard projections originating from MCH value specific points along the ODC projection in Osmonomogram©.

Radiating Line (RL) is the MCHC value specific graphical projection in the HBS Graphics© model, which is the basic part of the HBS Nomogram©.

The present invention is referred to as Homeostatic Blood States method or HBS Method. It is also referred to as new method in the following text. It consists of the mathematical model HBS Trends and five major hypotheses supported by five new schematic models.

The HBS Nomogram, later referred to as Nomogram, is the final result of the present invention. It is made on the basis of the new mathematical model—HBS Trends and complements one basic and two optional components: the graphical background provided by HBS Graphics (basic component), Osmonomogram and Devi-safe nomograms (optional components).

The Homeostatic Blood States method consists of five discovered concepts incorporated in the components of the present invention:

1) The homeostasis of the human body strives to maintain the red cell mass specific homeostatic target blood volume. It is equal to ideal (normal) blood volume and maintains ideal plasma volume only once per physiologic hematocrit scale—at hematocrit of Ideal Total Match.

Physiologic blood volume endpoints maintained throughout the physiologic range of human blood Hct are characterized by BV to PV ratio ranging from ideal blood volume (IBV) to ideal plasma volume (IPV) targets. The new method hypothesizes that homeostasis strives to maintain only one endpoint, which is in the center of the range—the red cell mass (RCM) specific homeostatic target blood volume (tBV). Other blood volume endpoints are considered being homeostatically unstable derivatives of the target volume. At any target that value tBV maintains a unique endpoint BV to PV ratio—equal absolute volume deviations from ideal values—IBV and IPV—that are maintained exclusively at Hct of Ideal Total Match (ITM). Homeostatic setting or target state that maintains tBV also maintains other target parameters: plasma volume (tPV), osmolality (tOsm), mean cell volume (tMCV) and mean cell hemoglobin concentration (tMCHC).

2) At physiologically critical—lowest and highest—hematocrit limits target states maintain the Maximal Target Deviation, which is equal to Constant k. It is the maximal homeostatically acceptable sum of target state specific absolute volume deviations in respect to ideal blood and plasma volumes.

In addition to its inherent role in reflecting blood's oxygen carrying capacity, blood Hct is one of the five major factors that affect plasma viscosity and red blood cell (RBC) function. The new method refers to physiologically critical Hct limits as Homeostatic Hematocrit Limits (HHL) considering only plasma viscosity. In physiology textbooks (110) and laboratory investigation handbooks (59-62), the highest critical Hct value or Lower Homeostatic Limit (LHL) is unanimously considered being 60% and the lowest Hct value or Higher Homeostatic Limit (HHL) being below 15%, meanwhile ideal plasma viscosity is considered being Hct-40%. The Maximal Target Deviation (MTD) is the maximal sum of absolute blood and plasma volume deviations from ideal values (IBV and IPV). The MTD is applicable only to target states at HHL and its value is referred to as Constant k, which is a fraction of IBV. This value depends on the preferred values of ITM and HHL. The new method hypothesizes that ITM hematocrit is consistent with ideal plasma viscosity Hct-40% and HHL values as described above. Therefore Constant k and MTD should be equal to 0.29·IBV.

3) Plasma hydration limits in respect to target states are reached, when either blood or plasma volume overcome ideal values by the Maximal Safe Deviation, which is half the value of Constant k.

Ideal values—IBV and IPV—are maintained as homeostatic targets only at ITM. Target states maintain progressively increasing tBV and tPV deviations in respect to IBV and IPV, when approaching critical Hct limits (HHL). Therefore reserve of safe (isoosmotic) plasma hydration origin deviations from target states also decreases. Homeostasis induces compensatory osmotic accommodations to oppose plasma hydration shifts that override either IBV or IPV by Maximal Safe Deviation (MSD), which is half of the Constant k value. Target Hct value specific maximal isoosmotic plasma volume expansion (PVE) from target state that reaches MSD is referred to as maximal Expansion (mE) for dilution and maximal Depletion (mD)—for dehydration. Compensatory hypoosmotic plasma accommodations oppose plasma dilution that overrides mE and compensatory hyperosmotic plasma accommodations oppose plasma dehydration that overrides mD. Plasma volume is the first to reach MSD and determine the mE volume, when plasma dilution affects target states at that lower than ITM (tHct range from UHL to ITM). Meanwhile BV is the first to reach MSD and determine the mE volume, when plasma dilution affects target states at that higher than ITM (tHct range from ITM to LHL). Unlike plasma dilution cases, the BV is the first to reach MSD and determine the mD volume, when plasma dehydration affects target states at that lower than ITM (tHct range from UHL to ITM). Also PV is the first to reach MSD and determine the mD volume, when plasma dehydration affects target states at tHct higher than ITM (tHct range from ITM to LHL).

4) Compensatory osmotic accommodations are homeostatically induced to oppose the advanced deterioration of plasma hydration that overrides the MSD limits or target states maintain similar blood and plasma volume deviation patterns in respect to ideal blood and plasma volume.

Compensatory homeostatic osmotic accommodations oppose plasma hydration shifts that override the MSD limits striving to recover target plasma viscosity. Accommodations are tissue perfusion-expansion and lymphatic loop protein turnover dependent. Hypooncotic states in blood are mainly due to protein trapping in the lymphatic loop as they enter the high compliance state resulting from volume expansion, when plasma hydration overcomes safe (isoosmotic) dilution limits. Hyperoncotic states are mainly due to excessive protein release from the lymphatic loop as they enter the high compliance state resulting from volume decrease, when plasma dehydration overcomes safe (isoosmotic) limits. All target states are subject to that kind of compensatory osmotic accommodations, because normal vasomotor tone adjusts low priority tissue perfusion and consequently lymphatic turnover to patterns of target blood volume—decreases tone, when volume overcomes ideal, and increases, when volume is lower than ideal. Consequently such accommodations should be induced even by minute plasma hydration shifts in respect to target states at homeostatic hematocrit limits. Resulting plasma osmolality changes and consequently safe deviation limits can be traced by mean cell hemoglobin concentration (MCHC) shifts resulting from osmotic mean cell volume (MCV) changes.

5) Target tissue perfusion focused vasomotor tone maintains target tissue perfusion despite different patterns of target blood volume.

Vasomotor tone under the control of intact sympathetic stimulation and homeostatic guidance is considered as normal or target tissue perfusion focused (TPF) by the new theory. It is considered ideal only when ideal blood volume is present, which is inherent to target states at ITM, but may be reached in a variety of deviations from target states at other tHct values. Therefore TPF can be increased (TPFi) or decreased (TPFd) in respect to ideal pattern, when striving to maintain red cell mass and target blood volume specific target hematocrit value consistent with target perfusion of high (HPT) and regular (RPT) priority tissues maintaining their target expansion. Target expansion of HPT is consistent with their minimal compliance features, meanwhile maintaining threshold compliance in between high and low in RPT sites. At the same time it maintains threshold compliance in between low and high in low priority (LPT) tissues and the lowest compliance of the lymphatics. Sympathetic tone (hypertension) increase above TPF results in approaching the safe dehydration profile limit of maximal safe (isoosmotic) deviation. Meanwhile sympathetic tone decrease (anaesthesia) below TPF promotes plasma dilution approaching safe hydration profile limits.

Mathematical Model HBS Trends

It is the mathematical model that describes hypotheses and provides numeric background values for the rest of models and the main developed nomogram—HBS Nomogram.

The model of Homeostatic Blood Volume Trends (HBV trends) mathematically derives hematocrit specific target values from ideal blood volume inherent to ITM hematocrit.

The key element of the model is the principle of deriving Constant k value from different countdown Hct values (ITM) and critical Hct limits—the lowest (UHL) and highest (LHL). However, the new method advocates ITM-Hct-40%, UHL-Hct-13.3% and LHL-Hct-60%. The HBS Trends model mathematically describes the major hypothesis of red cell mass (and consequently target Hct and Hb) specific homeostatic target states providing its specific values.

The model is introduced using the widely preferred method for ideal blood volume calculation—Nadler's formula (9), but alternative formulas (11) can also be used. The Nadler's formula utilizes two individual specific physical variables—body height and weight:

$$IBV = 0.3669 \cdot H^3 + 0.03219 \cdot W + 0.6041 \quad [1]$$

where H—body height in meters and W—body weight in kilograms.

Target states are mathematically described in the following formulas:

$$tBV = 0.5 \cdot (IBV + IPV + RCMn) \quad [2]$$

where IBV—ideal blood volume, IPV—ideal plasma volume and RCMn—target hematocrit value n specific red cell mass.

Ideal plasma volume is calculated as follows:

$$IPV = IBV \cdot (1 - Hct_{ITM}) \quad [3]$$

where IPV—ideal plasma volume, IBV—ideal blood volume and $Hct_{ITM}$—hematocrit of the Ideal Total Match.

Target hematocrit value n specific red cell mass is calculated as follows:

$$RCMn = Cn \cdot (IBV + IPV \cdot (1 - tHct_n)^{-1})) \cdot Hct_n \quad [4]$$

where RCMn—red cell mass inherent to target state at target Hct value n, Cn—coefficient inherent to target Hct value n, IBV—ideal blood volume, IPV—ideal plasma volume and tHct—target hematocrit value n.

Coefficient inherent to target Hct value n is calculated as follows:

$$Cn = ((IBV + IPV) \cdot (2 - Hct_n)^{-1}) \div (IBV + IPV \cdot (1 - Hct_n)^{-1}) \quad [5]$$

where Cn—target Coefficient C inherent to target Hct value n,

IBV—ideal blood volume,

IPV—ideal plasma volume, tHct—target hematocrit n.

Consequently:

$$Cn = ((IBV + IBV \cdot (1 - tHct_{ITM})) \cdot (2 - Hct_n)^{-1}) \div \quad [6]$$
$$(IBV + IBV \cdot (1 - tHct_{ITM}) \cdot (1 - Hct_n)^{-1}))$$

where Cn—coefficient inherent to target Hct value n, IBV—ideal blood volume, $Hct_{ITM}$—hematocrit of the Ideal Total Match and tHct—target hematocrit n.

Target hematocrit specific maximal iso-osmotic or safe deviations (MSD) are mathematically described as following.

Maximal safe plasma dilution in respect to target states at hematocrit values lower than Ideal Total Match hematocrit is calculated as follows:

$$mE_n = IPV + 0.5 \cdot k - tPV_n \quad [7]$$

where $mE_n$—maximal safe plasma dilution volume inherent to target state at target hematocrit value n<ITM (tHctn<$Hct_{ITM}$), IPV—ideal plasma volume, k—constant k and tPVn—target plasma volume at target hematocrit value n<ITM.

Maximal safe plasma dehydration in respect to target states at hematocrit values lower than Ideal Total Match hematocrit is calculated as follows:

$$mD_n = tBV_n - IBV + 0.5 \cdot k \quad [8]$$

where $mD_n$—maximal safe plasma dehydration volume inherent to target state at target hematocrit value n<ITM, tBVn—target blood volume at target hematocrit value n<ITM, IBV—ideal blood volume and k—constant k.

Maximal safe plasma dilution in respect to target states at hematocrit values higher than Ideal Total Match hematocrit is calculated as follows:

$$mE_m = IBV + 0.5 \cdot k - tBV_m \quad [9]$$

where $mE_m$—maximal safe plasma dilution volume inherent to target state at target hematocrit value m>ITM (t$Hct_m$>$Hct_{ITM}$), IBV—ideal blood volume, k—constant k and tBVn—target blood volume at target hematocrit value m>ITM.

Maximal safe plasma dehydration in respect to target states at hematocrit values higher than Ideal Total Match hematocrit is calculated as follows:

$$mD_m = tPV_m - IPV + 0.5 \cdot k \quad [10]$$

where $mD_m$—maximal safe plasma dehydration volume inherent to target state at target hematocrit value m>ITM, tPVn—target plasma volume at target Hct value m>ITM, IPV—ideal plasma volume and k—constant k.

Constant k is calculated as following:

$$k = IPV + RCM_{LHL} - IBV = IBV \cdot (1 - Hct_{ITM}) + RCM_{LHL} - IBV \quad [11]$$

where k—constant k, IPV—ideal plasma volume, IBV—ideal blood volume, $Hct_{ITM}$—hematocrit of ideal total match and $RCM_{LHL}$—red cell mass at the lower homeostatic hematocrit limit (LHL), which is the highest Hct value that preserves physiological plasma viscosity at its highest normal value.

Alternatively Constant k may be calculated as following:

$$k = IBV - RCM_{UHL} - IPV = IBV - RCM_{UHL} - IBV \cdot (1 - Hct_{ITM}) \quad [12]$$

where k—constant k, IBV—ideal blood volume, IPV—ideal plasma volume, $Hct_{ITM}$—hematocrit of ideal total match and $RCM_{UHL}$—red cell mass at the upper homeostatic hematocrit limit (UHL), which is the lowest Hct value that preserves physiological plasma viscosity at its lowest normal value.

It is clear from the above that Constant k is the key element in the formulas for maximal safe (isoosmotic) blood and plasma volume deviations in respect to ideal values and target states. Calculation of case specific ideal blood volume by means of any preferred formulas, i.e. Nadler's, is the only initial value needed to make mathematical model individual person specific. However, consensus agreement has to be reached regarding values of ITM hematocrit ($Hct_{ITM}$) and upper or lower homeostatic hematocrit limits (UHL and LHL) as determinants of Constant k value.

The main numeric values derived by the mathematical model HBS Trends are shown in TAB.1: target hematocrit (tHct) specific target values—red cell mass (tRCM), plasma volume (PV), coefficient (Cn), blood volume (tBV), plasma volume (tPV), normal or ideal blood volume (IBV) and plasma volume (IPV), target state specific plasma volume's deviation in respect to normal or ideal value (IPVE), target state specific blood volume's deviation in respect to normal or ideal value (IBVE), maximal isoosmotic (safe) volume deviation—dilution—from target state specific plasma dilution and blood volume (mE) and its hematocrit value (mE-Hct), plasma volume at its maximal safe or isoosmotic dilution (mE-PV), blood volume at its maximal safe dilution (mE-BV), maximal isoosmotic (safe) volume deviation—dehydration—from target state specific plasma dilution and blood volume (mD) and its hematocrit value (mD-Hct), plasma volume at its maximal safe or isoosmotic dehydration (mD-PV), blood volume at its maximal safe dehydration (mD-BV).

New Models

Five discovered concepts deployed by the new method are described by five schematic models. The earlier introduced model—HBS Trends—mathematically describes all concepts and provides numeric background values for the other five models, which are disclosed in the following chapters.

Blood Component Compartments (BCC Model)

The present inventor has discovered the blood component compartments model or BCC model which is a schematic model that describes Hct specific RCM to PV ratios (BCC) based on the concept that homeostasis of the human body strives to maintain red cell mass specific homeostatic target blood volume. It is equal to ideal (normal) blood volume and maintains ideal plasma volume only once per physiologic hematocrit scale—at hematocrit of Ideal Total Match. (Concept #1)

The model of Blood Component Compartments (BCC model) refers to BV, PV and RCM as blood components. The model shows plasma volume to red cell mass ratio at different Hct in three blood volume (BV) endpoint trends: ideal blood volume trend maintains ideal blood volume at any Hct (FIG.

Figure 1:
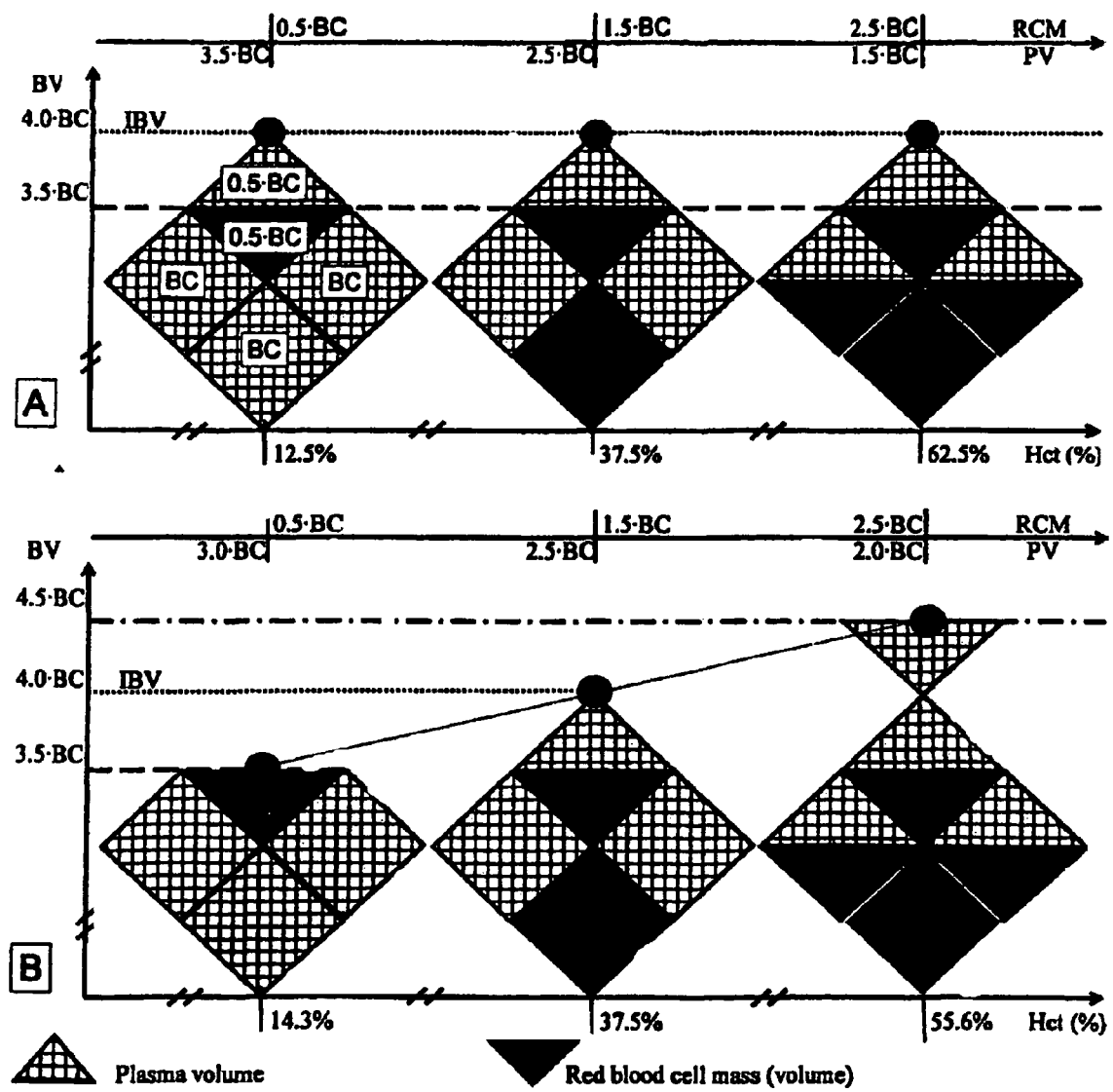
Figure 1:
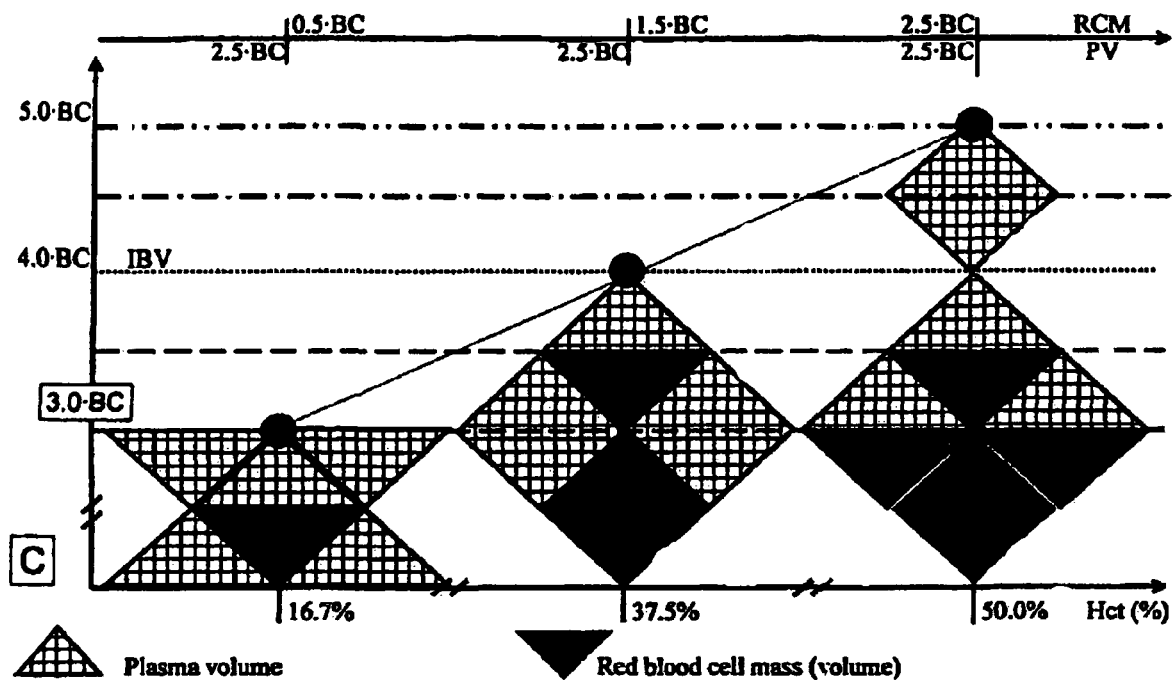

1A); target blood volume endpoint trend at any Hct maintains equal absolute blood and plasma volume deviations from ideal values (FIG. 1B); ideal plasma volume endpoint trend maintains ideal plasma volume at any Hct (FIG. 1C).

Blood component compartment (BC) is equal to Constant k, which in turn is equal to quarter of ideal blood volume (0.25·IBV). All trends maintain equal BV, RCM and PV to RCM ratio only at hematocrit 37.5%. They maintain different PV, but equal RCM at different Hct values: RCM=0.5·BC=0.5 k at Hct 12.5, 14.3 and 16.7%; RCM=2.5·BC=2.5 k at Hct 62.5, 55.6 and 50.0%.

Only the target blood volume trend at any Hct maintains equal absolute blood and plasma volume deviations (0.5·BC or 0.5 k) in respect to ideal values at ITM-Hct-37.5%. Meanwhile ideal blood volume trend maintains extreme plasma volume deviations while keeping ideal blood volume. The ideal plasma volume endpoint trend on the contrary—maintains extreme blood volume deviations.

The BCC model shows that target blood volume trend (TBV trend) maintains the most homeostatically justified plasma to blood volume ratio. It supports the hypothesis (Hypothesis 1) that target blood volume is maintained as homeostatic target at any Hct within the physiologic range. It also describes the origin and the meaning of Ideal Total Match hematocrit, which is the value, where ideal blood and plasma volumes are maintained in any endpoint target trend. In every trend, deviations in respect to proper ideal value (IBV, IPV or both) are shown equal at the lowest and highest hematocrit values. The sum absolute deviations are equal to Constant k or quarter of the ideal blood volume, too.

Different ITM hematocrit patterns would result in different number of compartments and different compartment volume, consequently other value of Constant k. The ITM-Hct-37.5% value has been chosen for the explanation of the BCC model, because of its simplicity. Meanwhile the new method advocates ITM-Hct-40%, but it is much more complex to analyze schematically. The BCC model leads to the concept of homeostatic Hct limits described in the following model.

Homeostatic Hematocrit Limits (HHL Model)

The present inventor has discovered the Homeostatic hematocrit Limits model or HHL model which is a schematic model that describes target blood volume trend specific blood and plasma volumes and their deviations from ideal values. It is described in association with the dynamics of the vasomotor tone. Model is based on the concept that at physiologically critical—lowest and highest—hematocrit limits target states maintain the Maximal Target Deviation, which is equal to Constant k. It is the maximal homeostatically acceptable sum of target state specific absolute volume deviations in respect to ideal blood and plasma volumes. (Concept #2) Plasma hydration limits in respect to target states are reached, when either blood or plasma volume overcome ideal values by the Maximal Safe Deviation, which is half the value of Constant k. (Concept #3)

The new method refers to physiologically critical Hct limits as Homeostatic Hematocrit Limits (HHL) considering only plasma viscosity. The highest critical Hct value or Lower Homeostatic Limit (LHL) is considered 60% and the lowest Hct value or Higher Homeostatic Limit (HHL)—15%, meanwhile ideal plasma viscosity maintaining value—40%—is attributed to Ideal Total Match.

Like in the previous model (BCC model), for clarity of explanation the ITM-Hct-37.5% value has been chosen for the description of the HHL model. Although the new method advocates ITM-Hct-40%, it is much more complex to analyze schematically. Note that the purpose of these models is to describe the principle relationship of ITM, UHL, LHL and Constant k.

Like it was disclosed in the BCC model, the ITM-Hct-37.5% value corresponds to Constant k that is equal to quarter of ideal blood volume at the lowest critical Hct-14.3% (UHL) and the highest critical Hct-55.6% limits applicable to target states. These limits are schematically described by the HHL model in FIG. 2-4. Both—target plasma volume deviation and blood volume deviation from ideal values are shown being equal to [0.5 k] at UHL and LHL, therefore resulting in sum absolute deviation k referred to as Maximal Target Deviation (MTD). Intact vasomotor tone is shown as homeostatically adjusted to maintain target tissue perfusion with any target blood volume. However it can be modified to facilitate reaching IBV during osmotic shifts or when sympathetic stimulation is blunted by such factors like anesthesia.

TABLE 4

Normal and critical values of hemoglobin concentration (Hb), hematocrit (Hct), mean cell volume (MCV), mean cell hemoglobin (MCH), mean cell hemoglobin concentration (MCHC) and plasma osmolality (osm).

| Literature source | Parameter applicability | Hb (g/L) | | Hct (%) | | MCV (fL) | | MCH (pg) | | MCHC (g/L) | | osm (mOsm/kgH$_2$O) | |
|---|---|---|---|---|---|---|---|---|---|---|---|---|---|
| | | Min | Max | Min | Max | Min | Max | Min | Max | Min | Max | Min | Max |
| 1* | Male | 140 | 180 | 42 | 52 | 80 | 95 | 27 | 31 | 320 | 360 | 285 | 295 |
| | Female | 120 | 160 | 37 | 47 | 80 | 95 | 27 | 31 | 320 | 360 | 285 | 295 |
| | Critical | <50 | >200 | <15 | >60 | | | | | | | <265 | >320 |
| 2** | Microcytic | | | | | <80 | | | | | | | |
| | Macrocytic | | | | | | >100 | | | | | | |
| | Critical | <50 | | <15 | >60 | | | | | <300 | >360 | | |
| 3† | Male | 136 | 175 | 39 | 49 | 80 | 100 | 26 | 34 | 310 | 360 | 285 | 293 |
| | Female | 120 | 155 | 35 | 45 | 80 | 100 | 26 | 34 | 310 | 360 | 285 | 293 |
| 4‡ | Male | 135 | 160 | 40 | 48 | 82 | 95 | 25 | 35 | 330 | 348 | 275 | 295 |
| | Female | 120 | 150 | 36 | 42 | 82 | 95 | 25 | 35 | 330 | 348 | 275 | 295 |

*Mosby's manual of diagnostic and laboratory tests. 3rd ed. Pagana K D, Pagana T J, eds. Mosby Inc. USA 2006
**Delmar's guide to laboratory and diagnostic tests. Daniels R, Deaniels R eds. Thomson Delmar Learning; Canada 2002
†Oxford Handbook of Clinical and Laboratory Investigation. 2nd ed. Provan D. editor. London, UK 2005
‡Manual of laboratory tests [Laboratoriniu tyrimu zinynas]. Kucinskienė Z A. Vaistu Zinios Inc. Vilnius, Lithuania 2001

Figure 2:
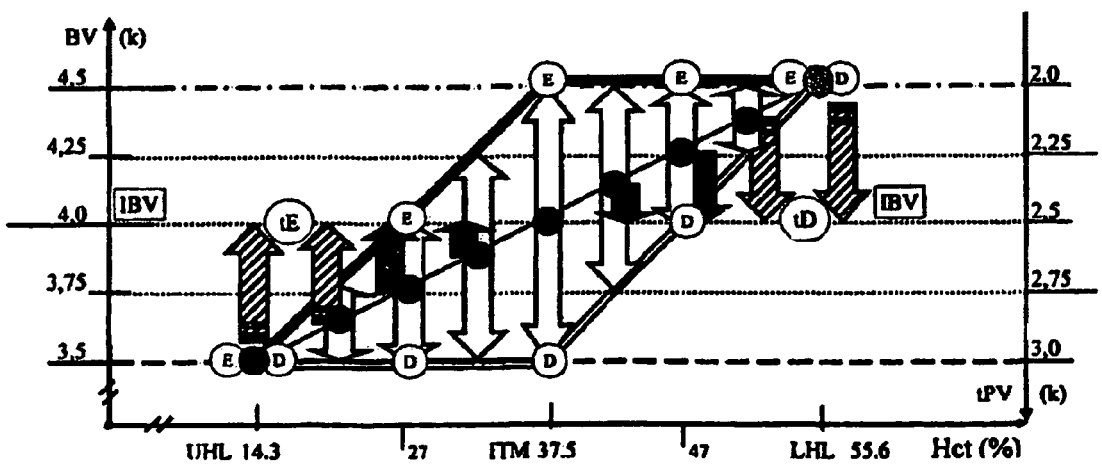
Figure 2:
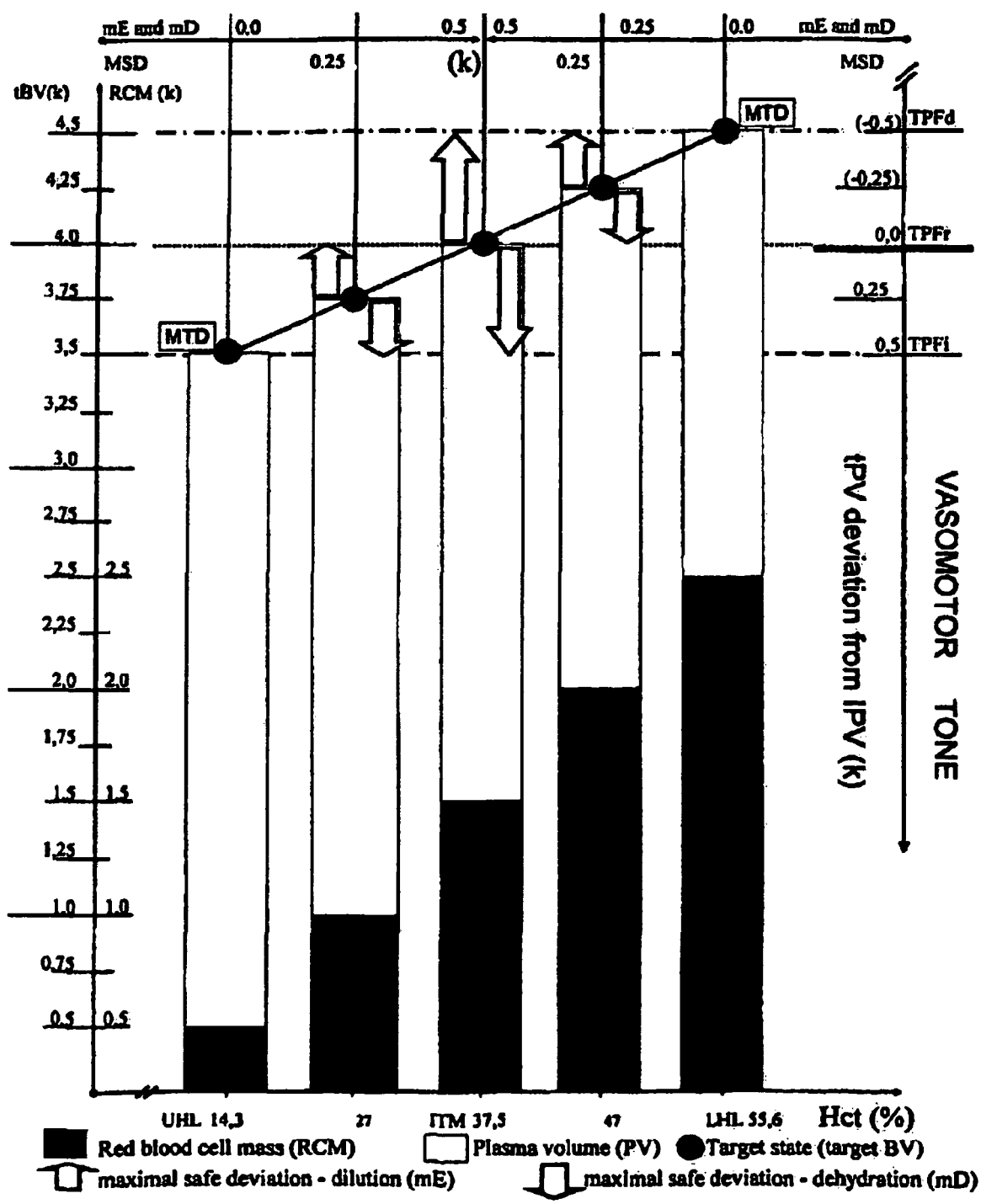

Target states are shown as heavy black dots in FIG. 2. The maximal safe deviation limits (E—for dilution and D—for dehydration) in respect to target states are shown as heavy white arrows. The IBV-target focused deviations from target states that are within maximal safe deviation limits are shown as heavy black arrows. These shifts are referred to as IBV-target plasma deviations. The IBV-target focused deviations that override maximal safe deviation limits are shown as striated arrows. These shifts are referred to as osmotic IBV-target plasma deviations (tE and tD). Definitions of the above described deviations from target states refer specifically to plasma, because they are applicable to isoosmotic or osmotic origin plasma hydration shifts.

Maximal Safe (Isoosmotic) Deviations from Target States

The present inventor has discovered that safe (isoosmotic) plasma hydration limits in respect to target states are reached, when either bBV or PV overcome ideal values by the value Maximal Safe Deviation, which is half the value of Constant k (Hypothesis 3). Thus, it is essential to obtain an individual value of Constant k in order to establish target states specific limits of safe plasma hydration deviations. As described in the mathematical model of HBS Trends, these ITM and LHL or UHL hematocrit values are the only determinants in calculating Constant k as fraction of individual ideal blood volume IBV, which in turn is obtained from formulas for normal blood volume, i.e. Nadler's.

The new method advocates ITM hematocrit value 40% because of its consistency with ideal physiological plasma viscosity. It also advocates LHL-Hct-60% value because of its consistency with the well established physiologically critical plasma viscosity. Under assumption of ITM-Hct-40% and LHL-Hct-60%, the calculated Constant k is approximately equal to 0.29·IBV. This Constant k value is used to calculate the corresponding UHL hematocrit, which appears to be 13.3% in the described setting. Similarly, UHL and ITM values are used to obtain corresponding LHL value. Target state specific limits of safe deviations are described in FIGS. 3, 4.

Reaching IBV state by plasma hydration origin deviations from target states within safe (isoosmotic) limits is homeostatically available within proper intervals of target hematocrit values: ideal blood volume can be reached within limits of safe dilution in respect to target states within target hematocrit limits; ideal blood volume can be reached within limits of safe dehydration in respect to target states within target hematocrit limits.

As shown in FIG. 3-A, target hematocrit specific absolute tBV and tPV deviations from ideal values inherent to ITM Hct-40%, reach maximal target deviation (MTD) at physiologically critical hematocrit values—UHL 13.3 and LHL 60.0(%). Therefore target states at UHL and LHL have no reserves for safe (isoosmotic) plasma hydration origin deviations (MSD) as shown in FIG. 3-B. Maximal plasma hydration origin blood volume deviations consistent with MSD are applicable to ITM Hct-40%. Constant k consistent with that ITM value is equal to 0.3·IBV.

As shown in FIG. 4-B, the maximal safe dilution B (mE) in respect to target state Y at tHct-27% maintains plasma volume diluted to MSD state (IPV+0.5 k) in respect to ideal (IPV) value (G), when k=0.3·IBV. Meanwhile maximal safe dehydration H (mD) in respect to target state Z at tHct-50% maintains absolute plasma dehydration by maximal value (IPV−0.5 k) Both states maintain IBV as homeostatically unstable state (deteriorated target state). As shown in FIG. 4-B hematocrit 27 and 50(%) specific MSD maintain ideal plasma volume (IPV). Maximal safe dehydration G (mD) in respect to target state Y at Hct-27% maintains blood volume depletion (MSD) by maximal value (IBV−0.5 k). Meanwhile maximal safe dilution D (mE) in respect to target state Z at tHct-50% maintains blood volume expansion (MSD) by maximal value (IBV+0.5 k).

Osmotic Deviation Limits Model (ODL Model)

The present inventor has discovered the Osmotic Deviation Limits model or ODL model which is a schematic model that schematically describes compensatory and artificially induced osmotic shifts from target states. Model is based on the discovered concept that compensatory osmotic accommodations are homeostatically induced to oppose the advanced deterioration of plasma hydration that overrides the MSD limits or target states maintain similar blood and plasma volume deviation patterns in respect to ideal blood and plasma volume. (Concept #4)

The present inventor has discovered that homeostasis activates numerous compensatory mechanisms to prevent or counteract overriding of critical parameters in a variety of settings. In case of critical plasma hydration states, compensatory osmotic erythrocyte volume shifts can oppose Hct and related plasma viscosity deteriorations. Ability to accommodate cellular size is known as RBC's osmotic resistance or fragility. The hemolysis normally begins in the hypotonic media of 0.5% normal saline (NS) solution and ends in 0.3% NS solution. Osmotic resistance decreases with increasing RBC size reflected by MCV. Maximally expanded RBCs cannot accommodate by swelling, while maximally small— by shrinking.

The present inventor has discovered target plasma osmolality (tOsm) is an individual and case specific osmolality in a long-term homeostatic equilibrium. It applies proper erythrocyte surface tension (EST), what means that part of coexisting erythropoietic RBC brands in blood maintain the brand specific RBC size (ebMCV), resting surface tension (RST) and osmotic resistance features (ebEOR), while other brands maintain target RBC size (tMCV) and target osmotic resistance (tEOR) features under the influence of target surface tension (TST). Note that target osmolality—tOsm—is maintained only by equilibrated homeostatic states (EHS), while any plasma osmolality deviations from target value are considered relatively hyperosmotic or hypoosmotic, although they stay within normal osm limits per se. The MCHC and MCV values also have target values that are case specific as being inherent to the target trend, but only in the setting of unchanging RBCs erythropoietic brand content. Target trend is hyper-osmotic in respect to trends with lower MCHC and hypo-osmotic in respect to trends with higher MCHC. Osmotic shifts induce deviation from tOsm value and appropriate MCV shift related MCHC and RCM changes. Then the blood state enters the pre-target homeostatic trend (PHT).

Figure 5:
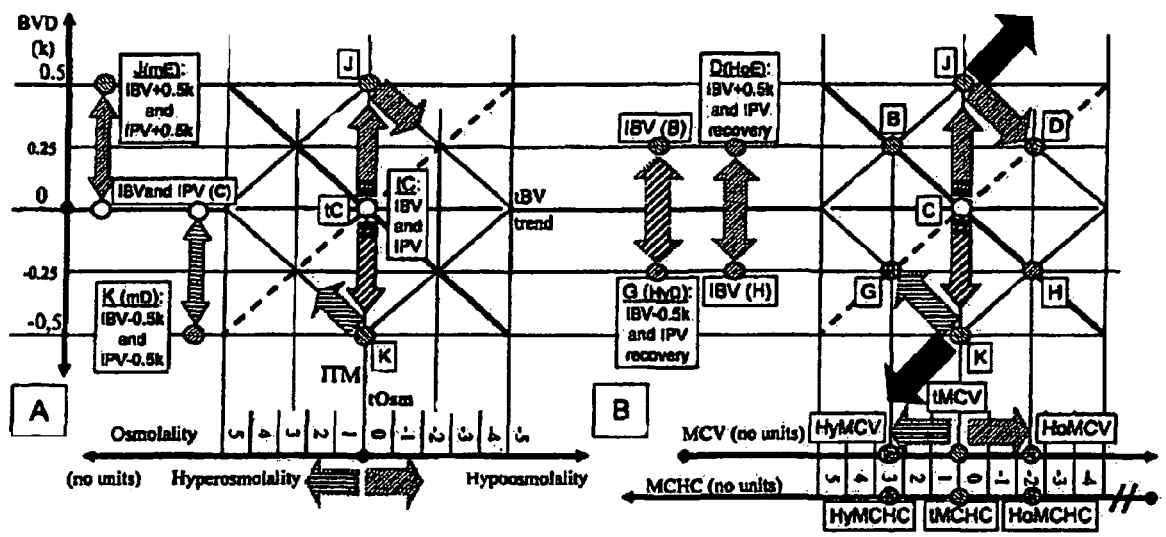

The present inventor has discovered an interfering MCV, MCH and MCHC parameter dynamics is investigated by means of ODL-model in respect to trends of osmotic deviations from target tMCV and tMCHC values. Homeostatic limits of maximal physiological (functional) osmotic deviations from target MCV and MCHC are referred to as osmotic deviation limits (ODL). The ODL model is described in FIGS. 5 and 6. FIG. 5-A shows overridden maximal safe deviation—MSD—limits J and K induced plasma osmolality shift: hypoosmotic originating from J (mE) and hyperosmotic from K (mD). FIG. 5-B shows the following shifts: a) Osmolality shifts to from J to D and from K to G recover ideal plasma volume in "isolated" case (no fluid exchange with extravascular compartment, so blood volume is not changing): osmotic plasma volume shifts were considered as a result of fluid released from or absorbed by red blood cells (RBC). b) Osmolality shifts from J to D and from K to G preserve plasma volume in "open" case (fluid exchange with extravascular compartment): the heavy black arrow leading from J (mE) shows that the overwhelming intravascular fluid shift in the setting of diluted to MSD plasma volume promotes blood volume increase, while RBC swelling preserves plasma volume (IPV+0.5 k) by absorbing fluid entering circulation. Heavy dark arrow originating from K (mD), overwhelming plasma dehydration in the setting of dehydrated to MSD plasma volume decreases blood volume, but RBC shrinking preserves plasma volume (IPV−0.5 k) consistent with MSD limit. c) Osmolality shifts are indirectly reflected by mean cell volume (MCV): it increases from target (tMCV) to hypoosmotic (HoMCV) or decreases to hyperosmotic (HyOsm). d) In the setting of unchanging erythropoietic RBC content, osmolality shifts are indirectly reflected by mean cell hemoglobin concentration (MCHC): it decreases from target (tMCHC) to hypoosmotic (HOMCHC) or increases to hyperosmotic (HyOsm).

*Example 1*
Isolated hyperosmotic MCV shift
calculation summary:
100 tMCV
1,4 RCM at tOsm
0,5 absolute osmotic RCM deviation
0,9 RCM at HyOsm
64 HyMCV
285 tOsm (mnOsm)
443 HyOsm

Figure 6:
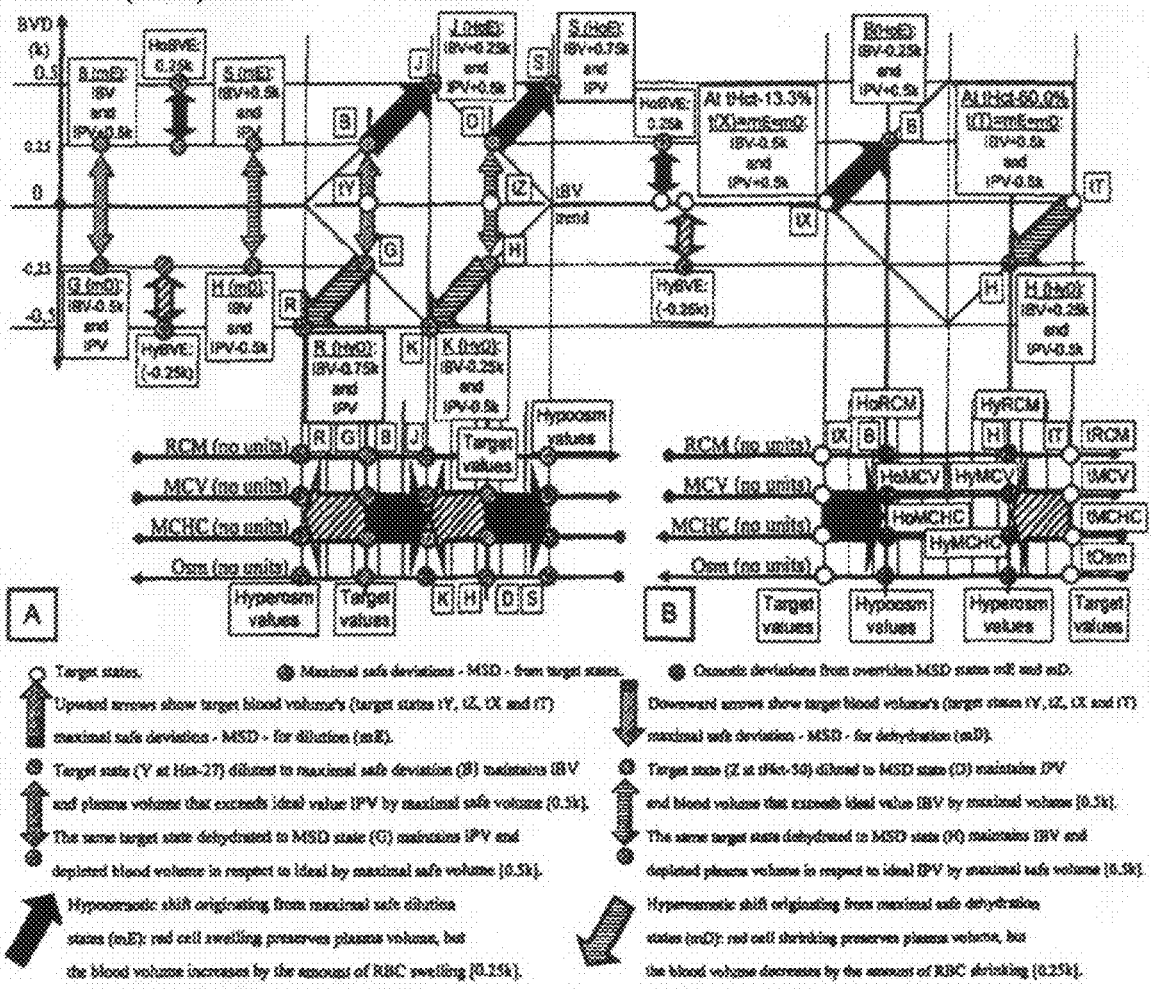
Figure 7:
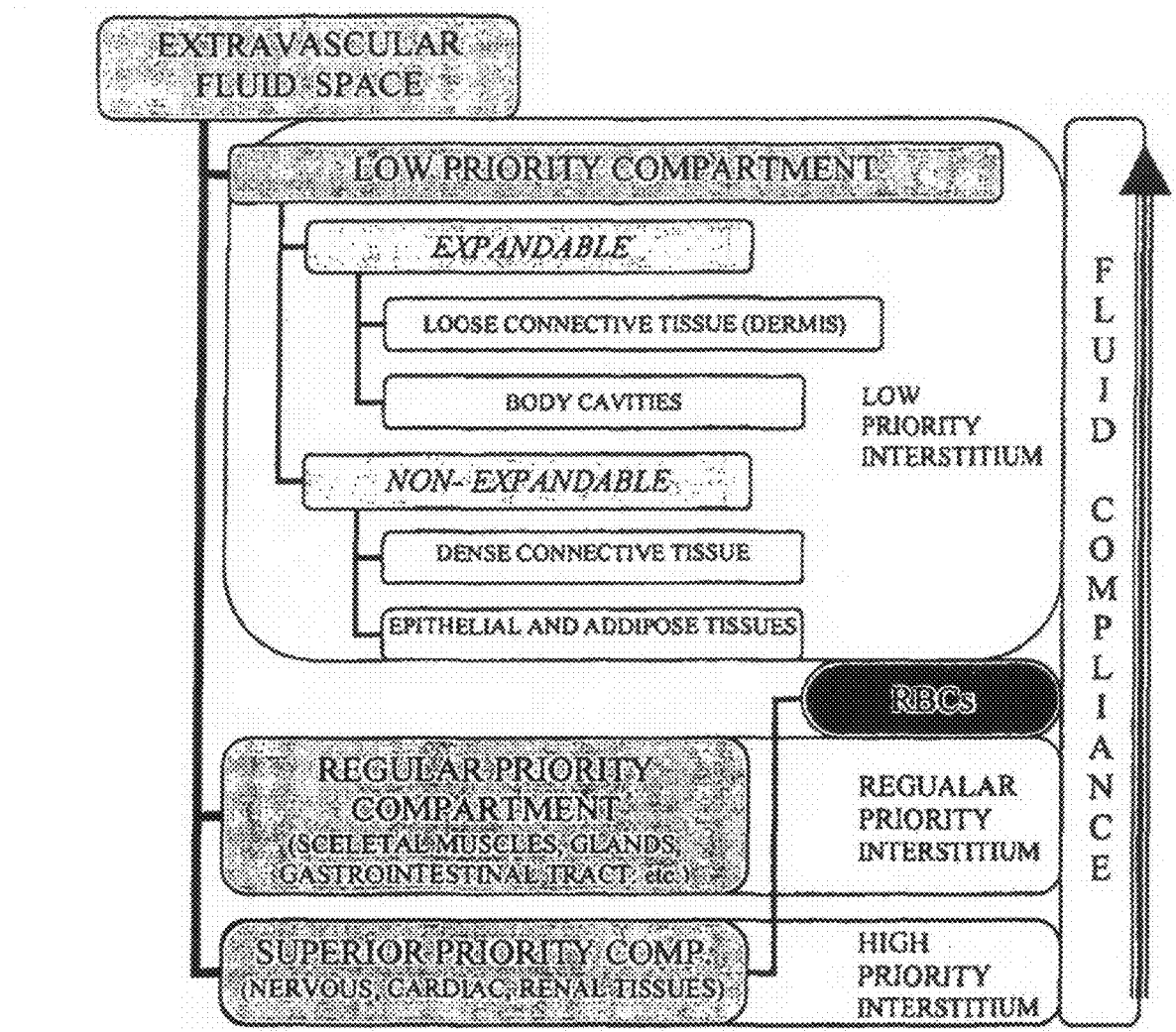
Figure 8:
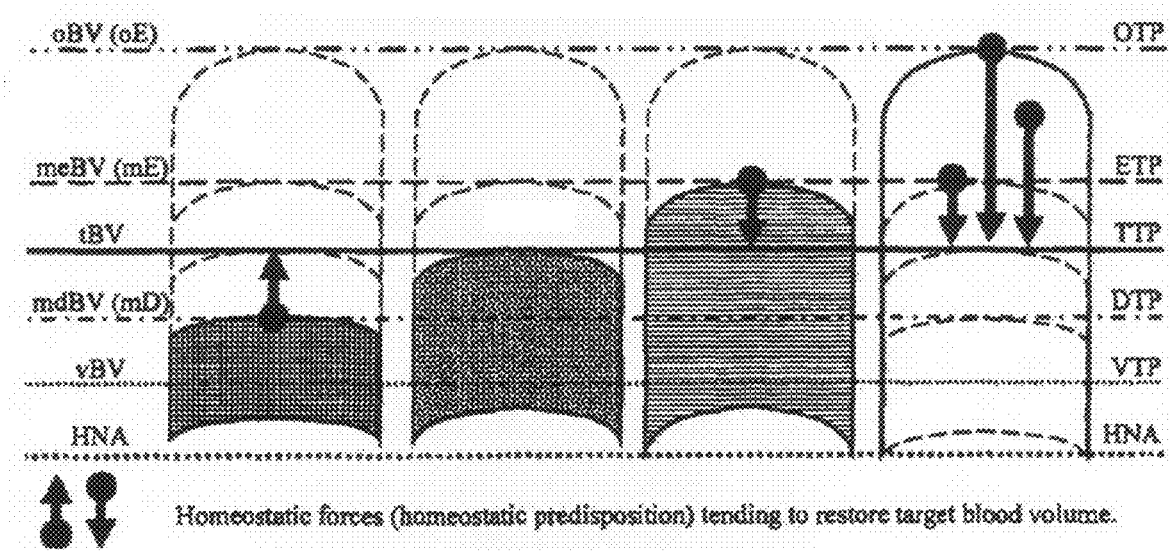
Figure 9:
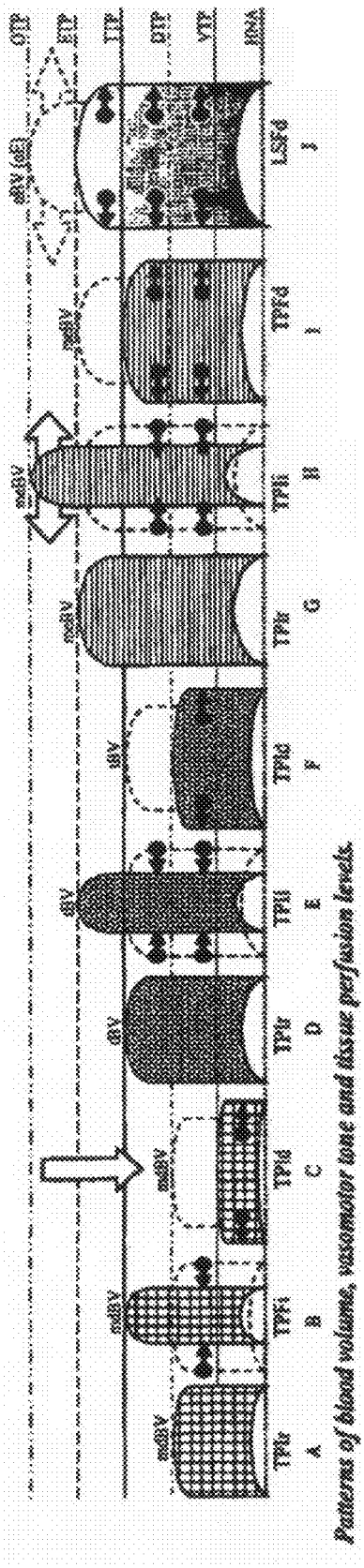

*Example 2*
Isolated hypoosmotic MCV shift
calculation summary:
80 tMCV
1,4 RCM
0,5 absolute osmotic RCM deviation
1,9 RCM at HyOsm
109 HyMCV
295 tOsm (mxnOsm)
217 HoOsm FIG. 6-A shows overridden MSD limits for dilution B and D induced hypoosmotic shifts to J (HoE) and S (HoE). Overridden MSD limits for dehydration G and H induced hyperosmotic shifts to R (HyD) and K (HyD). Hypoosmotic shifts resulted in RBC swelling by the amount of excessive fluid retained in circulation after equilibration with extravascular (peripheral) compartment. Blood volume expands by volume of RBC swelling [0.25 k], meanwhile plasma volume is preserved at its maximal safe dilution [IPV+0.5 k] in respect to target state tY at tHct-27% and remains ideal (IPV) in respect to target state tZ at tHct-50%. Hyperosmotic shifts resulted in RBC shrinking by the amount of residual plasma fluid loss after equilibration with the extravascular (peripheral) compartment. Blood volume decreases by volume of RBC shrinking [0.25 k], meanwhile plasma volume is preserved at its maximal safe dehydration [IPV−0.5 k] in respect to target state tZ at tHct-50%. Hypoosmotic blood volume deviation S [+0.75 k] in respect to target state tZ and hyperosmotic G [−0.75 k] in respect to target state tY overcome the maximal homeostatic limits [±0.5 k] for blood volume deviation in respect to ideal (IBV), therefore they can be induced artificially (osmotically active intravenous infusion solutions) or by appropriate pathologic conditions. FIG. 6-B shows that target states tX and tT maintain maximal safe deviations (MSD) for dilution and dehydration. Any plasma hydration shifts induce immediate compensatory osmolality accommodations: hypoosmotic to B (HoE) and hyperosmotic to H (HyE). Hypoosmotic shifts result in RBC swelling by the amount of excessive fluid retained in circulation after equilibration with extravascular (peripheral) compartment. Blood volume expands by volume of RBC swelling [0.25 k], meanwhile plasma volume is preserved at its maximal safe dilution [IPV+0.5 k] in respect to target state tX at tHct-13.3% (UHL). That shift increases blood volume in the setting of preserved plasma dilution, what is a plausible effect at critically low hematocrit values. Hyperosmotic shift from tT resulted in RBC shrinking by the amount of residual plasma fluid loss after equilibration with extravascular (peripheral) compartment. Blood volume decreases by the volume of RBC shrinking [0.25 k], meanwhile plasma volume is preserved at its maximal safe dehydration [IPV−0.5 k] in respect to target state tT at tHct-60% (LHL). That shift decreases blood volume in the setting of preserved plasma dilution, what is a plausible effect at such high hematocrit values. Examples describing interfering numeric value dynamics of parameters involved in osmolality shifts affecting plasma are presented in the FIG. 6-C and TAB.2.

Homeostatic Tissue Perfusion Levels (TPL Model)

The present inventor has discovered the Homeostatic Tissue Perfusion model or TPL model which is a schematic model that proposed tissue stratification according to fluid compliance and homeostatic perfusion priority referred to as tissue perfusion levels (TPL). The new model also introduced the corresponding standardized patterns of tissue perfusion, circulating blood volume and vasomotor tone (FIGS. 7-10).

This model is essential for clinical verification of target states. The Nomogram's applicability would be compromised without this model. The new method hypothesizes that homeostasis guides tissue perfusion according to the vital importance being stratified to homeostatic priority patterns. There are three major tissue compartment patterns (FIG. 7): superior and high homeostatic priority tissues (HPT), regular homeostatic priority tissues (RPT) and low homeostatic priority tissues (LPT). There are also three major tissue perfusion priority levels (TPL): the high or HPP (includes superior and high priority cells and their interstitium), regular (RPP) and low (LPP). Red blood cells are considered specific, independent and expandable fluid compartment that equilibrates with plasma just like extravascular space. Target perfusion setting in respect to perfusion of different tissue spaces varies with different BV states. However, in extremes, the major task of homeostasis is to protect and supply the higher priority tissue sites at the expense of lower priority sites. The corresponding patterns of tissue perfusion levels, blood volume and vasomotor tone are described in FIGS. 8 and 9.

Clinical evaluation of the circulating blood volume is of major importance and pretty challenging though. Addressing this issue, the new method proposed the following new processes.

Figure 10:
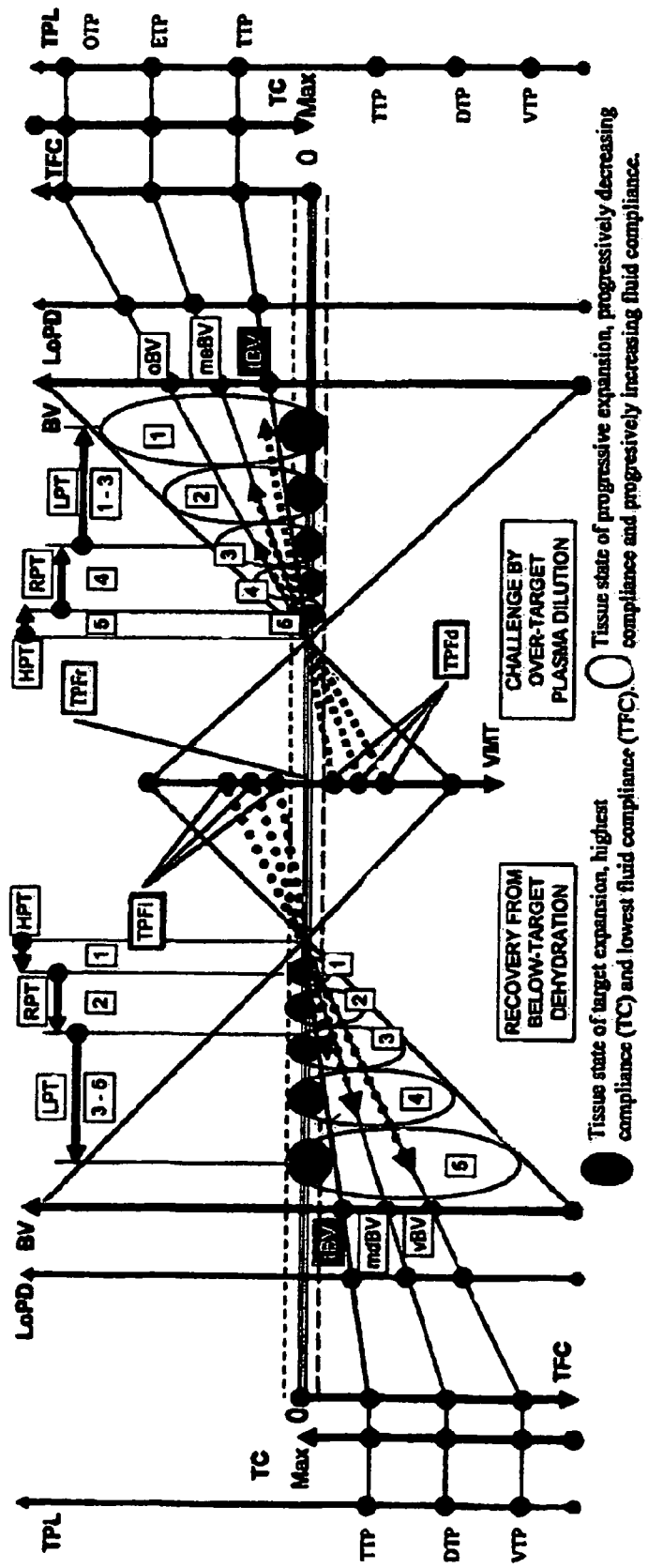

(1) Tissue perfusion levels have significant influence on tissue fluid compliance (TFC), which is the fluid accumulation capacity, and tissue compliance (TC), which is the resistance to volume expansion. Note that the bigger the size of the body fluid space or tissue displayed as ovals in FIGS. 10-A-C, the lower the homeostatic perfusion priority. Tissues maintain different inherent patterns of TC and TFC according to the following principle: the lower homeostatic priority, the lower inherent TC and higher TFC. Nevertheless, all tissues maintain progressively increasing TFC and decreasing TC, when their volume is expanded (swell) or depleted (shrink) in respect to normal or target anatomical volume. It means that the more expanded the compartment, or the more advanced the shrinking, the more efficiently the tissue accumulates fluid. There is a similarity to inflating a balloon: it is very easy in the beginning (it is empty), later it becomes very difficult (target volume) and then resistance starts slowing down again (advanced expansion). All tissues within their target volume maintain tissue-specific lowest TFC and highest TC features referred to as high-TC/low-TFC state. Superior priority cells and high priority tissues—HPT—are minute in volume and have negligible range of expansion. Their supplies are nearly totally perfusion dependent. Thus, their TFC and TC features can be ignored in the overall clinically traceable intercompartment fluid equilibration. The body fluid compartments maintain different patterns of compliance with the same pattern of homeostatically managed distribution of tissue perfusion. The upper limit of the high-TC/low-TFC state is for the threshold between high and low TC (also, low and high TFC), when plasma and tissues are challenged by excessive fluid (tissues start swelling). The lower limit of the high-TC/low-TFC state is for the similar threshold between high and low TC (also, low and high TFC), when plasma and tissues are challenged by fluid deficit—dehydration (tissues start shrinking). Mainly because of homeostatic blood flow distribution, the high inherent volume maintaining low priority tissues (LPT) deliver a very special homeostatic function—excessive plasma fluid drainage, accumulation and release-upon-demand back to circulation. Both LPT and RPT maintain threshold compliance in between low and high at target tissue perfusion (TTP) maintained by target blood volume and target-perfusion-focused increased vasomotor tone (TPFi). Note that resting TPF tone (TPFr) is assumed to be present only on the tiny limit-line consistent with clinically undetectable "super-normal" condition, where tissues of any priority maintain their normal anatomic fluid volume and the highest-TC/lowest-TFC state. The relatively small increases in blood volume that overcome the target state, result in significantly increasing level of perfusion decentralization (LoPD) and TFC (FIG. 10-C). The TFC increase and TC decrease affects LPT sites to much more extent, and leads to excessive plasma fluid drainage and accumulation there.

(2) Therefore plasma hydration that recovers the target state after advanced dehydration is equilibrating with relatively small volume of high (HPT) first. Demands of the lower priority tissues are satisfied in the sequence of homeostatic hierarchy according to the tissue specific vital importance. As shown in FIG. 10-B, it is reflected in the numbers attached to the ovals or expandable fluid spaces. These numbers reflect the sequence of major fluid equilibration: the number one (FIG. 10-B) is the highest homeostatic priority but small volume sites that "drink first", because their fluid compliance is the highest of all in that tissue perfusion and blood volume setting. Blood flow centralization also has an important role there. To some extent, these hypotheses echo with the concepts of volume kinetics revealing that crystalloid is distributed in the expandable space that is significantly smaller than the traditional extracellular volume (ECV), which approximates 20% lean body mass, particularly in the first 30 minutes after completion of the infusion.

(3) Similarly, the plasma hydration that tends to override target state is equilibrating with relatively large volume of LPT that enters the progressively increasing high-TFC state. As shown in FIG. 10-C, the plasma fluid equilibration takes part in the lower priority tissues first, if plasma hydration is over-the-target. It is reflected in the numbers attached to the ovals or expandable fluid spaces. These numbers reflect the sequence of major fluid equilibration: the number one (FIG. 10-C) is the lowest homeostatic priority but large volume sites that "drain" the excessive fluid delivered by plasma, because their fluid compliance is the highest of all in that tissue perfusion and blood volume setting. Blood flow decentralization also has an important role there.

(4) In summary, only extremely high rate of isoosmotic IV infusion can achieve residual plasma dilution that overrides target state. The upper limit of the high-TC/low-TFC state as threshold for steeply increasing fluid accumulation efficacy in low priority tissues, is proposed by the new method for uncovering target states by volume loading test (Chapter 4.4.3.) with intravenous short high-rate isotonic crystalloid infusions. It complies with the findings of the volume kinetic studies that report plasma volume expansion efficacy (PVEE) as high as 80%, when resuscitating the preexisting dehydration origin hypovolemia by isotonic crystalloid solutions. Meanwhile, PVEE is reported as low as 5% in case of isotonic crystalloid volume load in the setting of preexisting euvolemic normal (target) plasma hydration.

Body Fluid Equilibration Model (BFE Model)

Figure 11:
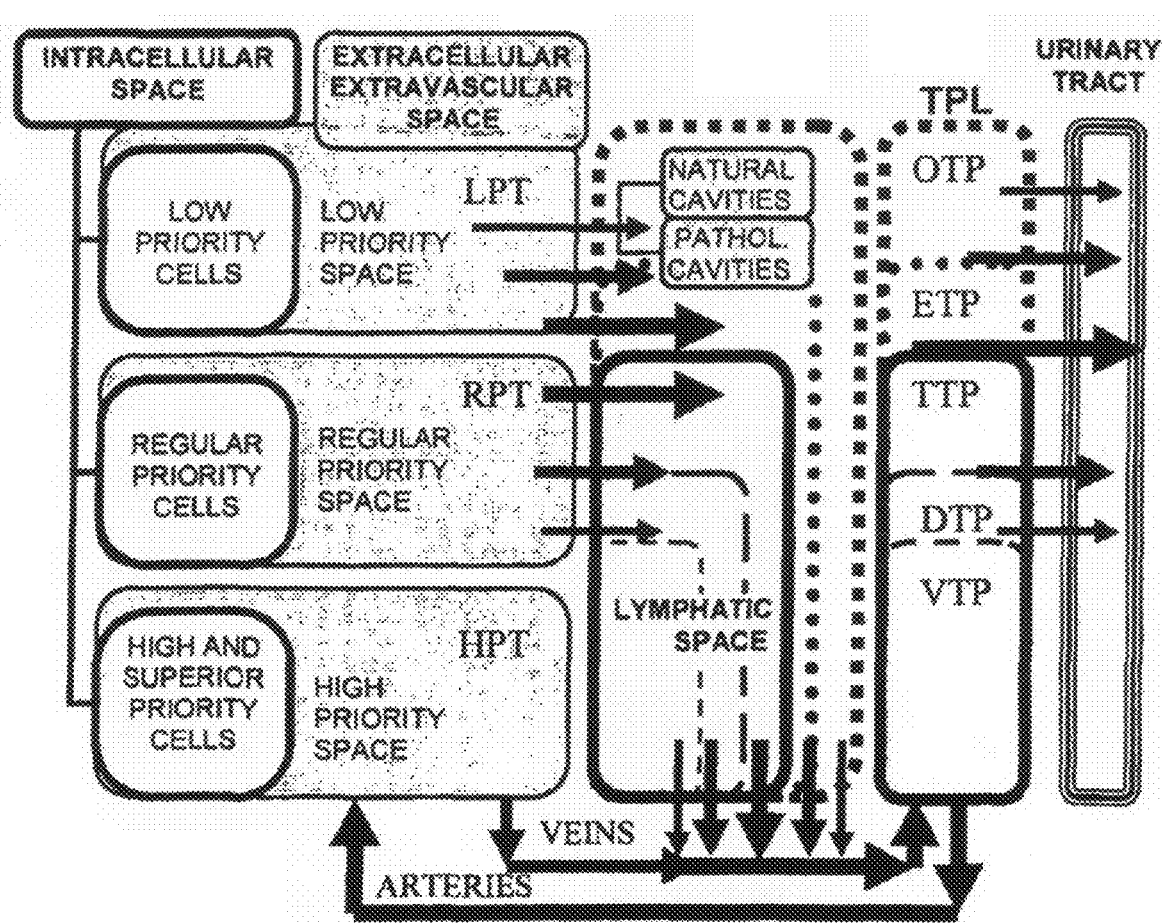

The present inventor has discovered the Body Fluid Equilibration model or BFL model which is the major schematic model (FIGS. 11-12) that summarizes concepts of the above described models and systemizes an overall process of inter-compartment body fluid circulation, equilibration and elimination, also incorporating the corresponding urine output, lymphatic loop fluid and protein turnover processes.

Figure 12:
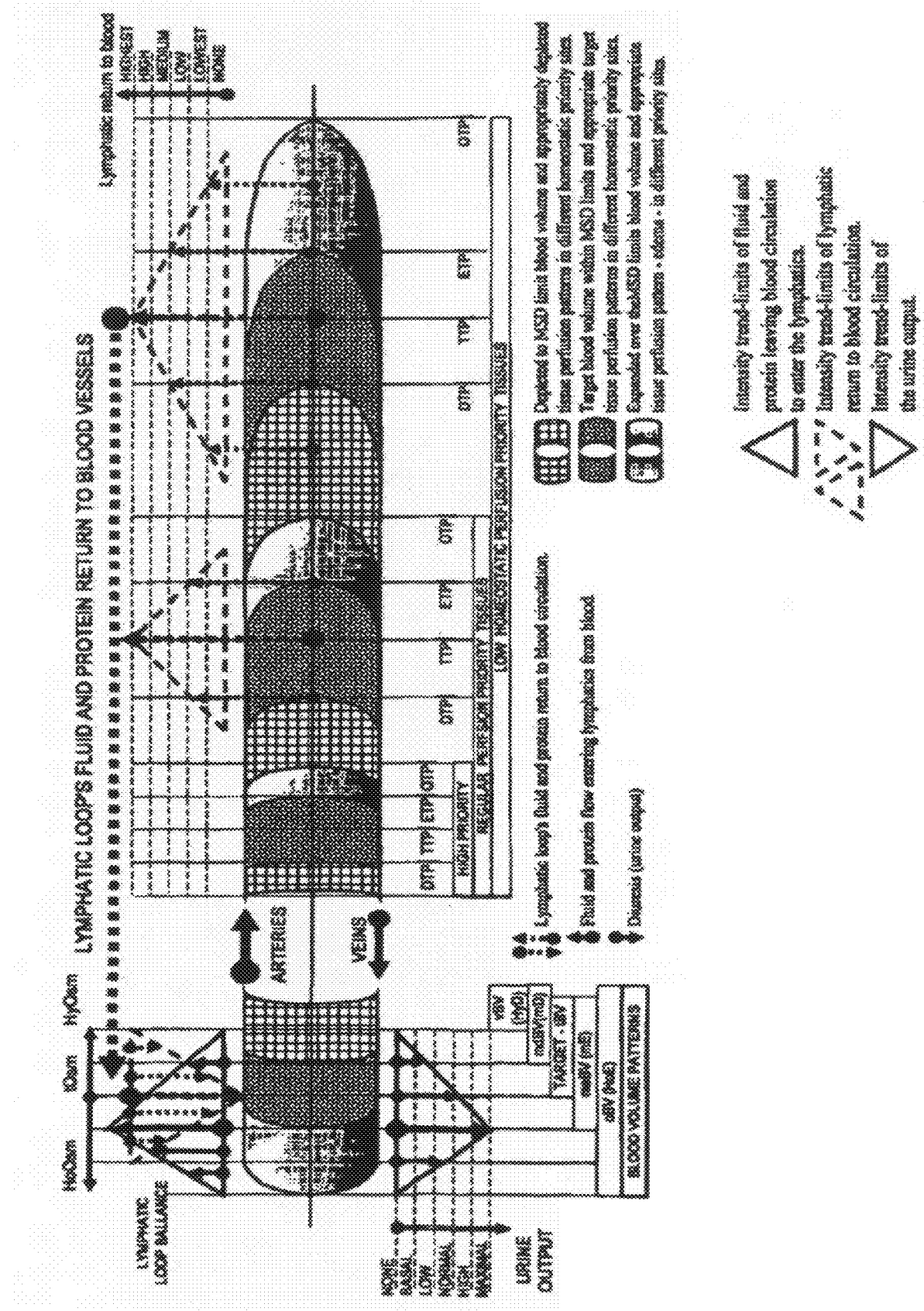

The present inventor has discovered that advanced over-target plasma hydration (dilution), fluid and protein trapping in the lymphatics is induced as it enters the progressing high-FC state. Also, the lymphatic vessels are progressively obstructed by the advancing interstitial edema. The resulting plasma hypoosmolality bares the compensatory pattern (FIGS. 5, 6). Similarly, in hypovolemic dehydration, an excessive lymphatic loop fluid and protein release to circulation facilitates plasma fluid resuscitation by means of the compensatory plasma hyperosmolality. Urine output is shown as directly proportional to the turnover rate of the lymphatic loop (FIG. 12).

Patterns of Homeostatic Stability

The present inventor has discovered the blood homeostatic stability patterns (HSP) described as predisposition to retain in or eliminate from circulation an additional load of isotonic non-colloid fluid. Pre-set potentials as definitions of HSP, were proposed by the new method to describe osmotic and volemic blood state's stability in the sense of predisposition to plasma dilution for maintaining adequate effective circulating volume and plasma osmolality. The pre-set volume potential $[PVP^{-/0/+}]$ describes predisposition of proper homeostatic blood state to isotonic plasma hydration solely for blood volume increase, while pre-set osmotic potential $[POP^{-/0/+}]$ describes predisposition to isotonic plasma hydration solely for decrease of osmolality (dilution).

The proposed classification is as follows:
1. $[PVP^0]$ euvolemic state consistent with target state specific blood volume,
2. $[POP^0]$ iso-osmotic blood state with target osmolality,
3. $[PVP^+]$ hypervolemic state—an over-target expanded blood volume,
4. $[POP^+]$ relative hyperosmolality (HyOsm) in respect to target state (tOsm),
5. $[PVP^-]$ hypovolemic state—the below-target decreased blood volume,
6. $[POP^-]$ relative hypoosmolality (HoOsm) in respect to target state (tOsm)

Homeostatic stability states are described by both potentials as follows:
1. $[POP^0/PVP^0]$ isoosmotic/euvolemic (homeostatic target) state,
2. $[POP^0/PVP^-]$ isoosmotic/hypovolemic (pre-target) state,
3. $[POP^0/PVP^+]$ isoosmotic/hypervolemic (pre-target) state,
4. $[POP^-/PVP^0]$ hypoosmotic/euvolemic (hypoosmotic pre-target) state,
5. $[POP^-/PVP^-]$ hypoosmotic/hypervolemic (hypoosmotic pre-target) state,
6. $[POP^-/PVP^-]$ hypoosmotic/hypovolemic (hypoosmotic pre-target) state
7. $[POP^+/PVP^0]$ hyperosmotic/euvolemic (hyperosmotic pre-target) state,
8. $[POP^+/PVP^+]$ hyperosmotic/hypervolemic (hyperosmotic pre-target) state,
9. $[POP^+/PVP^-]$ hyperosmotic/hypovolemic (hyperosmotic pre-target) state From the nine potentials above, the physiologically maintained are the following:
1. $[POP^0/PVP^0]$ isoosmotic/euvolemic (homeostatic target) state,
2. $[POP^0/PVP^-]$ isoosmotic/hypovolemic (safe isoosmotic dehydration) state,
3. $[POP^0/PVP^+]$ isoosmotic/hypervolemic (safe or isoosmotic dilution) state,
4. $[POP^-/PVP^+]$ hypoosmotic/hypervolemic (advanced plasma dilution) state,
5. $[POP^+/PVP^-]$ hyperosmotic/hypovolemic (advanced dehydration) state The rest of potentials are considered as pathologically or artificially induced states. The homeostatically most stable are the homeostatic target states [$POP^0/PVP^0$] maintained and protected by the overall homeostasis of the human body. Meanwhile plasma osmolality or volume deviations from target states are considered homeostatically unstable derivatives of the target state. It results in proper "homeostatic tension" or forces (FIG. 9) tending to recover the target values of proper parameter.

Steady State (Equilibration Pause)

The present inventor has discovered that blood samples for evaluation of residual plasma dilution should be taken at least 20 minutes after the end of infusion or an appropriate equilibration pause (EQP) has to be made in course of intravenous fluid resuscitation.

Volume Loading Test (VLT-Test)

The present inventor has discovered an algorithm—the Volume Loading Test (VLT-test)—that serves for clinical verification of target states, which is essential for the accuracy of Nomogram's application, especially in monitoring and planning the infusion therapy measures or calculating blood transfusion amount for target Hct and Hb increase. The VLT-test also serves for balancing intravenous fluid resuscitation interfering with measures of blood component transfusion.

As described in TPL model (FIG. 10-C, Chapter 4.3.4.), plasma hydration that tends to override target state is equilibrating with relatively large volume of LPT that quickly enters the progressively increasing high-TFC state. Therefore, only the extremely high rates of isoosmotic intravenous infusions can achieve residual plasma dilution that overrides target state. The upper limit of the high-TC/low-TFC state as threshold for steeply increasing fluid accumulation efficacy in low priority tissues, is used by the new method for uncovering target states by intravenous (IV) isotonic crystalloid infusion.

The present inventor has discovered kinetics of isotonic or nearly isotonic fluids are dependent on the state of hydration, so that more crystalloid fluid is retained in plasma in the setting of mild to moderate dehydration. Therefore, boluses of parenteral crystalloid fluid can provide valuable diagnostic information in uncovering the preexisting homeostatic stability patterns and verifying target states.

The present inventor has discovered that intravenous test volume load of isotonic crystalloid solution recovers the target state in case of preexisting dehydration or to confirm the presence of normal plasma hydration as marker of preexisting target state. However target state has to be differentiated with preexisting over-target plasma hydration, which can demonstrate similar VLT-test results. Therefore, specific procedure of uncovering preexisting over-target plasma hydration as overridden target state is also proposed by the new method.

The present inventor has discovered that intravenous infusion amount should be capable of expanding the dehydrated plasma volume by the amount of maximal isoosmotic plasma volume expansion (PVE) in respect to target volume. The tHct specific PVE values are described by the HBS Trends model as mE parameter (TAB.1) and included in the Nomogram. The mE values are expressed in fractions of Constant k, which in turn is equal to ~0.3 fraction of calculated normal or ideal blood volume. It makes the test-infusion amount individual. Assuming that up to 80% of infused solution will be retained in circulation (Chapter 4.3.4.) in case of preexisting advanced dehydration, the infusion amount is proposed to be equal to appropriate mE value at pre-test Hct level in the Nomogram.

The present inventor has discovered an algorithm or steps of VLT-test procedure:
1. Baseline (bHct) or pre-test Hct value has to be established by taking the blood test referred to as T1;
2. By the time when blood test results are available, normal or ideal blood volume should be calculated by any preferred formula;
3. The mE value is taken from the PVE column in the Nomogram on the level of Hct value obtained from T1 blood test results;
4. The VLT-PVE value are provided in k units (Constant k is the new unit for measuring volume in the Nomogram). Therefore appropriate VLT-PVE value is multiplied by the calculated value of normal blood volume (IBV), providing the crystalloid infusion test-volume (TVL) in milliliters, if IBV was calculated in milliliters, too;
5. High rate bolus TVL amount infusion is then started. Author's preferred rate in preliminary investigations is 10 ml/kg/h. Usually, infusion takes 10-15 minutes;
6. An equilibration pause—EQP-1—of 20 minutes is then applied;
7. The $2^{nd}$ blood sample—T2—is then taken;
8. Urine output if available is collected and measured from the start of the infusion;
9. Result interpretation:
    a) if Hct decreases isoosmotically (along one MCHC specific radiating line in the HBS Nomogram) for more than 1%, target state is supposed to be recovered, consequently, considering that T2 test has provided the tHct value for; (note that it means that hematocrit decreases >1%, i.e., from 40% to <39%),
    b) if Hct decreases heteroosmotically (inducing inter-trend or inter MCHC specific radiating line shift in the HBS Nomogram) for more than 1%, target state is suspected being not completely recovered, consequently, another similar amount and rate TVL is required; it should definitely recover the target state,
    c) if Hct decreases for less than 1%, there are two options:
        preexisting target state is verified, consequently, considering that mean value from both T1 and T2 tests have provided the that value, or
        preexisting over-target plasma dilution state is confirmed, consequently additional investigation is needed—following to the next step (N10).
10. Infusions induce the so called controlled urine output rate that exceeds the basal rate; therefore, urine output evaluation is of great importance in differentiating preexisting target state from preexisting over-target plasma dilution: if urine output approximates basal rate or is below it (i.e., $\leq$0.5 ml/kg/h or even $\leq$20 ml/h), there is a suspicion of deteriorated renal fluid elimination resulting in over-target plasma dilution. Meanwhile urine output exceeding basal would support the assumption of verified preexisting target state. As the last measure of differentiation, the mini dose IV diuretic-test could be attempted (i.e., 20 mg IV furosemide administration). For a period like 30 minutes, steady state requirements should be obeyed (no IV infusion or other route fluid intake). Then the $3^{rd}$ blood test is taken. In case of uncovered target state, the resulting Hct increases is less than 1%, meanwhile it is more than 1% in case of preexisting plasma over-target dilution, although urine output after diuretic administration may be similar in both cases.
11. Note that limits of maximal isoosmotic deviation from target states—mE-Hct and mD-Hct—are less than 1% at that value below 22% and above 57%. Therefore VLT-test is not applicable at these baseline (pre-test) Hct values.

12. The Hb to Hct ratio (MCHC) decrease in the consequent blood tests means that the preexisting relative plasma hyperosmolality due to advanced dehydration has been also recovered by the isotonic IV crystalloid infusion.

HBS Nomogram

Figure 13:
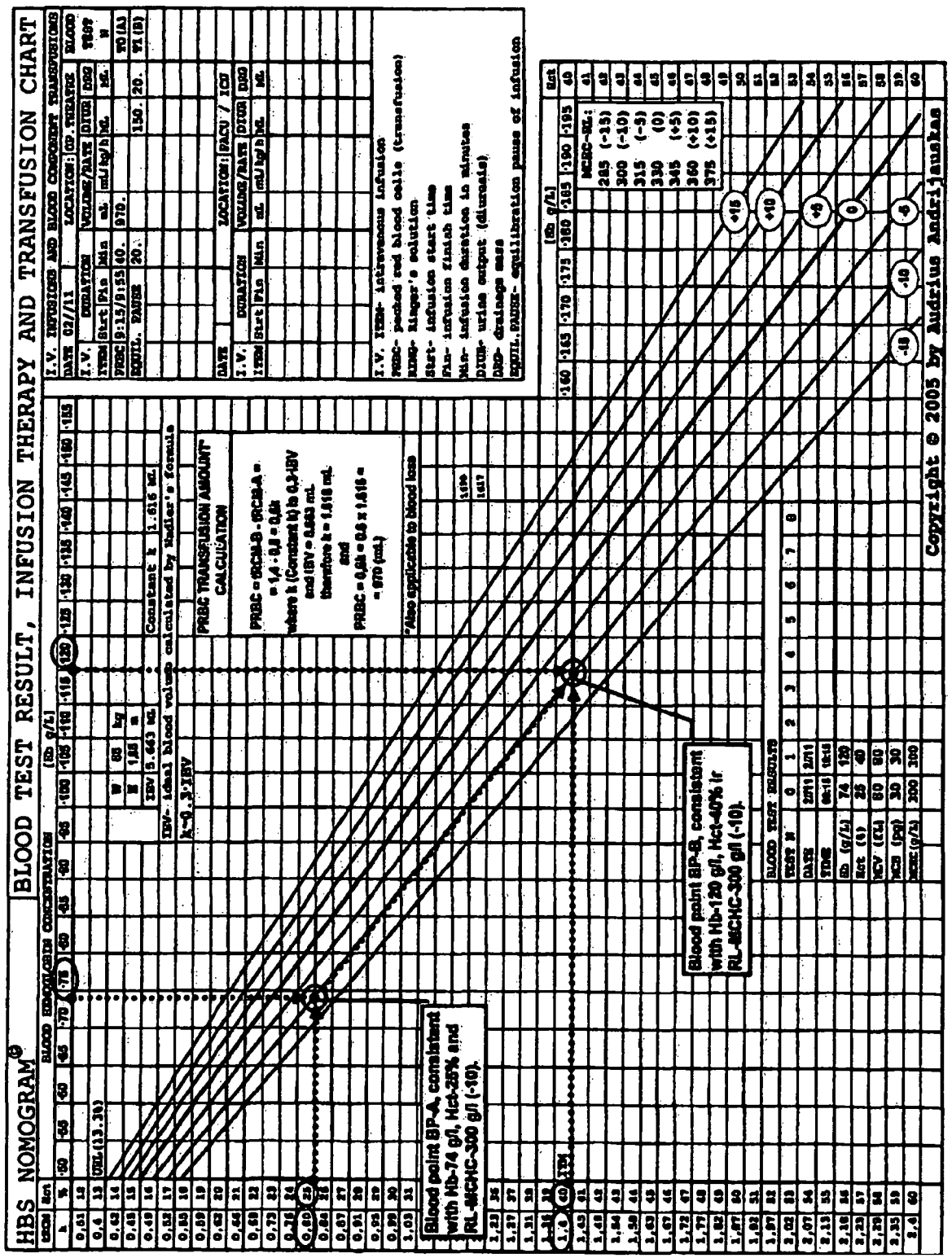
Figure 14:
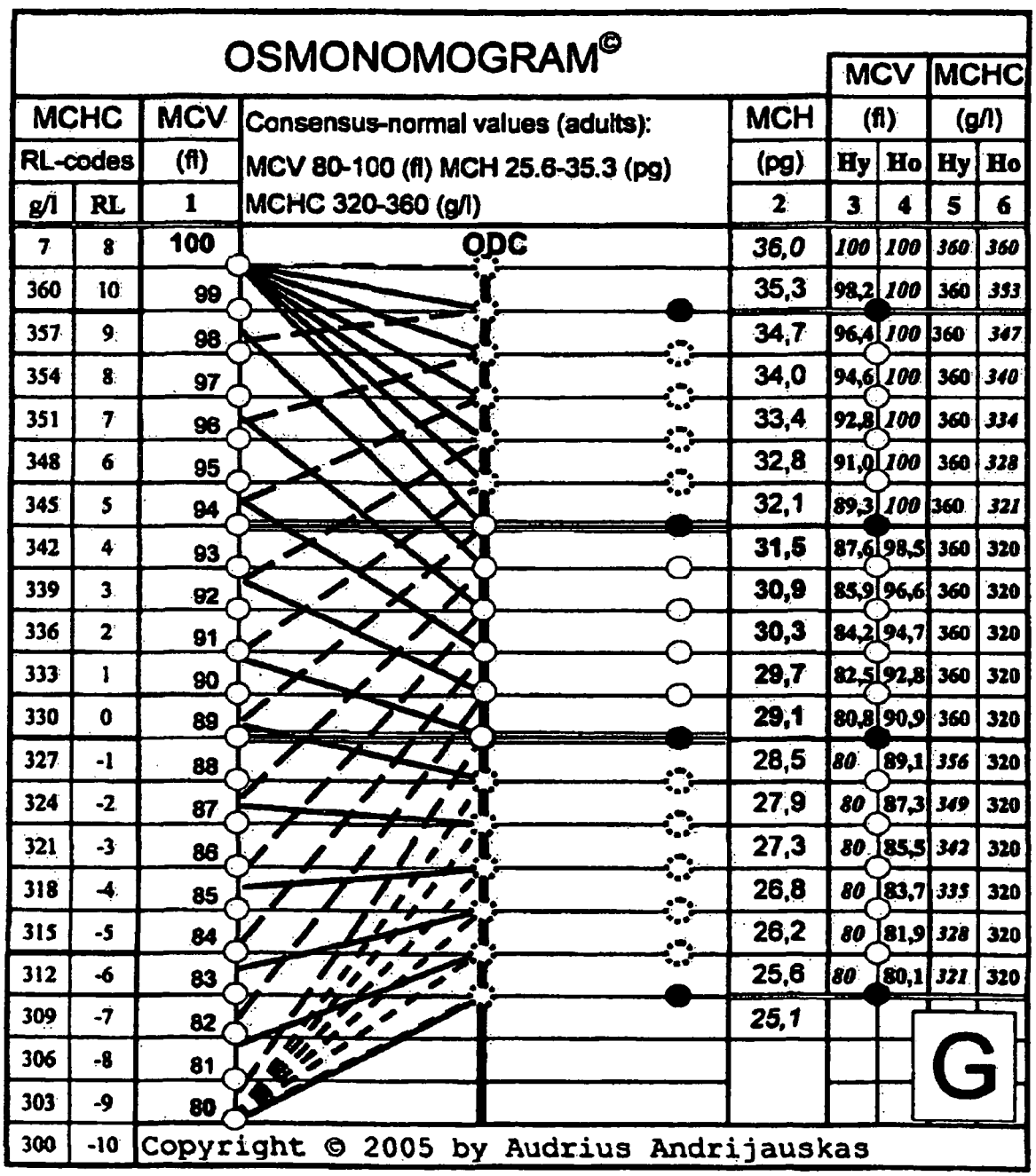
Figure 15:
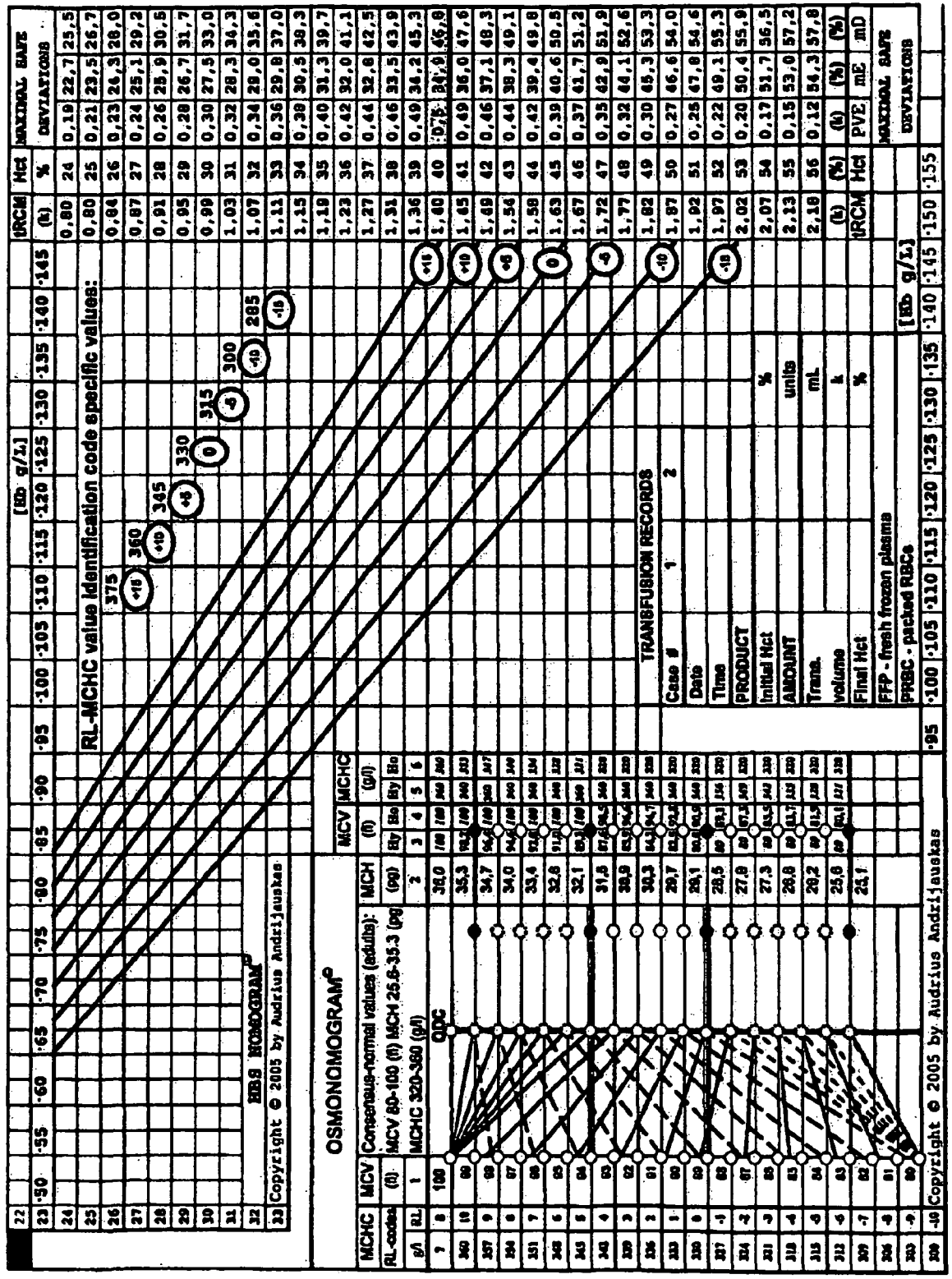
Figure 16:
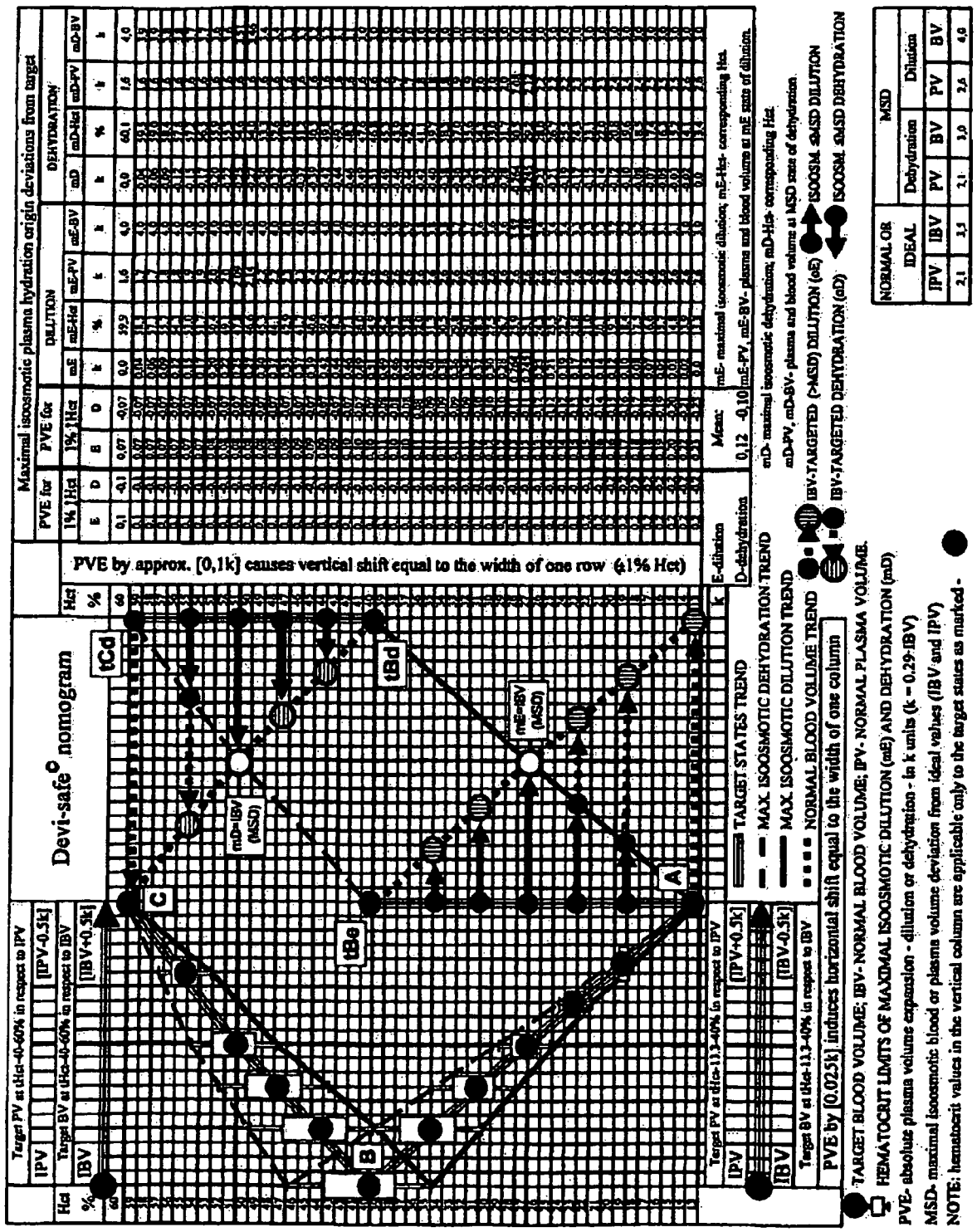
Figure 16:
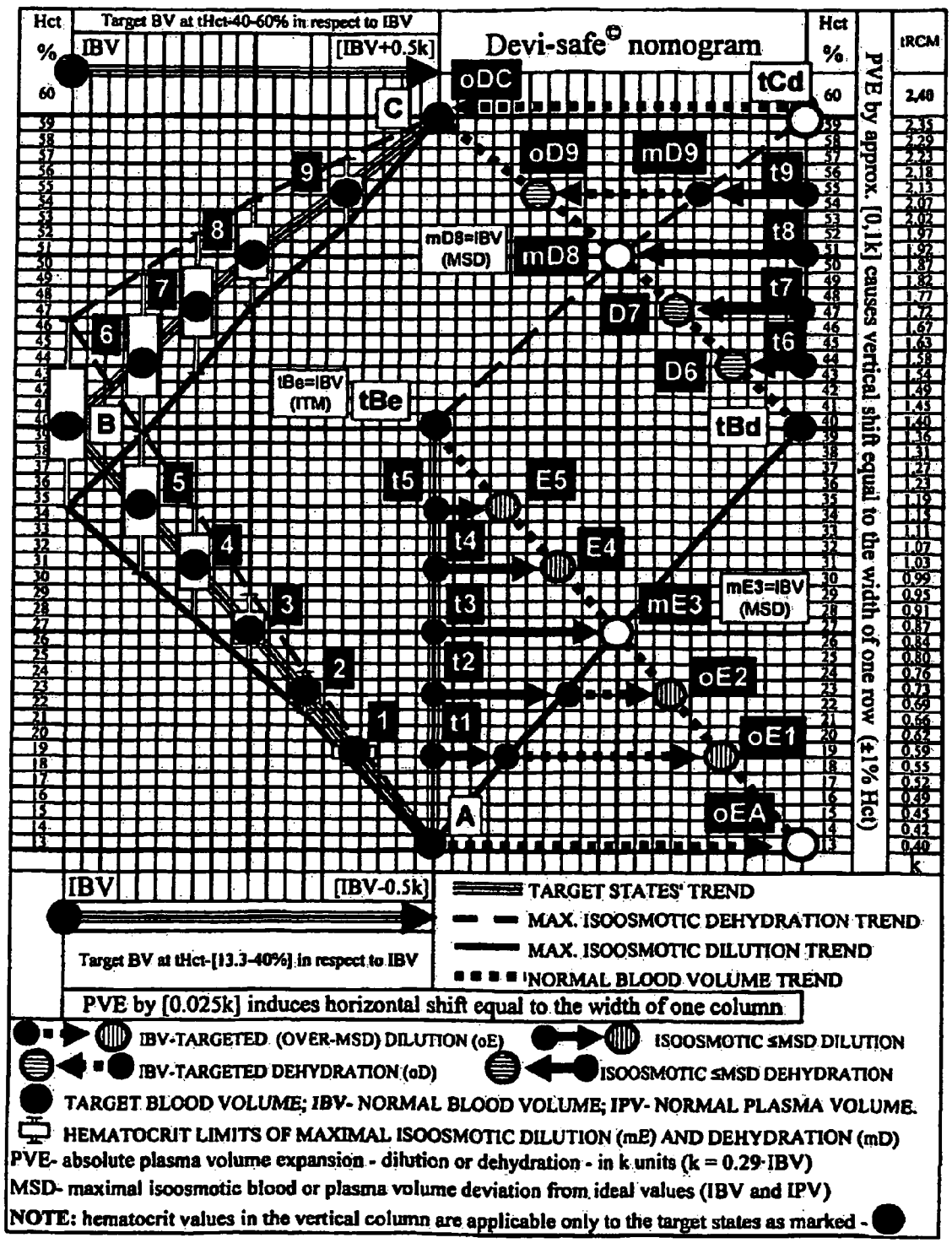
Figure 16:
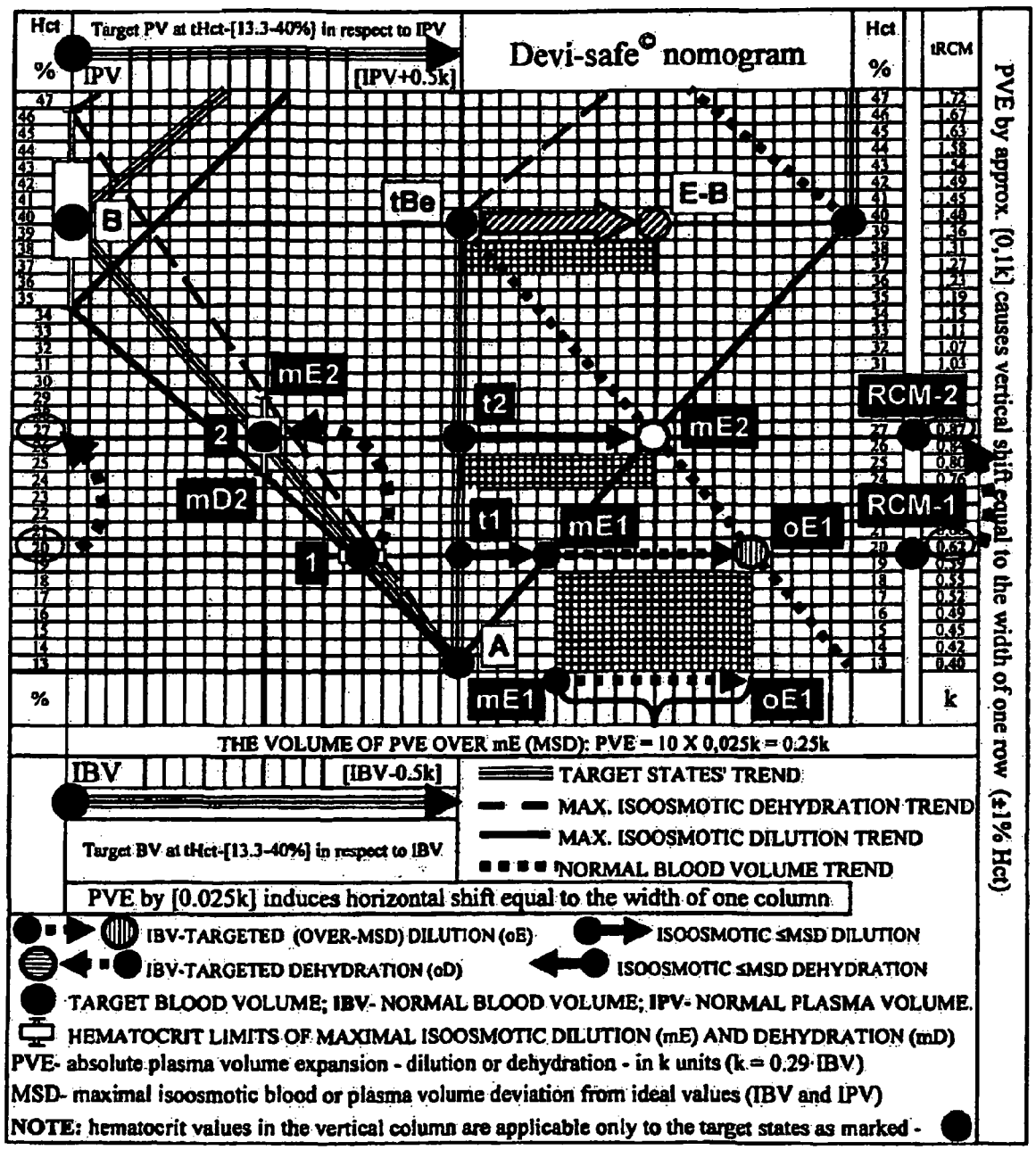
Figure 16:
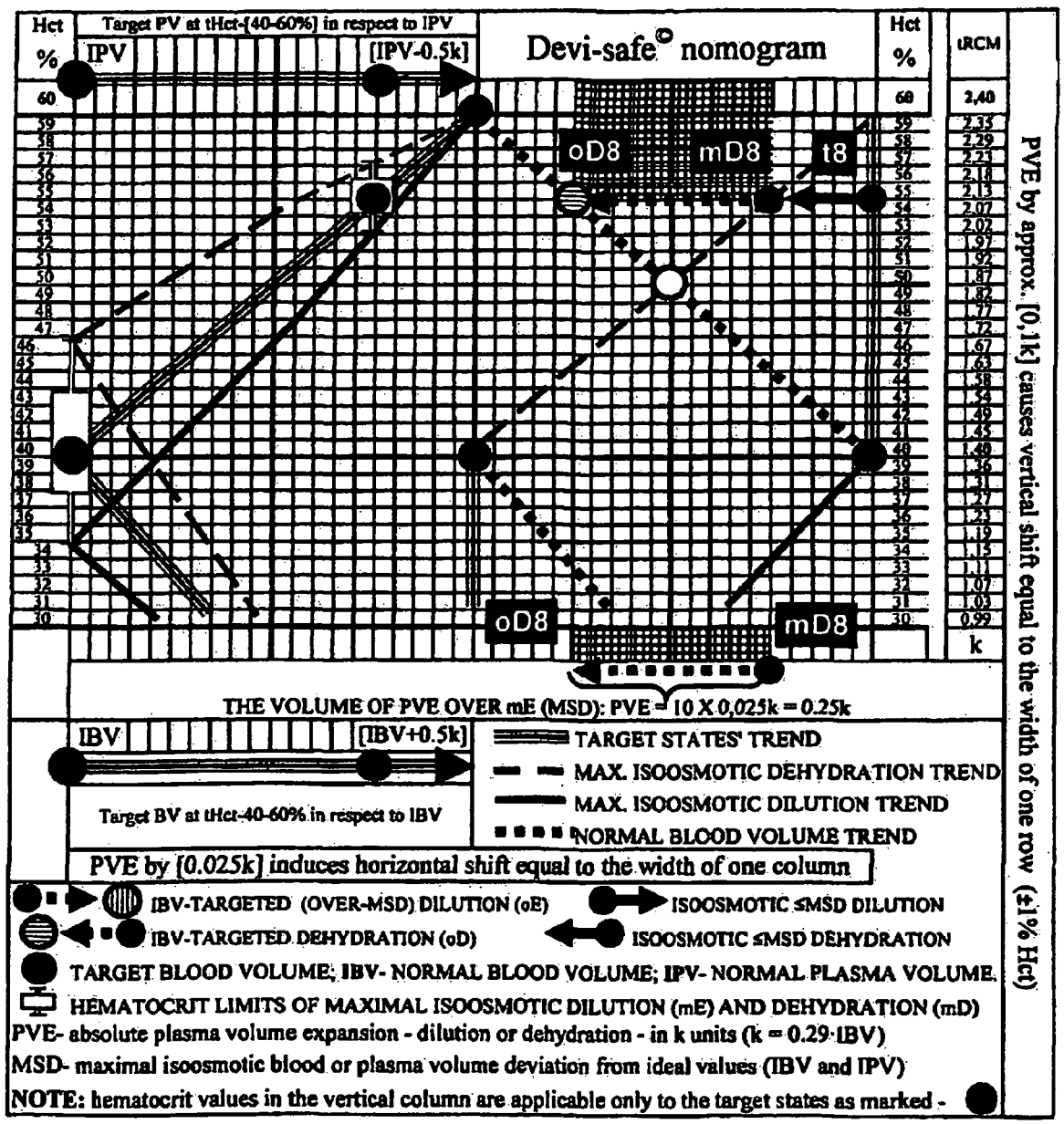

The present inventor has discovered the HBS Nomogram, later referred to as Nomogram, which is created on the basis of the above described mathematical model—HBS Trends. The graphical background for the Nomogram is provided by the HBS Graphics (FIG. 13). The Nomogram has two optional components: the Devi-safe nomogram and Osmonomogram (FIG. 14). They can be used independently from the HBS Nomogram. The Devi-safe nomogram provides an easy and fast evaluation of proper target state (and consequently that) specific limits of isoosmotic deviations. It is also more accurate than basic version of the Nomogram (FIG. 15), which accounts for maximal isoosmotic Hct deviation limits mE and mD on every 1% step of target Hct, meanwhile Devi-safe provides all intermediate values. A modified version of the Nomogram provides the intermediate limits, too (FIG. 16).

HBS Graphics

The present inventor has discovered the HBS Graphics. Linear graphical trends are well known to reflect Hb to Hct ratio dynamics during changes in red blood cell content and isoosmotic plasma dilution. However, hematocrit is also affected by osmotic RCM shifts reflected by the dynamics of the mean cell volume (MCV). Thus, changes in plasma osmolality induce deviations from linear pattern of Hb to Hct ratio.

The HBS Graphics proposed a simple, objective and accurate method for graphical recording and evaluation of the interfering Hb, Hct and MCHC values. This nomogram has a horizontal Hb and vertical Hct coordinate axes, and also the radiating linear MCHC projections referred to as Radiating Lines (RL). All RLs radiate from the zero Hct and Hb point and split on the way downwards (FIG. 13). They are drawn on the basis of the corresponding Hb, Hct and MCHC values as shown in TAB.3. For the ease of locating proper MCHC specific RL, the identification numbers from [−15] to [+15] are used in the Nomogram (FIG. 15). The blood test derived Hb and Hct values are graphically spotted in the Graphics as "Blood Points (BP)" located on proper case specific RL projection, i.e. BP derived from Hb-120 g/l and Hct-35% is located in RL-MCHC-343 g/l encoded as RL[+4] (FIG. 13).

The present inventor has discovered that plasma osmolality fluctuations can be traced by graphical MCHC dynamics in the Graphics: isoosmotic plasma dilution shifts can be verified graphically by Hb to Hct ratio shift along one MCHC (RL) projection line (FIG. 13-A). Plasma osmolality shifts can be induced by blood component transfusions (i.e., fresh frozen plasma) and even by isotonic intravenous solutions, such as Ringer's solution. Therefore, if no changes are present in the contents of circulating erythropoietic brands, changes in plasma osmolality can be verified solely by detected inter-RL (inter-MCHC) shifts in Graphics: increasing MCHC in subsequent blood tests, indirectly shows the increasing osmolality and RBC shrinking (FIG. 13-B); meanwhile, decreasing MCHC reflects the decreasing osmolality and RBC swelling.

Osmonomogram

Figure 20:
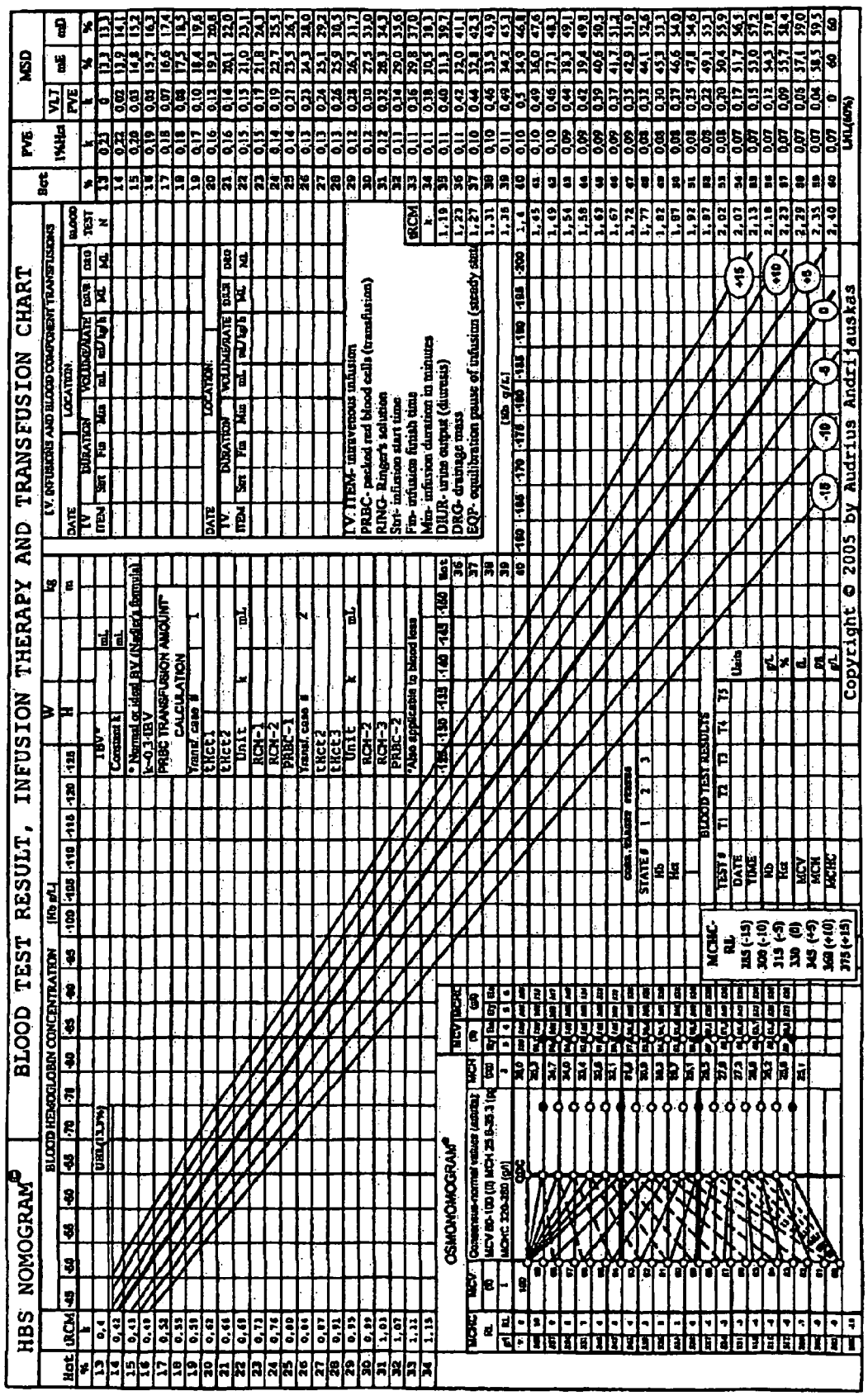
FIG. 20 depicts an optional version of HBS Nomogram with Osmonomogram as a component.
Figure 22:
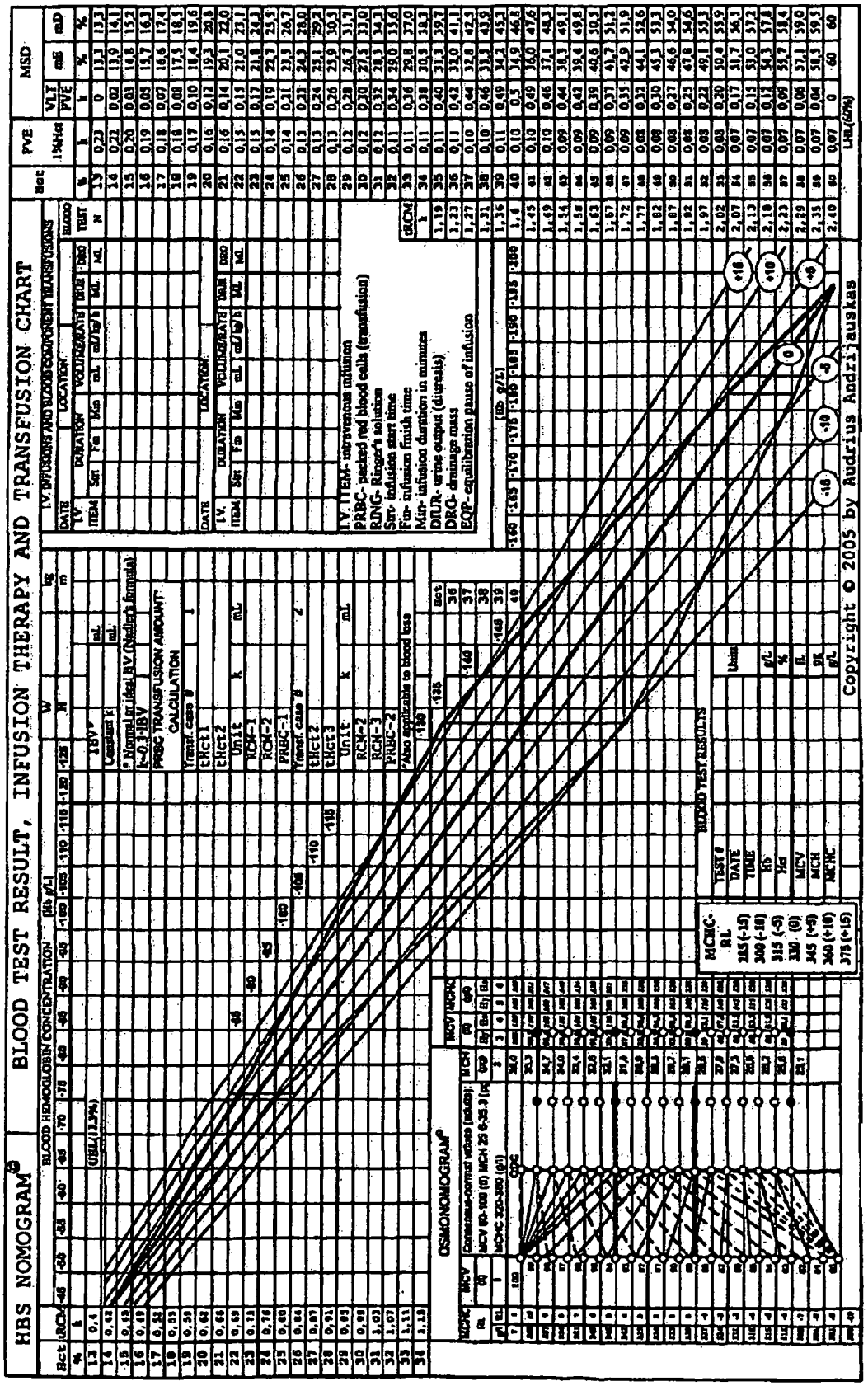
FIG. 22 depicts an optional version of HBS Nomogram with optional Devi-safe nomogram specific trends overlapping graphical background trends and Osmonomogram as component.

The present inventor has discovered Osmonomogram (FIGS. 14A-G) as an independent nomogram that also serves as an optional component of HBS Nomogram (FIGS. 15,20, 22). Earlier in the text, the new mathematical model HBS Trends has shown that plasma osmolality changes are traceable solely by MCHC parameter changes, if erythropoietic blood content remains stable. That concept serves as basis for monitoring plasma osmolality dynamics by inter-MCHC (inter-RL) shifts in HBS Graphics (the major graphical component of the basic HBS Nomogram). However, that method is subject to error resulting from changing erythropoietic blood content, because MCH are not being traced. Meanwhile, Osmonomogram enables more reliable and accurate nomographic evaluation of plasma osmolality shifts, because it traces MCH stability in consequent blood test results as indicator of erythropoietic blood content stability. It also traces the corresponding MCV dynamics. All these parameters are available from conventional blood tests. They are available from the same blood test as Hb and Hct parameters. as Hb and Hct parameters. To some extent that eliminates the need for separate osmolality tests.

An interfering dynamics of plasma osmolality and MCV, MCH, MCHC parameters was described by ODL-model earlier in the text. The nomographic interference of normal MCV, MCH and MCHC values have been investigated in the development of the Osmonomogram (FIGS. 14A-G).

As far as normal MCH interval is treated differently in existing art (FIG. 14A), the present invention has established the MCH limits corresponding to the normal MCV and MCHC intervals: the corresponding MCV trend (Columns 4 and 5 in FIG. 14A) was calculated from critical MCHC values 320 and 360 (g/L) and MCH values within 24-36 (pg) by means of the existing equation:

$$MCV = 1000 \cdot MCH \cdot MCHC^{-1}$$

where MCV—mean cell volume (fl), MCHC—mean cell hemoglobin concentration (g/l) and MCH—mean cell hemoglobin (pg).

The obtained MCV trend (column #1) revealed that only the MCH interval from 29.1 to 32.1 (pg) is consistent with corresponding normal MCV interval and critical MCHC values. With the out of this range normal MCH values 25.6 to 29.1 (pg), the minimal normal MCV is reached with lower than maximal normal MCHC, and similarly with MCH from 32.1 to 36.0 (pg), the maximal normal MCV is reached with higher than minimal normal MCHC. Thus, the new method considers MCH-32.1 pg as Homeostatic High and MCH-29.1 pg as Homeostatic Low limits of MCH parameter.

Based on the above calculations, the nomographic projections of maximal functional hypoosmotic (mHo) and hyperosmotic (mHy) deviations from target states were derived: the declining solid lines are for maximal functional hypoosmotic and dash-style for hyperosmotic MCV deviations from target (tMCV). The term functional means that the interfering parameters—plasma osmolality, MCV, MCH and MCHC—are within inherent normal or critical value intervals. As shown by ODL model (Chapter 4.3.3.), relatively small osm shifts induce big changes in MCV (TAB.2). Note that target osmolality—tOsm—is maintained equilibrated homeostatic target states, while any plasma osmolality deviations from target state are relatively hyperosmotic or hypoosmotic in its respect, although they may stay within normal osm limits.

The Osmonomogram has two standard Maximal Functional Osmotic Deviation (MFOD) projections that originate from every MCH value (column #2) specific points along the vertical Osmotic Deviation Center (ODC) projection: solid lines for maximal hypoosmotic deviations and dash-style for hyperosmotic. As shown in TAB.2 and FIGS. 14C-F, the proper MCH value specific maximal functional hyperosmotic MCV values (mHyMCV) are corresponding to critical plasma hyperosmolality (cmHyOsm-320 mOsm/l), and maximal functional hypoosmotic MCV values (mHoMCV) are corresponding to critical plasma hypoosmolality (cmHoOsm-265 mOsm/l). The corresponding critical MCHC values (hyperosmotic Hy and hypoosmotic Ho) are put in column #5 and #6 adjacent to the corresponding MCH value in column #2. Columns #7 and #8 are optional as they show the MCHC value specific radiating line (RL) codes applied in HBS Nomogram.

Clinical implication is as following. The blood test derived MCH and MCV values are marked in the Osmonomogram© as points connected by the functional osmotic deviation lines (FOD lines) between the corresponding MCV and MCH values, the latter being located on the vertical ODC projection. If consecutive test results reveal the same MCH value, but different MCV, then another connecting line is drawn and the MCV shift is evaluated in respect to osmolality dynamics: the upward inclination means hypoosmotic trend, and approaching the standard maximal functional hypoosmotic deviation limit (heavy line that originates from the same MCH point in ODC) signals about critical hypoosmolality pending; approaching the standard maximal hyperosmotic functional deviation limit (heavy dash-style line that originates from the same MCH point in ODC) signals about critical hyperosmolality pending. Planning and monitoring the osmotically active treatment could be based on that basis: monitoring the continuity of hyperosmotic or hypoosmotic treatment can be visualized and traced without additional blood tests. Baseline test revealed state that is close to critical osmotic deviation limits would alert that osmotic measures should be approached with proper caution.

Devi-Safe Nomogram

Figure 17:
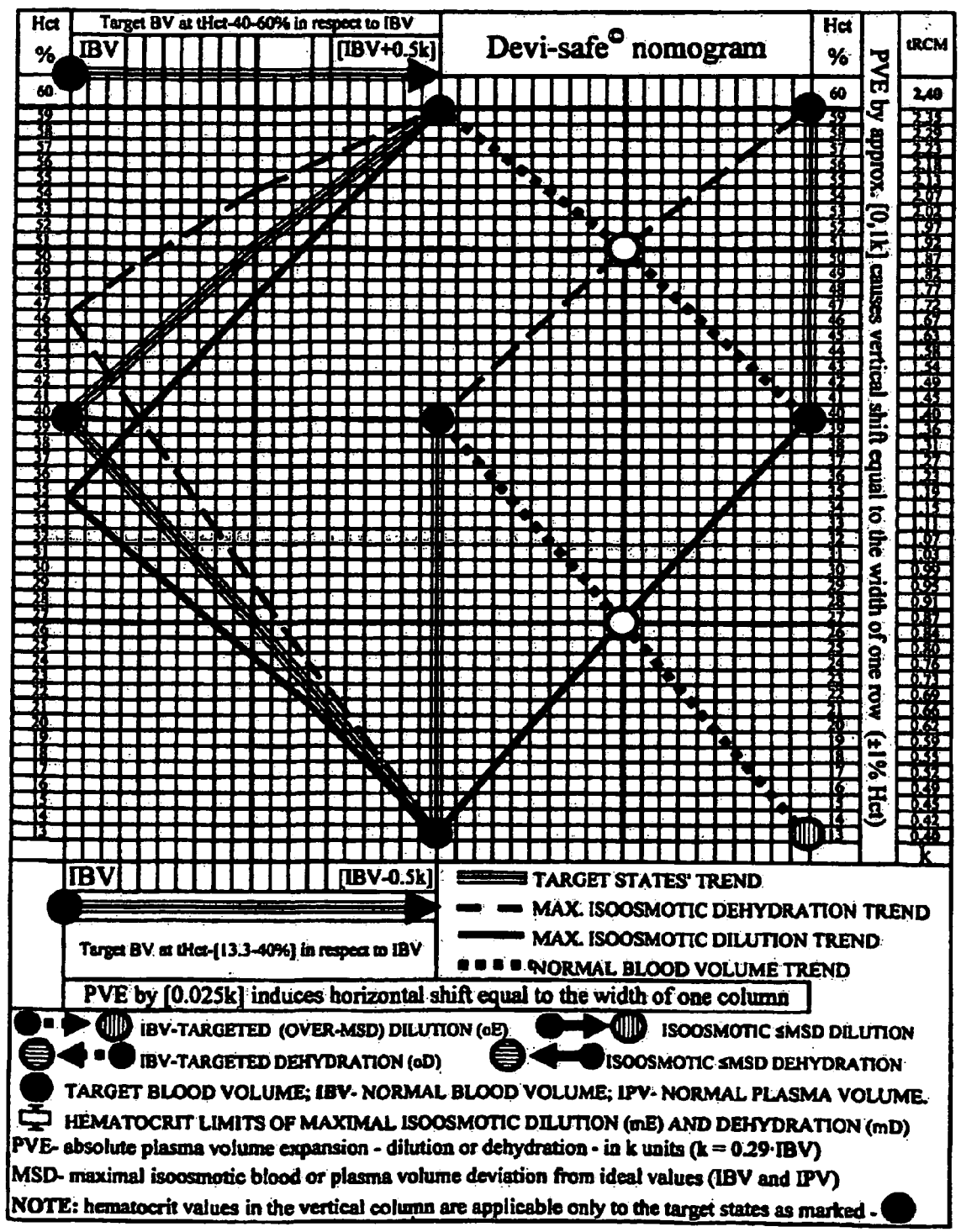
FIG. 17 depicts the Devi-safe nomogram in the form of independent clinical chart.
Figure 18:
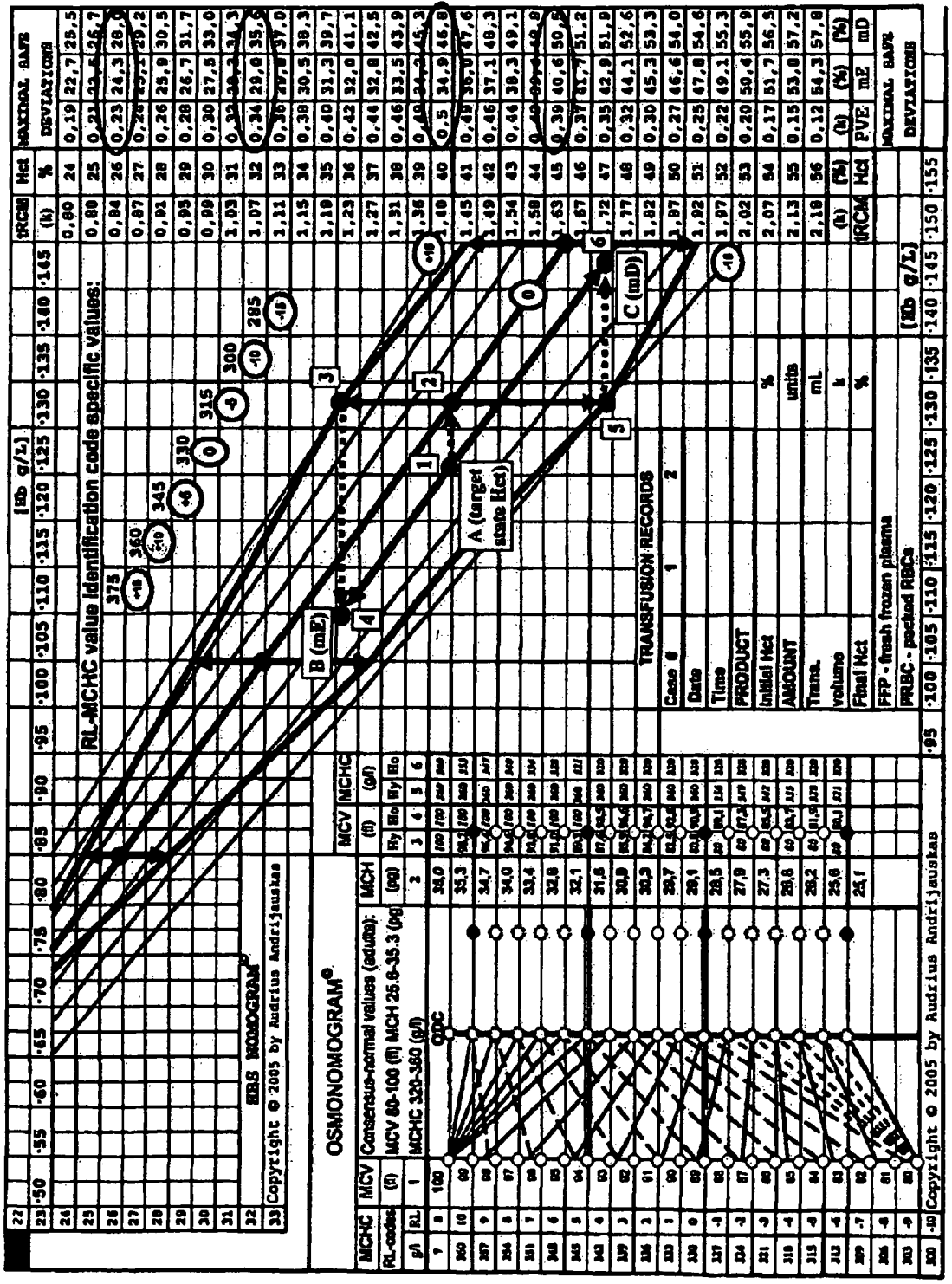
FIG. 18 depicts HBS Nomogram with optional Osmonomogram and Devi-safe nomogram (heavy line-projections provide target state specific limits of isoosmotic deviations: follow the numeric sequence for algorithmic actions).

The present inventor has discovered Devi-safe nomogram (FIGS. 16-17) as an independent nomogram that can also be used as optional part of the HBS Nomogram (FIG. 18). The independent is much more informative than its simplified version applied in the HBS Nomogram.

Independent Devi-Safe Nomogram

The present inventor has discovered an independent Devi-safe© nomogram that has two coordinates axes (FIG. 16A): the vertical is for red cell mass values (tRCM) that are specific to the corresponding values of target hematocrit (that) within the homeostatic Hct range from 13.3% (UHL) to 60.0% (LHL), and the horizontal axis for the target states specific plasma and blood volume deviations from normal.

Values and shifts evaluated in the vertical coordinate axis:
Hematocrit values in the Hct column are specific to target states along the vertical and the declining triple-line style projections (heavy black dots). These Hct values also apply to the vertical isoosmotic plasma dilution origin deviations from target states.
In the left half of the nomogram, the hematocrit values—Hct column—are also applicable to the specific limits of maximal isoosmotic deviations from target states: these limits are along dash-style lines for dehydration and heavy lines for dilution. Corresponding numeric values are provided in the numeric table (FIG. 16A). In the table, the target state specific limits of maximal isoosmotic Hct deviations (mE-Hct for dilution and mD-Hct for dehydration) are provided along with corresponding volumes of plasma volume expansion (mE and mD) and the resulting volumes of plasma (mE-PV, mD-PV) and blood (mE-BV, mD-BV). Mean plasma volume deviations (PVE) specific to maximal isoosmotic shifts from target states on every 1% Hct step-level are provided in the $3^{rd}$ and $4^{th}$ columns: they are exponentially increasing from 0.07 k to 0.23 k with the decreasing target states' Hct value. Their decimal values are shown in the $1^{st}$ and $2^{nd}$ column. The mean PVE per 1% Hct deviation is shown equal to 0.12 k for dilution and 0.1 k for dehydration, where k=0.29·IBV and IBV can be calculated by formula for individual normal blood volume preferred by the user. However, these mean values are unacceptable at low target hematocrit values (step-PVE reaches 0.16 k at tHct-20% and 0.22 k at tHct-14%). Note that plasma volume expansion and corresponding Hct shifts are exponential and compartment expansion dependent, as clearly shown by studies on volume kinetics. Therefore it is not recommended to use the mean value (vertical step value in the nomogram) in any calculations for plasma volume expansion and corresponding Hct shifts. However, the plasma expansion volume in respect to target states can be reliably calculated by means of horizontal step values as described below. Nevertheless, the mean PVE step-values can be used for general references. In general, the Hct trend is used there to monitor target Hct and dilution origin deviations from it per se.

Values and shifts evaluated in the horizontal coordinate axis:
The left half of the nomogram shows the target blood and plasma volume deviations from ideal (normal) values IBV and IPV, accordingly; they are specific to target states and circulating red cell mass (tRCM) at different Hct levels (heavy black dots on the declining triple line-style projections); normal values—IBV and IPV—are met only in target state B at ITM-Hct-40%; the horizontal nomographic deviation step-value is the mean value equal to 0.025 k, where k=0.29·IBV; the IBV value of an individual can be calculated by formula for normal blood volume preferred by the user. Example: target state at Hct-27% maintains tRCM-0.87 k and target blood volume that is by 10 horizontal nomographic steps from target state B, which is at ITM-Hct-40%; it means that its tBV is by 10×0.025 k or 0.25 k volume less than normal (IBV), while its tPV is by the same amount higher than normal (IPV). (FIG. 16B)
The right half of the nomogram shows deviations from target states referred to as plasma volume expansion (PVE) from target values tBV and tPV, accordingly; deviations are specific to target states at different Hct levels (heavy black dots on the vertical triple line-style projections); the declining heavy line is for limits of maximal isoosmotic dilution origin deviations (mE), and heavy dash-style line—for dehydration origin limits; the declining dot-style projections are for states that maintain normal blood volume, while being appropriately diluted or dehydrated in respect to corresponding target state. The horizontal nomographic deviation step-value is the same as for the left half of the nomogram.
Examples: target state at Hct-27% has a potential to be isoosmotically diluted up to the maximum plasma expansion (PVE) by 10 horizontal nomographic steps from target state t3 to mE3, and reach the state of normal blood volume: its maximal isoosmotic PVE is 10×0.025 k or 0.25 k (FIG. 16C). Meanwhile, target state t8 can be dehydrated up maximal isoosmotic limit mD8 by the same PVE-0.25 k volume and also reach normal blood volume then (FIG. 16D). Other target states have limits of maximal isoosmotic deviations that are less than normal blood volume (A, tCd, t9, t2, t1) or overcome it (t7, t6, B-tBe-tBd, t7, t6, t5, t4).

Mini Devi-Safe© Version as Optional Component of the HBS Nomogram

The present inventor has discovered the Mini Devi-safe version as optional part of Nomogram provides target state Hct specific limits of maximal safe (isoosmotic) deviations (FIG. 18A). Limits are shown as heavy lines crossing the radiating MCHC specific lines—RL—in the HBS Nomogram. These lines are referred to as Safe Deviation Lines (SDL). They meet twice in the RL-0 (MCHC-330 g/l): on the level of the homeostatic Hct limits—13.3% (UHL) and 60.0% (LHL). These projections also meet once close to RL(+15) and once—close to RL(−15), at Hct-34.9% and Hct-46.8%, accordingly. The vertical upward (maximal isoosmotic dilution) and downward (maximal isoosmotic dehydration) deviations from RL-0 to SDL are specific on every Hct level. Deviations are applicable to target states regardless of RL (MCHC) specificity. Therefore, proper algorithm is followed to obtain limits specific to target states in RLs other than RL-0 (MCHC values other than 330 g/l):

Step 1. Verify target state's (tl) Hct and Hb (MCHC value is unnecessary, because marking Hct and Hb in the Nomogram provides an approximate MCHC value); mark it #1 in the Nomogram; assume it is in RL-(−5) that is MCHC-315 g/l specific; (FIG. 18)

Step 2. Follow the horizontal projection to the RL-0; mark that point #2;

Step 3. Follow the vertical projection upwards till it hits the appropriate SDL projection for dilution; mark it #3;

Step 4. Follow the horizontal projection to the RL-(−5); mark it #4; this is the limit of maximal isoosmotic dilution for the target state t1;

Step 5. Follow the vertical projection downwards till it hits an appropriate SDL projection for dehydration; mark it #5;

Step 6. Follow the horizontal projection to the RL-(−5); mark it #6; this is the limit of maximal isoosmotic dehydration for the target state t1.

Although Hct deviation limits inherent to 1% Hct steps could be provided by the maximal safe deviation column in the Nomogram, the SDL projections provide values inherent to the intermediate Hct levels.

Figure 19:
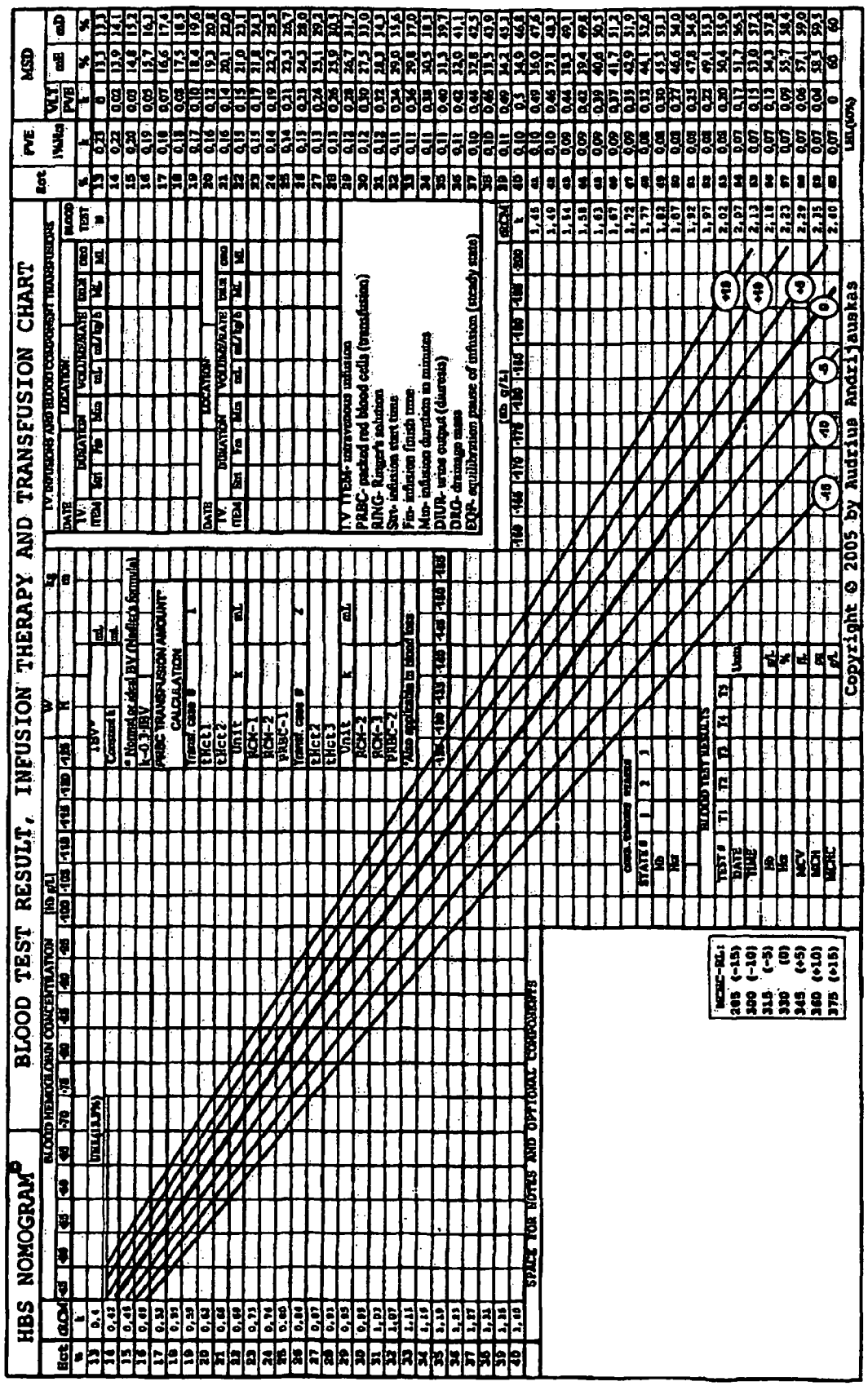
FIG. 19 depicts A the basic version of HBS Nomogram; B optional version of HBS Nomogram with optional Devi-safe nomogram specific trends overlaping graphical background trends.
Figure 19:
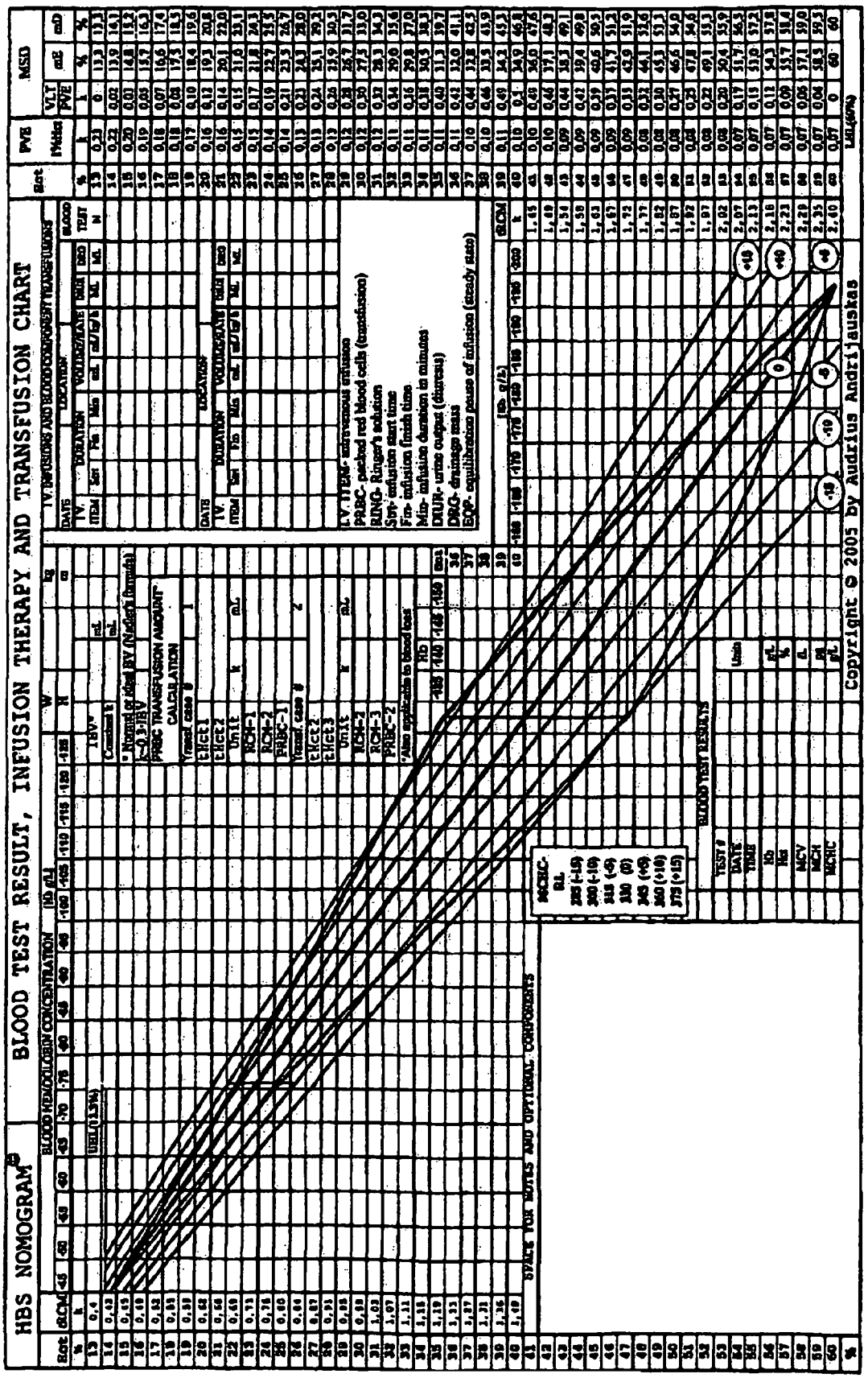
Figure 21:
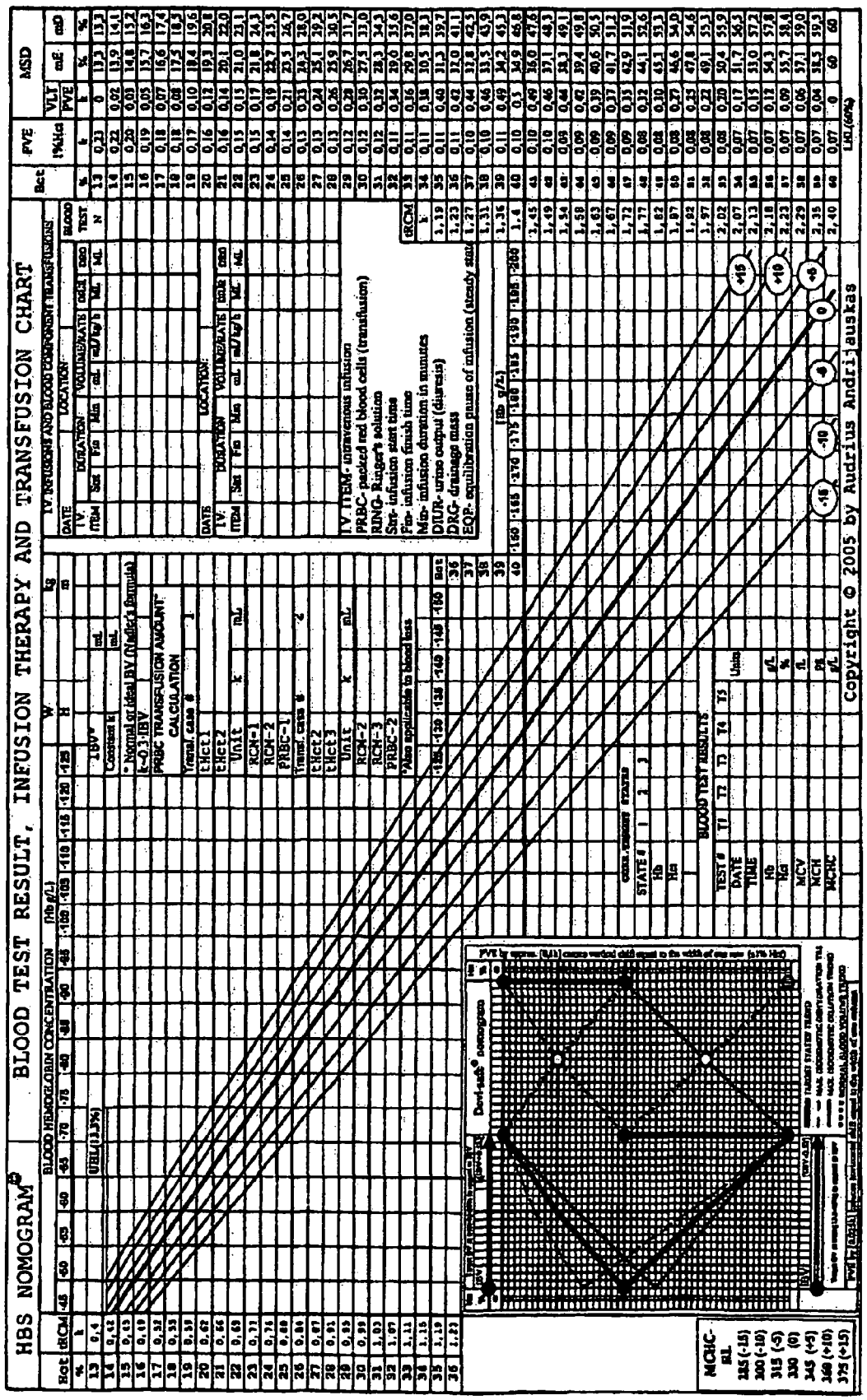
FIG. 21 depicts an optional version of HBS Nomogram with Devi-safe nomogram as a component.

The main versions of optional component combinations in the HBS Nomogram are shown in FIGS. 19B and 21, 22. Note that all nomograms contain numeric tables consisting of the following data columns:

Hct—blood hematocrit (%) applicable to target states and their derivatives tRCM—target state (and target Hct) specific circulating red cell mass PVE/1% Hct—the 1%Hct-step-specific mean plasma volume expansion in respect to target states on every horizontal target Hct level (applicable to estimation of approximate Hct decrease in respect to target states due to residual plasma dilution induced by intravenous colloid infusions; volume kinetic modeling should be applied for better accuracy)

VLT-PVE—volume of intravenous isotonic crystalloid solution (k units) to be used during the volume loading test—VLT-test—in target states' verification process (Chapter 4.4.3.)

mE—target state specific limit of maximal isoosmotic plasma dilution (maximal isoosmotic dilution state's Hct value in %)

mD—target state specific limit of maximal isoosmotic plasma dehydration (maximal isoosmotic dehydration state's Hct value in %).

APPLICABILITY

The present inventor has discovered the HBS Method and its major instrument—HBS Nomogram©—applicable to major experimental and clinical applications.

The key concept of the new method is the concept of homeostatically maintained red cell mass specific target blood volume instead of conventionally assumed normal or ideal blood volume. The concept claims that blood volume is homeostatically adjusted to circulating red cell mass in the way that absolute blood volume deviation from normal is equal to corresponding plasma volume deviation. Meanwhile, normal or ideal blood and plasma volumes are both assumed to be homeostatically maintained as homeostatic target state only at hematocrit of so called Ideal Total Match (ITM). The new theory advocates that ITM is the Hct-40% level, which is suggested as starting point in the verification process. The basic clinical and experimental algorithm—the Volume Loading Test (VLT-test)—was proposed for uncovering and verifying of target states and their derivatives. It sets the case for future research.

The proposed new unit of volume measure in the nomograms—Constant k—is the fraction of calculated normal blood volume. The latter can be calculated by any method for normal blood volume calculation preferred by the user. It makes nomographic values universally applicable to any individual.

The Constant k was also used for establishing target states specific (consequently, target Hct specific, too) limits of homeostatically justified isoosmotic plasma dilution in respect to target states. These limits were derived by means of new models—Homeostatic Hematocrit Limits (HHL) and Osmotic Deviation Limits (ODL). For the above purpose, the new theory advocates the critical Hct limits—the lowest or Upper Homeostatic Limit (UHL) equal to Hct-13.3%, and the highest or Lower Homeostatic Limit (LHL)—Hct-60%. Nevertheless, these models proposed a method of investigating alternative settings, thus encouraging further research.

Plasma volume expansion trends in respect to target states were introduced as target states specific volumes of critical (maximal isoosmotic) hydration or dehydration at every 1% Hct step. Fluid compartment expansion dependent and infusion solution specific kinetic data, however, are not provided. Therefore it is not clear what rates of specific infusion solutions can reach and maintain proper plasma dilution overriding target states. The same issue is choosing the type and infusion rate for maintenance of the target state. All it needs future investigation, most likely based on volume kinetics, which is developed by Dr. Hahn and his colleagues.

Osmotic plasma deviations were shown as being traceable by blood hemoglobin concentration, hematocrit and mean cell hemoglobin content parameters.

All the above is finally introduced in the way of clinical charts, also offering a new way of recording, filing and analyzing data in patient's medical records. The basic HBS Nomogram and its versions with optional Osmonomogram and Devi-safe nomograms are described in the following chapters by examples of clinical application. Some of the author's pilot clinical investigations, reported in recent publications and unpublished material, are also described.

Monitoring Red Blood Cell Content

The HBS Nomogram (FIG. 23A) and Devi-safe (FIG. 23B) nomograms are independently applicable to monitoring of circulating RBC content as target state hematocrit specific red cell mass (tRCM). Blood test derived Hb and Hct values can be graphically spotted as Blood Points (BP) located on case specific RL (MCHC) projection in all versions of the HBS Nomogram (FIGS. 19-22), while Devi-safe uses only the Hct parameter, and does not specify the corresponding Hb and MCHC values.

As shown in FIG. 23A, the BP-3 is derived from blood test results revealing the Hb-126 g/l and Hct-40%. The BP-3 is located in RL-MCHC-315 g/l projection encoded as radiating line RL(−5). The same BP-3 is spotted in the Devi-safe nomogram (FIG. 23D) by locating it on the triple-line style projections used for target states according to the only one parameter—target state specific Hct.

Target states Hct specific circulating red cell mass volumes are provided along the vertical numeric column (tRCM) in both nomograms. These values are put on the horizontal 1% Hct step levels within the homeostatic Hct range (13.3 to 60%). Volumes are expressed in fractions of the specific unit of measure—Constant k. It is a 0.3 fraction of the individual calculated normal blood volume—IBV, which is the body weight and height or the body surface area specific, depending on the method of calculation. That makes tRCM values individual.

The first thing to do when using HBS Nomogram, is to calculate individual normal blood volume by means of formulas preferred by the user. Then individual value of Constant k is derived and applied to calculation of target Hct specific tRCM values (and any other volumes provided in the Nomogram).

The target state 3 (BP-3) specific tRCM−3=1.4 k is on the horizontal Hct-40% level in nomograms as shown in FIGS. 23A, D. Assuming patient's weight 70 kg and height 1.70 meters, the calculated normal blood volume (IBV) is 4.660 ml (Nadler's formula). Thus, target state 3 (BP-3) and tHct-40% specific circulating red cell mass (tRCM-3) is calculated as following:

tRCM−3=1.4 $k$=1.4×0.3IBV=1.4×0.3×4660=1864 (mL)

The tRCM values are specific only to target states and their plasma dilution origin derivatives. Therefore, clinical verification of these states has the major importance. The new method has introduced the VLT-test (FIG. 24A) for this purpose. However, states of advanced abnormal body fluid handling make the task challenging. Blunted sympathetic tone (i.e., anaesthesia) also has a specific influence on the homeostatic processes involved. Therefore nomographic red cell mass values are to be used with caution. In complex cases, they need to be supported by data derived from specific modalities of circulatory monitoring, etc. Specific algorithms need to be developed by future research.

Calculating Transfusion Amount and Blood Loss

Amount of PRBC transfusion required for proper tHct, tHb and tRCM increase from target states can be calculated by means of HBS Nomogram or an independent Devi-safe nomogram. Blood loss can be evaluated in the very similar way.

When the pre-transfusion target state specific tRCM is established as described in the previous chapter on an example of patient weight 70 kg and height 1.70 meters, the next step is to determine the post-transfusion target state that is to be approached by means of PRBC transfusion.

In FIGS. 23A, B, the pre-transfusion target state #1 (Hb-63 g/L, Hct-20% and MCHC-315 g/L) spotted as BP-1 is shown "upgraded" by PRBC-1 (0.25 k or 335 ml) transfusion up to the target state 2 (Hb-85 g/l, Hct-27% and MCHC-315 g/l). The amount of PRBC transfusion is the difference of post-transfusion tRCM-2 (0.87 k or 1.164 ml) and pre-transfusion RCM-1 (0.62 k or 828 ml): the difference is equal to 0.25·k or 335 ml volume of PRBC transfusion.

The Nomogram offers an advantage of calculating the PRBC volume required to reach either Hb or Hct increase targets monitoring both of them, while Devi-safe considers only Hct parameter.

CLINICAL CASE EXAMPLE #1

A 35 years old male patient has been delivered to the emergency room by an ambulance with acute bleeding from the cut of the femoral artery. The bleeding has been temporary stopped by an ambulance paramedics. Two intravenous infusion lines were established and high rate IV infusions of isotonic crystalloid solutions were maintained on the way to the hospital. On the arrival, the patient was conscious, there were no signs of pending shock. Patient's initial evaluation suggested that he was ASA physical state class I, his weight was about 70 kg and height approximately 1.70 m. He was taken to the operating theater immediately after arrival. The initial blood test results showed low Hct (23%). Surgery has been made under the local anesthesia, because patient refused to be other way anaesthetized. Visible blood loss in the suction device was 500 ml. During the 30 minute long surgery, patient has been managed by an anesthetist, who transfused him with several units of packed red blood cells and delivered 800 ml of isotonic crystalloid (NS) solution. Urine output was negligible.

Suddenly, the patient's blood pressure started decreasing, although bleeding has been completely stopped. The 335 ml of HES hetastarch (concentration 6%, Mw 450 kDa, MS 0.7) solution has been infused and another blood test (T1) was taken. It revealed Hct-18.6% and Hb-58.5 g/l. Based on the nomographic calculations, the 335 ml of PRBC were transfused with a purpose to reach Hct-25.1-27.0% and the corresponding Hb-80-85 g/l, which are appropriate values for a young ASA I patient. Afterwards, the patient was taken to the recovery unit, and for another 20 minutes patient was stable with the low maintenance rate (3 ml/kg/h) infusion of isotonic crystalloid (NS) solution. At that time another blood test (T2) has been taken, revealing immediate postoperative Hct-25.1% and Hb-79.0 g/l. Unexpectedly, the patient has developed signs of severe anemia intolerance. Additional 700 ml PRBC were transfused with a purpose of reaching Hct-37.5-40% and corresponding Hb-118-126 g/l values, which are close to normal. For another 20 minutes after transfusion the patient was stable with the low maintenance rate (3 ml/kg/h) infusion of isotonic crystalloid (NS) solution. At that time another blood test (T3) has been taken, revealing immediate postoperative Hct-37.5% and Hb-118 g/l. Note that 20 minutes long low maintenance rate (3 ml/kg/h) infusion of isotonic crystalloid was performed prior to blood samples for the purpose of providing a kind of steady state for the plasma fluids to complete an acute equilibration with the extravascular space (equilibration pause).

Acknowledging that there is not much use of the nomogram in the management of the intensive bleeding, the 'Blood test result, infusion therapy and transfusion chart' (FIG. 23) has been started by anaesthetist in the operating theater after the bleeding has been completely stopped. The initial bleeding management measures were also ignored in the Chart. However, it has been used for the rest of the patient's stay in the hospital. After surgery, the Chart has been used for guiding the postoperative infusion therapy and monitoring for occult bleeding as described in Clinical Case Examples #2 and #3.

Nomographical (FIGS. 23A-D) and clinical interpretation:

The 'Blood test result, infusion therapy and transfusion chart' (FIG. 23), later referred to as Chart, has been started by anaesthetist in the operating theater after the bleeding has been completely stopped. It was just after 335 ml of HES hetastarch (concentration 6%, Mw 450 kDa, MS 0.7) has been infused for patient's hemodynamic stabilization. At that time, the first recorded in the Chart blood test (T1) has been taken. It has revealed Hct-18.6% and Hb-58.5 g/l recorded as nomographic point T1 in the nomograms. Is it the characteristics of homeostatic target state or its hydration origin derivative? To answer the question, proper clinical evaluation has been made at the time of blood sampling:

a) Patient's hydration state evaluation. There were no signs of dehydration or overhydration: the current basal diuresis and prior infusion therapy regimen were considered as adequate to maintain the normal hydration state;

b) Evaluation of residual plasma dilution resulting from prior infusion therapy measures. An expected residual effect of treatment with isotonic crystalloid solutions was the maintained target plasma dilution (homeostatic target state); meanwhile, the colloid infusion (335 ml of HES hetastarch 6%, Mw 450 kDa, MS 0.7) just before obtaining the blood test (20 minutes prior to sampling) suggests an excessive—over the target state—residual plasma dilution that approximates 100% of the infused HES volume. That residual colloid-induced plasma dilution is expected to last for another couple of hours at minimum; therefore, appropriate over the target state plasma dilution has to be considered in the evaluation of blood test results obtained throughout the colloid solution specific duration of volume expanding effect.

Conclusion At the time of taking blood tests T1, T2 and T3, the temporary over the target state plasma dilution—plasma volume expansion (PVE)—should be equal to the volume of the recently infused colloid solution (335 ml HES).

Action An independent Devi-safe© nomogram has been used in addition to the basic HBS Nomogram [the Chart] (FIGS. 23B-D) in order to evaluate the influence of the over-target plasma dilution on blood test results:

Corrections to the blood test results. Blood test T (FIG. 23A) is assumed to reflect the persisting temporary plasma volume expansion (PVE) of 335 ml over target volume; conversion of PVE volume into specific units of measure—constant k—is made as following: the normal blood volume (IBV) calculated by Nadler's formula on the basis of patient's weight and height was 4.660 ml. Therefore k is equal to 1.330 ml (~0.3·IBV), and consequently the PVE is 335 ml or 0.25 k. The mean over-target PVE=0.16 k consistent with 1%-Hct decrease specific to the target state #1 at Hct-20%, is taken from the numeric column [PVE/1%Hct] in the Chart (FIG. 23A). Therefore, target state's plasma dilution by 0.25 k (335 ml HES) would result in the calculated Hct decrease from target state specific value tHct-20% (point 1) to 18.6% (point T1), the latter confirmed by blood test T1. Conclusion: the tHct-20% specific target state #1 (t1) corresponds to over-target dilution origin derivative state E1 at Hct-18.6% (blood test T1).

Spotting blood test results and corresponding target states in nomograms. Blood test T1 results (Hct-18.4%, Hb-58.5 g/l) were marked as blood point T1 on the RL(−5)—MCHC-315 g/l projection in the Chart (FIG. 23A), also as point E1 in the middle of the osmotic shift [mE1-oE1] towards normal blood volume on the target level (tHct-20%) in the independent Devi-safe© nomogram (FIG. 23B). This nomographic location (E1) shows that blood volume is by 0.125 k lower than normal (dot-style IBV projection) despite plasma expansion over the target state by colloid infusion: point E1 is by 5 horizontal steps below IBV, and additional volume expansion of PVE=0.25 k would be required to reach normal blood volume (note that the horizontal shift step-value for plasma volume expansion is equal to 0.025 k; see Chapter 4.5.3.). With no further PRBC transfusions, the blood would approach the corresponding target state #1 after the resolution of colloid induced over target plasma dilution. In FIG. 23B, the corresponding target state #1 specific point 1 is by 15 horizontal steps away from the vertical IBV projection, and similarly, point t1 is by the same number of steps away from the dot-style IBV projection; thus, the maximal isoosmotic dilution over the target t1 up to point mE1 needs PVE1=0.125 k consistent with 5 horizontal steps from target states specific vertical triple-line style to the declining heavy solid line projection. However, mE1 is far below normal blood volume, and additional volume expansion of PVE2=0.25 k by 10 horizontal steps is required to reach IBV). The normal blood volume (IBV) would have been reached if additional 0.125 k (166 ml) volume of colloid solution was infused and the nomographic point oE1 would have been reached. However, it would be justified if no PRBC are planned, because residual plasma expansion by colloid could cause circulatory overload following the PRBC transfusion. Another possibility of reaching IBV is reaching the maximal isoosmotic plasma dilution point (mE) by crystalloids and then inducing the osmotic (oncotic) shift to oE by 0.25 k volume load of colloids. However, in the case discussed, the crystalloid solution volume load was not as one needed for maximal isoosmotic plasma dilution over the target (volume kinetic studies have provided overwhelming evidence confirming that over the target volume plasma expansion is achieved by I.V. isotonic crystalloid solution load accounting for 3-5% residual plasma volume expansion; it would require up to 5.541 ml of high rate infusion).

Calculating the amount of PRBC transfusion. Minimal acceptable Hb for that young ASA I patient, like the one discussed, could be Hb 70-80 g/l. Thus, the anesthesiologist's decision was to increase target state specific Hct up to 27%, which is consistent with Hb-85 g/l (FIG. 23A). The pre-transfusion tHct-20% specific red cell mass was tRCM1-0.62 k, therefore transfusion 0.25 k volume of packed red cells (PRBC) would increase tHct from 20% to 27% (FIGS. 23A, B). The PRBC volume is calculated as RCM difference: 0.87 k-0.62 k=0.25 k, where k is equal to 1.330 ml (~0.3·IBV), and consequently the PRBC is 335 ml.

Residual plasma dilution after PRBC transfusion. Target state #1 spotted on the triple-line style projection in the left half of the Devi-safe© nomogram (FIG. 23B) shows that specific target blood volume at Hct-20% is by 0.375 k less than IBV and plasma volume exceeds normal by the same volume. The post-transfusion target state #2 spotted on the triple-line style projection at Hct-27% in the left half of the nomogram shows that specific target blood volume is by 0.25 k less than IBV and plasma volume exceeds normal by the same volume. These values will be reached after colloid induced temporary plasma dilution resolves. As far as residual plasma dilution by colloids was persistent at the moment of transfusion, the post-transfusion state should maintain IBV at post-transfusion nomographic point mE2 (FIG. 23C). Note that this is not a target state, but an osmotic plasma dilution derivative that maintains the maximal isoosmotic plasma dilution mE-Hct-25.1% confirmed by the blood test T2. This state maintains normovolemia under the normal vasomotor tone, which is a plausible clinical effect. The post-transfusion test (T2) revealed Hct-25.1% that was by 1.9% lower than corresponding target state #2 specific value (Hct-27%), because tHct-27 specific mean PVE=0.19 k/1% Hct. The residual PVE caused by previous colloid infusion has reached the post-transfusion IBV target without corresponding extravascular space expansion (edema), meanwhile the same state (mE) of over the target plasma expansion could have been reached by nearly 20 times bigger intravenous load of isotonic crystalloid solutions. It would cause generalized edema with negative consequences that could overcome the clinical benefit of maintaining IBV. However, both cases may cause dilution origin coagulopathy, but it should not be significant, because plasma volume expansion is not high (335 ml). Higher volume of pre-transfusion colloid infusion (conventional practice!) would have caused the more significant post-transfusion plasma dilution and coagulopathy due to overridden maximal isoosmotic plasma dilution limit (mE). It has been avoided by tailoring the corresponding colloid infusion volume and blood transfusion amount by means of new nomograms.

Similar investigations of the 2nd recorded PRBC (0.53 k or 700 ml) transfusion show that the post-transfusion homeostatic state E3 maintains temporary osmotic plasma dilution over the target state #3 for the amount of previous colloid infusion (FIG. 23D): the corresponding target state #3 (t3) would maintain normal blood volume, but residual plasma dilution due previous colloid infusion resulted in plasma dilution causing blood volume overload by the amount of infusion (335 ml or 0.25 k). However, male individuals are used to blood volume that exceeds normal calculated value, because inherent normal male Hct and Hb values are over the ITM-Hct-40%. Thus, the patient discussed has tolerated it perfectly.

Monitoring Plasma Hydration

Conventional methods for monitoring plasma hydration as reflection of the whole body hydration state cannot effectively and reliably deploy the consequent blood tests derived Hct and Hb dynamics. The new method proposed a brand new approach.

CLINICAL EXAMPLE #2

The same patient as in example #1 was monitored for plasma hydration state by means of the new nomograms on the next day following surgery. He was hyperthermic during the night after surgery, but has not received intravenous fluid resuscitation. He was not taking fluids orally either. Signs of dehydration were obvious in the morning. The volume loading test (VLT-test, Chapter 4.4.3.) in the beginning of infusion therapy showed advanced dehydration and plasma hyperosmolality.

During the postoperative night, the patient became severely dehydrated due to hyperthermia induced increased fluid loss with no rehydration measures applied. The temporary plasma over the target state dilution (T3 in FIG. 23A and E3 in FIG. 23D) due to previous (perioperative) colloid infusion has resided by that time, too. Therefore, during the night plasma dilution has returned to normal (target state #3) and later decreased to the state of the maximal isoosmotic dehydration (T5 in FIG. 24A and mD3 in FIG. 24B), later advancing to hyperosmotic state (T4 in FIG. 24A). The volume loading test (VLT-test) has recovered the target state #3 specific plasma hydration and provided target state tHct-40% specific blood volume, also established the target state's characteristics: tHct-40%, tHb-126 g/l, circulating tRCM-1.4 k, where k is equal to 1.330 ml (~0.3·IBV), and consequently tRCM-3=1.864 ml, tBV3=4.660 ml, tPV3-2.756 ml.

The process (FIGS. 24A,B):

Baseline or pre-test Hct value was established by taking the blood test T1;

Individual normal blood volume (IBV) calculated by Nadler's formula has been recorded in 'Blood test result, infusion therapy and transfusion chart' (FIG. 23A) a day before (during surgery).

Amount or test volume load (TVL) of Ringer's solution was calculated as following:
1). The TVL value was taken from the numeric column [VLT-PVE] in nomograms—it is on the level of previously established target tHct-ITM-40% (the last postoperative target state #3 specific value). Note that baseline Hct-42.7% value (T4) would be used instead, if previously established target state was not available or bleeding was present; the TVL is equal to 0.5 k at tHct-40% level; 2). As described in Example #1, an individual k value is equal to 1.330 ml (~0.3·IBV), and consequently TVL=0.5 k=665 ml.

Figure 24:
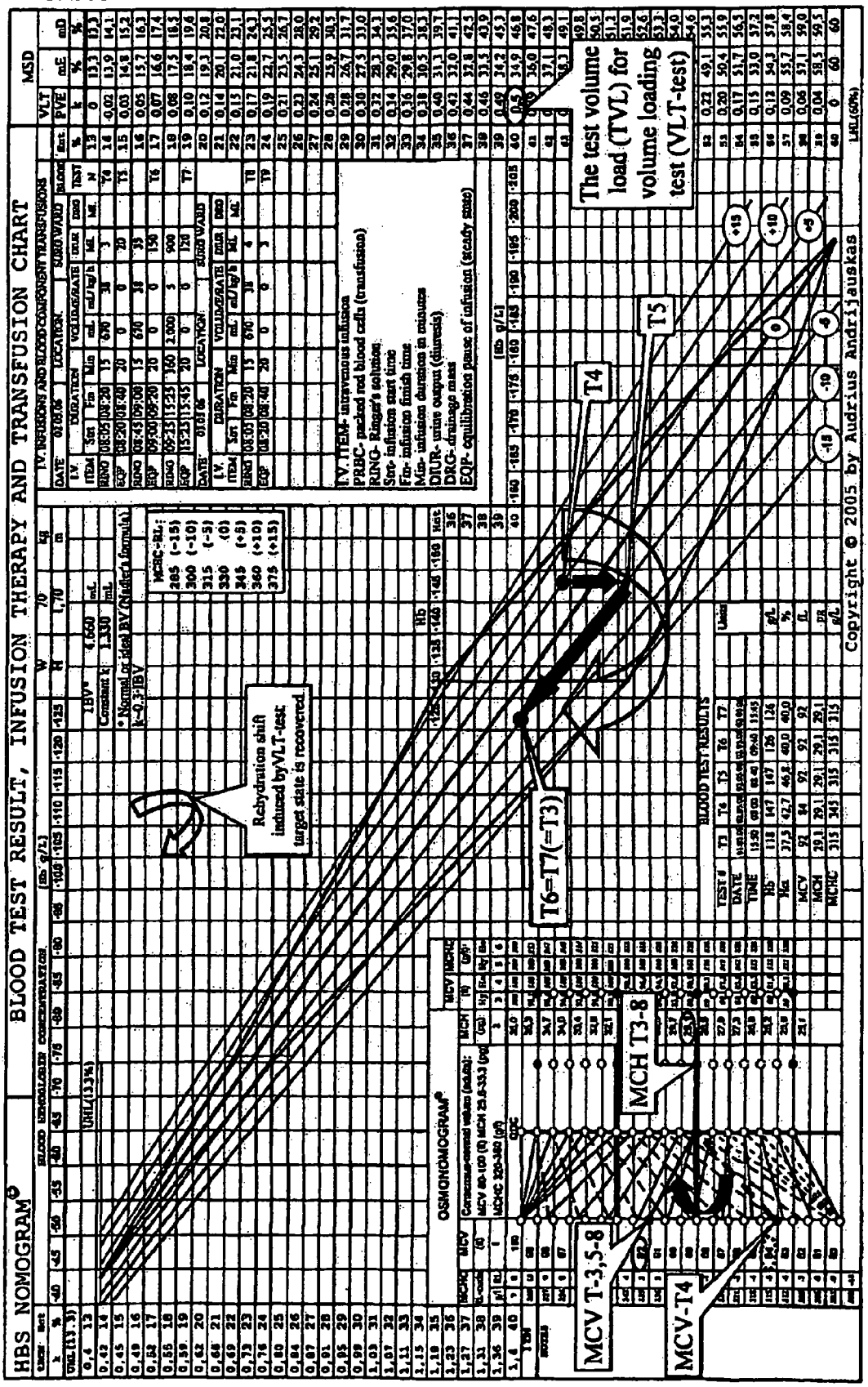
Figure 24:
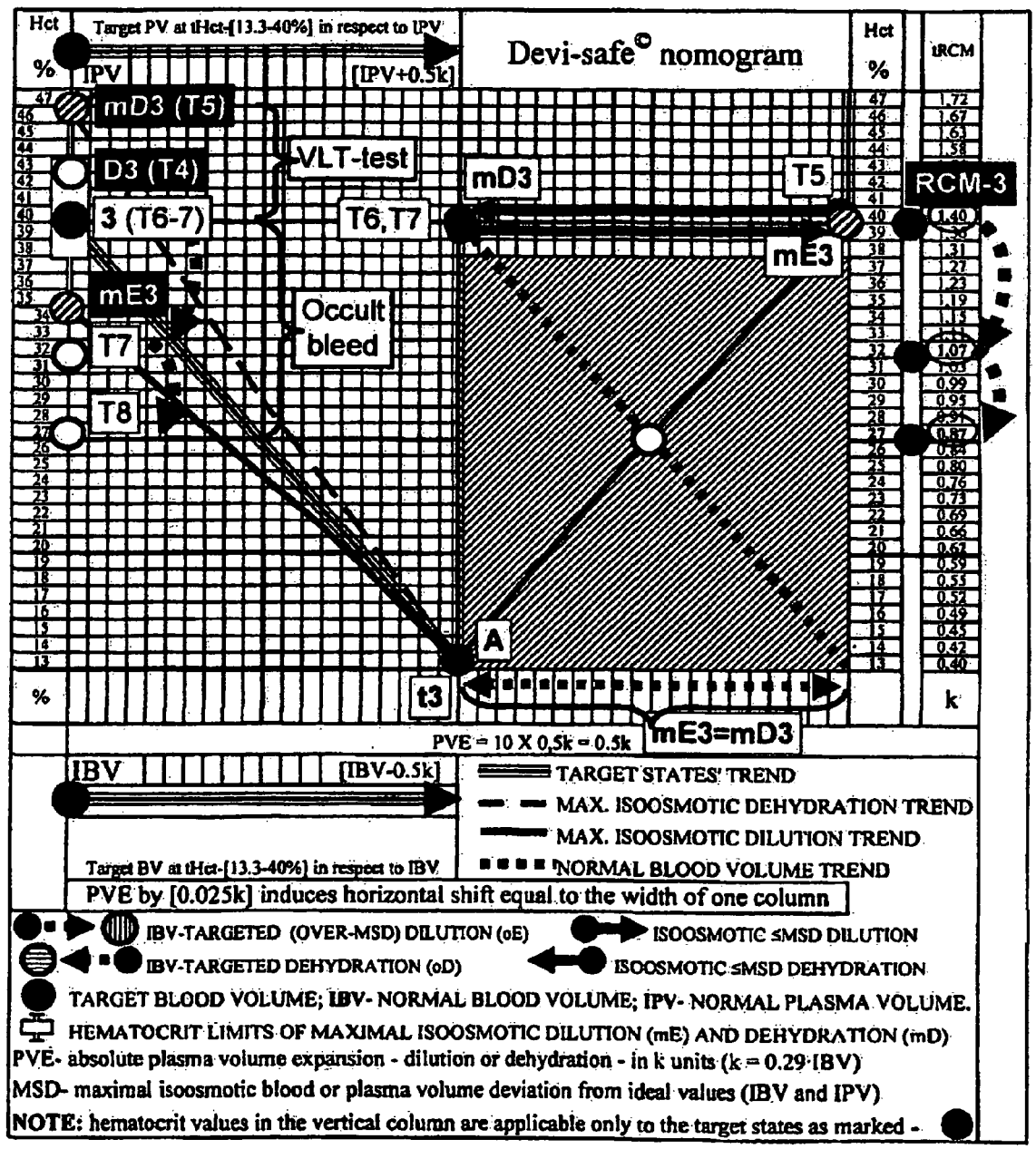

High rate (38 ml/kg/h) bolus infusion (TVL-665 ml) of Ringer's solution was started (FIG. 24A, table "I.V. Infusions and Blood Component Transfusions" in the Chart).

An equilibration pause (steady state without infusion)—EQP-1—was then applied for 20 minutes.

The $2^{nd}$ blood sample in a row—T5—was taken immediately after EQP-1. It revealed Hct-46.8% and Hb-147 g/l (note that isotonic infusion has induced Hct increase, but not the decrease that would be an appropriate reflection of plasma dilution). It suggested the preexisting hyperosmotic dehydration state and warranted another similar volume loading test. As shown in FIG. 24B, blood test T5 results suggest the state of maximal isoosmotic dehydration (mD3), which is by 20 horizontal steps away from the corresponding target state T5 (the horizontal shift step-value is 0.025 k, therefore it is consistent with both plasma and blood volume decreased by 0.5 k from normal).

Consequent similar volume loading test (VLT-2) was made followed by EQP-2 and blood test T6, revealing Hct-40.0% and Hb-126 g/l. It is consistent with the characteristics of the target state #3 determined a day before (after the surgery and the last PRBC transfusion).

Urine output was collected from the start of procedure: it was a total of 3 ml during VLT-1 and increased to 20 ml during EQP-1; it further increased to a total of 35 ml during VLT-2 and 150 ml during EQP-2. That is consistent with normal urine output dynamics during recovery from severe dehydration.

The later maintenance rate (5 ml/kg/h) Ringer's solution infusion of 2000 ml resulted in the normal urine output (900 ml over 6 hours of infusion), while blood test T7 obtained after that infusion and EQP-3 showed no Hct, Hb or MCHC changes from the values of the targets state #5 (blood sample T5 in VLT-test).

As described in Chapter 4.4.1., the blood homeostatic stability patterns can be described as predisposition to retain in or eliminate from circulation an additional load of isotonic non-colloid fluid. These states are described by preset potentials: the pre-set volume potential [$PVP^{-/0/+}$] describes predisposition of proper homeostatic blood state to isotonic plasma hydration solely for blood volume increase, while pre-set osmotic potential [$POP^{-/0/+}$] describes predisposition to isotonic plasma hydration solely for decrease of osmolality (dilution).

The proposed classification of pre-set homeostatic potentials can be applied to the blood test results discussed above as follows:

Test T4 [$POP^+/PVP^+$] —hyperosmotic/hypovolemic (hyperosmotic pre-target) state Test T5 [$POP^0/PVP^+$] —isoosmotic/hypovolemic (isoosmotic pre-target) state Tests T3, 6, 7 [$POP^0/PVP^0$] —isoosmotic/euvolemic (homeostatic target) state The dynamics of plasma osmolality and erythropoietic RBC content could be monitored by an optional component of the clinical Chart—the Osmonomogram (Chapter 4.5.2.). This nomogram enables the more reliable and accurate nomographic evaluation of plasma osmolality shifts, because it traces MCH stability and corresponding MCV dynamics in consequent blood test results as indicator of erythropoietic blood content stability. These parameters are available from the same blood test as Hb and Hct parameters. To some extent it eliminates the need for separate osmolality tests. Two standard maximal functional osmotic deviation projections (MFOD lines) originate from all the patient's tests derived MCH-29.1 pg value (FIG. 24C; column #2) on the vertical projection of the osmotic deviation center (ODC): heavy solid line for maximal functional hypoosmotic and dash style for hyperosmotic deviations from target mean cell volume (tMCV). In the current case, all blood tests except T4 show MCV-92 fl, thus, it is assumed to be the target MCV value. The T4 test provided MCV4-84 fl, which is hyperosmotic in respect to target value. The MCH and MCV values are marked in the Osmonomogram© as points connected by the functional osmotic deviation lines (FOD lines) between the corresponding MCV and MCH values, the latter being located on the vertical ODC projection. These lines show that all the consecutive tests revealed the same MCH value, but the MCV was different in T4, therefore MCV shift was evaluated in respect to osmolality dynamics: the downward inclination of the FOD line corresponding to test T4 means hyperosmotic shift, where approaching standard maximal hyperosmotic functional deviation limit (standard dash-style line that originates from the same MCH-29.1 point in ODC) signals about critical hyperosmolality pending. The critical MCV-81 and 92 (fl) corresponding critical MCHC values (hyperosmotic HyMCHC-360 g/l and hypoosmotic HoMCHC-320 g/l) are in column #5 and #6 adjacent to the MCH-29.1 value in column #2. Columns #7 and #8 are optional as they show the MCHC value specific radiating line (RL) codes applied in HBS Nomogram©.

Clinical interpretation is as following. The consecutive tests revealed the same MCH value, but the MCV was different in T4: the resulting nomographical MFOD line upward inclination visualized the hyperosmotic shift from target state; its approaching of standard maximal functional hyperosmotic deviation limit signals about approaching critical plasma hyperosmolality. There is a possibility (Chapter 4.5.2.) that MCH-29.1 pg value specific maximal functional hyperosmotic MCV value (mHyMCV=81 fl) may be corresponding to critical plasma hyperosmolality (cmHyOsm-320 mOsm/l), and maximal functional hypoosmotic MCV (mHoMCV=92 fl) corresponding to critical plasma hypoosmolality (cmHoOsm-265 mOsm/1). As far as target MCV-92 fl is the same as nomographically suggested maximal limit of functional osmotic deviation from target, there is a possibility that either this is the patient specific pattern of erythropoietic brand or the long term plasma osmolality (target Osm) is hypoosmotic in respect to limits of normal plasma osmolality. Thus, just one test of plasma osm would be justified. If it is not available, caution should be applied to all hypoosmotic measures including hypoosmotic I.V. solutions.

Occult Bleeding Detection

Conventional methods for monitoring blood test results in detection of moderate occult bleeding cannot reliably deploy the dynamics of consequent blood tests unless bleeding has reached significant blood loss. The new method proposed a brand new approach to an early detection of occult bleeding.

CLINICAL EXAMPLE #3

The same patient as in examples #1 and #2 was monitored for plasma hydration state by means of the new nomograms on the $2^{nd}$ day following surgery. The patient was not hyperthermic anymore and has been on the normal oral diet and fluid intake with no I.V. infusions for the last 12 hours. However, the patient's complains and physical investigation raised suspicion of bleeding. Initial investigation did not provide clues for the presence of bleeding The VLT-test and additional blood test an hour later have uncovering occult gastrointestinal (GI) bleeding later confirmed by instrumental investigation.

In the morning of the $2^{nd}$ day following surgery, the VLT-test has been made in the same way (VLT-1) as a day before (Case #2). However, this time it was justified by the suspicion of the occult bleeding, but not the evaluation of patient's hydration state. Only one stage of volume loading has been made, because the consecutive blood tests (T8, T9) revealed the increasing deviation from target state #3 (target state #3 was established a day before; see Case #2): blood test T8 showed Hct-32.0%, Hb-101 g/l and T9 showed Hct-27.0%, Hb-85.1 g/l. These results are consistent with overridden hematocrit of the maximal isoosmotic plasma dilution deviation from target state #3 (FIG. 25; the mE-Hct-34.9% value in the mE column of the numeric table of the Chart is target state #3 tHct-40% specific). There were no changes in plasma osmolality as confirmed by unchanging MCH (29.1 pg) and MCHC (315 g/l) parameters; note that deviation from target state occurred along the same nomographic radiating line RL(-5) in FIG. 25. Therefore even one blood test (T8) was enough to support the clinical suspicion of occult bleeding. The VLT-test has finally confirmed the diagnosis by showing further isoosmotic Hct and Hb decrease. Note that even maximal isoosmotic plasma dilution deviation from target state #3 could haven been induced only by overwhelming isoosmotic intravenous crystalloid volume load, such as 5000-6000 ml, with signs of generalized edema.

Author's Theoretical Investigations

The current practice applies normal calculated blood volume to the calculations of blood donation induced Hb and Hct decrease, also to the estimation of the allowable donation amount for maintaining the safe post-donation Hc and Hb values. The new method debates it, and argues that RCM specific blood volume should be used instead.

Current EU regulations quote the standard amount of 450 ml for donor's whole blood per collection unit. The established minimal pre-donation baseline Hct-34% value seeks patient's safety and allows collection of 50-60 g of hemoglobin per collection unit at baseline Hct≧34%. Due to different baseline values, even packed red blood cells (PRBC) units processed from the consecutive collection containers of the same donor have different volume of red cells, but hemoglobin load is always in the range between 50 and 60 grams. Different erythropoietic RBC brands contain different mean cell hemoglobin content (MCH) and mean cell volume (MCV). Thus, different volume of PRBC may contain the same amount of total hemoglobin. In most clinical settings the blood volume is unknown, therefore knowing the hemoglobin content of the PRBC unit does not help much in predicting the post-transfusion Hb and Hct values. For the same reason, the mathematical methods for predicting the post-donation Hb and Hct decrease in acute normovolemic hemodilution (ANH) are very approximate: they assume that baseline blood volume is normal calculated blood volume. Application of average Hct decrease is an additional source of possible error.

Addressing these issues, the new method proposed the use of transfusion unit specific PRBC (RCMt) volume per se as criteria for predicting the transfusion induced Hb and Hct increase by means of HBS Nomogram, which provides Hct specific RCM values on every 1% Hct steps. Similarly, the Hb and Hct decrease after donation of proper amount of whole blood can be estimated, because the HBS Nomogram provides Hct specific target blood volume values on every 1% Hct steps. Alternatively, mathematical formulas from the new mathematical model HBS Trends can also be used for the above purposes in a variety of applications—starting from calculator and ending in software of clinical monitors. Target plasma hydration state is the major condition for the method's precision, therefore it has to be applied in accordance with target state's verification by the volume loading test (VLT-test) prior to blood donation procedure and after the procedure in case of blood transfusion (Reminder: note that at tHct<27%, the maximal plasma hydration shifts are negligible—they are Hct<1%).

In order to evaluate the initial accuracy of the new method, the calculated post donation Hct decrease has been compared to the clinically and experimentally obtained values reported in the published materials. Calculations were made by formulas used in ANH, but the assumption of baseline Hct specific RCM and target blood volume (tBV) was made instead of "estimated blood volume". Assumption of baseline ideal or normal calculated blood volume (IBV) applied to the same calculations was used as a control for evaluation of accuracy in predicting post-donation Hct decrease.

The 1st investigation (Theoretical investigation 1) evaluated the credibility of the hypothesis that only the RCM specific baseline target blood volume but not the baseline normal blood volume states are capable of demonstrating the progressive pattern of Hct and Hb decrease consistently observed during the blood donation procedures.

The 2nd investigation (Theoretical investigation 2) evaluated the credibility of the hypothesis that only the RCM specific baseline target blood volume but not the baseline normal blood volume states are capable of demonstrating the Hct decrease by 3% and 10% after donation of 1 and 3 units of whole blood, when the exchangeable blood volume in the collection bags is calculated to result in that decrease. Such calculations are used in tailoring donation volumes for proper Hct decrease during the blood donation. (xlix)

The 3rd investigation (Theoretical investigation 3) evaluated the credibility of the hypothesis that only the RCM specific baseline target blood volume but not the baseline normal blood volume states are capable of inducing the Hct decrease by 3% and 10% after the donation of 1 and 3 units of whole blood, accordingly, when donation volume per collection bag is equal to the EU standard—450 ml. These patterns of Hct decrease are widely reported as observed during the blood donation. (xlix) The influence of body mass index (BMI) on the accuracy of predictions was investigated by evaluation of the three BMI patterns—20, 24 and 29.

No clinical or experimental investigations were made by the author for the evaluation of the above hypotheses, because the overwhelming data in the published reports serves as excellent controls perfectly suitable for current pilot investigations.

Theoretical Investigation 1

This theoretical investigation evaluated the credibility of the hypothesis that only the RCM specific baseline target blood volume but not the baseline normal blood volume states are capable of demonstrating the progressive pattern of Hct and Hb decrease consistently observed during the blood donation procedures.

As shown in FIG. 27, the two numerical trends are described in columns adjacent to the HBS Nomogram: the target states' Hct specific red cell mass (tRCM) values are derived by the new method, and the parallel values of ideal or normal blood volume specific RCM are calculated on the assumption that normal calculated blood volume is maintained at any Hct level. The RCM volume values are provided in fractions of Constant k, which is equal to 0.29·IBV.

The new method specific numeric column adjacent to tRCM is the packed red blood cell (PRBC) volume that has to be withdrawn to induce the 3%-Hct decrease. Similarly, the next numeric column to the right provides the PRBC that has to be withdrawn in order to induce the 4%-Hct decrease. The progressively increasing PRBC values in parallel with Hct increase along both columns indicate that the same volume of withdrawn whole blood requires decreasing RCM for the same 3% or 4% Hct decrease from baseline, when baseline Hct value decreases. That happens during blood donation, therefore the new method's trend is capable of maintaining the progressive pattern of Hct and Hb decrease even when the withdrawal amount is equal regardless of baseline Hct value, because the Hct decrease trend is steeper than the corresponding PRBC decrease (the Hct increases by 2.42, while PRBC only by 1.57 in the Hct range from 58 to 24%. (FIG. 27) The adjacent columns tBV↓/Hct↓ show the decrease of tBV that corresponds to 3% and 4% Hct decrease. These numeric trends show that autotransfusion compensates for the most of the withdrawn blood volume, which is equal to 450 ml or 0.27 k as shown in adjacent columns "1 UNIT—[ml][k]": the baseline blood volume is restored for the whole amount of plasma loss and then plasma is expanded to compensate up to 60% of the RCM loss.

The corresponding numeric values in the normal or ideal blood volume trend show that equal amounts of RCM loss (PRBC columns) are needed for the 3% or 4% Hct decrease at any Hct levels. (FIG. 27) Therefore, equal volumes of donated whole blood at decreasing baseline Hct values would result in progressively decreasing, but not increasing drop in Hct, what is not consistent with the acknowledged progressive pattern of Hct and Hb decrease in blood donation processes.

Conclusion. Only the RCM specific target blood volume endpoint trend (new method), but not the ideal or normal calculated blood volume endpoint trend is capable to induce the post whole blood donation Hct shifts of the progressive pattern, which is repeatedly described in the published investigations.

6.2.2. Theoretical Investigation 2

The 2nd investigation (Theoretical investigation 2) evaluated the credibility of the hypothesis that only the RCM specific baseline target blood volume but not the baseline normal blood volume maintaining homeostatic states are capable of demonstrating the Hct decrease by 3% and 10% after donation of 1 and 3 units of whole blood, when the exchangeable blood volume (EBV) is calculated for target Hct decrease by 3% and 10%. Such calculations are used in estimating donation volumes for proper Hct decrease during the pre-operative blood donation in ANH processes.

Numerous published studies reported the very similar trends of Hct and Hb decrease after blood withdrawal in healthy volunteers, blood donors and surgery patients, who pre-donated their blood for later retransfusion: studies unanimously report the progressive pattern of Hct and Hb decrease with increasing number of donated units: they report an approximate Hct decrease by 3% and 10% after donation of 1 and 3 units of whole blood, accordingly. In contrast to Hct, the corresponding increasing Hb decrease is not well specified: it is reported to be increasing with every consequently donated unit, and progressively exceeding the initial 10 g/l decrease per first unit.

Shander recommends several formulae that deploy the Hct parameter for estimates of the EBV:

$$EBV=BV \times (bHct-fhct)/avgHct \quad [1]$$

and (the most accurate)

$$EBV=BV \times (bHct-fHct) \times (3-avgHct) \quad [2]$$

and average hematocrit is $$avgHct=(bHct-fHct)/2+fHct$$

where EBV—exchangeable whole blood volume, bHct—measured baseline, fHct—preferred post-donation and avgHct—average hematocrit.

Conventional formulae for EBV calculation use the estimated blood volume (BV), which is usually calculated by Nadler's formula. (ix)

Prognostic accuracy of the two methods—the new method (HBS-method) and conventional or standard (Std-method)—was compared in predicting the Hct decrease by 3% and 10% after the donation of 1 and 3 units of whole blood, accordingly.

The $2^{nd}$ formula (the more accurate) was chosen for EBV estimates (TAB.4A-D) in the current investigation: two patterns of BV have been applied to the formula—the RCM specific target blood volume (tBV) representing the new method (HBS-method), and the normal blood volume (IBV) calculated by Nadler's formula representing the standard method (Std-method).

It was assumed by the new method that tBV was decreasing from tBV1 to tBV2 by adjusting plasma volume to the decreasing red cell content from tRCM1 to tRCM2, meanwhile standard method assumed unchanging normal BV. In both cases the RCM decrease (wRCM) was calculated similarly:

$$wRCM=EBV \times (bHct-avgHct) \quad [3]$$

where wRCM—red cell mass decrease, EBV—exchangeable whole blood volume, bHct—measured baseline and avgHct—average hematocrit.

Then the post-donation RCM (RCM2) is calculated as follows:

$$RCM2=RCM1-wRCM \quad [4]$$

where RCM2—the post-donation red cell mass, RCM2—the post-donation red cell mass and wRCM—the red cell mass decrease.

The corresponding post-donation RCM2 specific target blood volume (tBV2) and post-donation Hct are calculated from the obtained RCM2 value by formulas described in the new mathematical model. The derived post-bleeding (donation) Hct values (column #11 for the HBS-method and column #12 for Std) were compared to the expected Hct decrease by 3% and 10%. A1

Numbers of patients in pre-donation groups were simulated following patterns reported in the study of Mercuriali et al., who analyzed data from 2183 patients undergoing surgical procedures in the Orthopaedic Institute of the University of Milan, see FIG. 29. A2

As shown in FIG. 30, for each first unit of autologous blood (350-450 ml) collected, authors reported a mean decrease of 10 g L-1 of Hb and 3% of packed cell volume (PCV or Hct). In patients with baseline Hct less than 39-40% the value decreases to less than 34% (threshold value for donation) after collection of one or two units. It has precluded donation for 10% of patients and limited the number of units collected in 31% of them. Authors discovered that when baseline Hct was less than 37%, patients could deposit only 0 or 1 unit. In the current theoretical investigation, patient and parameter data has been derived from the table above and the figure below in order to mimic the number of patients and baseline Hct groups that allowed donation of 1 and 3 units in the study of Mercuriali et al.

With collection of 3 units of blood, the packed cell volume was reduced by approximately 10%. Therefore, only when Hct was greater than 40%, patients could deposit 3 units. Hematocrit decrease shifts resulting from withdrawal of two units were also excluded from current investigation.

Therefore simulated baseline Hct interval from 34% to 40% was investigated in respect to withdrawal of one unit (TAB.4A-C) and interval from 44% to 56%—in respect to withdrawal of three units (TAB.D). The body mass index (BMI) was calculated by dividing weight in kilograms by height in meters squared. The BMI has the advantage of being gender and frame size independent. Overweight is defined as BMI of 25-29.9 kilograms/meters squared. Therefore three patterns of BMI—20, 24 and 29—were used in the study to represent the lower, medial and higher values within the BMI interval usually met in clinical practice. Three patterns of body height and weight combination—1.70/70, 1.85/70 and 170/85 (m/kg)—were used to represent the chosen BMI values. The same body height and weight combinations were used in the calculation of normal blood volume value (IBV), which was used for different purposes in both methods. The Nadler's formula was chosen for IBV calculations, because it is probably the most popular in related research. Note that BMI had no effect on Hct decrease predictions (TAB.4A-C), therefore BMI stratification was not applied in the three donation units group (TAB.4D).

Statistical analysis. To compare the results of the HBS-method (new) and the Std-method (conventional) to results reported in the study of Mercuriali et al., we generated data for analysis, supposing that baseline Hct distribution is the same like in that study. For each generated observation we calculated deviance Hct↓ with HBS and Std methods. Continuous variable Hct↓ was analyzed and presented as mean±SD. A hypothesis on distribution's normality for the Hct↓ was rejected, therefore nonparametric Wilcoxon test for homogeneity of two Hct↓ groups in location were performed. A value of $p \leq 0.05$ was considered to be significant in the test. In all patient and donation protocol groups the new method showed the significantly better prognostic stability and accuracy than the conventional method. (TAB.4E, Suppl.P-1,2) Statistical analysis was performed with SPSS 13.

6.2.3. Theoretical Investigation 3

The 3rd investigation (Theoretical investigation 3) evaluated the credibility of the hypothesis that only the RCM specific baseline target blood volume but not the baseline normal blood volume states are capable of inducing the Hct decrease by 3% and 10% after the donation of 1 and 3 units of whole blood, accordingly, when donation volume per collection bag is equal to—450 ml (current EU standard). Such values of Hct decrease are repeatedly reported as being observed during the blood donation procedures. (Two methods—the new method (HBS) and standard (Std)—were compared for the prognostic accuracy in predicting Hct decrease induced by two patterns of donated blood volume (EBV)—450 ml (1 unit) and 1350 ml (3 units). Collection of 1 (TAB.5A-C) or 3 (TAB.4D-F) such units was expected to reduce baseline Hct approximately by 3% or 10% according to numerous published reports.

Patient and baseline Hct groups were the same like in the previous investigation, but in this investigation the exchangeable blood volume (EBV) was equal for all baseline Hct values and patient groups.

The RCM decrease (wRCM), was calculated the same way like in the previous investigation (formula #3), and the corresponding post-donation RCM2 specific target blood volume (tBV2) and post-donation Hct were calculated from the obtained RCM2 value by formulas described in the new mathematical model. (HBS Trends, Chapter 4.1.)

The derived post-bleeding (donation) Hct values (column #11 for the HBS-method and column #12 for Std) were compared to the expected Hct decrease by 3% and 10%.

Just like in the previous investigation, the new method showed the significantly better prognostic stability and accuracy than the conventional method in all patient BMI, baseline Hct and donation volume groups. (TABS.5-G,H, Suppl.P-3-6)

Discussion (on Theoretical Investigations)

Acute normovolemic hemodilution (ANH) is an established procedure for the avoidance of allogeneic blood transfusions in elective surgery. Between induction of anesthesia and start of surgery, fresh whole blood is withdrawn from the patient and simultaneously replaced by the identical volume of a colloid solution or the triple volume of a crystalloid solution. Presuming that normovolemia is maintained, hemodilution entails a reduction of red blood cells, and thus of hemoglobin concentration.

The blood volume that has to be exchanged for crystalloids and/or colloids during acute normovolemic hemodilution (ANH) in order to reach a preset target hemoglobin concentration is calculated by different formulas based on baseline and predicted post ANH procedure Hb or Hct. However, they systematically overestimate the exchangeable blood volume (EBV), a fact that may potentially endanger patients because the target Hb will be missed and the normovolemic anemia might turn out to be more severe than a priori intended.

The EBV used to be predicted by the Bourke and Smith formula developed in 1974, but it systematically overestimated the volume actually exchanged (overestimation: dogs 15%, patients 20%). In 2003, the exchangeable blood volume (EBV) was shown being predicted more accurately by the new Meier's iterative model (overestimation: dogs 1%, patients 8%). The highest precision reached in dogs was mainly due to the direct measurement of blood volume before and after the ANH, while in patients the both methods assumed the ideal or normal calculated volume in both stages. Besides, dogs were splenectomized several weeks before experiments. Authors agree that the most possible source of error in human investigations is the unknown blood volume maintained throughout ANH procedure. Surprising is the finding that Hb decrease is faster, when blood removal is made before the replacement of removed volume.

Conclusion. The existing formulae and nomograms for modeling the blood volume and plasma dilution dynamics reflected in Hb and Hct changes are not accurate, mainly because the direct measures of blood volume are not applicable in most clinical settings, meanwhile assumption of normal calculated blood volume is found as unreliable.

As shown by the current investigations, the new method offers better accuracy in modeling and monitoring of the ANH induced blood volume and plasma dilution changes reflected by Hct an Hb decrease under the assumption of RCM specific blood volume being maintained throughout the procedure. These values are easily accessible in the HBS Nomogram© and its optional component Devi-safe© nomogram: the difference in pre-donation and the preferred post-donation RCM values in the nomogram is the amount of PRBC to be withdrawn to the collection bag; measured baseline, preferred post-donation and average Hct values determines the whole blood amount for donations, just like in the current theoretical investigation 2.

The author argues that it is the target blood volume, which is normally recovered and maintained by homeostasis immediately following any blood loss. Colloid solutions can override that trend for a while, but their effect can also be monitored and evaluated by the Devi-safe nomogram as shown earlier in clinical examples.

In conclusion, the blood donation induced Hct and Hb shifts can be more accurately predicted by the new method (HBS Method) and its main instrument—the HBS Nomogram© and its optional components. The new mathematical applied to appropriate software could significantly increase its applicability. Further research is encouraged.

6.3. Clinical Investigations

There follow the author's pilot clinical investigations on the way of the new method's validation.

6.3.1. Clinical Investigation 1

The following pilot clinical investigation was made by the author for the purpose to evaluate prognostic precision of the RCM specific target blood volume (HBS method) compared with rule of thumb (Habibi et al.) in predicting the post-transfusion Hct and Hb values.

Background. Total hip arthroplasty is associated with significant bleeding, which continues through early postoperative hours. Choosing amount of packed red blood cells (PRBC) for transfusion to reach hematocrit targets is challenging. The two methods of predicting post-transfusion hematocrit were compared: the new—HBS Method, referred to as method A and conventional "Rule of Thumb" (Habibi et al.) referred to as method B.

Methods. The retrospective investigation of immediate postoperative blood transfusions included sixteen adult patients, who were ASA physical status II, five of them males and eleven females, mean age 64.75±10.427 (range, 45-79 yr) after total hip arthroplasty. Patients received routine procedures: venous blood samples taken just before starting transfusion (20 minutes after stopping all infusions), then 20 minutes after transfusion. Eight patients received one PRBC unit, others received two. Amount of wound drainage has been measured. Perioperative infusion and transfusion data, timing, blood test results, urine output and drainage amounts were recorded using new type of chart—HBS Nomogram. The post-transfusion hematocrit predicted by both methods was calculated. (TAB.6) The method A deploys mathematical formulas for calculating hematocrit specific homeostatic circulating erythrocyte mass. Corrections for simultaneous blood loss were applied to calculations by method A protocol A-cor. Corrections are not applicable to method B, which accounts only for units transfused: protocol B1 predicts 3% hematocrit increase, B2-4% and B3-5%.

Results. Method B-1 ($p=0.019$) predicted hematocrit better than method A, but method A did better than B-2 ($p=0.04$) and B-3 ($p<0.0001$), while method A-cor was the best of all, predicting better than A ($p<0.0001$), B-1 ($p<0.009$), B-2 ($p<0,0001$) and B-3 ($p<0.0001$). Method B does not account for simultaneous bleeding, and there are no criteria for choosing proper protocol—B1, B2 or B3, therefore providing the overall advantage to method A and its modification A-cor. (Suppl. P7)

Conclusion: The new method is a promising tool for transfusion amount selection, therefore further investigations are needed.

Comparison of two methods for predicting hematocrit increase after immediate postoperative transfusions following the total hip arthroplasty Materials and Methods Records of immediate postoperative blood transfusions administered after total hip arthroplasty were retrospectively investigated in sixteen patients, who were ASA physical status II, five of them males and eleven females, mean age 64.75±10.427 (range, 45-79 yr). Patients were selected from the latest list of those operated by the same two surgery and anaesthesia teams, excluding only patients, who were physical status other than ASA II. All patients have undergone the similar routine procedures. Baseline venous blood hematocrit (that) tests were obtained just before starting PRBC transfusion 20 minutes after stopping maintenance rate intravenous crystalloid infusion for equilibration of plasma dilution. Blood samples were obtained through peripheral intravenous catheter after flushing it with 3 ml of withdrawn blood, which was later returned to the vein. Post-transfusion hematocrit (pthct) tests were obtained 20 minutes after commencing of transfusion and before restarting crystalloid infusion. Eight patients received transfusions of one PRBC unit, while another eight received two units. The standard PRBC transfusion rate was one unit in 30 minutes. All blood Hct tests have been processes by the same laboratory equipment: hematological analyzer COULTER®HmX, Beckman Coulter, Inc. USA, 2004. The amount of wound drainage has been measured before and after the transfusion. Perioperative infusion and transfusion data, timing, blood test results, urine output and drainage amounts were recorded on the new chart based on the HBS Nomogram. It enabled recording of the blood Hb, Hct and mean MCHC, also tracing the osmolality dynamics in plasma.

Predicted post-transfusion Hct values were compared as calculated by method A (HBS Method) and method B (Rule of thumb). Calculation correction for the simultaneous blood loss through drainage was applied to method A referred to as modified method A (A-cor). Blood loss correction is not applicable to method B.

Method A

This method is based on the new mathematical model HBS Trends assuming that Ideal Total Match (ITM) hematocrit is 40% and the critical Hct limits are 13.3% and 60%. Thus, Constant k is equal to 0.3·IBV. Mathematically target state is described in formulas below:

$$tBV = 0.5 \cdot (IBV + IPV + tRCM) \quad [1]$$

where IBV—ideal blood volume—can be calculated by any preferred method and tRCM is tHct specific, meanwhile IPV—ideal plasma volume is originally described as following:

$$IPV = IBV \cdot (1 - tHct_{ITM}) \quad [2]$$

Where $Hct_{ITM}$—hematocrit of the Ideal Total Match, which is considered universally equal to 0.4, consequently:

$$IPV = 0.6 \cdot IBV \quad [3]$$

The formula for calculating tRCM is as following:

$$tRCMn = Cn \cdot (IBV + 0.6 \cdot IBV \cdot (1 - tHct_n)^{-1})) \cdot Hct \quad [4]$$

where tRCM—red cell mass in target state at target Hct value n, Cn—coefficient inherent to target Hct value n:

$$Cn = \left( \frac{(IBV + IPV) \cdot (2 - Hct_n)^{-1} \div}{(IBV + IPV \cdot (1 - Hct_n)^{-1}} \right) \quad [5]$$

$$= \left( \frac{(IBV + 0{,}6 \cdot IBV) \cdot (2 - Hctn)^{-1} \div}{(IBV + 0{,}6 \cdot IBV \cdot (1 - Hct_n)^{-1}} \right)$$

Consequently the predicted post-transfusion eHctA value was calculated by method A as following:

$$eHctA = (tRCMn + PRBC) \cdot tBVx^{-1} \quad [6]$$

$$= 2 \cdot (tRCMn + PRBCx) \cdot (tRCMn + PRBC + 1{,}6 \cdot IBV)$$

where tRCMn—is the red cell mass at pre-transfusion Hct value n, assuming that homeostatic target state is being maintained at the time of blood sampling, which has been obtained after 20 minutes long equilibration pause of maintenance rate isotonic crystalloid infusion, and PRBC—is the volume of transfused packed red blood cells.

Predictive values of post-transfusion Hct were calculated by means of the formulas [4], [5] and [6], where patient physical state specific IBV value has been calculated by means of Nadler's formula as following:

$$IBV = 0.3669 \cdot H^3 + 0.03219 \cdot W + 0.6041 \quad [7]$$

where H—body height in meters and W—body weight in kilograms.

The measured and calculated results are disclosed in TAB 6.

Method A-Cor (Modified Method A)

Appropriate correction to calculations by method A has been made accounting for the recorded simultaneous blood loss through the wound drainage during the transfusion:

$$eHctA\text{-}cor=2\cdot(tRCMn+PRBC-cLEM)\cdot(tRCMn-cLEM+PRBC+1.6\cdot IBV) \quad [8]$$

where cLEM—is the calculated loss of erythrocyte mass through the wound drainage. It is calculated as following:

$$cLEM=MDM\cdot dmHct \quad [9]$$

where MDM—is the measured drainage mass, and dmHct—the Hct of the drainage mass. However measuring dmHct is not a routine practice in our institution, therefore a pilot test for dmHct has been made. It revealed that dmHct was in the midst of the interval between measured baseline (tHct) and post-transfusion (ptHct) values. Therefore an assumption of dmHct as the mean value of tHct and ptHct has been made. Thus the calculation of corHct value has been made by calculating cLEM value as following:

$$cLEM=0.5\cdot MDM\cdot(ptHct-tHct) \quad [10]$$

Method B

Method B accounts only for transfused PRBC units: the rule of thumb predicts that administration of one unit of PRBC will increase Hct by 3-5%. Therefore three different protocols of this method have been determined: protocol B1 predicted 3% hematocrit increase, B2-4% and B3-5%. The predicted values were calculated as following:

$$eHctB1=tHct+3\cdot NU \quad [11]$$

$$eHctB2=tHct+4\cdot NU \quad [12]$$

$$eHctB3=tHct+5\cdot NU \quad [13]$$

where eHct-B1 (B2, B3)—is the predicted (expected) post-transfusion Hct value, tHct—the baseline or pre-transfusion Hct value and NU—the number of transfused PRBC units.

Results

Statistical analysis was performed with SAS/STAT® 9.0. Continuous variables were analyzed and presented as mean±SD. Normal distribution of collected data was first verified with the Kolmogorov Smirnov test. A hypothesis on distribution's normality for all variables wasn't rejected, therefore parametric t-test for paired samples was used to compare mean of deviance Hct between method A and method B. A value of $p \leq 0.05$ was considered to be significant in tests. The difference between all the methods was significant: method B-1 (p=0.019) predicted hematocrit better than method A, but method A did better than B-2 (p=0.04) and B-3 (p<0.0001), while method A-cor was the best of all, predicting better than A (p<0.0001), B-1 (p<0.009), B-2 (p<0.0001) and B-3 (p<0.0001). (Suppl. P7)

Conclusion

The new method proposed has demonstrated good performance in transfusion amount selection and bleeding evaluation in the very challenging clinical setting. Further investigations are encouraged.

Conclusions and Practical Considerations

The HBS Method as part of the HBS Theory leads to improvement in patient safety and provides physiologically adequate basis for future studies investigating the processes related to blood component transfusion, blood saving strategies and optimization of intravenous infusion therapy measures. The statement is based on the following findings of the current study:

1. The HBS Graphics as part of the HBS Nomogram is an objective and accurate method for the graphical tracing of the interfering values of blood hemoglobin concentration, hematocrit and mean cell hemoglobin concentration.
2. The HBS Nomogram enables nomographical tracing of blood volume and red blood cell content, also plasma hydration and osmolality dynamics by means of blood hemoglobin concentration and hematocrit.
3. Nomograms can be used alone and, for more efficiency, in line with effective circulating blood volume monitoring modalities, methods of volume kinetics and guidelines for infusion and transfusion therapy.

There are specific areas within the prior art that can be enhanced by the new method: 1) blood test evaluation in patients medical records and clinical charts; 2) blood loss evaluation and transfusion amount estimates; 3) infusion therapy measures; 4) suggestions for the future research. The potential solutions and suggestions for each of these areas are specified as following:

1. Blood hemoglobin concentration and hematocrit are probably the most widely used parameters for outpatient and inpatient examination. Blood test derived results are conventionally recorded on multiple pages in patient's medical records making dynamical investigations tedious and time-consuming. Research results describing plasma dilution by means of hemoglobin or hematocrit are presented in a clinically unpractical way. The HBS Nomogram as part of clinical charts is a solution for the above problems. The new method provides a nomographic system and a simple algorithm for tracing the interfering dynamics of three major blood test parameters in relation to osmotic state of plasma: the interfering blood hemoglobin concentration and hematocrit shifts along the graphical mean corpuscular hemoglobin concentration (MCHC) specific trends reflect both plasma dilution and osmotic dynamics. Osmotic dynamics in plasma is reflected by inter-trend shifts, so it allows interpretation without knowing the osmotic values from separate blood tests. Life threatening conditions can be detected more effectively, when tracing the blood tests dynamics on a single page of HBS Nomogram or on a screen of computers and monitors. Nomograms can be used on site along with circulatory monitoring devices, providing a useful tool for tracing and evaluation of derived data.
2. Perioperative pulmonary edema related to infusion therapy remains an issue for decades and results in significant number of fatal outcomes. The HBS Nomogram along with the methods for target states verification (VLT-test elaboration) deployed for planning and monitoring infusion therapy measures may prevent dehydration and volume overload related threats.
3. The HBS Nomogram leads to the more accurate estimates of blood component transfusion amounts in approaching the clinical targets. Increased precision of blood loss evaluation also contributes to improvement of transfusion strategies.
4. Unrecognized in a timely manner occult bleeding is a common cause of otherwise avoidable deaths. The HBS Nomogram deployed for detection of internal bleeding can save lives by early indicating appropriate treatment.

5. The new method can lead to optimization of acute normovolemic hemodilution (ANH) processes and improvement in patient safety.
6. The HBS Theory proposed the homeostatic principles applicable for the mathematical modeling of homeostatic target states specific red cell mass, target blood and plasma volume, also proposed homeostatic deviation limits in respect to homeostatic target states. Thus, different preset key values, such as normal blood volume and critical hematocrit limits, can be deployed in computer simulations enabling their experimental evaluation.
7. In future experiments, mathematically derived volumes should be compared to values obtained by direct measurements. Development of methods for the clinical target state's verification could be a priority. Investigations should lead to development of infusion and blood transfusion therapy nomograms that would combine the new method and methods of volume kinetics, volume turnover kinetics and other. The HBS Nomogram could be significantly improved if target state specific infusion protocols are applied by means of methods based on volume kinetics. All that could lead to the creation of the gold standard.
8. Tracing the osmotic state in plasma may become continuous and non-invasive if combined with hemoglobin and hematocrit dynamics obtained by apparatus for non-invasive, real-time, accurate, continuous monitoring of hemoglobin and hematocrit.

A method of increasing blood hemoglobin concentration in a patient requiring such treatment is taught by the instant invention, comprising the steps of determining hemoglobin concentration (Hb) in a patient's blood sample, determining the ideal blood volume (IBV) of the patient, determining a first red cell mass value corresponding to the patient's hemoglobin concentration based on a predetermined mean cell hemoglobin concentration (MCHC) parameter, determining a target red cell mass (tRCM-B) of the patient based on the predetermined MCHC, calculating a therapeutically effective amount of packet red blood cells for transfusion into a patient to increase the patient's red cell mass to approximately the tRCM-B level, wherein the therapeutically effective amount is directly proportional to k, wherein k is equivalent to about 30% of the IBV value, further wherein the therapeutically effective amount of packet red blood cells (PRBC) is defined by the mathematical formula: k((target red cell mass)—(first red cell mass)), wherein the first four steps can occur in any order, and administering to the patient the calculated therapeutically effective amount of packet red blood cells thereby increasing the hemoglobin concentration in the patient's blood.

Preferably, k is defined by one of the mathematical formulas:

$$k = IPV + RCM_{LHL} - IBV = IBV \cdot (1 - Hct_{ITM}) + RCM_{LHL} - IBV \text{ and}$$

$$k = IBV - RCM_{UHL} - IPV = IBV - RCM_{UHL} - IBV \cdot (1 - Hct_{ITM}).$$

As described above, IBV may be calculated by known methods and preferably based on height and width of the patient using Nadler's formula. Referring to FIG. 13C, showing an HBS Nomogram, which can be used in the method of increasing blood hemoglobin concentration according to the invention, and in which the predetermined mean cell hemoglobin concentration (MCHC) parameter is selected using a HBS nomogram, wherein the HBS nomogram comprises a two-dimensional plot of red cell mass scale verses blood hemoglobin concentration, further wherein the HBS nomogram comprises at least one radiating line defining mean cell hemoglobin concentration (MCHC-RL). Additionally, as shown in FIG. 13C, the HBS nomogram comprises a plot of blood hematocrit (Hct) verses blood hemoglobin concentration.

In one preferred method of increasing blood hemoglobin concentration, the tRCM-B corresponds to a desired target blood hemoglobin concentration in the patient's blood, wherein the target blood hemoglobin concentration is selected to correspond to a MCHC of 300 g/l (+/−15 g/l). Moreover, a therapeutic amount of artificial hemoglobin may be administered to the patient, wherein the therapeutic amount of artificial hemoglobin is equivalent to the amount of hemoglobin contained in the therapeutic amount of packet red blood cells (PRBC) defined by the mathematical formula.

In one preferred method of increasing blood hemoglobin concentration, the predetermined mean cell hemoglobin concentration (MCHC) parameter is selected using a HBS nomogram in combination with an Osmonomogram, wherein the Osmonomogram defines tables of normal mean cell hemoglobin content (MCH), mean cell volume (MCV), and mean cell hemoglobin concentration (MCHC) values, wherein the HBS nomogram comprises a two-dimensional plot of red cell mass scale verses blood hemoglobin concentration, further wherein the HBS nomogram comprises at least one radiating line defining mean cell hemoglobin concentration (MCHC-RL).

Furthermore, the predetermined mean cell hemoglobin concentration (MCHC) parameter may be selected using a HBS nomogram in combination with at least one nomogram selected from the group consisting of: an Osmonomogram and a Devi-safe nomogram, wherein the Osmonomogram defines tables of normal mean cell hemoglobin content (MCH), mean cell volume (MCV), and mean cell hemoglobin concentration (MCHC) values, wherein the Devi-safe nomogram comprises a two-dimensional plot of blood hematocrit (Hct) verses ideal blood circulating volume (IBV), and wherein the HBS nomogram comprises a two-dimensional plot of red cell mass scale verses blood hemoglobin concentration, further wherein the HBS nomogram comprises at least one radiating line defining mean cell hemoglobin concentration (MCHC-RL).

In FIG. 13C, a HBS nomogram is shown comprising a two-dimensional plot of red cell mass scale verses blood hemoglobin concentration, further wherein the HBS nomogram comprises at least one radiating line defining mean cell hemoglobin concentration (MCHC-RL). Additionally, the HBS nomogram may further comprise a plot of blood hematocrit (Hct) verses blood hemoglobin concentration.

In another method of the present invention, a calculated volume of packed red blood cells (PRBC) can be administered to achieve a therapeutically appropriate post-transfusion Hct (ptHct) in a patient requiring such treatment, comprising the steps of: determining baseline venous blood hematocrit (tHct) in the patient's blood sample just before starting PRBC transfusion and about 20 minutes after stopping maintenance rate intravenous crystalloid infusion for equilibration; determining tRCM of patient based on tHct; determining the ideal blood volume (IBV) of the patient; calculating a therapeutically effective amount of packed red blood cells (PRBC) for transfusion into the patient to achieve the post-transfusion hematocrit (ptHct), wherein the therapeutically effective amount is directly proportional to k, where k is equivalent to about 30% of the IBV value, further wherein the therapeutically effective amount of packed red blood cells (PRBC) is defined by the mathematical formula: PRBC=(ptHct×tBV)−tRCM ; and the calculated therapeutically effective amount of packet red blood cells can be administered to the patient to achieve the therapeutically appropriate post-transfusion Hct in the patient's blood. Preferably, k may be determined by one of the following mathematical formulas:

$$k=IPV+RCM_{LHL}-IBV=IBV\cdot(1-Hct_{ITM})+RCM_{LHL}-IBV \text{ and}$$

$$k=IBV-RCM_{UHL}-IPV=IBV-RCM_{UHL}-IBV\cdot(1-HC-t_{ITM}).$$

Additionally, when calculating the volume of packed red blood cells (PRBC) to achieve a therapeutically appropriate post-transfusion Hct, the therapeutically appropriate post-transfusion Hct (ptHct) may be limited to a range of 13.3% to 60%.

In another preferred method of administering a calculated volume of packed red blood cells (PRBC) to achieve a therapeutically appropriate post-transfusion Hct, the therapeutically appropriate post-transfusion Hct (ptHct) may approximate an ideal total match hematocrit (Hct$_{ITM}$).

Furthermore, the therapeutically appropriate post-transfusion Hct (ptHct-cor) may comprise the further step of calculating loss of erythrocyte mass (cLEM) through wound drainage as follows: ptHct-cor=½ (tHct+ptHct) and cLEM=0.5·MDM·(ptHct−tHct), whereby the calculated volume of packed red blood cells (PRBC) take into account loss of erythrocyte mass (cLEM) through wound drainage to achieve the therapeutically appropriate post-transfusion Hct (ptHct-cor).

The method of administering a calculated volume of packed red blood cells (PRBC) may further comprise the predetermined mean cell hemoglobin concentration (MCHC) parameter being selected using a HBS nomogram, wherein the HBS nomogram comprises a two-dimensional plot of Hct verses blood hemoglobin concentration, further wherein the HBS nomogram comprises at least one radiating line defining mean cell hemoglobin concentration (MCHC-RL).

Additionally, the tRCM may correspond to a desired target blood hemoglobin concentration in the patient's blood, wherein the target blood hemoglobin concentration is selected to correspond to a MCHC of 300 g/l (+/−15 g/l).

In the method of administering a calculated volume of packed red blood cells (PRBC), a therapeutic amount of artificial hemoglobin may be administered to the patient, wherein the therapeutic amount of artificial hemoglobin is equivalent to the amount of hemoglobin contained in the therapeutic amount of packet red blood cells (PRBC) defined by the mathematical formula.

Moreover, the predetermined mean cell hemoglobin concentration (MCHC) parameter may be selected using a HBS nomogram in combination with an Osmonomogram, wherein the Osmonomogram defines tables of normal mean cell hemoglobin content (MCH), mean cell volume (MCV), and mean cell hemoglobin concentration (MCHC) values, wherein the HBS nomogram comprises a two-dimensional plot of red cell mass scale and corresponding hematocrit (Hct) verses blood hemoglobin concentration, further wherein the HBS nomogram comprises at least one radiating line defining mean cell hemoglobin concentration (MCHC-RL).

In another preferred aspect of the method of administering a calculated volume of packed red blood cells (PRBC) of this important invention, the predetermined mean cell hemoglobin concentration (MCHC) parameter may be selected using a HBS nomogram in combination with at least one nomogram selected from the group consisting of: an Osmonomogram and a Devi-safe nomogram, wherein the Osmonomogram defines tables of normal mean cell hemoglobin content (MCH), mean cell volume (MCV), and mean cell hemoglobin concentration (MCHC) values, wherein the Devi-safe nomogram comprises a two-dimensional plot of blood hematocrit (Hct) verses ideal blood circulating volume (IBV), and wherein the HBS nomogram comprises a two-dimensional plot of red cell mass scale verses blood hemoglobin concentration, further wherein the HBS nomogram comprises at least one radiating line defining mean cell hemoglobin concentration (MCHC-RL).

An HBS nomogram is taught for graphic representation of a quantitative relationship among homeostatic blood states in a patient, comprising: a plurality of scales and a solid support, the plurality of scales being disposed on the support and comprising a scale for a plurality factors including Hb, tRCM, Hct, and at least one scale for MCHC, wherein the scales for Hb, tRCM, Hct, and MCHC each have values on the scales, and wherein the scales for Hb, tRCM, Hct, and MCHC are disposed on the solid support with respect to the points scale so that each of the values on Hb, tRCM, Hct, and MCHC can be correlated to predict a therapeutically effective amount of packet red blood cells for transfusion into a patient to increase the patient's red cell mass.

An apparatus for increasing blood hemoglobin concentration in a patient requiring such treatment, comprising: one or more processors, and a memory communicatively coupled to the one or more processors, the memory including one or more sequences of one or more instructions which, when executed by one or more processors, cause the one or more processors to perform the steps of: acquiring hemoglobin concentration (Hb) and hematocrit (Hct) in a patient's blood sample, acquiring the ideal blood volume (IBV) of the patient, determining a first red cell mass value corresponding to the patient's hemoglobin concentration based on a predetermined mean cell hemoglobin concentration (MCHC) parameter, determining a target red cell mass (tRCM-B) of the patient based on the predetermined MCHC, calculating a therapeutically effective amount of packet red blood cells for transfusion into a patient to increase the patient's red cell mass to approximately the tRCM-B level, wherein the therapeutically effective amount is directly proportional to k, wherein k is equivalent to about 30% of the IBV value, further wherein the therapeutically effective amount of packet red blood cells (PRBC) is defined by the mathematical formula: k((target red cell mass)—(first red cell mass)), wherein first four steps can occur in any order; and producing the calculated therapeutically effective amount of packet red blood cells that can be administered for increasing the hemoglobin concentration in the patient's blood.

In another apparatus of the present invention for determining a calculated volume of packed red blood cells (PRBC) to achieve a therapeutically appropriate post-transfusion Hct (ptHct) in a patient requiring such treatment, comprising one or more processors, and a memory communicatively coupled to the one or more processors, the memory including one or more sequences of one or more instructions which, when executed by one or more processors, cause the one or more processors to perform the steps of: acquiring baseline venous blood hematocrit (that) in the patient's blood sample just before starting PRBC transfusion and about 20 minutes after stopping maintenance rate intravenous crystalloid infusion for equilibration, determining tRCM of patient based on tHct, determining the ideal blood volume (IBV) of the patient, calculating a therapeutically effective amount of packed red blood cells (PRBC) for transfusion into the patient to achieve the post-transfusion hematocrit (ptHct), wherein the therapeutically effective amount is directly proportional to k, where k is equivalent to about 30% of the IBV value, further wherein the therapeutically effective amount of packed red blood cells (PRBC) is defined by the mathematical formula: PRBC=(ptHct×tBV)−tRCM , and producing the calculated therapeutically effective amount of packet red blood cells to be administered to the patient to achieve a therapeutically appropriate post-transfusion Hct in the patient's blood.

In another method of the present invention for determining an ideal intravascular fluid replacement strategy in a patient requiring such strategy, comprising:
 a. determining hemoglobin concentration (Hb) in the patient's blood sample;
 b. determining the ideal blood volume (IBV) of the patient;
 c. determining the ideal plasma volume (IPV) according to the mathematical formula: IPV=0.6 IBV;
 d. determining a target red cell mass (tRCM) corresponding to the patient's hemoglobin concentration based on a predetermined mean cell hemoglobin concentration (MCHC) parameter, wherein steps (a) to (d) can occur in any order; and
 e. determining tBV according to the mathematical formula:

tBV=0.5(IBV+IPV+tRCM), whereby, the physiologic target blood volume (tBV) can be achieved by appropriate fluid replacement.

Another method taught by the present invention for diagnosing and treating dehydration in a patient requiring such treatment, comprises:
 (a) obtaining a first blood sample from the patient at time T1 and determining a first blood hematocrit (Hct) value;
 (b) estimating the patient's ideal blood volume (IBV) to determine volume loading test-plasma (VLT) and volume expansion (PVE) values for calculating Hct values;
 (c) administering to the patient an infusion and begin collection of patient's urine, wherein the infusion is a high rate intravenous bolus of isotonic crystalloid infusion, wherein the volume for infusion into the patient is read off a plasma volume expansion (PVE) column, wherein the plasma expansion column forms part of a nomogram;
 (d) inducing blood equilibration by stopping the infusion and waiting for sufficient time to allow the patient's blood to equilibrate;
 (e) obtaining a second blood sample from the patient at time T2 and determining a second Hct value; and
 (f) determining the hydration state of the patient,
 wherein the patient had mild dehydration immediately prior to step (a) if blood Hct decreases more than 1% isoosmotically between the first and second Hct values,
 wherein the patient had severe isoosmotic dehydration prior to step (a) if blood Hct decreases more than 1% isoosmotically between the T1 and T2 blood samples in which case the patient is provided with another infusion in accordance with step (c), which is repeated until target hydration is achieved, wherein if Hct decreases by less than 1% isoosmotically between the T1 and T2 blood samples and if urine output of the patient during steps (c) and (d) exceeded 20 ml/hour, the patient's plasma has achieved a target level of hydration and no further medical intervention required,
 wherein if Hct decreases by less than 1% isoosmotically between the T1 and T2 blood samples and if urine output of the patient during steps (c) and (d) was approximate to or less than 20 ml/hour, the patient's plasma is suspected of over-target state plasma dilution and patient is administered an I.V. diuretic and hydration level of the patient is monitored until target hydration is achieved, and
 wherein if Hct increases by more than 1% and if urine output of the patient during steps (c) and (d) exceeded 20 ml/hour then patient is administered an I.V. diuretic and state of hydration of the patient is monitored until stabilization.

The approach described herein for increasing blood hemoglobin concentration in a patient requiring such treatment is particularly well suited for handheld or system based computers, or Internet-based applications. The invention may be implemented in hardware circuitry, in computer software, or a combination of hardware circuitry and computer software and is not limited to a particular hardware or software implementation.

Also disclosed is a devi-safe nomogram comprising two coordinate axes, wherein one axis comprises a target red cell mass (tRCM) scale specific to the corresponding values of target hematocrit (tHct) within the homeostatic Hct range from 13.3% (UHL, upper homeostatic hematocrit limit) to 60.0% (LHL, lower homeostatic hematocrit limit), wherein the other axis comprises a scale specific to plasma and blood volume deviations from normal,
 wherein the Devi-safe nomogram enables a medical worker to determine a patient's target state's blood volume (tBV) deviation from ideal value (IBV) and thereby determine an appropriate plasma volume expansion for a given volume of plasma to facilitate a patient in achieving normovolemia.

FIG. 28 is a block diagram that illustrates a computer system 700 upon which an embodiment of the invention may be implemented. Computer system 700 includes a bus 702 or other communication mechanism for communicating information, and a processor 704 coupled with bus 702 for processing information. Computer system 700 also includes a main memory 706, such as a random access memory (RAM) or other dynamic storage device, coupled to bus 702 for storing information and instructions to be executed by processor 704. Main memory 706 also may be used for storing temporary variables or other intermediate information during execution of instructions to be executed by processor 704. Computer system 700 further includes a read only memory (ROM) 708 or other static storage device coupled to bus 702 for storing static information and instructions for processor 704. A storage device 710, such as a magnetic disk or optical disk, is provided and coupled to bus 702 for storing information and instructions.

Computer system 700 may be coupled via bus 702 to a display 712, such as a cathode ray tube (CRT), for displaying information to a computer user. An input device 714, including alphanumeric and other keys, is coupled to bus 702 for communicating information and command selections to processor 704. Another type of user input device is cursor control 716, such as a mouse, a trackball, or cursor direction keys for communicating direction information and command selections to processor 704 and for controlling cursor movement on display 712. This input device typically has two degrees of freedom in two axes, a first axis (e.g., x) and a second axis (e.g., y), that allows the device to specify positions in a plane.

The invention is related to the use of computer system 700 for determining homeostatic blood states for patients and their doctors. According to one embodiment of the invention, parameters for determining homeostatic blood states is provided by computer system 700 in response to processor 704 executing one or more sequences of one or more instructions contained in main memory 706. Such instructions may be read into main memory 706 from another computer-readable medium, such as storage device 710. Execution of the sequences of instructions contained in main memory 706 causes processor 704 to perform the process steps described herein. One or more processors in a multi-processing arrangement may also be employed to execute the sequences of instructions contained in main memory 706. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 704 for execution. Such a medium may take many forms, including but not limited to, non-volatile media, volatile media, and transmission media. Non-volatile media includes, for example, optical or magnetic disks, such as storage device 710. Volatile media includes dynamic memory, such as main memory 706. Transmission media includes coaxial cables, copper wire and fiber optics, including the wires that comprise bus 702. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 704 for execution. For example, the instructions may initially be carried on a magnetic disk of a remote computer. The remote computer can load the instructions into its dynamic memory and send the instructions over a telephone line using a modem. A modem local to computer system 700 can receive the data on the telephone line and use an infrared transmitter to convert the data to an infrared signal. An infrared detector coupled to bus 702 can receive the data carried in the infrared signal and place the data on bus 702. Bus 702 carries the data to main memory 706, from which processor 704 retrieves and executes the instructions. The instructions received by main memory 706 may optionally be stored on storage device 710 either before or after execution by processor 704.

Computer system 700 also includes a communication interface 718 coupled to bus 702. Communication interface 718 provides a two-way data communication coupling to a network link 720 that is connected to a local network 722. For example, communication interface 718 may be an integrated services digital network (ISDN) card or a modem to provide a data communication connection to a corresponding type of telephone line. As another example, communication interface 718 may be a local area network (LAN) card to provide a data communication connection to a compatible LAN. Wireless links may also be implemented. In any such implementation, communication interface 718 sends and receives electrical, electromagnetic or optical signals that carry digital data streams representing various types of information.

Network link 720 typically provides data communication through one or more networks to other data devices. For example, network link 720 may provide a connection through local network 722 to a host computer 724 or to data equipment operated by an Internet Service Provider (ISP) 726. ISP 726 in turn provides data communication services through the world wide packet data communication network now commonly referred to as the "Internet" 728. Local network 722 and Internet 728 both use electrical, electromagnetic or optical signals that carry digital data streams. The signals through the various networks and the signals on network link 720 and through communication interface 718, which carry the digital data to and from computer system 700, are exemplary forms of carrier waves transporting the information.

Computer system 700 can send messages and receive data, including program code, through the network(s), network link 720 and communication interface 718. In the Internet example, a server 730 might transmit a requested code for an application program through Internet 728, ISP 726, local network 722 and communication interface 718. In accordance with the invention, one such downloaded application provides for the calculating of transfusion strategies as described herein.

The received code may be executed by processor 704 as it is received, and/or stored in storage device 710, or other non-volatile storage for later execution. In this manner, computer system 700 may obtain application code in the form of a carrier wave.

While this invention has been described in connection with the best mode presently contemplated by the inventor for carrying out his invention, the preferred embodiments described and shown are for purposes of illustration only, and are not to be construed as constituting any limitations of the invention. Modifications will be obvious to those skilled in the art, and all modifications that do not depart from the spirit of the invention are intended to be included within the scope of the appended claims. Those skilled in the art will appreciate that the conception upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

My invention resides not in any one of these features per se, but rather in the particular combinations of some or all of them herein disclosed and claimed and it is distinguished from the prior art in these particular combinations of some or all of its structures for the functions specified.

With respect to the above description then, it is to be realized that the optimum dimensional relationships for the parts of the invention, including variations in size, materials, shape, form, function and manner of operation, assembly and use, and all equivalent relationships to those illustrated in the drawings and described in the specification, that would be deemed readily apparent and obvious to one skilled in the art, are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A method of increasing blood hemoglobin concentration in a patient requiring such treatment, comprising:
 (a) determining hemoglobin concentration (Hb) in a patient's blood sample;

(b) determining the ideal blood volume (IBV) of the patient;

(c) determining a first red cell mass value corresponding to the patient's hemoglobin concentration based on a predetermined mean cell hemoglobin concentration (MCHC) parameter;

(d) determining a target red cell mass (tRCM-B) of the patient based on the predetermined MCHC;

(e) calculating a therapeutically effective amount of packet red blood cells for transfusion into a patient to increase the patient's red cell mass to approximately the tRCM-B level, wherein the therapeutically effective amount is directly proportional to k, wherein k is equivalent to about 30% of the IBV value, further wherein the therapeutically effective amount of packet red blood cells (PRBC) is defined by the mathematical formula:

k((target red cell mass)−(first red cell mass)), wherein steps (a) to (d) can occur in any order; and (f) administering to the patient the calculated therapeutically effective amount of packet red blood cells thereby increasing the hemoglobin concentration in the patient's blood.

2. The method of increasing, blood hemoglobin concentration according to claim 1, wherein k is defined by one of the mathematical formulas:

$k = IPV + RCM_{LHL} - IBV = IBV(1 - Hct_{ITM}) + RCM_{LHL} - IBV$ and $k = IBV - RCM_{UHL} - IPV = IBV - RCM_{UHL} - BV(1 - Hct_{ITM})$.

3. The method of increasing blood hemoglobin concentration according to claim 1, wherein IBV is calculated based on height and width of the patient using Nadler's formula.

4. The method of increasing blood hemoglobin concentration according to claim 1, wherein the predetermined mean cell hemoglobin concentration (MCHC) parameter is selected using a HBS nomogram, wherein the HBS nomogram comprises a two-dimensional plot of red cell mass scale verses blood hemoglobin concentration, further wherein the HBS nomogram comprises at least one radiating line defining mean cell hemoglobin concentration (MCHC-RL).

5. The method of increasing blood hemoglobin concentration according to claim 4, wherein the HBS nomogram further comprises a plot of blood hematocrit (Hct) verses blood hemoglobin concentration.

6. The method of increasing blood hemoglobin concentration according to claim 1, wherein the tRCM-B corresponds to a desired target blood hemoglobin concentration in the patient's blood, wherein the target blood hemoglobin concentration is selected to correspond to a MCHC of 300 g/l(+/−15 g/l).

7. The method of increasing blood hemoglobin concentration according to claim 1, wherein a therapeutic amount of artificial hemoglobin is administered to the patient, wherein the therapeutic amount of artificial hemoglobin is equivalent to the amount of hemoglobin contained in the therapeutic amount of packet red blood cells (PRBC) defined by the mathematical formula.

8. The method of increasing blood hemoglobin concentration according to claim 1, wherein the predetermined mean cell hemoglobin concentration (MCHC) parameter is selected using a HBS nomogram in combination with an Osmonomogram, wherein the Osmonomogram defines tables of normal mean cell hemoglobin content (MCH), mean cell volume (MCV), and mean cell hemoglobin concentration (MCHC) values, wherein the HBS nomogram comprises a two-dimensional plot of red cell mass scale verses blood hemoglobin concentration, further wherein the HBS nomogram comprises at least one radiating line defining mean cell hemoglobin concentration (MCHC-RL).

9. The method of increasing blood hemoglobin concentration according to claim 1, wherein the predetermined mean cell hemoglobin concentration (MCHC) parameter is selected using a HBS nomogram in combination with at least one nomogram selected from the group consisting of: an Osmonomogram and a Devi-safe nomogram, wherein the Osmonomogram defines tables of normal mean cell hemoglobin content (MCH), mean cell volume (MCV), and mean cell hemoglobin concentration (MCHC) values, wherein the Devi-safe nomogram comprises a two-dimensional plot of blood hematocrit (Hct) verses ideal blood circulating volume (IBV), and wherein the HBS nomogram comprises a two-dimensional plot of red cell mass scale verses blood hemoglobin concentration, further wherein the HBS nomogram comprises at least one radiating line defining mean cell hemoglobin concentration (MCHC-RL).

\* \* \* \* \*